(12) United States Patent
Sillers et al.

(10) Patent No.: US 11,685,938 B2
(45) Date of Patent: Jun. 27, 2023

(54) MUCONIC ACID PRODUCTION FROM GENETICALLY ENGINEERED MICROORGANISMS

(71) Applicant: PTT GLOBAL CHEMICAL PUBLIC COMPANY LIMITED, Bangkok (TH)

(72) Inventors: Ryan Sillers, Reading, MA (US); Theron Hermann, Arlington, MA (US); Michelle Spencer, Woburn, MA (US); Russell Udani, Arlington, MA (US); R. Rogers Yocum, Lexington, MA (US)

(73) Assignee: PTT GLOBAL CHEMICAL PUBLIC COMPANY LIMITED, Bangkok (TH)

( * ) Notice: Subject to any disclaimer, the term of this patent is extended or adjusted under 35 U.S.C. 154(b) by 112 days.

(21) Appl. No.: 17/326,643

(22) Filed: May 21, 2021

(65) Prior Publication Data

US 2021/0277429 A1 Sep. 9, 2021

Related U.S. Application Data

(62) Division of application No. 16/081,504, filed as application No. PCT/US2017/020263 on Mar. 1, 2017, now abandoned.

(60) Provisional application No. 62/302,558, filed on Mar. 2, 2016.

(51) Int. Cl.
*C12P 7/46* (2006.01)
*C12N 9/88* (2006.01)
*C12N 15/70* (2006.01)

(52) U.S. Cl.
CPC ............ *C12P 7/46* (2013.01); *C12N 9/88* (2013.01); *C12N 15/70* (2013.01); *C12Y 402/01118* (2013.01)

(58) Field of Classification Search
CPC ..... C12P 7/46; C12P 7/44; C12N 9/88; C12N 15/70; C12N 15/52; C12Y 402/01118; C12Y 401/01063; C12Y 101/01025; C12Y 205/01054; C12Y 207/01002; C12Y 401/01031; C12Y 604/01001
See application file for complete search history.

(56) References Cited

U.S. PATENT DOCUMENTS

| | | | |
|---|---|---|---|
| 4,480,034 A | 10/1984 | Hsieh | |
| 4,535,059 A | 8/1985 | Hsieh et al. | |
| 4,588,688 A | 5/1986 | Maxwell | |
| 4,603,338 A | 8/1986 | Hsieh | |
| 4,681,852 A | 7/1987 | Tribe | |
| 4,753,883 A | 6/1988 | Backman et al. | |
| 4,833,078 A | 5/1989 | Hsieh | |
| 4,968,612 A | 11/1990 | Hsieh | |
| 5,168,056 A | 12/1992 | Frost | |
| 5,272,073 A | 12/1993 | Frost et al. | |
| 5,487,987 A | 1/1996 | Frost et al. | |
| 5,616,496 A | 4/1997 | Frost et al. | |
| 6,180,373 B1 | 1/2001 | Wich et al. | |
| 6,210,937 B1 | 4/2001 | Ward et al. | |
| 6,472,169 B1 | 10/2002 | Frost et al. | |
| 6,600,077 B1 | 7/2003 | Frost et al. | |
| 6,613,552 B1 | 9/2003 | Frost et al. | |
| 6,962,794 B2 | 11/2005 | Vaile et al. | |
| 7,244,593 B2 | 7/2007 | Yocum et al. | |
| 7,638,312 B2 | 12/2009 | Park et al. | |
| 7,790,431 B2 | 9/2010 | Frost | |
| 8,809,583 B2 | 8/2014 | Bui | |
| 8,871,489 B2 | 10/2014 | Grabar et al. | |
| 9,017,976 B2 | 4/2015 | Gong et al. | |
| 2009/0191610 A1 | 7/2009 | Zelder et al. | |
| 2010/0314243 A1 | 12/2010 | Frost et al. | |
| 2013/0337519 A1 | 12/2013 | Dole et al. | |
| 2014/0234923 A1 | 8/2014 | Yocum et al. | |
| 2015/0044755 A1 | 2/2015 | Yocum et al. | |
| 2015/0240270 A1* | 8/2015 | Yocum | C12N 9/93 435/254.2 |
| 2016/0017381 A1 | 1/2016 | Beckham et al. | |

FOREIGN PATENT DOCUMENTS

| | | |
|---|---|---|
| EP | 0 190 921 A2 | 8/1986 |
| WO | WO 2011/017560 A1 | 2/2011 |
| WO | WO 2011/085311 A1 | 7/2011 |
| WO | WO 2011/123154 A2 | 10/2011 |
| WO | 2013/116244 | 8/2013 |

OTHER PUBLICATIONS

Curran et al., Metabolic engineering of muconic acid production in *Saccharomyces cerevzszae*. Metabol. Eng., 2013, vol. 15: 55-66. (Year: 2013).*
Gulmezian et al., The role of UbiXin *Escherichia coli* coenzyme Q biosynthesis. Arch Biochem. Biophys., 2007, vol. 467: 144-153. (Year: 2007).*
Payer et al., Regioselective para-carboxylation of catechols with a prenylated flavin dependent decarboxylase. Agnew. Chem. Int. Ed., 2017, vol. 56: 13893-13867, vol. 394: 335-344) (Year: 2017).*
Sonoki T., Enhancement of a platform chemical (catechol) production from cellulosic materials. NSIR 2014 Young Investigator Research Grant; Outline of Research Result, pp. 33-34. (Year: 2014).*
Stephen F. Altschu et al.; "Basic Local Alignment Search Tool"; J. Mol., Biol. 215, pp. 403-410 (1990).
Stephen F. Altschul et al.; "Gapped BLAST and PSI-BLAST: a new generation of protein database search programs"; *Nucleic Acids Research*, 1997, vol. 25, No. 17, pp. 3389-3402.

(Continued)

*Primary Examiner* — Ganapathirama Raghu
(74) *Attorney, Agent, or Firm* — Oblon, McClelland, Maier & Neustadt, L.L.P.

(57) ABSTRACT

The subject of this invention is improvements in the yield and titer of biological production of muconic acid by fermentation. Increased activity of one or more enzymes involved in the muconic acid pathway leads to increased production of muconic acid.

13 Claims, 13 Drawing Sheets

Specification includes a Sequence Listing.

(56) References Cited

OTHER PUBLICATIONS

Laurent Aussel, et al.; "Biosynthesis and physiology of coenzyme Q in bacteria☆";Biochimica et Biophysica Acta 1837 (2014), pp. 1004-1011.

Tomoya Baba et al.; "Construction of *Escherichia coli* K-12 in-frame, single-gene knockout mutants: the Keio colkection"; Molecutar Systems Biology (2006), pp. 1-11.

Vale'rie Barbe et al.; "Unique features revealed by the genome sequence of *Acinetobacter* sp. ADP1, a versatile and naturally transformation competent bacterium";Nucleic Acids Research, 2004, vol. 32, No. 19, pp. 5766-5779.

J. A. Bird et al.; "cis-cis-Muconate, the Product Inducer of Catechol 1,2-Oxygenase in Pseudomonas aeruginosa"; Biochem. J. (1968) vol. 109, pp. 479-481.

Sunil S. Chandran et al.; "Phosphoenolpyruvate Availability and the Biosynthesis of Shikimic Acid"; Biotechnol. Prog. 2003, 19, pp. 808-814.

Ruizhen Chen et al.; "Metabolic Consequences of Phosphotransferase (PTS) Mutation in a Phenylalanine-Producing Recombinant *Escherichia coli*"; Biotechnol. Prog. 1997, vol. 13, pp. 768-775.

Kai Chen et al.; "Deletion of the aroK gene is essential for high shikimic acid accumulation through the shikimate pathway in *E. coli*"; Bioresource Technology, vol. 119 (2012), pp. 141-147.

Ve'ronique de Berardinis et al.; "A complete collection of single-gene deletion mutants of Acinetobacter baylyi ADP1"; Molecular Systems Biology 4; Article No. 174, 2008.

K. M. Draths et al.; "Biocatalytic Synthesis of Aromatics from D-Glucose: The Role of Transketolase"; J. Am. Chem. Soc., vol. 114, No. 10, pp. 3956-3962, 1992.

K. M. Draths et al.; "Environmentally Compatible Synthesis of Catechol from D-Glucose"; J. Am. Chem. Soc., vol. 117, No. 9, pp. 2395-2400, 1995.

David A. Elsemore et al.; "Unusual Ancestry of Dehydratases Associated with Quinate Catabolism in Acinetobacter calcoaceticus†"; Journal of Bacteriology, vol. 177, No. 20, Oct. 1995, p. 5971-5978.

Adelfo Escalante et al; "Metabolic engineering for the production of shikimic acid in an evolved *Escherichia coli* strain lacking the phosphoenolpyruvate: carbohydrate phosphotransferase system"; Escalante et al. Microbial Cell Factories , 9:21, pp. 1-12, 2010.

Flores, N. et al, "Pathway engineering for the production of aromatic compounds in *Escherichia coli*"; Nature Biotechnology vol. 14, pp. 620-623, 1996.

David T. Fox et al; "The Missing Link in Petrobactin Biosynthesis: asbF Encodes a (#)-3-Dehydroshikimate Dehydratase"; Biochemistry , vol. 47, pp. 12251-12253, 2008.

Ya-Ming Ger et al; A Single Ser-180 Mutation Desensitizes Feedback Inhibition of the Phyenylalanine-Sensitive 3-Deoxy-D-Arabino-Hepulosonate 7-Phosphate (DAHP) Synthetase in *Escherichia coli*[1], J Biochem. vol. 116, pp. 986-990, 1994.

D. J. W. Grant and J. C. Patel; "The non-oxidative decarboxylation of p-hydroxybenzoic acid, gentisic acid, protocatechuic acid and gallic acid by Klebsiella aerogenes (Aerobacter aerogenes)"; Antonie van Leeuwenhoek 35 (1969) pp. 325-343.

Esben H. Hansen et al; "De Novo Biosynthesis of Vanillin in Fission Yeast (*Schizosaccharomyces pombe*) and Baker's Yeast (*Saccharomyces cerevisiae*)"; Applied and Environmental Microbiology, vol. 75, No. 9, May 2009, p. 2765-2774.

Andrew A. Horowitz et al, "Efficient Multiplexed Integration of Synergistic Alleles and Metabolic Pathways in Yeasts via CRISPR-Cas." Cell Systems. 1(1): pp. 88-96, 2015.

Changyun Hu et al; "Mutation analysis of the feedback inhibition site of phenylalanine-sensitive 3-deoxy-D-arabino-heptulosonate 7-phosphate synthase of *Escherichia coli*"; J. Basic Microbiol. vol. 43 (2003) 5, pp. 399-406.

Sakura G. Iwagami et al: "Characterization of the Protocatechuic Acid Catabolic Gene Cluster from *Streptomyces* sp. Strain 2065"Applied and Environmental Microbiology, vol. 66, No. 4, Apr. 2000, p. 1499-1508.

Kaemwich Jantama et al; "Combining Metabolic Engineering and Metabolic Evolution to Develop Nonrecombinant Strains of *Escherichia coli* C That Produce Succinate and Malate"; Biotechnology and Bioengineering, vol. 99, No. 5, Apr. 1, 2008, pp. 1140-1153.

Kaemwich Jantama et al; "Eliminating Side Products and Increasing Succinate Yields in Engineered Strains of *Escherichia coli* C"; Biotechnology and Bioengineering, vol. 101, No. 5, Dec. 1, 2008, pp. 881-893.

Natalia Jiménez et al; "Uncovering the Lactobacillus plantarum WCFS1 Gallate DecarboxylaseInvolved in Tannin Degradation"; Applied and Environmental Microbiology, Jul. 2013 vol. 79 No. 14, p. 4253-4263.

Christopher W.Johnson et al; "Enhancing muconic acid production from glucose and lignin-derived aromatic compounds via increased protocatechuate decarboxylase activity";Metabolic Engineering Communications, vol. 3, 2016, pp. 111-119.

Yoshimi Kikuchi et al; "Mutational Analysis of the Feedback Sites of Phenylaianine-Sensitive 3-Deoxy-D-arabino-Heptulosonate-7-Phosphate Synthase of *Escherichia coli*";Applied and Environmental Microbiology, vol. 63, No. 2, Feb. 1997, p. 761-762.

Yutaka Kojima et al; "Studies on pyrocatechase. I. Purification and spectral properties", The Journal of Biological Chemistry, vol. 242, No. 14, 1967, p. 3270-3278.

Claude G.Lerner et al; "Low copy number plasmids for regulated low-level expression of cloned genes in *Escherichia coli* with blue/white insert screening capability"; Nucleic Acids Research, vol. 18, No. 15, 1990, p. 4631.

Kai Li and J. W. Frost; "Microbial Synthesis of 3-Dehydroshikimic Acid: A Comparative Analysis of D-Xylose, L-Arabinose, and D-Glucose Carbon Sources"Biotechnol. Prog. 1999, 15, p. 876-883.

Henry Lin et al; "Increasing the Acetyl-CoA Pool in the Presence of Overexpressed Phosphoenolpyruvate Carboxylase or Pyruvate Carboxylase Enhances Succinate Production in *Escherichia coli*"; Biotechnol. Prog. vol. 20, No. 5, 2004, p. 1599-1604.

Fengming Lin et al; "Isofunctional Enzymes PAD1 and UbiX Catalyze Formation of a Novel Cofactor Required by Ferulic Acid Decarboxylase and 4-Hydroxy-3-polyprenylbenzoic Acid Decarboxylase";ACS Chem. Biol., vol. 10, 2015, p. 1137-1144.

Jia-ling Luand James C. Liao; "Metabolic Engineering and Control Analysis for Production of Aromatics: Role of Transaldolase";Biotechnology and Bioengineering, vol. 53, pp. 132-138 (1997).

Boguslaw Lupa et al; "Distribution of genes encoding the microbial non-oxidative reversible hydroxyarylic acid decarboxylases/phenol carboxylasesi"; Genomics vol. 86 (2005), p. 342-351.

Tina Lütke-Eversloh & Gregory Stephanopoulos; "L-Tyrosine production by deregulated strainsof *Escherichia coli*";Appl Microbiol Biotechnol vol. 75: (2007), p. 103-110.

Sumiko Mizuno et al; "Microbial production of cis, cis-muconic acid from benzoic acid"; Appl Microbiol Biotechnol vol. 28 (1988) p. 20-25.

Atsushi Nakazawa et al; "Purification and properties of pyrocatechase from Pseudomonas fluorescens, Biochim Biophys Acta 147, (1967) p. 189-199".

Ellen L. Neidle and L. Nicholas Ornston;"Cloning and Expression of Acinetobacter calcoaceticus Catechol 1,2-Dioxygenase Structural Gene catA in *Escherichia coli*"; Journal of Bacteriology, vol. 168, No. 2, Nov. 1986, p. 815-820.

Wei Niu et al; "Benzene-Free Synthesis of Adipic Acid"; Biotechnol. Prog., vol. 18, No. 2, 2002, p. 201-211.

Matthew R. Parsek et al; "Roles of CatR and cis,cis-Muconate in Activation of the catBC Operon, Which Is Involved in Benzoate Degradation in *Pseudomonas putida*"; Journal of Bacteriology, vol. 174, No. 23, Dec. 1992, p. 7798-7806.

Ranjan Patnaik et al; "Engineering of *Escherichia coli* Central Metabolism for Aromatic Metabolite Production with Near Theoretical Yield"; Applied and Environmental Microbiology, vol. 60, No. 11, Nov. 1994, p. 3903-3908.

Karl A.P. Payne et al; "New cofactor supports αβ-unsaturated acid decarboxylation via 1,3-dipolar cycloaddition"; Nature.; 522(7557), 2015, p. 497-501.

(56) References Cited

OTHER PUBLICATIONS

Brian F. Pfleger et al; "Structural and functional analysis of AsbF: Origin of the stealth 3,4-dihydroxybenzoic acid subunit for petrobactin biosynthesis"; Proc Natl Acad Sci USA, vol. 105, No. 44, Nov. 4, 2008, p. 17133-17138.

Danilo Perez-Pantoja et al; "Metabolic reconstruction of aromatic compounds degradation from the genome of the amazing pollutant-degrading bacterium Cupriavidus necator JMP134"; FEMS Microbiol Rev 32 (2008) p. 736-794.

Danilo Pérez-Pantoja et al; "Genomic analysis of the potential for aromatic compounds biodegradation in Burkholderiales"; Environmental Microbiology (2012) 14(5), p. 1091-1117.

James Pittard and B. J. Wallace; "Distribution and Function of Genes Concerned with Aromatic Biosynthesis in *Escherichia coli*"; Journal of Bacteriology, vol. 91. No. 4, Apr. 1966, p. 1494-1508.

Tino Polen et al; "Toward biotechnological production of adipic acid and precursors from biorenewables"; Journal of Biotechnology 167 (2013) p. 75-84.

Barbara J. Rutledge; "Molecular characterization of the qa-4 gene of Neurospora crassa", Gene 32, (1984) p. 275-287.

F. Schirmer et al; "The Acinetobacter caicoaceticus NCIB8250 *mop* operon mRNA is differentially degraded, resulting in a higher level of the 3' CatA-encoding segment than of the 5' phenolhydroxylase-encoding portion", *Mol Gen Genet* (1998) 257, p. 330-337.

Igor A Shumilin et al.; "Crystal structure of phenylalanine-regulated 3-deoxy-D-arabinoheptulosonate-7-phosphate synthase from *Escherichia coli*"; Structure, vol. 7, No. 7, 1999, p. 865-875.

E. S. Shumkova et al; "Phenol Degradation by *Rhodococcus opacus* Strain 1G"; Applied Biochemistry and Microbiology vol. 45, No. 1, 2009, p. 43-49.

R. Sietmann et al; "Novel metabolic routes during the oxidation of hydroxylated aromatic acids by the yeast *Arxula adeninivorans*"; The Society for Applied Microbiology, Journal of Applied Microbiology 108 (2010) p. 789-799.

Mark R. Smith et al; "Quantitative biotransformation of catechol to cis, cis-muconate"; Biotechnology Letters vol. 11, No. 2 p. 105-110 (1989).

Jacky L. Snoep et al;"Reconstitution of Glucose Uptake and Phosphorylation in a Glucose-Negative Mutant of *Escherichia coli* by Using *Zymomonas mobilis* Genes Encoding the Glucose Facilitator Protein and Glucokinase"; Journal of Bacteriology, vol. 176, No. 7, Apr. 1994, p. 2133-2135.

Georg A. Sprenger; "Genetics of pentose-phosphate pathway enzymes of *Escherichia coli* K-12"; Arch Microbiol (1995) 164 : p. 324-330.

Georg A. Sprenger et al; "Transketolase A of *Escherichia coli* K12 Purification and properties of the enzyme from recombinant strains"; Eur. .I. Biochem. 230, p. 525-532 (1995).

Georg A. Sprenger et al; "Transaldolase B of *Escherichia coli* K-12: Cloning of Its Gene, talB, and Characterization of the Enzyme from Recombinant Strains"; Journal of Bacteriology, vol. 177, No. 20, Oct. 1995, p. 5930-5936.

Per Stroman et al; "Purification and Characterization of 3-Dehydroshikimate Dehydratase, an Enzyme in the Inducible Quinic Acid Catabolic Pathway of *Neurospora crassa*"; The Journal of Biological Chemistry, vol. 253, No. 13, Issue of Jul. 10. pp. 4593-4598, 1978.

Taka Tateoka and Ituko Yasuda; "3-Dehydroshi mate dehydratase in mung bean cultured cells"; Plant Cell Reports (1995) 15: p. 212-217.

G. N. Vemuri et al; "Effects of Growth Mode and Pyruvate Carboxylase on Succinic Acid Production by Metabolically Engineered Strains of *Escherichia coli*"; Applied and Environmental Microbiology, vol. 68, No. 4, Apr. 2002, p. 1715-1727.

Lisa M. Weaver et al; "Cloning of an aroF Allele Encoding a Tyrosine-Insensitive 3-Deoxy-D-arabino-Heptulosonate 7-Phosphate Synthase"; Journal of Bacteriology, vol. 172, No. 11, Nov. 1990, p. 6581-6584.

Christian Weber et al ; "Biosynthesis of cis,cis-Muconic Acid and Its Aromatic Precursors, Catechol and Protocatechuic Acid, from Renewable Feedstocks by *Saccharomyces cerevisiae*"; Applied and Environmental Microbiology, vol. 78 No. 23, Dec. 2012, p. 84218430.

Kerry A. Wheeler et al; "Control of metabolic flux through the quinate pathway in Aspergillus nidulans"; Biochem. J. (1996) 315, 195-205.

Mark D. White et al; "UbiX is a flavin prenyltransferase required for bacterial ubiquinone biosynthesis"; Nature. Jun. 25, 2015; 522(7557): 502-506.

Nengzhong Xie et al; "Characterization of benzoate degradation by newly isolated bacterium *Pseudomonas* sp. XP-M2"; Biochemical Engineering Journal 46 (2009) p. 79-82.

Neng-Zhong Xie et al; "Biotechnological production of muconic acid: current status and future prospects"; Biotechnology Advances 32 (2014) p. 615-622.

Jian Yi et al; "Altered Glucose Transport and Shikimate Pathway Product Yields in *E. coli*"; Biotechnol. Prog. 2003, vol. 19, p. 1450-1459.

Nobuji Yoshikawa et al; "Microbial production of cis, cis-muconic acid"; Journal of Biotechnology. 14 (1990) p. 203-210.

Sonoki T., Enhancement of a platform chemical (catechol) production from cellulosic materials. NISR Grant Outline of Research Result, 2014, pp. 33-34. (Year: 2014).

Niu et al., Benzene-free synthesis of adipic acid. Biotechnol. Prog., 2002, vol. 18: 201-211 (Year: 2002).

Chica et al., Semi-rational approaches to engineering enzyme activity: combining the benefits of directed evolution and rational design. Curr. Opi. Biotechnol., 2005, vol. 16: 378-384. (Year: 2005).

Miller et al., Production of phenylalanine and organic acids by phosphoenolpyruvate carboxylase-deficient mutants of *Escherichia coli*. J. Indus. Microbial. 1987, vol. 2: 143-149 (Year: 1987).

Payer et al., Regioselective para-carboxylation of catechols with a prenylated flavin dependent decarboxylase. Angew. Chem. Int. Ed. 2017, vol. 56: 13893-13897. (Year: 2017).

Sen et al., Developments in directed evolution for enzyme functions. Appl. Biochem. Biotechnol., 2007, vol. 143: 212-223. (Year: 2007).

Sonoki et al., Enhancement of protocatechuate decarboxylase activity for the effective production of muconate from lignin-related aromatic compounds. J. Biotechnol., 2014, vol. 192: 71-77 (Year: 2014).

Whisstock et al., Prediction of protein function from protein sequence. Q. Rev. Biophysics., 2003, vol. 36 (3): 307-340. (Year: 2003).

Johnson et al, "Enhancing muconic acid production from glucose and lignin-derived aromatic compounds via increased protocatechuate decarboxylase activity", Metabolic Engineering Communications vol. 3 (2016), pp. 111-119.

Lin et al., "Isofunctional Enzymes PAD1 and UbiX Catalyze Formation of a Novel Cofactor Required by Ferulic Acid Decarboxylase and 4-Hydroxy-3-polyprenylbenzoic Acid Decarboxylase", *ACS Chem. Biol*,, (2015), vol. 10, No. 4, pp. 1137-1144 (10 pages).

Payne et al, "New cofactor supports α,β-unsaturated acid decarboxylation via 1,3-dipolar cycloaddition", *Nature*, (2015), vol. 522, pp. 497-514.

Zhang et al, "Regulation of the isofunctional genes ubiD and ubiX of the ubiquinone biosynthetic pathway of *Escherichia coli*", *FEMS Microbiology Letters*, (2003) vol. 223, pp. 67-72.

Clarke et al, "Unexpected role for vitamin B2", *Nature*, (2015), vol. 522, pp. 427-428.

White et al, "UbiX is a flavin prenyltransferase required for bacterial ubiquinone biosynthesis", *Nature*. (2015), vol. 522, pp. 502-518.

Li et al, "Decarboxylation mechanisms in biological system", *Biorganic Chem.*, (2012), vol. 43, pp. 2-14 (15 pages).

Do et al, "Crystal structure of UbiX, an aromatic acid decarboxylase from the psychrophilic bacterium Colwellia psychrerythraea that undergoes FMN-induced conformational changes", *Sci. Rep.*, (2015) 5:8196, pp. 1-9.

\* cited by examiner

MUCONIC ACID PRODUCTION FROM GENETICALLY ENGINEERED MICROORGANISMS

CROSS-REFERENCE TO RELATED APPLICATION

This application is a divisional application of U.S. application Ser. No. 16/081,504, filed Aug. 31, 2018, which is the U.S. national stage application of International Application No. PCT/US2017/020263 filed Mar. 1, 2017, which claims priority to U.S. Provisional Patent Application No. 62/302,558 filed Mar. 2, 2016, the contents of each of which is herewith incorporated by reference herein.

REFERENCE TO SEQUENCE LISTING

This application contains a Sequence Listing which has been submitted electronically in ASCII format and is hereby incorporated by reference in its entirety. Said ASCII copy, created on Feb. 20, 2020, is named 524823US_ST25.txt and is 344,000 bytes in size.

FIELD OF THE INVENTION

The present invention is in the field of producing renewable chemical feedstocks using biocatalysts that have been genetically engineered in the central aromatic biosynthetic pathway. More specifically, the present invention provides processes for improving the production of muconic acid from renewable carbon resources using genetically modified biocatalysts.

BACKGROUND OF THE INVENTION

Adipic acid is a major commodity chemical and is used in the production of nylon 6,6 and polyurethanes. Adipic acid is currently derived from petrochemical feedstocks. Current synthesis of adipic acid is environmentally harmful releasing nitrous acid (Xie et al., 2014). Alternatively, adipic acid can be made from any of the three isomers of muconic acid (cis, cis; cis, trans; trans, trans isomers) by chemical hydrogenation. It would be desirable to produce muconic acid from renewable resources by fermentation with a microorganism, followed by hydrogenation process to yield adipic acid, since such a route to adipic acid would be more environmentally friendly than the traditional petrochemical route (Niu, Draths and Frost, 2002; Frost and Draths, 1997). Many other chemicals can be made by chemical conversion of one or more muconic acid isomers, including, but not limited to 1.6 hexane diol, 3-hexenedicarboxylic acid, 1,6-hexanediamine, and terephthalic acid.

The international patent application publication No. WO 2011/017560 claims biocatalysts having a muconate pathway and a method for producing muconic acid using these biocatalysts. In brief, this published patent application discloses four different pathways for producing muconic acid. The first pathway for muconic acid production starts with succinyl-CoA and acetyl-CoA. The second pathway for muconic acid production begins with pyruvate and malonate semialdehyde. The third pathway for muconic acid production starts with pyruvate and succinic semialdehyde. The fourth pathway for muconic acid production starts with lysine. All these pathways for muconic acid production proposed in this patent application are based on computer modeling and it is yet to be seen whether such biocatalysts can ever be created with commercially acceptable productivity and yield for muconic acid.

A fermentation route to produce cis, cis-muconic acid using a genetically engineered E. coli system has been described in the scientific literature (Niu et al., 2002; Frost and Draths, 1997) and in patent literature (U.S. Pat. Nos. 5,487,987; 5,616,496; WO 2011/085311 A1). However, the prior art process for muconic acid production suffered from significant drawbacks such as expensive medium components (aromatic amino acids and vitamins) and chemical inducers, as well as yields lower than required for industrial production. A recent United States Patent Application Publication No. US2015/0044755, which is incorporated herein by reference in its entirety, provides improved biocatalysts for muconic acid production involving constitutive expression of relevant gene, improved heterologous genes and novel "leaky" AroE enzymes. The present invention provides further improvements in the muconic acid biocatalysts described in the United States Patent Application Publication No. US2015/0044755.

SUMMARY OF THE INVENTION

This present invention provides genetically engineered microorganisms that produce cis, cis-muconic acid starting from non-aromatic carbon sources, such as sugars and carbohydrates including, but not limited to glucose, sucrose, glycerol and cellulosic hydrolysate.

In one embodiment of the present invention, the activity of a negative regulator of aromatic amino acid biosynthesis is genetically manipulated. In one aspect of the present invention, the activity of the negative regulator TyrR is substantially reduced by means of controlling the expression of the tyrR gene coding for the TyrR protein. In another aspect of the present invention, the activity of the negative regulator TyrR is totally eliminated by means of deleting or inactivating the tyrR gene in the chromosomal DNA of the microorganism.

In another embodiment of the present invention, the feedback inhibition of certain enzymes in the aromatic amino acid pathway by certain metabolites is overcome through genetic manipulations. In most wild type E. coli strains, deoxyarabino-heptulosonate 7-phosphate synthase ("DAHP synthase") functioning at the beginning of the aromatic amino acid pathway occurs as three different isozymes which are known to be encoded by three different genes namely aroG, aroF and aroH. The proteins encoded by each of these three genes are subjected to feedback inhibition by one or more metabolites of aromatic amino acid pathway. In one aspect of the present invention, the wild type aroG gene is replaced by a modified aroG gene which codes for an AroG protein that is resistant to feedback inhibition by one or more metabolites of the aromatic amino acid pathway within the microbial cell. Such a feedback resistant form of AroG protein is referred as "AroG$^{FBR}$". In another aspect of the present invention, the wild type aroF gene is replaced by an aroF gene which codes for an AroF protein that is resistant to feedback inhibition by one or more metabolites of the aromatic amino acid pathway within the microbial cell (AroF$^{FBR}$). In yet another aspect of the present invention, the wild type aroH gene is replaced by an aroH gene which codes for an AroH protein that is resistant to feedback inhibition by one or more metabolites of the aromatic amino acid pathway within the microbial cell (AroH$^{FBR}$). In yet another aspect of the present invention the biocatalyst selected for the commercial production of cis, cis-muconic acid may have more than one feedback resistant isozyme for DAHP synthase.

In another embodiment of the present invention, the activity of one or more of the enzymes involved in the central aromatic biosynthetic pathway within the microbial cell is enhanced. In one aspect of the present invention, the enhancement of the activity of one or more enzymes involved in the operation of an aromatic pathway and/or a muconic acid pathway is accomplished through genetic manipulation. In a preferred aspect of the present invention, the expression of one or more of the genes coding for the proteins AroF, AroG, AroH, AroB, TktA, TalB, AroZ, QutC, Qa-4, AsbF, QuiC, AroY, Rpe, Rpi, Pps, CatA and CatX or their homologs or analogs are enhanced leading to the increased activity of said proteins. Rpe is a ribulose-5-phosphate epimerase, Rpi is a ribulose-5-phosphate isomerase, and Pps is a phosphoenol pyruvate synthetase (Neidhardt and Curtiss, 1996). If the host strain is yeast, for example *Saccharomyces cerevisiae*, or a filamentous fungus, for example, *Neurospora crassa*, several of the enzymes that catalyze reactions in the shikimate pathway can be combined into one large protein or polypeptide, called Aro1p, encoded by the ARO1 gene in the case of *S. cerevisiae*. Aro1p combines the functions of AroB, AroD, AroE, AroK (or AroL), and AroA). As such, for the purposes of this invention, Aro1p, and ARO1, or a portion thereof, can be used as a substitute, or in addition to, AroB, AroD, AroE, AroK, and/or AroA.

In yet another embodiment of the present invention, flux through erythrose-4-phosphate within the bacterial cell is enhanced by means of overexpressing enzymes in the operation of the pentose phosphate pathway. In one aspect of the present invention, the expression of transaldolase enzyme, for example one coded by the talB or talA gene is enhanced by genetic modification. In another aspect of the present invention, the expression of a gene encoding transketolase enzyme, for example, the tktA gene is enhanced by genetic manipulations. In yet another aspect of the present invention, the expression of the genes encoding either or both ribulose-5-phosphate epimerase and ribulose-5-phosphate isomerase are enhanced by genetic manipulations.

In another embodiment of the present invention, the pool of the phosphoenol pyruvate (PEP) necessary for the functioning of the aromatic amino acid pathway is increased through genetic manipulation. In one aspect of the present invention, competition for the use of PEP pool is decreased through elimination and/or complementation of a PEP-dependent phosphotransferase system (PTS) for glucose uptake with a PEP independent system for glucose uptake. In another aspect of the present invention, the GalP based sugar uptake system is inactivated for the purpose of conserving ATP within the microbial cells. In yet another aspect of the present invention, in the microbial cells defective in the functioning of both PTS system and GalP based sugar uptake system (ΔPTS/ΔgalP), the sugar uptake is accomplished by means of introducing an exogenous gene encoding for Glf (protein facilitating the glucose diffusion), or exogenous genes encoding for both Glf and Glk (glucokinase) proteins. In yet another aspect of the present invention, the availability of PEP is increased by increasing the expression of a gene that encodes a PEP synthetase, such aspps.

In yet another embodiment of the present invention, the activity of 3,4-dihydroxybenzoic acid decarboxylase (AroY) is enhanced. In one aspect of this embodiment, the expression of AroY is enhanced by genetic manipulation. In another aspect of the present invention, the expression of a protein acting as an accessory protein to AroY, selected from a group comprising UbiX, KpdB, Elw, Kox, Lpl and homologs thereof, is increased by genetic manipulation leading to an increase in 3,4-dihydroxybenzoic acid decarboxylase activity.

In another embodiment of the present invention, PEP availability is increased by the reduction or elimination of phosphoenolpyruvate carboxylase (Ppc) activity. In one aspect of the present invention, pyruvate carboxylase (Pyc) activity is increased and/or substituted for Ppc activity, particularly when Ppc activity is eliminated.

DETAILED DESCRIPTION OF THE PREFERRED EMBODIMENTS

Figure 1:
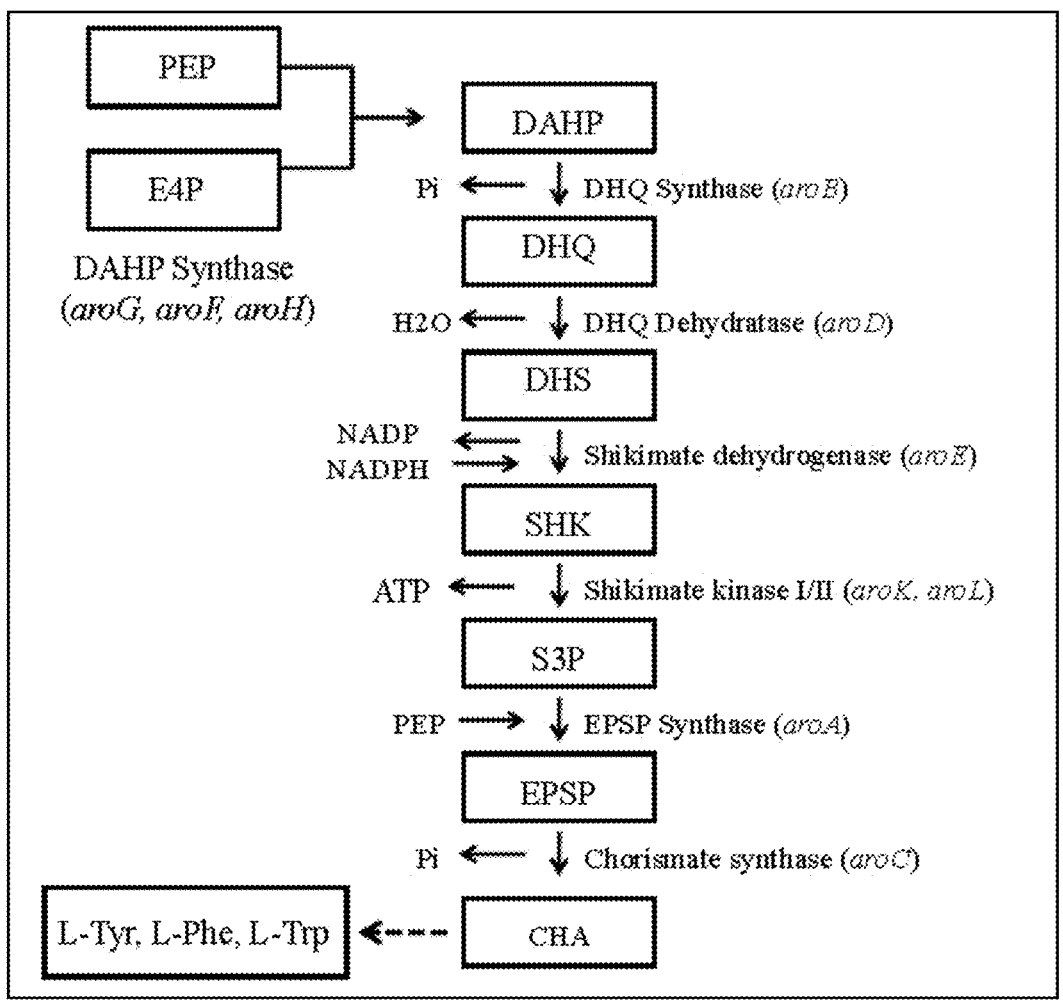
FIG. 1. Pathway for aromatic amino acid biosynthesis in *E. coli*.

All the patents, patent applications, publications, sequences, and other published materials are incorporated herein are incorporated by reference.

As used in this patent application, the phrase "for example" or "such as" is meant to indicate that there are more than one method, approach, solution, or composition of matter for the subject at hand, and the example given is not meant to be limiting to that example.

The term "heterologous" refers to a gene or protein that is not naturally or natively found in an organism, but which can be introduced into an organism by genetic engineering, such as by transformation, mating, or transduction. A heterologous gene can be integrated (inserted) into a chromosome or contained on a plasmid. The term "exogenous" refers to a gene or protein that has been introduced into, or altered, in an organism for the purpose of increasing, decreasing, or eliminating an activity, by genetic engineering, such as by transformation, mating, transduction, or mutagenesis. An exogenous gene or protein can be heterologous, or it can be a gene or protein that is native to the host organism, but altered by one or more methods, for example, mutation, deletion, change of promoter, change of terminator, duplication, or insertion of one or more additional copies in the chromosome or in a plasmid. Thus, for example, if a second copy of the aroB gene is inserted at a site in the chromosome that is distinct from the native site, the second copy would be exogenous.

The term "microorganism" as used in this present invention includes bacteria, archaea, yeast, algae and filamentous fungi that can be used for the commercial production of cis, cis-muconic acid through a fermentation process. The term "genetically engineered microorganism" refers to microorganisms that are not present in the Nature but generated using one or other genetic modifications as described in this patent application.

For nomenclature, a gene or coding region is usually named with lower case letters in italics, for example "aroZ", while the enzyme or protein encoded by a gene can be named with the same letters, but with the first letter in upper case and without italics, for example "AroZ". The enzyme or protein can also be referred to by a more descriptive name, for example, AroZ can also be referred to as 3-dehydroshikimate dehydratase. A gene or coding region that encodes one example of an enzyme that possess a particular catalytic activity can have several different names because of historically different origins, or because the gene comes from different species. For example the gene that encodes 3-dehydroshikimate dehydratase from *Bacillus anthracis* can be named asbF instead of aroZ, the same gene from *Aspergillus nidulans* can be named qutC, the same gene from *Neurospora crassa* can be named qa-4, and the same gene from *Acinetobacter baylyi* can be named quiC.

A "plasmid" means a circular or linear DNA molecule that is substantially smaller than a chromosome, separate from the chromosome or chromosomes of a microorganism, and that replicates separately from the chromosome or chromosomes. A "plasmid" can be present in about one copy per cell or in more than one copy per cell. Maintenance of a plasmid within a microbial cell in general requires an antibiotic selection, but complementation of an auxotrophy can also be used.

The term "chromosome" or "chromosomal DNA" as used in this invention in the context of a bacterial cell is a circular DNA molecule that is substantially larger than a plasmid and does not require any antibiotics selection.

The term an "expression cassette" or a "cassette" means a DNA sequence that can be part of a chromosome or plasmid that contains at least a promoter and a gene or region that codes for an enzyme or other protein, such that the coding region is expressed by the promoter, and the enzyme or protein is produced by a host cell that contains the DNA sequence. An "expression cassette" can be at least partly synthetic, or constructed by genetic engineering methods, so that the coding region is expressed from a promoter that is not naturally associated with the coding region. Optionally, the "expression cassette" can contain a transcription terminator that may or may not be a terminator that is naturally associated with the coding region. An "expression cassette" can have coding regions for more than one protein, in which case it can be called an operon, or a synthetic operon.

The term "overexpression" of a gene or coding region means causing the enzyme or protein encoded by that gene or coding region to be produced in a host microorganism at a level that is higher than the level found in the wild type version of the host microorganism under the same or similar growth conditions. This can be accomplished by, for example, one or more of the following methods: 1) installing a stronger promoter, 2) installing a stronger ribosome binding site, such as a DNA sequence of 5'-AGGAGG, situated about four to ten bases upstream of the translation start codon, 3) installing a terminator or a stronger terminator, 4) improving the choice of codons at one or more sites in the coding region, 5) improving the mRNA stability, and 6) increasing the copy number of the gene, either by introducing multiple copies in the chromosome or placing the cassette on a multicopy plasmid. An enzyme or protein produced from a gene that is overexpressed is said to be "overproduced". A gene that is being "overexpressed" or a protein that is being "overproduced" can be one that is native to a host microorganism, or it can be one that has been transplanted by genetic engineering methods from a different organism into a host microorganism, in which case the enzyme or protein and the gene or coding region that encodes the enzyme or protein is called "foreign" or "heterologous". Foreign or heterologous genes and proteins are by definition overexpressed and overproduced, since they are not present in the unengineered host organism.

The term a "homolog" of a first gene, DNA sequence, or protein is a second gene, DNA sequence, or protein that performs a similar biological function to that of said first gene, DNA sequence or protein, and that has at least 25% sequence identity (when comparing protein sequences or comparing the protein sequence derived from gene sequences) with said first gene or protein, as determined by the BLAST computer program for sequence comparison (Altschul et al., 1990; Altschul et al., 1997), using default parameters and allowing for deletions and insertions. An example of a homolog of the *E. coli* aroG gene would be the aroG gene from *Salmonella typhimurium*.

Two enzymes or proteins that are very distantly related by homology can carry out the same biochemical function but be only relatively weakly homologous to each other. For example, the FumA fumarase from *E. coli* K-12 (GenBank NP 416129) is about 26.9% homologous to a fumarase from *Clostridium botulinum* (GenBank GAE03909.1) over their region of overlap, and about 25.1% homologous to a fumarase beta subunit from *Pyrococcus* sp. ST04 (GenBank AKF23146.1) over their region of overlap. As another example, a *Klebsiella* AroZ and a *Neurospora crassa* Qa-4 enzyme that both function to convert DHS to PCA are 29.3% identical. Therefore, since for the genetic engineering of a metabolic pathway, the important feature of a heterologous enzyme or protein is the function or reaction carried out by that enzyme or protein, not the source organism or the precise amino acid sequence, we define "homologous" enzymes or proteins or "homologs" to comprise any pair of enzymes or proteins that are 25% or higher in the identity of their amino acid sequences, allowing for gaps, as shown for example by using the default parameters for alignment using the LaserGene 12 (DNAStar, Madison, Wis.) MegAlign program with the Lipman-Pearson method (Ktuple=2, Gap penalty=4, and Gap length penalty=12).

The term an "analog" of a first gene, DNA sequence, or protein is a second gene, DNA sequence, or protein that performs a similar biological function to that of said first gene, DNA sequence, or protein, but where there is less than 25% sequence identity (when comparing protein sequences or comparing the protein sequence derived from gene sequences) with said first gene, DNA sequence or protein, as determined by the BLAST computer program for sequence comparison (Altschul et al., 1990; Altschul et al., 1997), and allowing for deletions and insertions. An example of an analog of the *Klebsiella pneumoniae* AroZ protein would be the QutC protein from *Aspergillus nidulans*, since both proteins are enzymes that catalyze the 3-dehydroshikimate dehydratase reaction, but there is no significant sequence homology between the two enzymes or their respective genes. A scientist knowledgeable in the art will know that many enzymes and proteins that have a particular biological function, for example DAHP synthase or 3-dehydroshikimate dehydratase, can be found in many different organisms, either as homologs or analogs, and since members of such families of enzymes or proteins share the same function, although they may be slightly or substantially different in structure, different members of the same family can in many cases be used to perform the same biological function using current methods of genetic engineering. Thus, for example, the AroZ enzyme and the QutC enzyme catalyze the same reaction, DHS dehydratase, so either one will result in production of cis, cis-muconic acid in the proper context, and the choice of which one to use ultimately can be made by choosing the one that leads to a higher titer of cis, cis-muconic acid under similar fermentation conditions.

The terms a "non-aromatic carbon source" or a "non-aromatic compound" means a carbon-containing compound that can be used to feed a microorganism of the invention as a source of carbon and/or energy, in which the compound does not contain a six-membered ring related to benzene. Examples of non-aromatic carbon sources include glucose, xylose, lactose, glycerol, acetate, arabinose, galactose, mannose, maltose, or sucrose. An "aromatic compound" is a compound that contains one or more six-membered rings related to benzene. An example of an aromatic compound is catechol, or 1,2-dihydroxy benzene. A microorganism selected for producing muconic acid using glucose as a source of non-aromatic carbon source can further be engineered to use other types of non-aromatic carbon sources such as glycerol, sucrose and xylose using the genetic engineering techniques as provided in the patent documents U.S. Pat. No. 8,871,489 and US Patent Application Publication Nos. US2013/0337519A1 and US2014/0234923A.

The term a "strong constitutive promoter" means a DNA sequence that typically lies upstream (to the 5' side of a gene when depicted in the conventional 5' to 3' orientation), of a DNA sequence or a gene that is transcribed by an RNA polymerase, and that causes said DNA sequence or gene to be expressed by transcription by an RNA polymerase at a level that is easily detected directly or indirectly by any appropriate assay procedure. Examples of appropriate assay procedures include 1) quantitative reverse transcriptase plus PCR, 2) enzyme assay of an encoded enzyme, 3) Coomassie Blue-stained protein gel, or 4) measurable production of a metabolite that is produced indirectly as a result of said transcription, and such measurable transcription occurring regardless of the presence or absence of a protein that specifically regulates level of transcription, a metabolite, or inducer chemical. An example of a promoter that is not a "strong constitutive promoter" is the $P_{lac}$ promoter of *E. coli*, since it is repressed by a repressor in the absence of lactose or the inducer IPTG. By using well known methods in the art, a "strong constitutive promoter" can be used to replace a native promoter (a promoter that is otherwise naturally existing upstream from a DNA sequence or gene), resulting in an expression cassette that can be placed either in a plasmid or chromosome and that provides a level of expression of a desired DNA sequence or gene at a level that is higher than the level from the native promoter. A strong constitutive promoter can be specific for a species or genus, but often a strong constitutive promoter from a bacterium can function well in a distantly related bacterium. For example, a promoter from *Bacillus subtilis* or a phage that normally grows on *B. subtilis* can function well in *E. coli*. A "strong constitutive promoter" is substantially different from inducible promoters, such as $P_{tac}$, which have been used in the prior art production of cis, cis-muconic acid and typically require an expensive chemical or other environmental change for the desired level of function (Niu et al., 2002). Examples of strong constitutive promoters are $P_{15}$, $P_{26}$, from *Bacillus subtilis* phage SP01, and *coli* phage lambda $P_R$.

A "mutation" is any change in a DNA sequence that makes it different from a related wild type sequence. A "mutation" can comprise a single base change, a deletion, an insertion, a replacement, a frameshift, an inversion, a duplication, or any other type of change in a DNA sequence. Usually a "mutation" refers to a change that has a negative effect on function or reduce the activity of a gene or gene product, however, herein, the term "mutation" can also refer to a change that increases the activity of a gene or gene product. For example, a feedback resistant mutation in the aroG gene increases the activity of AroG in the presence of an inhibitor such as phenylalanine. Replacement of a promoter with a different, stronger promoter, also result in a mutation that can increase the activity of a gene or gene product. A "null mutation" is a mutation, such as a deletion of most or all of a gene, is a mutation that effectively eliminates the function of a gene. A "mutant" is a strain or isolate that comprises one or more mutations.

The biological production of cis, cis-muconic acid (herein referred to as simply "muconic acid") is based on the redirection of carbon from the aromatic amino acid pathway. Native production of aromatic amino acids and vitamins requires the metabolites erythrose-4-phosphate (E4P) and phosphoenolpyruvate (PEP). The first committed step in aromatic amino acid synthesis is catalyzed by the enzyme 3-deoxy-arabino-heptulonate 7-phosphate (DAHP) synthase. In *E. coli*, this step can be performed by three different isozymes, AroG, AroF, or AroH. Each of these enzymes is regulated at the transcriptional level by a repressor protein TyrR, as well as at the protein level by inhibition from terminal products of the pathway, phenylalanine, tyrosine, and tryptophan, respectively. The production of muconic acid proceeds from an intermediate in the aromatic amino acid pathway, dehydroshikimic acid (DHS) and requires the expression of three heterologous enzymes, dehydroshikimate dehydratase (AroZ), 3,4-dihydrobenzoate decarboxylase (AroY), and catechol 1,2-dioxygenase (CatA). This pathway is shown in FIGS. 1 and 2.

Figure 3:
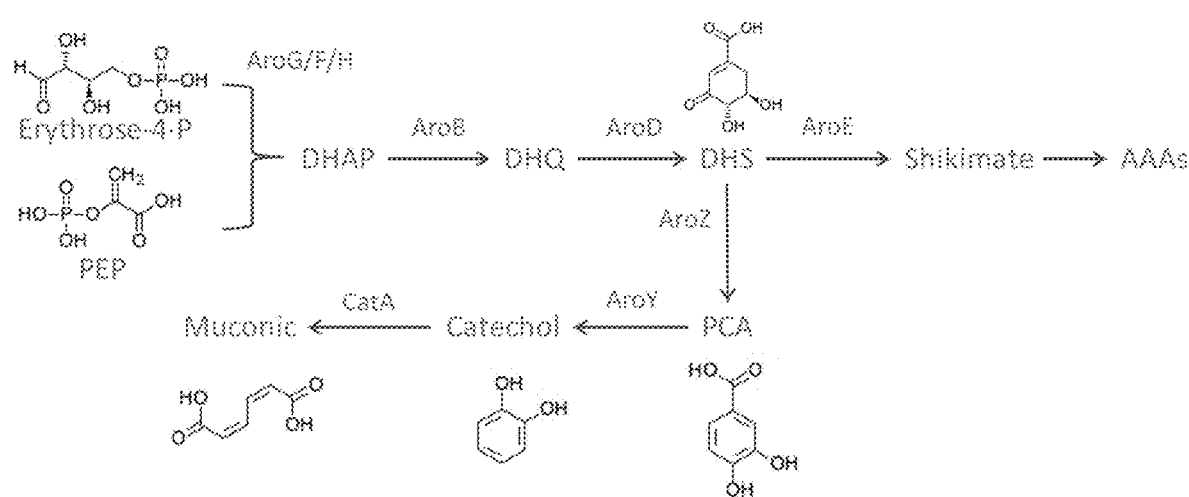
FIG. 3. Reaction steps in the conversion of 3-deoxy-arabino-heptulonate 7-phosphate (DHAP) to muconic acid.

A "muconic pathway" or "muconic acid pathway" refers to a biochemical pathway from DHS to PCA to catechol to cis, cis-muconic acid, and a "muconic pathway gene" is a gene that encodes an enzymes that catalyzes a step in a muconic pathway, or encodes an auxiliary function that serves to enhance the activity of one of said enzymes, for example, aroZ, aroY, catA, catX, and qutC (FIG. 3). DHS is an abbreviation for 3-dehydroshikimate, and PCA is an abbreviation for protocatechuic acid. A "muconic plasmid" is a plasmid that contains one or more muconic pathway genes.

Figure 2:
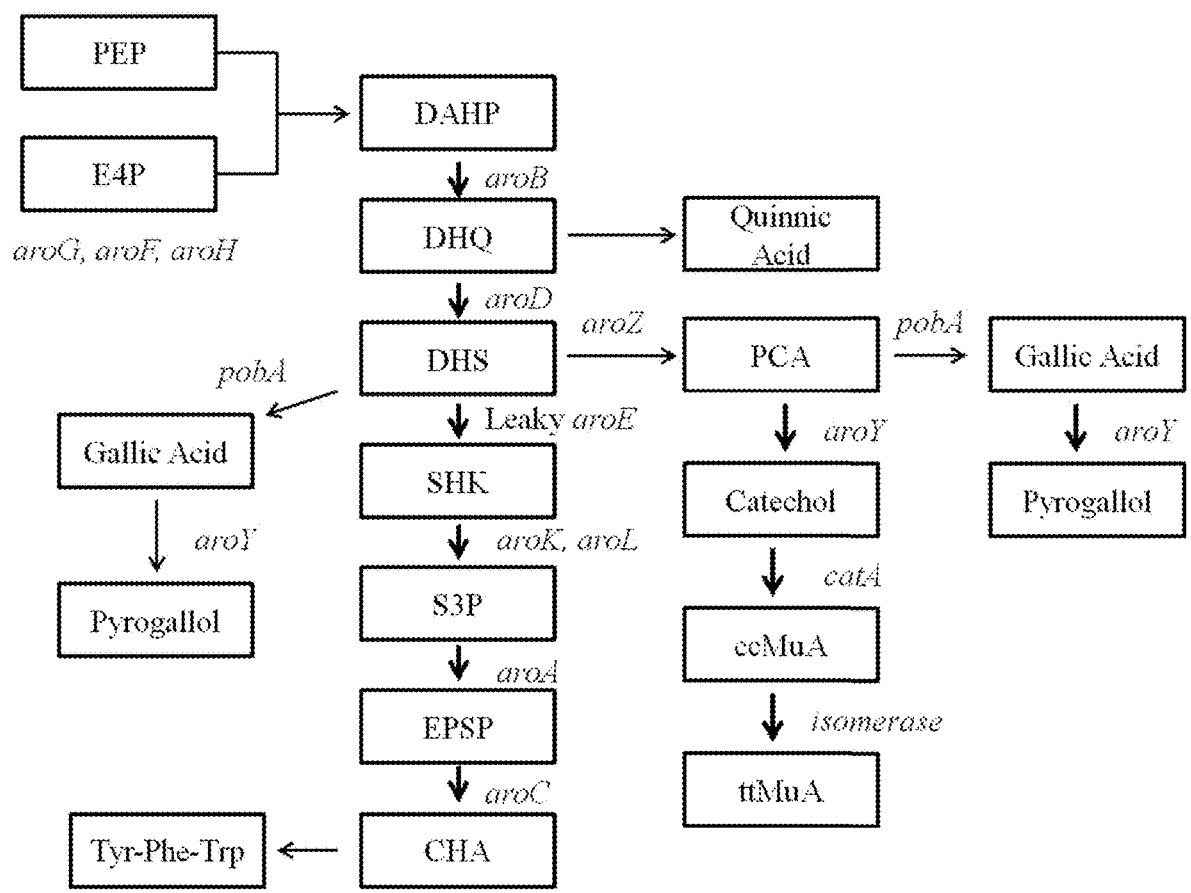
FIG. 2. Pathway for muconic acid biosynthesis in *E. coli*.

The genetic manipulations used in the present inventions are centered around the common pathway for aromatic amino acid and aromatic vitamin (or vitamin-like) biosynthesis present in many microbial cells as shown in FIG. 1. The common pathway for aromatic amino acid biosynthesis as depicted in FIG. 1 can be referred to as the "shikimic acid" or "shikimate" pathway, the "chorismic acid" or "chorismate" pathway, or the "central aromatic" or "central aromatic biosynthetic" pathway.

There is a substantial volume of published work on genetic engineering of microorganisms for the production of the aromatic amino acids, phenylalanine, tyrosine, and tryptophan (U.S. Pat. Nos. 4,681,852, 4,753,883, 6,180,373, European Patent Application 86300748.0). The approaches for the production of aromatic amino acids include using various combinations of feedback resistant enzymes (AroF, AroG, PheA, TyrA), deregulation of repression of transcription (tyrR$^-$), increasing promoter strength (P$_{tac}$, P$_{lac}$) and increasing the copy number of one or more genes (tktA). Many specific combinations of the above mentioned genetic modifications can be followed to obtain a biocatalyst suitable for muconic acid production.

According to the disclosure in the International Patent Application Publication No. WO2013/116244, incorporated herein in its entirety by reference, the genetically engineered microorganisms do not need to contain any exogenous plasmids in order to produce muconic acid, although they have certain exogenous or heterologous genes necessary to achieve the desired phenotype. In the preferred embodiment of the present invention, the exogenous genes introduced into the microorganisms are stably integrated into the chromosomal DNA. As a result of this chromosomal DNA integration of the exogenous genes, the need for the use of antibiotics or other selective methods to maintain the plasmids carrying exogenous DNA is totally eliminated. In addition, strong promoters that do not require chemical inducers are used to express genes necessary for the operation of the pathway from carbon source, such as glucose, to cis, cis-muconic acid.

When an exogenous coding sequence is integrated into the chromosomal DNA, it is integrated at a locus, the deletion of which has been reported not to cause any adverse effects. For example, the coding region at the physical location 0039 in *E. coli* bacterium, also known as ydeM, is annotated as a lipoprotein and has been demonstrated to have no adverse effects upon deletion. Similarly, the coding region at the physical location 2160 in *E. coli* bacterium, also known as nlpA, is annotated as a radical SAM domain protein and has been demonstrated to have no adverse effects upon deletion. In the present invention, a copy of P$_R$-catAX was inserted at the physical location 0039 in *E. coli* bacterium and a copy of P$_R$-aroG$^{FBR}$ was inserted at the physical location 2160 in *E. coli* bacterium. In other examples described herein, an insertion is made in gene that is advantageous to knockout or deleted, such as a gene encoding for an unwanted function, for example a ptsI gene or a tyrR gene.

The aromatic amino acid biosynthetic pathway is well known for many microorganisms, especially for *E. coli* (Neidhart and Curtiss 1996). In a wild type cell, the pathway is tightly regulated by both feedback inhibition and repression of transcription. The first committed step is catalyzed by deoxy-arabino-heptulosonate 7-phosphate (DAHP) synthase, of which there are three isozymes encoded by aroF, aroG, and aroH. The three isozymes, AroF, AroG, and AroH, are feedback inhibited by the products of aromatic amino biosynthetic pathway namely by tyrosine, phenylalanine, and tryptophan. Feedback resistant mutants of AroF, AroG, and AroH are well known (Hu et al. 2003; Lutke-Eversloh and Stephanopoulos 2007). One aspect of the present invention involves use of feedback resistant alleles of aroF, aroG, and aroH genes in order to express AroF, AroG and AroH enzyme proteins that are resistant to feedback inhibition by the products of aromatic amino acid biosynthetic pathway. The AroF, AroG and AroH enzyme proteins that are resistant to feedback inhibition are referred as AroF$^{FBR}$, AroG$^{FBR}$ and AroH$^{FBR}$.

Transcription of several of the operons involved in the aromatic pathway is regulated by either the repressor encoded by the tyrR gene or the repressor encoded by the trpR gene, or both (Neidhardt and Curtiss 1996). Of particular importance is the negative regulation of transcription of aroG and aroF by the TyrR protein when it is bound with one or more of the aromatic amino acids. One aspect of the present invention involves the removal of negative regulation by tyrR or trpR genes by means of eliminating these genes from the chromosome of the host bacterial strains.

The present invention teaches certain combinations of genetic elements in the biocatalysts suitable for muconic acid production, for example, but not limited to, various combinations of an overproduced feedback resistant AroG, an overproduced feedback resistant AroF, an overexpressed tktA, an overexpressed talA, chromosomally integrated cassettes for expressing an aroZ, aroY, and a catAX (or analogs or homologs thereof) from strong constitutive promoters, and a leaky aroE allele, which we define as a gene that encodes an AroE enzyme that confers prototrophy for the aromatic amino acids and vitamins, but without leading to significant secretion of unwanted aromatic compounds.

All specific examples of strain constructions disclosed herein are based on wild type *Escherichia coli* C strain (ATCC 8739), or *Escherichia coli* W strain (ATCC 9637). However, it should be realized at this point that the expression cassettes or appropriate analogs and homologs of the genetic elements disclosed herein can be assembled in any other suitable microorganism, such as any other suitable *E. coli* strains and other species of bacteria, archaea, yeast, algae, and filamentous fungi that can be used for the commercial production of muconic acid through a fermentative process.

In *E. coli*, the aromatic amino acid biosynthesis pathway from glucose starts with the non-oxidative branch of the pentose phosphate pathway (PPP). Four key enzymes in the non-oxidative pentose phosphate pathway are transketolase, transaldolase, ribulose-5-phosphate epimerase and ribulose-5-phosphate isomerase. These enzymes catalyze the reactions that lead to the formation of erythrose 4-phosphate (E4P) from hexose or pentose sugars. To increase the availability of E4P in *E. coli*, the tktA gene encoding transketolase can be overexpressed (Niu et al., 2002). Similarly, the overexpression of the transaldolase gene is also expected to increase the availability of E4P in some circumstances (Bongaerts et al., 2001). In yet another aspect of the present invention, the expression of both the transketolase and transaldolase genes are enhanced through genetic manipulations leading to an increase in the activity of transketolase and transaldolase enzymes. In yet another aspect of the invention, flux through the non-oxidative branch of the PPP is increased by overproducing ribulose-5-phosphate epimerase and ribulose-5-phosphate isomerase.

The first committed step and most tightly regulated reaction in the common aromatic amino acid pathway is the condensation of phosphoenolpyruvate (PEP) and E4P to produce deoxyarabino-heptulosonate 7-phosphate (DAHP) by DAHP synthase (encoded by aroG, aroF, and aroH). D-glucose consumed by E. coli is brought into aromatic biosynthesis partly through the PPP, and partly through glycolysis. The flow of glucose into the aromatic pathway is greatly increased when transketalose (tktA) and an isozyme of DAHP synthase (aroG) are amplified through transformation with a plasmid that increases their expression by increasing their copy number (Niu et al., 2002). In a preferred aspect of the present invention, the exogenous aroG and tktA genes are integrated into the chromosomal DNA for the purpose of amplification of activities transketolase and DAHP synthase enzymes.

In another embodiment of the present invention, the flux through PEP within the microbial cell is improved by increasing the PEP available for the synthesis of DAHP by reducing the flux of PEP to other pathways. Many genera of bacterial cells consume PEP in the transport of glucose across the cell membrane using a phosphotransferase system (PTS) in which one PEP molecule is consumed for every molecule of glucose transported across the bacterial outer membrane. By replacing or complementing the PEP-dependent PTS with a non-PEP dependent (PEP independent) glucose uptake mechanisms, it is possible to increase the pool size of the PEP available for the aromatic amino acid biosynthetic pathway within the microbial cell. For example, the PTS system for sugar uptake can be replaced or complemented by a GalP-based sugar uptake system or the sugar transporter system based on Glf/Glk proteins (Chandran et al., 2003; Yi et al., 2003). In a preferred aspect of the present invention besides deleting the PTS system for sugar uptake for the purpose of conserving PEP pool within the microbial cell, the GalP based sugar uptake system is also inactivated for the purpose of conserving ATP within the microbial cell. In a microbial cell which is defective in the functioning of both PTS system and a Gal-P based sugar uptake system (ΔPTS/Δga/P), the sugar uptake can be accomplished by means of introducing an exogenous gene coding for Glf (glucose facilitated diffusion protein), or exogenous genes encoding both Glf and Glk (glucokinase) proteins. As used in the present invention, the term functional glucose-facilitated diffusion protein refers to any Glf protein as well as any other protein which is functionally equivalent to Glf and functions to transport sugars into the microbial cells by facilitated diffusion. In one aspect of the present invention, the gene coding for the glucose facilitator protein Glf is introduced into the microbial cell which is ΔPTS/Δga/P and the glucose transported into the microbial cell is phosphorylated by endogenous glucose kinase. In another aspect of the present invention the genes coding for both Glf and Glk proteins are introduced into a microbial cell which is ΔPTS/ΔgalP. In a preferred aspect of the present invention, the exogenous glf and glk genes introduced into the microbial cell are integrated into the host chromosomal DNA.

In another embodiment of the present invention, when the carbon source for growth and energy requires gluconeogenesis (for example if the carbon source is acetate or succinate), the PEP pool can be increased by increasing the activity of carboxylating enzymes already present within the cell, for example PEP carboxykinase, which is encoded by pck in E. coli, or by introducing an exogenous carboxylating enzyme. In a preferred embodiment, the introduced exogenous gene coding for a carboxylating enzyme is stably integrated into the host chromosome. Genes coding for the carboxylating enzyme can be derived from a variety of microbial species. The genes coding for the carboxylating enzymes can further be subjected to genetic manipulations so that the expression of the carboxylating enzyme within the biocatalyst for cis, cis-muconic acid production is significantly enhanced.

PEP is one of two major metabolites for the aromatic pathway and reduction or elimination of Ppc activity preserves PEP for the aromatic pathway and muconic acid production. Ppc catalyzes the anaplerotic reaction forming oxaloacetate, an intermediate in the TCA cycle. Ppc activity is essential for wild type E. coli and some other organisms in minimal media, but it is absent in others. Some organisms, such as yeast that lack Ppc, utilize Pyc to replenish oxaloacetate. Lowered or absent Ppc activity can be complemented with Pyc activity, by providing an alternate route to oxaloacetate from pyruvate instead of PEP, which results in increased availability of PEP for muconic acid production as well as for production of other compounds, such as aromatic compounds, that require PEP as an intermediate. In at least one example disclosed herein, substituting Pyc for Ppc can reduce flux from PEP to OAA, which in turn conserves PEP for the central aromatic pathway.

In yet another embodiment of the present invention, the PEP pool inside the microbial cell is increased by decreasing or eliminating the activity of pyruvate kinase enzymes such as PykA and PykF which use PEP as a substrate.

From DAHP, the aromatic amino acid pathway proceeds via a number of intermediates to chorismate (CHA), a branch point for the biosynthesis of three aromatic amino acids namely L-Tyrosine (L-Tyr), L-Phenylalanine (L-Phe), and L-Tryptophan (L-Trp).

In the initial stages of the common aromatic amino acid pathway, 3-dehydroquinate (DHQ) synthase (AroB) removes the phosphate group from DAHP leading to the formation of DHQ. The enzyme DHQ dehydratase (AroD) removes a water molecule from DHQ leading to the formation of 3-dehydroshikimate (DHS) which is subsequently reduced to shikimate (SHK) by shikimate dehydrogenase (AroE). Shikimate kinase I/II (AroK, AroL) phosphorylates shikimate to shikimate 3-phosphate (S3P). There is a condensation of S3P with PEP leading to the formation of 5 enolpyruvoylshikimate 3-phosphate (EPSP). The formation of EPSP is mediated by EPSP synthase (AroA). A phosphate group from EPSP is removed by chorismate synthase (AroC) leading to the formation of chorismate (CHA).

As shown in the FIG. 2, the aromatic amino acid pathway can be blocked at the level of conversion of 3-dehydroshikimate (DHS) to shikimate (SHK) due to a mutation in an aroE gene leading to the accumulation of DHS (Niu et al., 2002). Introduction of an exogenous aroZ gene functions to convert DHS into protocatechuate (PCA). PCA is subsequently converted into catechol through a decarboxylation reaction mediated by an AroY enzyme. Catechol is ultimately converted into cis-cis-muconic acid (ccMuA) through the action of a catA gene product. ccMuA can be acted upon by maleyl acetoacetate isomerase to yield trans-trans muconic acid (ttMuA). The biosynthetic pathway from DHS to ccMuA and/or ttMuA is referred to as a muconic acid pathway. The three different genes responsible for the conversion of DHS to ccMuA can be obtained from various microbial species and introduced into a microorganism selected for muconic acid production such as Escherichia coli. In a preferred embodiment of the present invention, the exogenous genes coding for the proteins involved in muconic acid pathway are integrated into host chromosomal DNA.

In redirecting the aromatic amino acid pathway to the production of cis, cis-muconic acid, the mutation of the aroE gene is critical. The aroE gene can be completely inactivated leading to a total block in the biosynthesis of aromatic amino acids as was done with the WN1/pWN2.248 strain of *E. coli* described for the muconic acid production (Niu et al., 2002). An important drawback with the WN1/pWN2.248 *E. coli* strain and related strains is that due to the complete inactivation of the aroE gene, this strain has become auxotrophic for the aromatic acids such as phenylalanine, tyrosine and tryptophan, and aromatic vitamins or vitamin-like compounds mentioned above. As a result, this strain during its growth for the production of cis, cis-muconic acid requires the exogenous addition of these compounds (or a common intermediate such as shikimate), thereby adding substantially to the cost of commercial production of cis, cis-muconic acid using such a strain. A novel approach to overcome this dependency on an exogenous source of aromatic amino acids is to use a strain with a leaky mutation in aroE. The leaky aroE mutant would allow a limited flow of carbon to shikimic acid while accumulating significant amounts of DHS which is then available for the conversion into PCA by the action of an AroZ enzyme. Thus the use of a leaky mutant form of aroE would eliminate the dependence on exogenous aromatic amino acids, while still diverting the flow of carbon to cis, cis muconic acid.

The genes coding for the synthesis of AroZ, AroY and CatA proteins essential for the conversion of DHS into cis, cis-muconic acid can be derived from any one of many microbial species. In one embodiment, these exogenous genes are integrated into the host chromosome of the biocatalyst being developed. In a preferred embodiment, the expression of these exogenous genes within the biocatalyst is driven by a constitutive promoter without the need for any inducers.

The enzyme 3-dehydroshikimate dehydratase (AroZ; EC 4.2.1.118) is required for biosynthesis of the intermediate protocatechuate. In this specification, "AroZ" shall refer to any enzyme that catalyzes the 3-dehydroshikimate dehydratase reaction. In the prior art, this enzyme is expressed from the aroZ gene of *Klebsiella pneumoniae* strain A170-40 (ATCC25597) (Niu et al., 2002; Draths and Frost, 1995). However, the specific activity of AroZ varies widely among organisms, from 0.1 to 261 micromoles/min/mg (Wheeler et al, 1996; Fox et al, 2008; Pfleger et al, 2008), so a significant improvement can be had by expressing an aroZ gene also known as asbF (Fox et al, 2008; Pfleger et al, 2008), qutC (Wheeler et al, 1996), qa-4 (Rutledge, 1984), and quiC, from an organism that has a higher specific activity than *K. pneumoniae*, for example Acinteobacter baylyi, *Aspergillus nidulans* (Wheeler et al, 1996), now also known as *Emericella nidulans*, or *Neurospora crassa* (Rutledge, 1984; Stroman et al, 1978), or Podospora *anserina*, also known as Podospora *pauciseta* (Hansen et al, 2009).

As one particular example, the coding sequence for the qa-4 gene from *N. crassa* that encodes 3-dehydroshikimate dehydratase can be obtained by any of several well-known methods, for example whole gene DNA synthesis, cDNA cloning, or by a combination of genomic DNA cloning and PCR or synthetic DNA linker synthesis. Since there are no introns in the qa-4 gene, the coding region can be obtained by PCR from genomic DNA (Rutledge, 1984). The protein sequence of the qa-4 enzyme (SEQ ID No. 4) and the DNA sequence of the native gene (SEQ ID No. 5) are known.

Alternatively, an expression cassette can be constructed for the 3-dehydroshikimate dehydratase from *A. nidulans*. The coding sequence for the QutC enzyme from *A. nidulans* can be obtained by any of several well-known methods, for example whole gene DNA synthesis, cDNA cloning, or by a combination of genomic DNA cloning and PCR or synthetic DNA linker synthesis. The protein sequence of QutC (SEQ ID No. 6) and the DNA sequence of the native gene, containing no introns, are known (SEQ ID No. 7; GenBank accession number M77665.1). An expression cassette can be obtained by DNA synthesis, or by a combination of genomic cloning and PCR, so that the QutC enzyme can be produced accurately in *E. coli*. By expressing a coding sequence for QutC from a strong, constitutive promoter in *E. coli*, sufficient expression can be obtained from one or two copies of the gene integrated in the chromosome, obviating the need for maintaining more than two copies of the expression cassette on a multicopy plasmid as has been disclosed in the prior art (Niu et al., 2002), and which can lead to instability. The method described above can be used in general to obtain a DNA sequence that codes for a desired enzyme, and that coding sequence can then be used to construct an expression cassette designed to function in *E. coli* or another appropriate microbial host organism.

The specific activity of AroZ can also be improved by using the protein sequence from the prior art (Niu et al., 2002) by constructing an improved expression cassette, for example, in which a stronger promoter and/or ribosome binding site (RBS) has been installed in front of the coding region, as described in Example 4.

The aroZ gene encoding AroZ (3-dehydroshikimate dehydratase) from *Klebsiella pneumoniae* strain A170-40 can be obtained as described in the prior art. The DNA sequence of the gene and surrounding DNA can be determined by methods well known in the art. A heterologous gene of the invention such as aroZ can be built into an expression cassette using a native DNA sequence or it can be synthesized with a codon optimized sequence for the intended host organism. An aroZ gene can be cloned as described (Draths and Frost, 1995) from any other microbe that contains an active aroZ gene, for example *K. pneumoniae* strain 342, *Acinetobacer* Sp. ADP1 (*Acinetobacter baylyi* ADP1), *Bacillus thuringiensis*, *Emericella nidulans*, *Envinia amylovora*, *Pseudomonas putida* W619, *Neurospora crassa*, *Aspergillus nidulans* and many others.

The enzyme protocatechuate decarboxylase (AroY; EC 4.1.1.63) is required for biosynthesis of the intermediate catechol. In this specification, "AroY" shall refer to any enzyme that catalyzes the protocatechuate decarboxylase reaction. In the prior art, this enzyme is expressed from the aroY gene of *Klebsiella pneumoniae* strain A170-40 (ATCC25597) on a multicopy plasmid (Niu et al., 2002). However, once again an improvement in the process can be gained by producing enough of the enzyme from one or two copies of an expression cassette integrated in the chromosome of the host organism. This can be accomplished by obtaining an aroY gene from an organism that naturally produces an AroY enzyme that has higher specific activity than that of the *K. pneumoniae* AroY enzyme of the prior art, or by increasing the level of expression of the *K. pneumoniae* AroY by constructing an expression cassette that, for example, uses a strong constitutive promoter and/or strong RBS as described above under Example 4. The protein sequence for AroY from *K. pneumoniae* strain A170-40 is given in SEQ ID No. 8. The corresponding gene, aroY, can be cloned as described above (Draths and Frost, 1995), or based on the protein sequence, it can be synthesized with optimized codons for the intended host organism.

The aroY gene can be obtained from any other microorganism that contains a homolog or analog, for example, *K.*

*pneumoniae* strain NCTC418 (ATCC15380), *Klebsiella pneumoniae* 342, and *Arxula adeninivorans* (Sietmann et al, 2010). The DNA sequence of the aroY gene from *Klebsiella pneumoniae* 342 and surrounding DNA is given as SEQ ID No. 9.

The enzyme catechol 1,2-dioxygenase (CatA; EC 1.13.11.1) is required for the last step of cis, cis-muconic acid biosynthesis. In this specification, "CatA" shall refer to any enzyme that catalyzes the catechol 1,2-dioxygenase reaction. In the prior art, this enzyme is expressed from the catA gene of *Acinetobacter calcoaceticus* strain ADP1 on a multicopy plasmid (Niu et al., 2002). The source strain, *Acinetobacter calcoaceticus* strain ADP1, apparently has been renamed *Acinetobacter* Sp. ADP1 and *Acinetobacter baylyi* ADP1 (Neidle and Ornston, 1986; Barbe et al, 2004; de Berardinis et al, 2008). In this prior art example, the catA gene was expressed from a $P_{tac}$ promoter, which requires either lactose or IPTG (isopropylthiogalactoside) as an inducer. These compounds are too expensive for use in commercial fermentations, so again, significant improvements in the process are needed, both to eliminate the need for an expensive inducer and to create a more stable strain by integrating the expression cassette in the chromosome. This can be accomplished by constructing an expression cassette for the catA gene that uses a strong constitutive promoter, strong RBS, and/or more stable mRNA as described above in the other Examples.

The DNA sequence of the catA gene and surrounding sequences from *Acinetobacter baylyi* ADP1 is given in SEQ ID No. 10. The protein sequence for CatA from the same strain is given in SEQ ID No. 11. In a preferred embodiment, the expression cassette for catA contains one or two additional open reading frames that exist naturally downstream from catA, in order to increase the expression level of the catA gene (Schirmer and Hillen, 1998). Many other organisms can be a source for a catA gene, for example *Pseudomonas arvilla, Pseudomonas fluorescens* (Nakazawa et al, 1967; Kojima et al, 1967), *Streptomyces* Sp. Strain 2065 (Iwagami et al, 2000), *Cupriavidus necator* 335T, and many others (Perez-Pantoj a et al, 2008).

In order to improve the flow of carbon towards cis, cis-muconic acid, it is necessary to block certain other pathways branching out of the aromatic amino acid pathway, besides reducing the flow of carbon from DHS to shikimate (SHK) by using a leaky aroE mutant. Some bacteria, for example in the genus *Acinetobacter* and *Pseudomonas*, contain a gene named pobA, which encodes an enzyme, p-hydroxybenzoate hydroxlase, that converts DHS into gallic acid. Although a PobA homolog or analog has not been found in *E. coli*, strains of *E. coli* engineered to produce DHS secrete measurable amounts of gallic acid (Li and Frost, 1999), so it is likely that such an enzyme does exist in *E. coli*. In addition, the PCA derived from DHS can be converted into gallic acid by the action of p-hydroxybenzoate hydroxlase (PobA) enzyme coded by the pobA gene. The gallic acid thus produced can be subsequently converted to pyrogallol. One way to block the carbon flow to gallic acid and pyrogallol in the biocatalyst selected for an improved cis, cis-muconic acid is to block or diminish the activity of p-hydrobenzoate hydroxlase (PobA) protein through genetic manipulations. Similarly, DHQ, the precursor to DHS can also be acted upon by shikimate dehydrogenase coded by aroE leading to the production of quinnic acid. In an embodiment of the present invention, the leaky AroE mutant enzyme is additionally selected or screened for its inability or reduced ability to convert DHQ into quinnic acid.

There are several advantages in producing trans, trans-muconic acid in place of cis, cis-muconic acid. Trans, trans-muconic acid is preferred over cis, cis-muconic acid in the Diels Alder reaction with ethylene for the production of terephthalic acid. A biocatalyst with a genetically manipulated aromatic pathway produces cis, cis-muconic acid which can be converted into trans, trans-muconic acid outside the cell using chemical conversion processes. On the other hand by means of introducing a maleylacetoacetate isomerase or similar isomerase enzyme into the biocatalyst, it is possible to convert the cis, cis-muconic acid into trans, trans-muconic acid within the bacterial biocatalyst.

In one embodiment, the present invention provides a genetic approach to enhance the activity of AroY protein involved in the conversion of 3,4-dihydroxybenzoic acid (protocatechuic acid or PCA) to catechol. The activity of AroY protein has been identified as a major limitation and bottleneck in the biological conversion of glucose to muconic acid (Horwitz et al 2015; Weber et al 2012; Curran et al 2013; Sonoki et al 2014). AroY belongs to a class of non-oxidative decarboxylases that are widespread among many bacteria and utilize a wide-variety of substrates (Lupa et al 2005). Many of these genes encoding non-oxidative decarboxylases are organized into three gene operons, encoding B, C, and D type genes. "C" type genes encode decarboxylases like AroY, and while the specific function of the B and D type genes are not known although they are sometimes shown to be necessary for realizing full activity of the C type decarboxylase (Lupa et al 2005; Jimenez et al 2013; Lin et al 2015; Sonoki et al 2014). Weber et al (2012) cloned the B, C and D genes from *Klebsiella pneumoniae* or *Sedimentibacter hydroxybenzoicus* into a high-copy-number yeast vector pRS4K-HKT7 and performed fermentation in a medium with externally added PCA to determine the presence of PCA decarboxylase activities from these gene clusters; however, neither was any effort made to determine whether the PCA decarboxylase encoded by the C gene was dependent on the B or D gene in these gene clusters, nor was any attempt made to determine whether the expression of these gene clusters comprising B, C and D genes were able to enhance the muconic acid production using a non-aromatic carbon source such as glucose.

The gene encoding AroY that is used in specific examples disclosed herein is from *Klebsiella pneumoniae*, but the local gene structure of this aroY gene reveals no transcriptionally linked genes that would encode either a B or D type enzyme. Previous studies have shown that inclusion of another B type gene, kpdB, from *Klebsiella pneumoniae* (part of an operon from a 4-hydroxybenzoic acid decarboxylase) can increase AroY activity when producing muconic acid from lignin-related aromatic compounds (Sonoki et al 2014). However, lignin is a complex mixture of chemicals, which requires costly downstream purification processes in order to produce a pure product such as muconic acid. Johnson et al (2016) have shown that in a *Pseudomonas putida* strain expressing AroY (PCA decarboxylase) from *Enterobacter cloaceae*, co-expression of an EcdB protein from *E. cloaceae* having 89.3% sequence identity to KpdB increased the muconic acid production using glucose as a source of carbon from 1.44 g/L to 4.92 g/L at the end of a 54 hour fermentation; however, the muconic acid yield in this *Pseudomonas putida* based system was still found to be extremely (0.077 mol/mol), thus making this *Pseudomonas putida* based system unsuitable for commercial scale applications. Therefore there is still a need for an improved muconic production process from inexpensive, purer, non-aromatic carbon sources such as carbohydrates and other non-aromatic compounds (see above). Recent studies have shown that UbiX, a homolog of KpdB, produces a prenylated flavin mononucleotide cofactor and this cofactor supports the decarboxylation activity of UbiD in ubiquinone formation (White et al 2015; Payne et al 2015). Although previous characterizations of UbiX and its homologs refer to the proteins as either 4-hydroxy-3-polyprenylbenzoate decarboxylases, hydroxybenzoate decarboxylasse, subunit B proteins, phenolic acid decarboxylases, or phenylacrylic acid decarboxylases, these proteins are now more accurately annotated as flavin prenyltranferases.

Additional limitations in the production of muconic acid can be attributed to the limitations of the precursor metabolites PEP and E4P. Changes that eliminate or lower the consumption of these metabolites have been shown in the present invention to improve product formation. For instance, PEP availability has been improved by replacing the native glucose transport, the phosphotransferase system, (PTS) with an alternate system (Glf-Glk from Zymomonas mobilis). E. coli's native use of the PTS requires the utilization of PEP for transport and phosphorylation of glucose. The Glf-Glk system utilizes a facilitated diffuser and a glucokinase plus ATP for transport and phosphorylation of glucose, respectively. Use of Glf-Glk in place of a PTS has been shown to improve the yield and titer for several aromatic products. PEP is a substrate for a variety of biological reactions. In addition to glucose transport by the PTS, PEP is a substrate for pyruvate kinase, resulting in the production of ATP and pyruvate providing half of the ATP generated in glycolysis. Inactivation of the genes encoding for pyruvate kinase (pykA or pykF) has been demonstrated to increase yield of products in the aromatic pathway (Escalante et al. 2010). PEP is also the substrate for the production of oxaloacetate by phosphoenolpyruvate carboxylase (Ppc). In E. coli, this is an essential gene (Baba et al. 2006), and strains deleted for ppc are unable to grow on minimal media. There are other organisms that do not have phosphoenolpyruvate carboxylase, but instead replenish oxaloacetate from pyruvate with pyruvate carboxylase (Pyc), e.g. S. cerevisiae. The addition of pyruvate carboxylase in E. coli has been investigated, but only for the improvement of succinate production (Lin et al. 2004; Vemuri, Eiteman, and Altman 2002) not for any aromatic products.

The specification in this patent application provides several different aspects of invention related to the construction of a microbial strain for efficient production of muconic acid. A person skilled in the art can compile several different aspects of the present invention to construct a biocatalyst with very high efficiency for the production of muconic acid.

EXPERIMENTAL SECTION

General Remarks

Strain and inoculum preparations: A list of the bacterial strains used in the present invention is provided in Tables 1 and 2. A list of the plasmids used in the present invention is provided in Table 3. All specific examples of strain constructions disclosed herein are derived from a wild type E. coli C strain (ATCC 8739), or E. coli K-12 strains (YMC9 or MM294) but the genetic elements disclosed herein can be assembled in any other suitable E. coli strain, and the expression cassettes or appropriate analogs and homologs of the genetic elements disclosed herein can be assembled in any other suitable microorganism, such as other species of bacteria, archaea, yeast, algae, and filamentous fungi that can be used for the commercial production of cis, cis-muconic acid through a fermentative process.

E. coli C is capable of fermenting 10% glucose in AM1 mineral media. AM1 medium contains 2.63 g/L $(NH_4)_2HPO_4$, 0.87 g/L $NH_4H_2PO_4$, 1.5 mM $MgSO_4$, 1.0 mM betaine, and 1.5 ml/L trace elements. The trace elements are prepared as a 1000× stock and contained the following components: 1.6 g/L $FeCl_3$, 0.2 g/L $CoCl_2.6H_2O$, 0.1 g/L $CuCl_2$, 0.2 g/L $ZnCl_2.4H_2O$, 0.2 g/L $NaMoO_4$, 0.05 g/L $H_3BO_3$, and 0.33 g/L $MnCl_2.4H_2O$. The pH of the fermentation broth is maintained at 7.0 with 1.0-10.0 M KOH or 1.0-9.0 M ammonium hydroxide.

Fermentations: Fermentations were started by streaking on a fresh NBS-2% glucose (Jantama et al., 2008a) plate from a 40% glycerol stock of E. coli strain genetically engineered and stored in a −80° C. freezer. Plasmids, if present, are retained by including the appropriate antibiotic(s) in the agar plates and liquid media. Ampicillin (sodium salt) is used at 150 mg/L, spectinomycin HCL at 100 mg/L, tetracycline HCl at 15 mg/l, and kanamycin sulfate at 50 mg/l. After 24 to 48 hours (37° C.), a single colony is picked into 25 ml of the same medium in a shake flask. After shaking at 200 rpm at 37° C. until the cells have grown to an $OD_{600}$ of about 1.0, the culture is cooled on ice and an equal volume of sterile 80% glycerol is added. 2 ml aliquots are then frozen at −80° C. to be used as inocula for fermentations. The term "titer" means the amount of fermentation product produced per unit volume of fermentation fluid and the term "yield" means the ratio of fermentation product produced to carbon source consumed (g/g or mol/mol).

Cell growth: Cell mass was estimated by measuring the optical density at 550 nm ($OD_{550}$) or 600 nm ($OD_{600}$) using a Thermo Electronic Spectronic 20 spectrophotometer.

Figure 4:
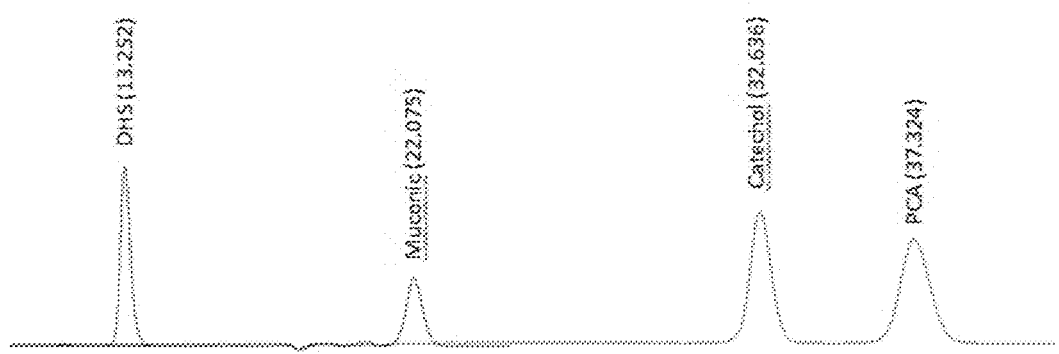
FIG. 4. Chromatograph showing standards used for HPLC analysis of total muconic acid and biochemical intermediates.

Analysis of intermediates in shikimic acid pathway and muconic acid pathways: Total muconic acid produced in fermentation broths, which includes cis, cis-muconic acid and cis, trans-muconic acid, and other biochemical intermediates were assayed by HPLC with a Waters Alliance instrument, and monitoring absorbance at 210 nm or refractive index at 45° C., using standards purchased from Sigma-Aldrich. The column was a BioRad Aminex HPX-87H run at 50° C. with 8 mM sulfuric acid as the mobile phase at a flow rate of 0.6 ml/min for 40 minutes. A chromatograph of purchased standards (Sigma-Aldrich) is shown in FIG. 4. To prepare for HPLC, fermentation samples are diluted 10 or 100 fold in 0.05 M potassium phosphate buffer, pH 7.0, to preserve the cis, cis-form of muconic acid from isomerizing to the cis, trans-form.

Figure 5:
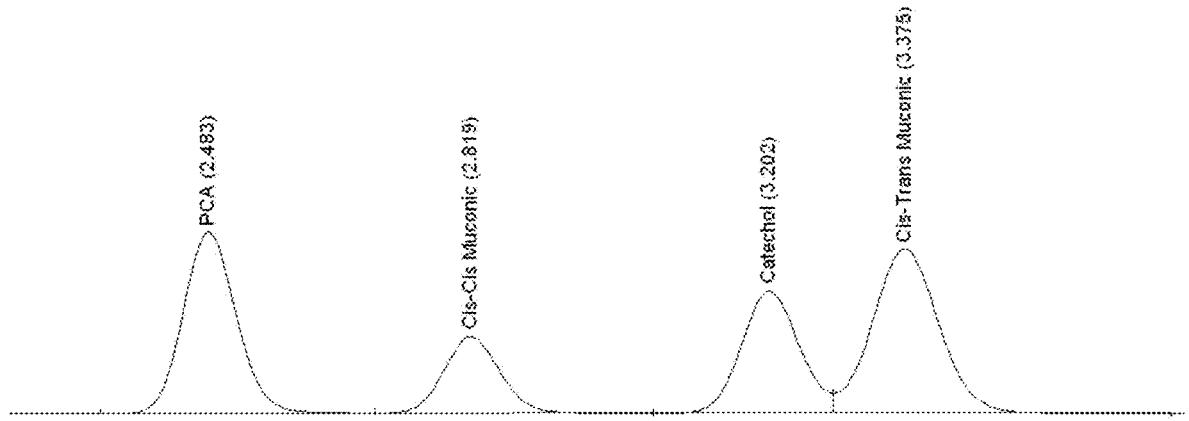
FIG. 5. Chromatograph showing standards used for HPLC analysis of muconic acid isomers.

To separate the isomers of muconic acid, the samples prepared as above were run in a second HPLC system. The instrument was an Agilent 1200 HPLC, the column was an Agilent Eclipse XDB-C18, 4.6×150 mm run at 30 degrees Centigrade with a mobile phase of 50 mM $KH_2PO_4$ in 30% methanol adjusted to pH 3.0 with phosphoric acid. The flow rate was 1 ml/min for 4 minutes, with detection by absorbance at 278 nm. The cis, trans-muconic acid standard was created by dissolving cis, cis-muconic acid in water and allowing it to undergo spontaneous acid catalyzed isomerization for about 2 hours at room temperature, until the HPLC peak had completely shifted to a new position. The other standards were purchased from Sigma-Aldrich. A chromatograph showing standards is shown in FIG. 5.

Composition of muconic acid production medium for the fermentation process: Each liter of fermentation medium contains 50 ml/L of 1M $KH_2PO_4$, 10 ml of 200 g/L Citric acid+25 g/L Ferric citrate, 1.2 ml of 98% Sulfuric acid, and a drop of Antifoam 204. These components were mixed with enough water to allow room for addition of other components below. After autoclaving, the following components were added: 10, 20, 30 or 40 ml of 50% glucose (to give 5, 10, 15, or 20 g/l final), 2 ml of 1M MgSO4, 1 ml of 0.1M CaCl2, 10 ml of 1000× Trace elements (Jantama et al. 2008a), and if necessary 1, 2, 4, or 8 ml of 50 g/L Phenylalanine+50 g/L Tyrosine+50 g/L Tryptophan (to give 0.5, 0.1, 0.2, or 0.4 g/l final), 10 ml of 1 g/L p-hydroxybenzoic acid+1 g/l p-aminobenzoic acid+1 g/L 2,3-dihydroxylbenzoic acid (the last three compounds are referred to as the aromatic "vitamins" or "vitamin-like componds", and, as necessary, 1 ml of 150 mg/ml Ampicillin (sodium salt) and/or 1 ml of 100 mg/ml Spectinomycin HCl. Aromatic amino acids and vitamins were not required and were not used for strains expressing functional AroE protein.

For shake flasks, NBS salts (Jantama et al. 2008a) plus 0.2 M MOPS buffer, pH 7.4 was substituted for the pre-autoclave mix described above, but the glucose and other additives were the same. For fed batch fermentation, the feed bottle contained 600 g/L of anhydrous glucose and, if necessary, 32 ml/L of 50 g/L phenylalanine+50 g/L tyrosine+50 g/L tryptophan. 9 M NH$_4$OH was used as base to maintain the pH of the fermentation medium. Aromatic amino acids and vitamins were not required and were not used for strains expressing a functional AroE protein.

Fed-batch fermentations were performed in 7 L New Brunswick Scientific Fermentors with pH, DO, temperature, glucose, and feed rate controlled by either DCU controllers or Biocommand Software. The medium was 50 mM K2HPO4, 20 mM K2SO4, 3 mM MgSO4 and trace elements. The trace elements are prepared as a 50× stock and contained the following components: 1.6 g/L FeCl$_3$, 0.1 g/L CuCl$_2$, 0.2 g/L ZnCl$_2$.4H$_2$O, 0.2 g/L NaMoO$_4$, 0.05 g/L H$_3$BO$_3$, and 0.55 g/L MnCl$_2$.4H$_2$O. The temperature was maintained at 37° C., the pH was maintained at 7.0 by 9N ammonium water. Aeration was at 0.5 vvm and the dissolved oxygen (DO) was maintained at 30% by automatically increasing the impeller's speed from 750 rpm to 1200 rpm. The initial glucose concentration in the medium was around 20 to 25 g/L. Feed glucose solution was added to the fermentor when the concentration dropped to below 5 g/L. The initial glucose feed rate was 4 g/L/hr and was ramped up to a feed rate of 7 g/L/hr by 48 hours after which it was maintained at 7 g/L/hr.

Construction of plasmids expressing muconic acid pathway genes: The three heterologous genes required for conversion of DHS to muconic acid were cloned either singly or in combination into a low-copy plasmid, pCL1921 (Lerner and Inouye, 1990). The DNA sequence of pCL1921 is given in SEQ ID No. 20 in Table 7. Briefly, the coding sequences of catAX, aroY and aroZ analogs or homologs were codon-optimized for expression in E. coli and commercially synthesized (GeneArt, Invitrogen). These sequences were then PCR amplified using a forward primer carrying a unique ribosome-binding site and a reverse primer carrying a unique terminator sequence for each gene. The resulting PCR fragment was digested with restriction enzymes and cloned downstream of a unique constitutive promoter sequence by standard molecular cloning procedures. The promoter sequences were cloned by PCR amplification from source DNA sequences previously described (United States Patent Application 20090191610; U.S. Pat. No. 7,244,593) followed by restriction digestion and standard molecular cloning. The promoter-RBS-coding sequence-terminator sequence together constituted an expression cassette. Individual expression cassettes were next combined to generate plasmids expressing one, two or all three muconic acid pathway genes.

The present invneiton is further illustrated using the following examples; however the examples provided herein in either alone or in any combination thereof should be construed to limit the scope or the embodiment of the invention. The claims provided at the end define the scope of the invention. A person skilled in the art can clearly understand the scope of the present invention as defined the claims. A person skilled in the art can make modifications or changes to the technical solutions provided by the invention without departing from the spirit and scope of the present invention.

Example 1

Increasing Expression of AroG and AroF Genes

The tyrR gene of E. coli can be mutated by any one of a number of well-known methods, such as chemical or radiation mutagenesis and screening (for example by PCR and DNA sequencing) or selection for analog resistance (for example, resistance to 4-fluorotyrosine), transposon mutagenesis, bacteriophage Mu mutagenesis, or transformation. In a preferred embodiment, the mutation in tyrR gene is a null mutation (a mutation that leaves no detectable activity), and in a more preferable embodiment, at least a portion of the tyrR gene is deleted. This can be accomplished, for example, by using a two-step transformation method using linear DNA molecules (Jantama et al, 2008a; Jantama et al, 2008b). In the first step, a cam$^R$, sacB cassette is integrated at the tyrR locus to replace most or all of tyrR open reading frame by double recombination and selecting for chloramphenicol resistance. In the second step, a linear DNA comprising a deleted version of the tyrR gene is integrated by double recombination, selecting for resistance to 5% sucrose in a rich medium such as LB. Correct deletions are identified and confirmed by diagnostic polymerase chain reaction (PCR). The purpose of deleting tyrR is to increase expression of aroG and aroF. An alternative approach that achieves a similar result is to replace the native promoter in front of aroG and/or aroF with a strong constitutive promoter and add, if necessary, a transcription terminator. More details on how this is accomplished in general are given in Example 4 below.

The latter of the two approaches described above for overcoming the repression of AroG and AroF activities by TyrR protein is preferable, since deletion of tyrR can cause unwanted overexpression of genes such as aroL111 (Neidhardt and Curtiss, 1996). More detail on how this is accomplished in general is given in Example 4 below.

Example 2

Feedback Resistant AroG and AroF

Mutations in the aroG gene that lead to a feedback resistant AroG enzyme (3-deoxy-D-arabinoheptulosonate-7-phosphate synthase or DAHPS) are well known in the art (Shumilin et al, 1999; Kikuchi et al, 1997; Shumilin et al, 2002). Also well known are methods for creating, identifying, and characterizing such mutations (Ger et al., 1994, Hu et al., 2003). A preferable mutation is one that leads to complete resistance to inhibition by phenylalanine. Any of the known published feedback resistant mutations can be introduced into an aroG gene contained in the chromosome or on a plasmid by any of a number of well known methods, one example of which is mutagenic PCR in which the desired mutation is synthesized as part of a PCR priming oligonucleotide (Hu et al., 2003). Correct installation of the mutation is confirmed by DNA sequencing. The sequence of the wild type aroG gene from *E. coli* C is given in SEQ ID No. 18. A preferred mutation is a point mutation that changes amino acid 150 of AroG from proline to leucine, for example by changing codon 150 from CCA to CTA (Hu et al, 2003). In a more preferred embodiment, codon 150 is changed from CCA to CTG, which is a preferred codon in *E. coli*. This particular allele of aroG is preferred, since the encoded DAHP synthase is completely resistant to inhibition by phenylalanine up to 3 mM, and it has a specific activity similar to the wild type enzyme (Hu et al., 2003).

Additional feedback resistant aroG alleles can be obtained by mutagenesis and selection for resistance to one or more phenylalanine analogs, such as beta-2-thienylalanine, p-fluorophenylalanine, p-chlorophenylalanine, o-fluorophenylalanine, and o-chlorophenylalanine, followed by demonstrating that the mutation causing the resistance is linked to the aroG gene (Ger et al., 1994; U.S. Pat. No. 4,681,852). Linkage to aroG can be demonstrated directly by DNA sequencing or enzyme assay in the presence and absence of phenylalanine, (Ger et al., 1994) or indirectly by phage mediated transduction and selection for a genetic marker at or near the aroG locus that can be selected, either for or against (U.S. Pat. No. 4,681,852). Such a genetic marker can be a deletion or point mutation in the aroG gene itself, or a mutation in any suitable closely linked gene such as nadA in case of *E. coli*. For an example in *E. coli*, after mutagenesis and selection for phenylalanine analog resistance, individual mutants or pools of mutants can be used as donors for P1 mediated transduction into a naïve recipient that is deleted for all three DAHP synthase genes, aroG, aroF, and aroH, and selecting for growth on an appropriate minimal medium. The transductants will then be enriched for mutations in the desired gene(s). Alternatively, after mutagenesis and selection for analog resistance, individual mutants or pools of mutants can be used as donors for P1 mediated transduction into a naïve recipient strain that contains a null mutation in the nadA gene, again selecting for growth on an appropriate minimal medium lacking nicotinamide. Another approach is to select for resistant mutants in a strain background that contains a transposon, for example Tn10, insertion near the aroG gene, such as in the nadA gene. P1 transduction from analog resistant mutants into a strain background that does not contain said transposon and selecting for tetracycline or other appropriate antibiotic resistance will enrich for the desired aroG mutations. In all such approaches, feedback resistance is ultimately confirmed by enzyme assay and DNA sequencing of the gene. We shall refer to alleles of aroG that are resistant to feedback inhibition as aroG*.

Strain WM191 (ΔtyrR, ΔaroF) was derived from YMC9 (ATCC 33927). The two step gene replacement method (Jantama et al., 2008a) was used to install clean deletions in both tyrR and aroF, to give strain WM191. Next, a nadA::Tn10 allele was transduced in from CAG12147 (CGSC 7351, *Coli* Genetic Stock Center, Yale University) to give strain WM189 (ΔtyrR, ΔaroF, nadA::Tn10). Selection was on LB plus tetracycline HCl (15 mg/l). Strain RY890 (ΔtyrR::kan, aroF363) was derived from MM294 (ATCC 33625) in three steps by P1 transduction. The donor strains, in order, were JW1316-1 (CGSC 9179, *Coli* Genetic Stock Center, Yale University), NK6024 (CGSC 6178, *Coli* Genetic Stock Center, Yale University), and AB3257 (CGSC 3257, *Coli* Genetic Stock Center, Yale University), and the three selections, in order, were LB plus kanamycin sulfate (50 mg/l), LB plus tetracycline hydrochloride (15 mg/l), and NBS minimal glucose (Jantama et al., 2008a) with thiamine HCl (5 mg/l).

WM189 was mutagenized with UV light to about 20% survival and plated on NBS minimal glucose medium (Jantama et al., 2008a) containing o-fluorophenylalanine (1 mM), thiamine (5 mg/l), and nicotinamide (1 mM). Colonies from each of several plates were collected into separate pools, and P1vir lysates were made on each pool. These lysates were used to transduce WM191 to tetracycline resistance (15 mg/l) on LB medium, and the colonies obtained were replica plated to NBS minimal glucose medium containing o-fluorophenylalanine at 1 mM, thiamine (5 mg/l), and nicotinamide (1 mM). Colony replicas that survived both tetracycline and analog were assumed to contain a feedback resistant mutation in aroG. Eight individual colonies from 5 independent pools were chosen for DNA sequencing. The aroG coding regions were amplified by polymerase chain reaction and sequenced. The results, shown in Table 4, revealed that each of the eight strains contained a point mutation in their aroG gene. Some of the alleles were identical to published alleles, but some were novel.

A P1vir lysate from one of the pools described above was used to transduce RY890 (which has an aroG wild type allele) to tetracycline resistance and resistance to o-fluorophenylalanine (0.3 mM) by replica plating as described above. Four colonies, named RY893, RY897, RY899, and RY901, were picked for DNA sequencing (Table 4), and again, two of the alleles were identical to a published allele, but two were novel. Strain RY902, which is isogenic to the latter four strains, but contains a wild type aroG gene, was constructed as a control, by transduction from CAG12147. These five strains were grown overnight in shake flasks in 25 ml NBS minimal glucose (15 g/l) plus thiamine HCl (5 mg/l) and nicotinamide (1 mM). The resulting cells were harvested by centrifugation, resuspended to be rinsed with 10 ml water, re-centrifuged, and resuspended in 0.5 ml of 50 mM potassium phosphate, pH 7.0. The suspended cells were lysed by vortexing with three drops of chloroform, and the crude lysate was assayed for DAHP synthase activity using a method similar to a method described in the literature (Hu et al., 2003), with the following modifications. The phosphate buffer was 50 mM (final concentration), pH 7.0, the final erythrose-4-phosphate concentration was 2 mM, the final phosphoenol pyruvate concentration was 5 mM, the incubation temperature was 30° C., and the reaction was stopped at 10 minutes. We define 1 mU as the activity that produced 1 nMole of DAHP per minute per milligram protein. To test for feedback resistance, each crude lysate was assayed with or without phenylalanine at a final concentration of 18 mM. The assay results are shown in Table 5. The enzymes showed varying specific activity and resistance to phenylalanine, but all of selected mutant versions that were tested were significantly more resistant than the wild type controls.

The aroG alleles from RY893, RY899, RY901, and RY902, described above, were introduced into a muconic acid producing strain background as follows. P1vir lysates from the aroG* and aroGwt donor strains were used to transduce MYR219 (*E. coli* C, ΔaroE, Δack::$P_{15}$-aroB, pMG37) to tetracycline HCl resistance (15 mg/l), to give new strains RY903, RY909, RY911, and RY912, respectively. Each of these strains was then transduced to kanamycin sulfate resistance (50 mg/l) using a P1vir lysate of JW1316-1, to introduce the ΔtyrR::kan allele, to give strains RY913, RY919, RY921, and RY922, respectively. Spectinomycin selection was maintained throughout to maintain the muconic plasmid. The resulting four strains were grown for 48 hours at 37° C. in shake flasks in 25 ml NBS minimal medium (Jantama et al., 2008a) containing supplements of 20 g/l glucose, 0.2 M MOPS buffer, pH 7.4, nicotinamide (1 mM), phenylalanine (100 mg/1), tyrosine (100 mg/1), tryptophan (100 mg/1), p-hydroxybenzoic acid (1 mg/1), p-aminobenzoic acid (1 mg/1), 2,3-dihydroxybenzoic acid (1 mg/1), phenol red (10 mg/1), and ammonium sulfate (1 g/l). The pH was kept close to 7 as estimated by eye from the color of the phenol red, against a pH 7.0 standard, by manual addition of 1 ml aliquots of 1.0 M KOH as called for to the shake flasks. The muconic acid produced was assayed by HPLC as described above, and the results are shown in Table 6. All three strains that contain a feedback resistant aroG* allele produced more muconic acid than the isogenic strain containing the wild type aroG allele. In a separate experiment disclosed herein, strain MYR205, containing aroG on multicopy plasmid pCP32AMP, produced 1.5 g/l muconic acid in a shake flask. Thus, the inventors have shown that the combination of ΔtyrR and single copy chromosomal aroG* can perform well compared to an isogenic aroG plasmid containing strain to produce muconic acid in shake flasks. The inherent superior genetic stability of the chromosomal alleles compared to plasmid alleles, plus the alleviation of the need for a selective medium to hold in a plasmid, makes the novel strains described herein more suitable for large scale commercial fermentations. Furthermore, no chemical inducer was required for expression of muconic acid pathway genes. Thus, strains of the instant invention described above are improved over those of the prior art (Niu et al., 2002), all of which contain the gene for overexpression of DAHP synthase on an undesirable multicopy plasmid.

In a similar fashion to that described above for AroG, a mutation that leads to an AroF or AroH isozyme that is resistant to feedback inhibition by tyrosine can be installed on a plasmid or in the chromosome. A preferred mutation is a point mutation that changes amino acid 148 of AroF from proline to leucine, for example by changing codon 148 from CCG to CTG (Weaver et al., 1990), to give a gene named aroF*. Other alleles of aroF* can be isolated by resistance to tyrosine analogs (for example o-fluorotyrosine, m-fluorotyrosine, p-fluorophenylalanine, etc.) in a fashion analogous to that described above for aroG* alleles. aroF* alleles can be selected, enriched for, and transduced by linkage to a transposon or a kanamycin resistance insertion, for example in a closely linked ΔyfiR::kan as in a strain such as JW2584 (CGSC 10051, *Coli* Genetic Stock Center, Yale University).

Example 3

Deletion of aroE from Chromosomal DNA and Muconic Acid Production

Figure 6:
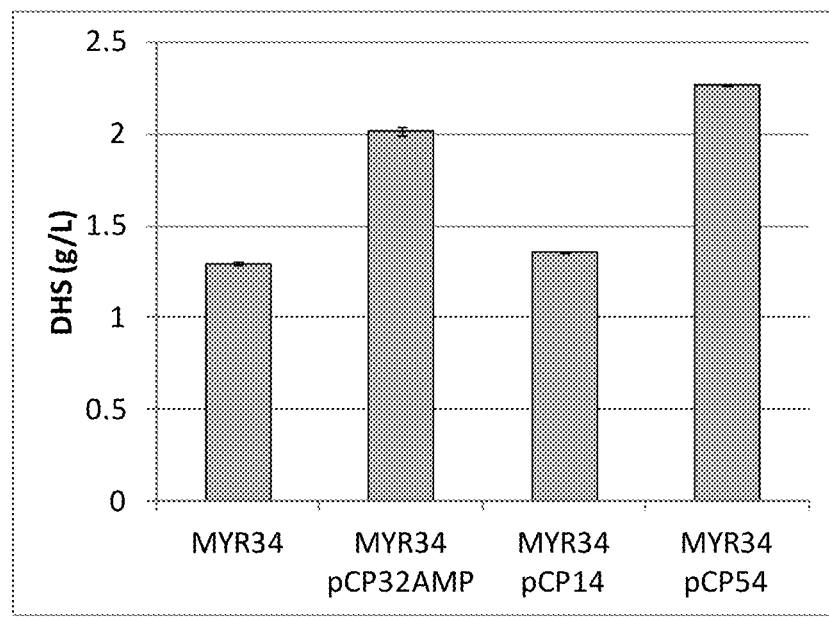
FIG. 6. Titer for the production of DHS in the *E. coli* strain MYR34 transformed with plasmids pCP32AMP, pCP14 and pCP54. MYR34 strain of *E. coli* has a deletion in aroE gene. The plasmid pCP32. AMP expresses the aroG gene coding for DAHP synthase. The plasmid pCP14 expresses the aroB gene coding for DHQ synthase. The plasmid pCP54 expresses both the aroB and aroG genes.

In this example the effect of overexpression of aroB and aroG on multicopy plasmids as well as the expression of genes coding for proteins functional in the muconic acid pathway was investigated. Strain MYR34 containing a deletion in the aroE gene coding for shikimate dehydrogenase was used as parent strain in these studies. The deletion of chromosomal copy of aroE was accomplished in a fashion similar to that described above in Example 1. When MYR34 was transformed with the plasmid pCP32AMP overexpressing the aroG gene coding for DAHP synthase protein functional in the shikimic acid pathway, there was a significant increase in the accumulation of DHS. When MYR34 was transformed with the plasmid expressing aroB from a constitutive promoter, no significant increase in the accumulation of DHS was noticed. However, when the *E. coli* strain MYR34 was transformed with the plasmid expressing both aroB and aroG genes, there was an increase in the accumulation of DHS than observed with MYR34 transformed with aroG alone thus suggesting aroB as a secondary bottleneck in DHS production (FIG. 6).

Figure 7:
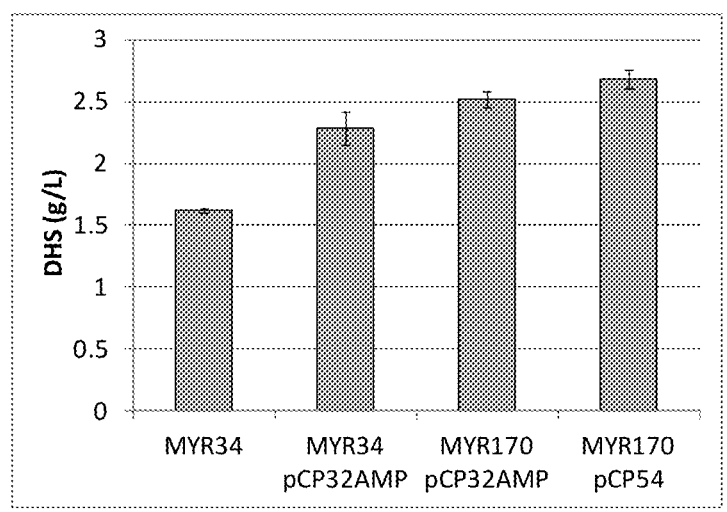
FIG. 7. Titer for the production of DHS in the *E. coli* strains MYR34 and MYR170 transformed with plasmids pCP32AMP and pCP54. The MYR34 strain of *E. coli* has a deletion of the aroE gene. The MYR170 strain has a deletion of the aroE gene and a second copy of the aroB gene under the control of $P_{15}$ promoter integrated at the ack locus of the host chromosomal DNA. The plasmid pCP32AMP expresses the aroG gene coding for DAHP synthase. The plasmid pCP54 expresses both aroB and aroG genes.

In the experiments presented in FIG. 7, the effect of an additional copy of the aroB gene integrated into the host chromosomal DNA was examined. In the *E. coli* strain MYR170 derived from MYR34, an additional copy of the aroB gene under the control of the $P_{15}$ promoter was integrated into the host chromosome at the ack locus. When MYR170 strain was transformed with the pCP32AMP plasmid, there was a slight increase in the DHS accumulation when compared to the DHS accumulation detected in the MYR34 strain transformed with the same plasmid. This slight increase in the accumulation of DHS in the MYR170 can be attributed to an additional copy of aroB gene integrated into the host chromosomal DNA. When MYR170 was transformed with pCP54 expressing both aroB and aroG genes, there was a further increase in the DHS accumulation suggesting aroB as a secondary bottleneck in DHS production.

Figure 8:
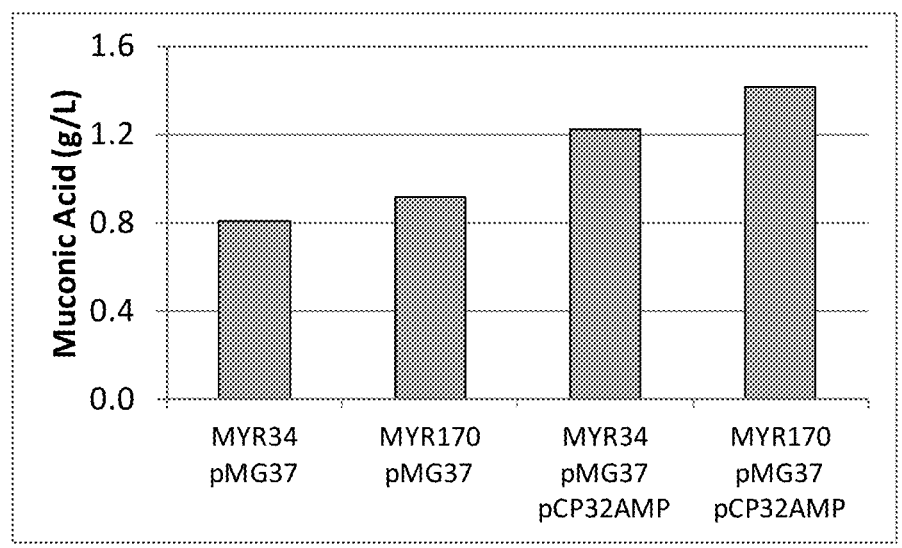
FIG. 8. Titer for the production of cis, cis-muconic acid in the *E. coli* strains MYR34 and MYR170 transformed with plasmid pMG37 alone or with both pMG37 and pCP32AMP plasmids. The MYR34 strain of *E. coli* has a deletion of the aroE gene. The MYR170 strain has a deletion of the aroE gene and a second copy of the aroB gene under the control of $P_{15}$ promoter integrated at the ack locus of the host chromosomal DNA. The plasmid pCP32AMP expresses the aroG gene coding for DAHP synthase. The plasmid pMG37 expresses the aroZ, aroY, and catAX, genes coding for proteins functional in the muconic acid pathway.

FIG. 8 provides the results on muconic acid production with the *E. coli* strains MYR34 and MYR170. Having established that in the aroE deletion strains MYR34 and MYR170, with overexpression of aroB and aroG genes there is an accumulation of DHS, efforts were made to see whether the expression of "muconic pathway" genes coding for the proteins functional in muconic acid production pathway would lead to conversion of DHS into cis, cis-muconic acid. In these experiments, the *E. coli* stains MYR34 and MYR170 were transformed either with the plasmid pMG37 alone or with both plasmids pMG37 and pCP32AMP. The plasmid pMG37 expresses aroZ, aroY and catAX genes coding for proteins functional in muconic acid pathway. The muconic acid production in both MYR34 and MYR170 increased when these bacterial strains were transformed with both the plasmids pCP32AMP and pMG37 when compared to the muconic acid production in these two strains transformed only with pMG37 plasmid suggesting that in these strains aroB expression is the bottleneck for cis, cis-muconic acid production.

Example 4

Overexpression of TktA

Transketolase encoded by tktA is a key enzyme in the pentose phosphate pathway and is thought to be limiting for the production of erythrose-4-phosphate, one of the key intermediates in the production of muconic acid. Overexpression of tktA, which encodes transketolase, by installing the gene with its native promoter on a multicopy plasmid (Sprenger et al, 1995, 1995a), is known to improve flux into the aromatic pathway (Draths et al., 1992). However, such plasmids are unstable, and often require antibiotic selection for maintenance. Another approach in the prior art was to add one additional copy of the tktA gene to the chromosome of the host strain (Niu et al., 2002). However, one additional copy of tktA with its native promoter is not sufficient to saturate the aromatic pathway with erythrose-4-phosphate, since its native promoter is not very close to the ideal. As such, the process needs substantial improvement.

Improved overexpression of tktA can be obtained, for example, by substituting the native tktA promoter in the chromosome with a strong constitutive promoter, for example a $P_{15}$ or $P_{26}$ promoter from *Bacillus subtilis* phage SPO1 (SEQ ID No. 1 and SEQ ID No. 2, respectively), or the $P_R$ promoter from bacteriophage lambda (SEQ ID No. 3). This is accomplished in two steps as described in Example 1, except that the $cam^R$, sacB cassette is used to replace the native chromosomal tktA promoter in the first step. In the second step, the strong constitutive promoter is installed by transforming with a linear DNA comprising the strong constitutive promoter, flanked by at least 50 bases of the 5' end of the tktA coding region on the downstream side and at least 50 base pairs of homology just upstream of the native tktA promoter on the upstream side of the strong constitutive promoter, and selecting for sucrose resistance. Improved expression from such an expression cassette is also accomplished by increasing the stability of the mRNA that is transcribed from the expression cassette. Improvement of the mRNA stability is accomplished by adding a stem loop structure at either the 5' end of the mRNA, the 3' end of the mRNA, or both. A stem-loop structure is often present at the end of an mRNA that is naturally terminated by a rho-independent transcription terminator, but if it is not, then a rho-independent transcription terminator can be added to the DNA sequence by well known methods of genetic engineering (ligation, PCR, etc.). Such a terminator can be comprised of an inverted repeat of between 4 and 20 bases in each repeat, separated by a "loop" of 3 or more bases, and followed by a region of one or more bases that is enriched for T's (deoxythymidine). The inverted repeats are rich in G's and C's (deoxyguanidine and deoxycytidine). Similarly, a stem-loop can be constructed into the 5' end of an mRNA by inserting a DNA sequence just downstream from the start point of transcription, but before the ribosome binding site, that contains a stem-loop as described above, but without the T-enriched region. An example of this is given in association with the $P_{15}$ promoter (SEQ ID No. 1).

In the analysis of the effect of overexpression of the tktA gene on the flow of carbon through the shikimic acid pathway, *E. coli* strain MYR170 was used as a parental strain. MYR170 has a deletion in the aroE gene coding for shikimate dehydrogenase enzyme and an additional copy of the aroB gene at the ack locus.

Figure 9:
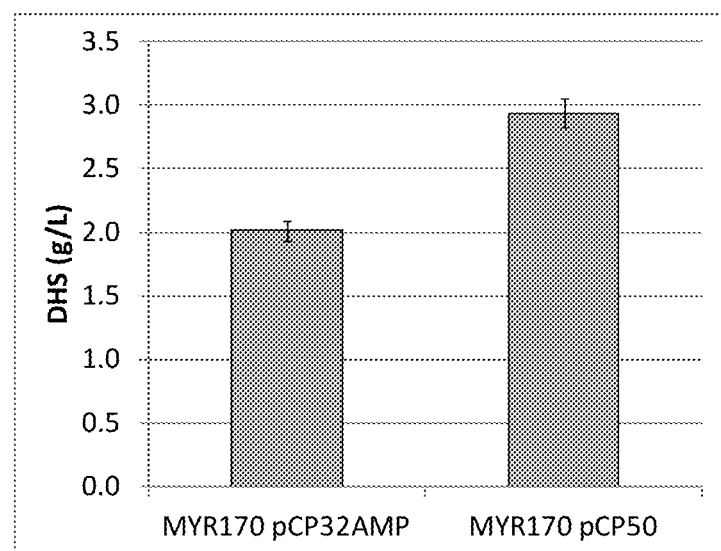
FIG. 9. Titer for the production of DHS in MYR170 strain of *E. coli* transformed with a plasmid expressing aroG gene alone (pCP32AMP) or aroG and tktA genes simultaneously (pCP50). The MYR170 strain has a deletion of the aroE gene and a second copy of the aroB gene under the control of the $P_{15}$ promoter integrated at the ack locus of the host chromosomal DNA.
Figure 10:
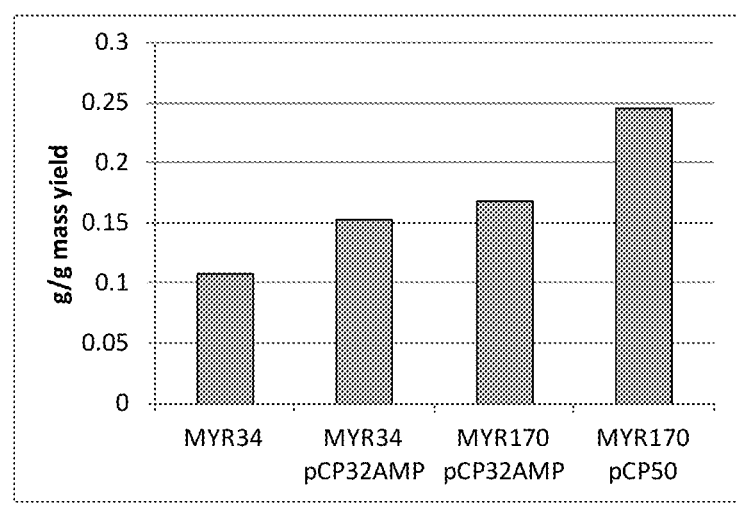
FIG. 10. DHS yield from MYR34 and MYR170 stains of *E. coli* transformed with plasmids pCP32AMP and pCP50. DHS yield is calculated as grams of DHS produced per gram of glucose consumed. The plasmid pCP32AMP expresses the aroG gene while pCP50 expresses aroG and tktA. The bacterial strain MYR34 has a deletion in the aroE gene. The MYR170 strain of *E. coli* is derived from MYR34 and has an additional aroB gene integrated at the ack locus on the chromosomal DNA.
Figure 11:
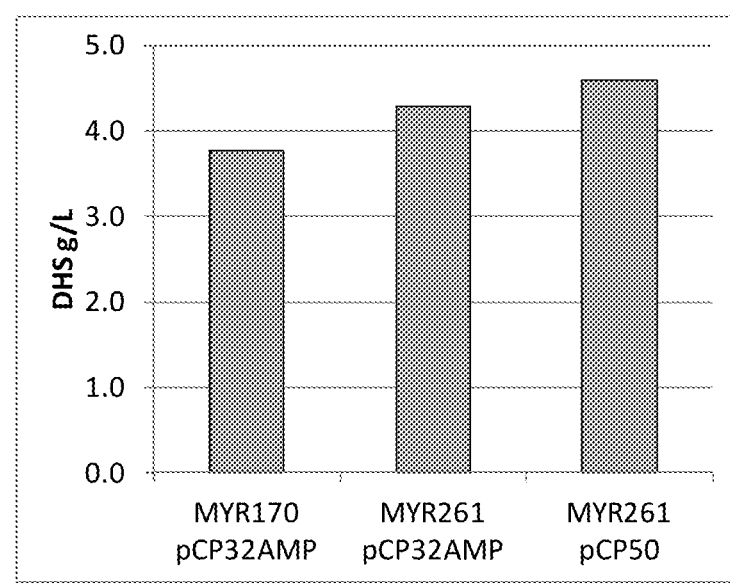
FIG. 11. DHS titer from MYR170 and MYR261 stains of *E. coli* transformed with plasmids pCP32AMP and pCP50. The plasmid pCP32AMP expresses the aroG gene while pCP50 expresses the aroB and tktA genes. The MYR170 strain has a deletion of the aroE gene and a second copy of the aroB gene under the control of $P_{15}$ promoter integrated at the ack locus of the host chromosomal DNA. MYR261 strain of *E. coli* is derived from the MYR170 strain of *E. coli*. MYR261 strain of *E. coli* has a second copy of the tktA gene with its native promoter integrated at the poxB locus of the chromosomal DNA.

In the experiments described in the FIGS. 9, 10 and 11 two different plasmids namely pCP32AMP and pCP50 were used. The plasmid pCP32AMP expresses only the DAHP synthase aroG gene from its native promoter and the plasmid pCP50 expresses the transketolase gene tktA from its native promoter along with aroG gene. MYR170, having an aroE deletion and an additional copy of aroB gene under the control of $P_{15}$ promoter integrated at the ack locus of the chromosomal DNA, was transformed individually with pCP32AMP and pCP50 plasmids. As shown in FIG. 8 the DHS accumulation was increased further with the expression of aroG gene along with tktA gene when compared to the *E. coli* cells expressing only aroG gene.

FIG. 10 provides data on the DHS yield in two different strains namely MYR34, MYR170 transformed with the plasmid pCP32AMP or pCP50. MYR34 strain having aroE gene deletion yielded 0.1 gram of DHS per gram of glucose consumed. The DHS yield in the MYR34 increased to 0.15 gram of DHS per gram of glucose consumed when this strain was transformed with the pCP32AMP plasmid with aroG gene overexpression. MYR170 has an additional copy of aroB gene inserted at the ack locus. As a result of the presence of this additional copy of the aroB gene, the yield for DHS production in the MYR170 strain transformed with pCP32AMP was slightly higher than the DHS yield noted in the MYR34 strain transformed with pCP32AMP. Thus the presence of an additional copy of aroB in MYR170 caused an increased carbon flow through shikimic acid pathway. Further increase in the DHS yield was observed when the MYR170 strain was transformed with plasmid pCP50 expressing both aroG and tktA genes. Thus the presence of additional copy of tktA accounted for an increase carbon flow through shikimic acid pathway. More specifically, the effect of presence of additional aroB and tktA genes caused an additive effect on DHS yield.

MYR261 used in the experiments described in FIG. 11 was engineered to integrate an additional copy of tktA gene into the chromosomal DNA of MYR170 at the poxB locus. The desired gene replacement (poxB::tktA) in the MYR261 strain was confirmed via PCR. MYR261 was transformed either with pCP32AMP (aroG overexpression) plasmid or pCP50 (aroG and tktA over expression) plasmid. As a control, MYR170 was transformed with pCP32AMP plasmid. As the result shown in FIG. 11 indicate, the presence of an additional copy of tktA gene in the chromosomal DNA of MYR261 increased the titer for DHS production with pCP32AMP plasmid when compared to the titer for DHS production observed in the MYR170 strain transformed with the same plasmid. Further increase in the transketolase level in the MYR261 strain when transformed with the plasmid pCP50 over expressing transketolase led to further increase in the titer for DHS production. The enzyme encoded by poxB, PoxB, or pyruvate oxidase, produces acetate as a reaction product. As such, the deletion of poxB that results from the insertion of tktA as described herein removes a potentially active pathway for acetate production. Similarly, simultaneous insertion of $P_{15}$aroB and deletion of ackA, which encodes AckA, or acetate kinase, as described below in Example 12 below, removes another potentially active pathway to acetate. Production of acetate is generally undesirable in fermentations (Jantama et al., 2008b). As such, these deletions can be useful for reducing acetate production.

Figure 12:
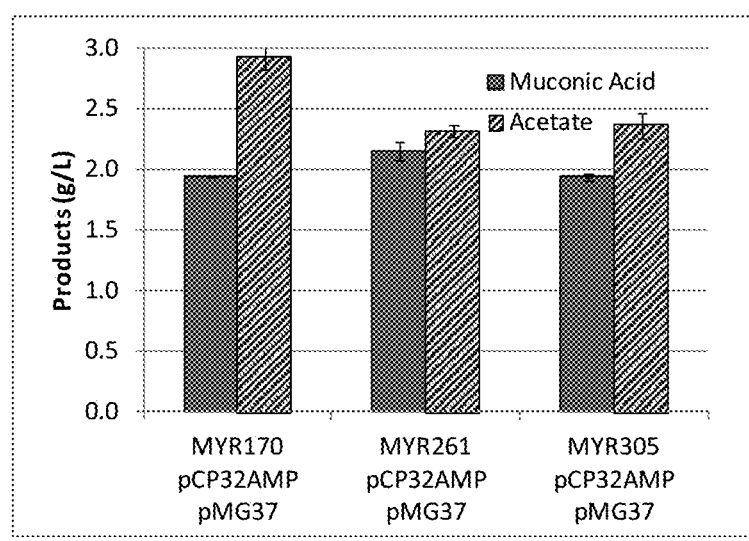
FIG. 12. Muconic acid and acetic acid production in the *E. coli* strains MYR170, MYR261 and MYR305 transformed with the plasmid pCP32AMP expressing aroG coding for DAHP synthase in the shikimic acid biosynthetic pathway and plasmid pMG37 expressing aroZ, aroY and catAX genes coding for proteins functional in the muconic acid pathway. MYR170 strain has a deletion in the aroE gene and an additional copy of aroB gene under the control of the $P_{15}$ promoter inserted at ack locus in the host chromosomal DNA. MYR261 and MYR305 are derivatives of MYR170 strain. MYR261 has an additional copy of tktA gene integrated at poxB locus on the host chromosomal DNA while MYR305 has a deletion in the poxB locus on the host chromosomal DNA.

FIG. 12 provides the titer for muconic acid and acetic acid production in MYR170, MYR261 and MYR305 strains of *E. coli* after transformation with the plasmids pCP32AMP and pMG37. MYR305 is derived from MYR170 by means of deleting poxB gene from the chromosomal DNA while MYR261 is a MYR170 derivative wherein the poxB gene has been inactivated by means of inserting an additional copy of the tktA gene. As mentioned above, the plasmid pCP32AMP expresses the aroG gene coding for DAHP synthase protein functioning in the shikimic acid biosynthetic pathway leading to the accumulation of DHS due to the deletion of aroE gene in the *E. coli* strains MYR170, MYR261 and MYR305. With the expression of muconic pathway genes namely aroZ, aroY and catAX on the plasmid pMG37, the DHS is converted into cis, cis-muconic acid as illustrated in FIG. 2. With the presence of an additional copy of the aroB gene and the tktA gene in the MYR261 strain, there was a slight increase in the production of muconic acid accompanied by a decrease in the accumulation of acetic acid.

Example 5

Overexpression of TalA or TalB

The talB gene encodes the predominant transaldolase in *E. coli*, but the talA gene also encodes a minor transaldolase.

Overproduction of transaldolase is known to improve flux into the aromatic pathway (Lu and Liao, 1997; Sprenger, 1995; Sprenger et al, 1995b). In the prior art, this was accomplished by overexpression of the tal gene (now known to be the talB gene) on a multicopy plasmid from its native promoter (Lu et al., 1997, Sprenger et al., 1995b). However, such plasmids are unstable, and require antibiotic selection for maintenance. Thus, there is a need for an improved process. Improved expression of talB can be obtained, for example, by substituting the native talB promoter in the chromosome with a strong constitutive promoter, for example a $P_{15}$ or $P_{26}$ promoter from *Bacillus subtilis* phage SPO1 (SEQ ID No. 1 and SEQ ID No. 2, respectively), or the $P_R$ promoter from bacteriophage lambda (SEQ ID No. 3). This is accomplished in two steps as described in Example 1, except that the $cam^R$, sacB cassette is used to replace the native chromosomal talB promoter in the first step. In the second step, the strong constitutive promoter is installed by transforming with a linear DNA comprising the strong constitutive promoter, flanked by at least 50 bases of the 5' end of the talB coding region on the downstream side and at least 50 base pairs of homology just upstream of the native talB promoter on the upstream side of the strong constitutive promoter, and selecting for sucrose resistance. The talA gene can also be overexpressed by a similar method, but it is preferred to over express the talB gene, since it encodes the predominant activity (Sprenger, 1995; Sprenger et al, 1995b). See Example 4 for more details on construction of the expression cassette designed for overexpression.

Example 6

Expression of AroZ, AroY and CatAX Genes

Figure 13:
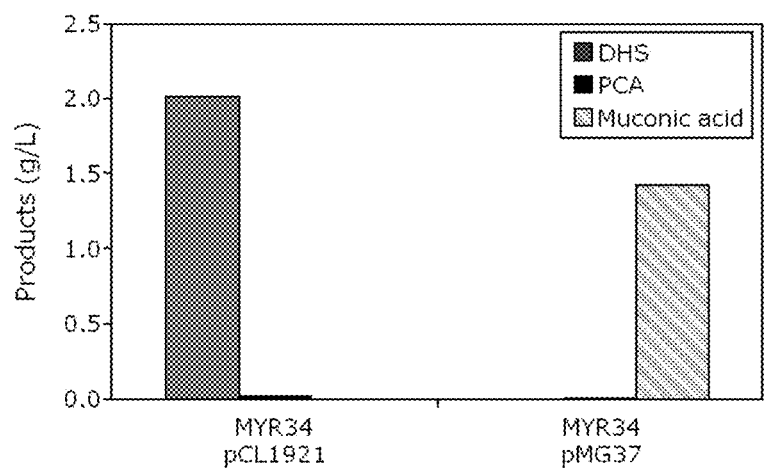
FIG. 13. Conversion of endogenous DHS produced by *E. coli* strain MYR34 into muconic acid. Strain MYR34 of *E. coli* has a deletion in the aroE gene coding of shikimate dehydrogenase. As a result there is an accumulation of DHS. When strain MYR34 is transformed with a plasmid expressing aroZ, aroY and catAX, genes coding for proteins functional in muconic acid pathway, there is conversion of DHS into muconic acid. However, no conversion of DHS into muconic acid occurs when MYR34 strain is transformed with the empty plasmid vector (pCL1921) without any exogenous genes.

To demonstrate conversion of endogenous DHS produced by *E. coli* into muconic acid, heterologous genes catAX from *Acinetobacter* sp. ADPJ, aroY from *Klebsiella pneumoniae*, and quiC from *Acinetobacter* sp. ADP1, were cloned under strong constitutive promoters ($P_{15}$, $P_R$, and $P_{26}$, respectively) in a low-copy plasmid, pCL1921 (Lerner and Inouye, 1990) to generate a 'muconic plasmid' pMG37. MYR34 strain derivatives carrying the empty vector (pCL1921) or pMG37 were grown at 37° C. for 17 hrs. in a shake flask medium (NBS minimal medium supplemented with aromatic amino acids and vitamins) containing 2% glucose. Supernatants were collected and analyzed by HPLC. In contrast to MYR34/pCL1921 which shows accumulation of DHS, MYR34/pMG37 shows production of muconic acid (FIG. 13). No significant amount of DHS, or intermediate products such as PCA and catechol were detected from the latter strain, suggesting that the heterologous genes expressed from pMG37 were functional and sufficient.

Example 7

Comparison of AroZ Homologs

Figure 14:
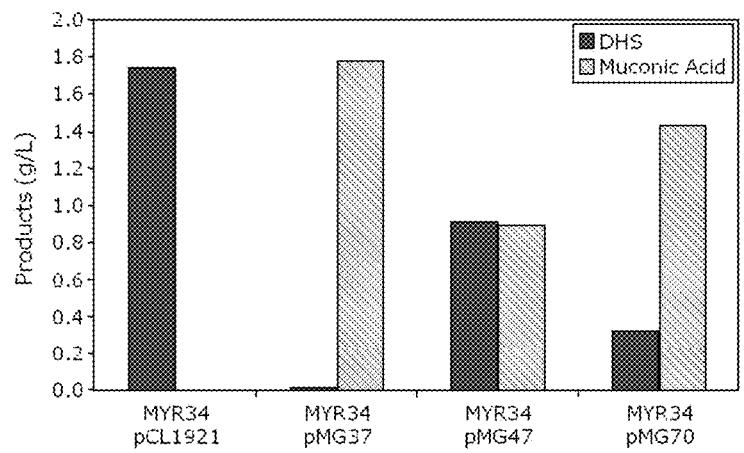
FIG. 14. Comparison of aroZ analogs for their ability to divert DHS into the muconic acid pathway. Three different aroZ analogs, namely quiC from *Acinetobacter* sp. ADPJ, asbF from *Bacillus thuringiensis*, and qa-4 from *Neurospora crassa* were cloned under the $P_{26}$ promoter in a low-copy plasmid which also expressed catAX and aroY genes from the $P_{15}$ and lambda $P_R$ promoters respectively. These three different plasmid constructs were expressed in MYR34 through transformation and the amount of muconic acid produced was measured.

Three different aroZ homologs and analogs were compared (FIG. 14) for their ability to divert DHS into the muconic acid production pathway. quiC from *Acinetobacter* sp. ADPJ, asbF from *Bacillus thuringiensis*, and qa-4 from *Neurospora crassa*, are reported to encode for proteins that have AroZ-like activity (Elsemore and Ornston, 1995; Fox et al, 1995; Rutledge, 1984). Each of these genes was codon-optimized for expression in *E. coli* and synthesized by GeneArt (Invitrogen), and cloned under a strong constitutive $P_{26}$ promoter in low-copy 'muconic plasmid' which also expressed catAX and aroY genes from the $P_{15}$ and $P_R$ promoters, respectively. MYR34/pCL1921, MYR34/pMG37 (muconic plasmid with quiC as aroZ), MYR34/pMG47 (muconic plasmid with asbF as aroZ), and MYR34/pMG70 (muconic plasmid with qa-4 as aroZ) were grown at 37° C. for 48 hrs. in a shake flasks with minimal medium containing 2% glucose, the aromatic amino acids and aromatic vitamins. Supernatants were collected and analyzed by HPLC. As expected, empty vector transformed MYR34 accumulated DHS and produced no muconic acid. The two aroZ homologs and the one analog examined were functional in diverting DHS towards muconic acid production, but to a varying degree. The MYR34 derivative expressing quiC gene was most robust and showed nearly 100% conversion of DHS to muconic acid with insignificant amount of DHS retention. The MYR34 derivative expressing the fungal aroZ homologue, qa-4, followed close with about 80% conversion of DHS to muconic acid and 20% DHS retention. Lastly, the MYR34 derivative expressing asbF gene showed only 50% conversion of DHS to muconic acid and 50% DHS retention. Taken together, under our shake flask assay conditions, the expression and/or activity of quiC gene appeared to be the highest compared to that of other aroZ homologs.

Example 8

Chromosomal Integration of CatAX, AroY and QuiC

Muconic acid can be produced by strains that contain only chromosomally integrated single copies of catA-X, aroY and quiC expressed from constitutive promoters at adhE locus.

Figure 15:
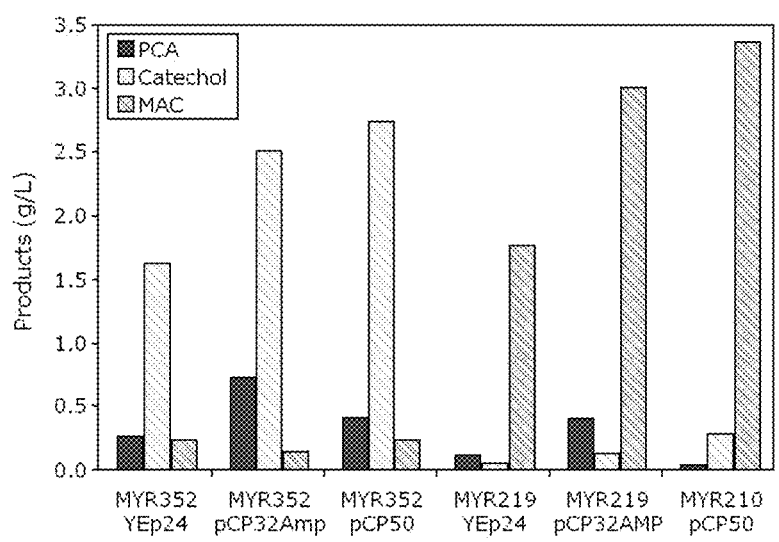
FIG. 15. Single copies of catAX, aroY and quiC were chromosomally integrated into MYR170 strain of *E. coli* (ΔaroE, Δack::$P_{15}$-aroB) resulting in MYR352 (SEQ ID No. 41). MYR170 was also transformed with low copy plasmid pMG37 carrying all genes necessary for the operation of muconic acid pathway leading to the MYR219 strain. Both MYR352 and MYR219 were transformed with YEp24 (medium-copy empty vector) or pCP32AMP (medium-copy aroG expressing plasmid) or pCP50 (medium-copy aroG and tktA expressing plasmid) and the amount of PCA, catechol and muconic acid produced were quantified using HPLC method.

MYR170 ($\Delta$aroE, $\Delta$ack::$P_{15}$-aroB), a high DHS producer, was the host strain used for integrating the muconic acid pathway genes at the adhE locus in the chromosome (SEQ ID No. 41). The resulting strain MYR352 was transformed with plasmids YEp24 (medium-copy, empty vector), pCP32AMP (medium-copy, aroG expressed from native promoter), or pCP50 (medium-copy, aroG and tktA expressed from their respective native promoters) to generate derivative strains. The latter two plasmids were used to increase DHS production. Strains were grown at 37° C. for 72 hrs. in shake flask medium containing 2% glucose as described above. Supernatants were collected at 72 hrs. and analyzed by HPLC. As expected, the aroG and aroG/tktA transformed MYR352 derivatives showed an overall increase in total product formation compared to an empty vector control (FIG. 15). All of the MYR352 transformants produced measurable titers of muconic acid, demonstrating for the first time that muconic acid can be produced by a strain that contains only integrated "muconic pathway" genes and without a fed chemical inducer of gene expression.

Not all DHS that was produced in any of these MYR352 derivative strains was converted to the end product muconic acid. Instead, there was a significant amount of catechol accumulation (FIG. 15), suggesting that expression or activity of catAX is limiting when it is expressed from a single copy on chromosome. Since the major accumulating intermediate was catechol, it is likely that quiC and aroY gene expression and/or activity is sufficient in the MYR352 strain background for muconic acid synthesis.

The MYR352 strain derivatives were compared in parallel with analogous MYR219 strain derivatives. MYR219 strain is same as MYR170 strain but contains low-copy plasmid pMG37 expressing muconic acid pathway genes. Thus, the main difference between MYR352 and MYR219 strains is with reference to the dosage of muconic acid pathway genes (1 copy vs. about 5 copies, respectively). In contrast to MYR352 derivative strains, MYR219 derivative strains showed very little accumulation of catechol or other intermediates, and successfully produced the end product muconic acid. Together, these results indicate the need for increasing catAX activity in strains such as MYR352.

Example 9

Expression of CatAX

Figure 16:
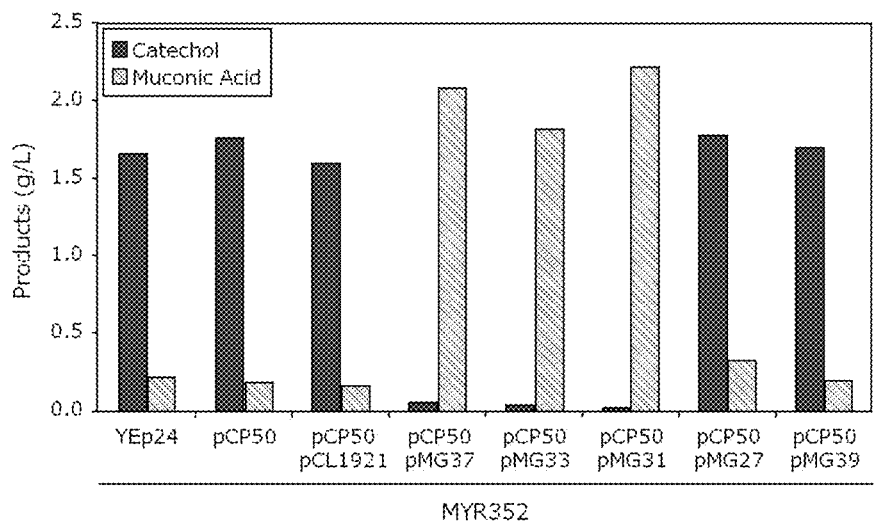
FIG. 16. Removal of catechol accumulation in MYR352 by means of increasing the expression of catAX. MYR352 was transformed with a plasmid expressing aroY alone (pMG27) or a plasmid expressing quiC alone (pMG39) or a plasmid expressing all three muconic acid pathway genes namely catAX, aroY and quiC (pMG37) or a plasmid expressing only two genes in the muconic acid pathway namely catAX and aroY (pMG33). Over expression of catAX alone was sufficient to prevent accumulation of catechol.

Accumulation of catechol and inefficient production of muconic acid in MYR352 strain is due to limiting dosage and/or activity of the catAX gene product(s). As described above, MYR352 contains ΔaroE, Δack::$P_{15}$-aroB and chromosomally integrated single copies of catAX, aroY and quiC genes under strong constitutive promoters. This strain was transformed with medium-copy empty vector control (YEp24) or aroG/tktA expression plasmid (pCP50) to increase carbon flow into the aromatic amino acid synthesis pathway and produce high amounts of DHS. Growth of transformed strains at 37° C. for 72 hrs in shake flask medium supplemented with 2% glucose as described above resulted in accumulation of catechol intermediate. This result suggested that catAX activity may be insufficient in MYR352. To confirm this hypothesis, the ability of one or more muconic acid pathway genes expressed from low-copy plasmid to alleviate catechol accumulation in MYR352/pCP50 was tested (FIG. 16). Specifically, MYR352/pCP50 was further transformed with low-copy empty vector control (pCL1921) or plasmids expressing all three genes, two genes, or one gene of the muconic acid production pathway. The derivative strains were assayed in a shake flask experiment as described above. While increasing the dosage of aroY alone (from pMG27) or quiC alone (from pMG39) did not alleviate catechol accumulation, expression of all of the muconic acid pathway genes (from pMG37) or catAX and aroY together (from pMG33), resulted in successful conversion of catechol to muconic acid. Further, expression of catAX alone (from pMG31) was sufficient for production of muconic acid and preventing accumulation of catechol.

Example 10

Constructing a Leaky AroE Mutation

In the prior art process for producing cis, cis-muconic acid, the host strain contains a mutation in the aroE gene named aroE353, which is a null mutation. As a result, the strain requires the feeding of the aromatic amino acids (phenylalanine, tyrosine, and tryptophan) and aromatic vitamins made from the shikimate pathway (p-hydroxy benzoic acid, p-amino benzoic acid, and 2,3-dihydroxy benzoic acid). The aromatic amino acids are too expensive to be fed in a commercially attractive process. As such, the prior art process needs a substantial improvement. This can be accomplished by installing a leaky version of the aroE gene, that we shall call aroE*. Leaky mutations are obtained by first generating a missense mutation that changes one amino acid in the aroE coding sequence that results in a null phenotype. This can be accomplished by any form of mutagenesis and screening for simultaneous auxotrophy for the six aromatic compounds listed above. A preferred method is to create a pool of mutant aroE genes by error-prone PCR mutagenesis, using Taq DNA polymerase, using wild type E. coli C genomic DNA as the template, and using PCR oligonucleotide primers that hybridize about 1000 base pairs upstream and 1000 base pairs downstream of the aroE coding region. The resulting pool of linear DNA molecules is used to transform an E. coli C derivative that produces cis, cis-muconic acid, and which contains an integrated cane, sacB cassette that has replaced the aroE coding region (see Example 4 for a related example), and selecting for sucrose resistance. The transformants are then screened for auxotrophs that have lost chloramphenicol resistance and require the six aromatic compounds listed above. Several independent auxotrophs are picked and tested for revertability by plating about $10^7$, $10^8$, or $10^9$ cells (rinsed in minimal glucose medium) on a minimal glucose plate without the six aromatic compounds. Revertants that give rise to colonies on the plates are picked and tested for production of cis, cis-muconic acid, but without production of substantial levels of aromatic amino acids. Among such revertants will be strains that carry one or more mutations in the aroE gene, such that the AroE enzyme provides enough aromatic amino acids and vitamins for growth, but not a surplus of these aromatic compounds. Another method to obtain a leaky aroE mutant is to install one of the classical revertable aroE mutants, such as aroE353 and aroE24 (both available from the Coli Genetic Stock Center at Yale University, New Haven, Conn., USA), into a cis, cis-muconic acid producing strain, and select for revertants as described above.

Example 11

Import of Glucose by Facilitated Diffusion

One of the substrates in the first committed step of the aromatic pathway is phosphoenolpyruvate (PEP). PEP is also the source of phosphate and energy for importing glucose and some other sugars by the bacterial phosphotransferase system (PTS). Thus, when a bacterium is growing on a PTS-dependent sugar, there is competition between the PTS and the aromatic pathway for PEP. As such, a significant improvement in increasing flux to the aromatic pathway can be achieved by deleting the PTS and providing an alternative pathway for sugar uptake. One solution to this problem is to replace the PTS with the E. coli GalP permease, a proton symporter that works reasonably well for glucose uptake (U.S. Pat. No. 6,692,794). However, the proton symporter still uses energy to maintain the proton gradient that is necessary to drive the permease. As such, there is a need for even further improvement in the process.

Some sugars, such as xylose, can be imported by a transporter protein that derives energy from hydrolysis of ATP (adenosine triphosphate). Once again, if the energy-dependent transporter can be replaced by a transporter that requires less energy, then an improvement can be made, since the energy inherent in the ATP can be conserved for other beneficial uses.

A significant improvement can be obtained by using a facilitated diffusion transporter, which expends no energy for the importation of the sugar (Parker et al, 1995; Snoep et al, 1994). For example, the glucose facilitator from Zymomonas mobilis, encoded by the glf gene, can be used in place of, or in addition to, the PTS in 3-dehydroshikimate (DHS) producing strains (Yi et al., 2003). However, these strains still rely at least partly on GalP for glucose import. Since GalP requires energy in the form of a proton gradient for importation of glucose, there is a need for improvements in the efficiency of glucose import for muconic producing strains.

A cassette for expression of glf plus a glucokinase gene, glk, also from Z. mobilis, can be assembled with a strong constitutive promoter, for example $P_{26}$. This cassette can then be integrated into the genome of a host strain at a location that will not interfere with production of the desired compound, which in this case is cis, cis-muconic acid. An example of such a location in the E. coli chromosome is the threonine degradation operon, tdcABCDEFG. If the growth medium contains no threonine, then this operon is not needed or expressed, so an insertion of an expression cassette in that operon does not interfere with metabolism.

To achieve the above described improvement, one or more of the genes encoding a PTS function are deleted, using a method similar to that disclosed in Example 1. For example, one or more of ptsH, ptsI, crr, or ptsG can be deleted. Next galP is deleted using the process as described in the U.S. Pat. No. 8,871,489. The $P_{26}$-g/f, glk cassette can then be installed in two steps, similar to those described in Example 1. In the first step, a $cam^R$, sacB cassette is integrated at the tdc operon, using a linear DNA derived from pAC21 (SEQ ID No. 15), and selecting for chloramphenicol (30 mg/l) resistance. In the second step, the $P_{26}$-g/f, glk cassette is integrated at the tdc operon, using a linear DNA derived from pAC19 (SEQ ID No. 15), selecting for sucrose resistance and screening for chloramphenicol sensitivity, and in this case, improved growth on minimal glucose medium.

Figure 17:
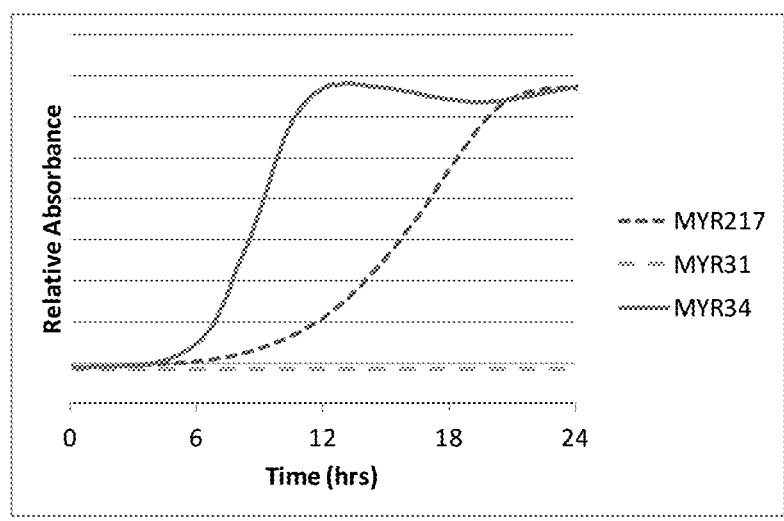
FIG. 17. Growth of strains using different systems for importing glucose. Deletion of ptsHI and galP (MYR31) leads to lack of growth in minimal glucose medium, while installation of glf and glk genes (MYR217) brings back growth. Control strain MYR34 is ΔaroE, but otherwise wild type. The three aromatic amino acids and three aromatic vitamins were added to the medium to allow growth of the auxotrophic strains.

To test whether facilitated diffusion of glucose could substitute for the conventional glucose import systems in E. coli, the ptsHI genes and the galP gene were deleted from MYR34 ($\Delta$aroE), and then the $P_{26}$-glf, glk cassette was integrated at the tdc operon, using a linear DNA derived from pAC19 (SEQ ID No. 15), to give strain MYR217. MYR217 grows reasonably well on a minimal glucose medium supplemented with the required three aromatic amino acids and three aromatic vitamin-like compounds (FIG. 17). However, strain MYR31, which contains deletions of ptsHI and galP, but does not contain the glf, glk cassette did not show any measurable growth (FIG. 17). Thus, facilitated diffusion is sufficient to replace the two conventional glucose import systems in our strain background.

Figure 18:
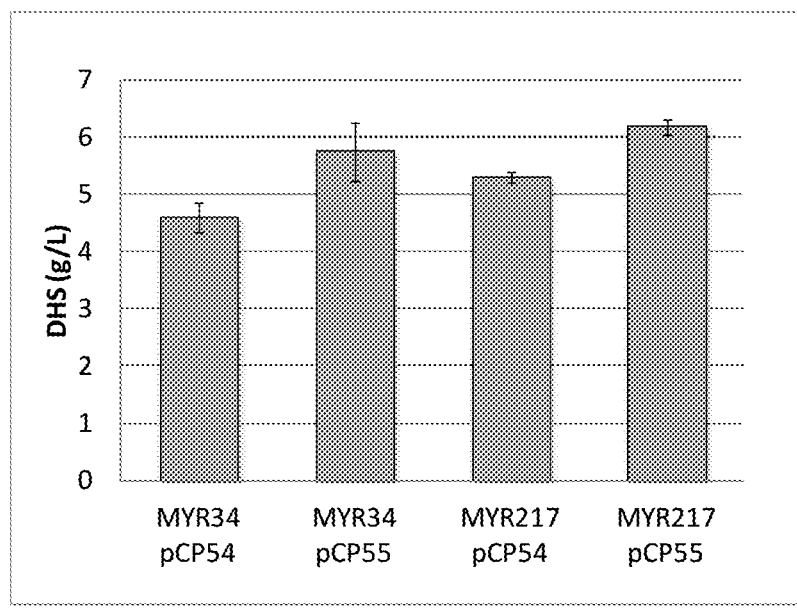
FIG. 18. DHS production in MYR34 and MYR217 strains of *E. coli*. When transformed with plasmids that lead to production of DHS, MYR217, which utilizes glf-glk for glucose import, produced a higher titer of DHS than transformants of MYR34, which utilizes the phosphotransferase system (PTS).

To test whether facilitated diffusion is useful for producing compounds derived from the aromatic pathway, MYR34 and MYR217 were transformed with pCP54 (aroG, aroB) and pCP55 (aroG, aroB, tktA). Production of the aromatic intermediate 3-dehydroshikimate (DHS) in shake flasks was compared for these two strains (FIG. 18). With either pCP54 or pCP55, the strain using facilitated diffusion produced as much or more DHS than the strains using the conventional glucose import systems. Production of DHS is a good proxy for muconic acid production in engineered E. coli strains, so we can conclude that facilitated diffusion of glucose is a useful improvement for muconic acid production.

Example 12

Overexpression of the AroB Gene

Expression of the aroB gene is reported to be rate limiting for cis, cis-muconic acid production (Niu et al., 2002). In the prior art, this was allegedly solved by integrating a second copy of the aroB gene with its native promoter. However, this is insufficient to alleviate the aroB limitation, since the native promoter and ribosome binding site of the aroB gene are far from ideal. As such, the process needs substantial improvement.

Improved overexpression of aroB can be obtained, for example, by replacing the native aroB promoter in the chromosome with a strong constitutive promoter, for example a $P_{15}$ or $P_{26}$ promoter from Bacillus subtilis phage SPO1 (SEQ ID No. 1 and SEQ ID No. 2, respectively), or the $P_R$ promoter from bacteriophage lambda (SEQ ID No. 3). This is accomplished in two steps as described in Example 4, except that the $cam^R$, sacB cassette is used to replace the native chromosomal aroB promoter and/or ribosome binding site in the first step. In the second step, the strong constitutive promoter is installed by transforming with a linear DNA comprising the strong constitutive promoter, followed by a ribosome binding site and at least 50 bases from the 5' end of the aroB coding sequence, including the ATG start codon, on the downstream side, and at least 50 base pairs of homology just upstream of the native aroB promoter on the upstream side of the strong constitutive promoter, and selecting for sucrose resistance. In addition to, or instead of, installing a stronger promoter, using a similar method, a stronger ribosome binding site, for example, AGGAGG, can be installed about 4 to 10 base pairs upstream of the ATG translation start codon of aroB. A copy of such a synthetic cassette, for example, a $P_{15}$-aroB cassette, can be integrated in the chromosome at a locus distinct from the native aroB locus, for example at the ack locus. Simultaneous deletion of the ack gene, as well as deleting the poxB gene as in Example 4 can help to reduce formation of unwanted acetate during fermentations.

Example 13

Decreasing Flux Through the Oxidative Branch of the Pentose Phosphate Pathway

The erythrose-4-phosphate that is needed for the first committed step in the aromatic pathway is derived from the non-oxidative portion of the pentose phosphate pathway (PPP). There are two different pathways by which carbon can enter the PPP. The first is from glucose-6-phosphate by the enzymes glucose-6-phosphate dehydrogenase (encoded by the zwf gene), 6-phosphogluconolactonase (encoded by the pgl gene), and 6-phophogluconate dehydrogenase (encoded by the gnd gene), to give ribulose-5-phosphate. In the last of these three steps, one carbon is lost as $CO_2$. This path into the PPP is called the oxidative branch of the PPP. Ribulose-5-phosphate is then converted into a variety of other sugar phosphates by the action of isomerases, epimerases, transketolase, and transaldolase. This group of reversible reactions, starting with ribulose-5-phosphate, is called the non-oxidative branch of the PPP. The second path by which carbon can enter the PPP is through fructose-6-phosphate and glyceraldehye-3-phosphate (both of which come from the Embden-Myerhoff pathway, also known as glycolysis), which are combined and rearranged by transaldolase and transketolase to give the variety of other sugar phosphates, one of which is erythrose-4-phosphate. If carbon enters the PPP through this second route, then no $CO_2$ is lost. In order to improve the yield of cis, cis-muconic acid from glucose, the loss of $CO_2$ can be prevented by blocking the oxidative branch of the PPP, such that all carbon entering the PPP must come through a non-oxidative route from fructose-6-phosphate and glyceraldehye-3-phosphate. The blocking of the oxidative branch of the PPP is accomplished by deleting the zwf gene, using a two-step method similar to that disclosed in Example 1 for deleting the tyrR gene.

Example 14

Increasing the Flux to and Through PEP to the Aromatic Pathway

It is desirable to ensure that PEP is not a rate limiting intermediate on the pathway to cis, cis-muconic acid. This is accomplished, for example, by increasing the recycling of pyruvate to PEP by the enzyme PEP synthetase, which is accomplished by integrating an overexpression cassette of the pps gene as described above in other examples. Another approach is to limit the consumption of PEP by pyruvate kinase, which in E. coli is encoded by the pykA and pykF genes. In this case, the approach is to decrease the activity of the enzyme(s). This is accomplished by deleting one or more genes that encode pyruvate kinase (as described in Example 1 for tyrR and in the U.S. Pat. No. 9,017,976), or reducing the strength of expression of one or more of these genes, for example, by mutating the promoter, ribosome binding site, or coding sequence, such that the level of pyruvate kinase activity is decreased. For example, the RBS in front of the E. coli pykA gene is 5'CGGAGTATTAC<u>ATG</u> (SEQ ID NO: 95). The ATG translation start codon is underlined. This sequence can be mutated to CaGAGTATTAC<u>ATG</u> (SEQ ID NO: 96), CaaAGTATTAC<u>ATG</u> (SEQ ID NO: 97), CaatGTATTAC<u>ATG</u> (SEQ ID NO: 98), CaataTATTAC<u>ATG</u> (SEQ ID NO: 99), and so on, such that the RBS sequence is made less like the consensus RBS of AGGAGG by one base change at a time. Each mutated version is then introduced into the chromosome at the pykA locus, replacing the wild type, and cis, cis-muconic acid production levels are measured for improvement.

Example 15

Conferring Growth on Sucrose

Strains derived from E. coli C do not grow on sucrose as a sole carbon source. However, they can be genetically engineered to do so as disclosed in the International Patent Application Publication No. WO2012/082720 and US Patent Application Publication No. US2013/0337519 which are hereby incorporated by reference in its entirety. As such, a cis, cis-muconic acid producing strain can be engineered to grow on sucrose as disclosed in the above mentioned application.

Example 16

An Improved Producer of Cis, Cis-Muconic Acid

All of the features described in Examples 1-15 can be combined in one strain of E. coli by installing the features one after another. The resulting strain comprises an improved cis, cis-muconic acid producer. The resulting strain can then be even further improved by integrating a second copy of each overexpression cassette described above, one at a time, at a location separate from the location of the first copy. An example of a convenient and safe location is at a BsrB1 restriction site just downstream from the terminator of rrfF, which encodes a ribosomal RNA. The desired cassette is ligated as a blunt linear DNA into the unique BsrB1 site of plasmid pMH17F (SEQ ID No. 17). An example is the ligation of the catAX expression cassette to give a plasmid named pcatAX. In parallel, a $cam^R$, sacB cassette is ligated as a blunt fragment into pMH17F to give pMH28F (SEQ ID No. 19). A linear DNA derived from pMH28 by PCR or by restriction enzyme cutting is used to deposit the $cam^R$, sacB cassette at the rrfF site. Next, a linear DNA derived from pcatAX by PCR or by restriction enzyme cutting is used to install the second copy of the catAX cassette at the rrfF locus, using selection on sucrose. The resulting strain is then compared with its grandparent strain for cis, cis-muconic acid production to determine that catAX was a limiting step. By a similar method, each cassette from Examples 2-15 is tested for a rate limiting step. If a step is found to be rate limiting, then one or more additional copies of the relevant cassette is/are integrated at yet other appropriate locations in the chromosome, leading to still further improvements in cis, cis-muconic acid production, without the need for plasmids or inducible promoters.

Example 17

Production of Cis, Cis-Muconic Acid by Fermentation

Cis, cis-muconic acid can be produced by genetically engineered microorganisms disclosed in the above Examples 1-15. The growth medium can vary widely and can be any medium that supports adequate growth of the microorganism. A preferred medium is a minimal medium containing mineral salts and a non-aromatic carbon source, such as glucose, xylose, lactose, glycerol, acetate, arabinose, galactose, mannose, maltose, or sucrose (see above for an example of a preferred minimal growth medium). For each combination of engineered microorganism and growth medium, appropriate conditions for producing cis, cis-muconic acid are determined by routine experiments in which fermentation parameters are systematically varied, such as temperature, pH, aeration rate, and compound or compounds used to maintain pH. As cis, cis-muconic acid is produced, one or more compounds must be fed into the fermentor to prevent pH from going too low. Preferred compounds for neutralizing the acid include alkaline salts such as oxides, hydroxides, carbonates, and bicarbonates of ammonium, sodium, potassium, calcium, magnesium, or a combination two or more of such alkaline salts.

Figure 19:
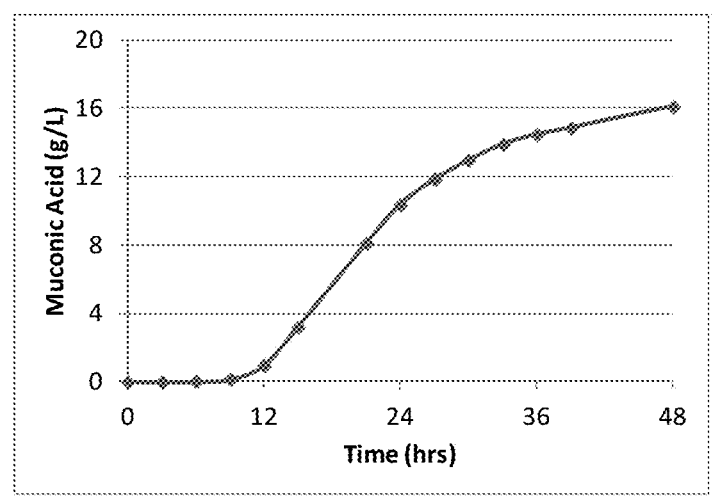
FIG. 19. Production of muconic acid by the MYR428 strain of *E. coli* in a 7 Liter fermentor. The MYR261 strain of *E. coli* with a genotype of ΔaroE ΔackA::$P_{15}$-aroB ΔpoxB::tktA was transformed with the plasmids pCP32AMP and pMG37 to generate the MYR428 strain of *E. coli*.

Muconic acid production by MYR428 strain of E. coli in a 7 Liter fermentor is shown in FIG. 19. MYR261 strain of E. coli with a genotype of ΔaroE ΔackA::P$_{15}$-aroB ΔpoxB::tktA was transformed with the plasmids pCP32AMP and pMG37 to generate MYR428. MYR428 was grown in a 7 liter fermentor as described above with glucose feeding for 48 hours. The final muconic acid titer was 16 g/l (see FIG. 19).

After fermentation is complete, cells are removed by flocculation, centrifugation, and/or filtration, and the cis, cis-muconic acid is then purified from the clarified broth by a combination of one or more subsequent steps, for example precipitation, crystallization, electrodialysis, chromatography (ion exchange, hydrophobic affinity, and/or size based), microfiltration, nanofiltration, reverse osmosis, and evaporation.

Example 18

Improvement of 3,4-Dihydroxybenzoic Acid (PCA) Decarboxylase (AroY) Activity

E. coli strain MYR993 with the genotype as provided in Table 2 was used a parental strain to generate strains with the deletion in either the ubiX gene or the ubiD gene. In constructing the *E. coli* strains with the deletion in ubiX, a kanamycin resistance cassette was amplified using primers MS608 and MS609 having 45 bp of homology to each end of the ubiX gene. In constructing the *E. coli* strains with the deletion in ubiD, a kanaymcin resistance cassette was amplified using primers MS604 and MS605 having 45 bp of homology to each end of the ubiD gene. The PCR products were column purified (QIAquick PCR Purification Kit, Qiagen) and used to transform the *E. coli* strain MYR993 (Table 2) using previously developed methods (Datsenko K A, Wanner B L (2000) One-step inactivation of chromosomal genes in *Escherichia coli* K-12 using PCR products. Proc Natl Acad Sci USA97: 6640-6645). to produce the *E. coli* stains with a deletion in either ubiX gene or ubiD gene (Table 2—MYR993 ΔubiX and MYR993 ΔubiD). The deletion stains are expected to be impaired in respiration so glucose was added to LB selection plates to provide for fermentative growth.

Figure 20:
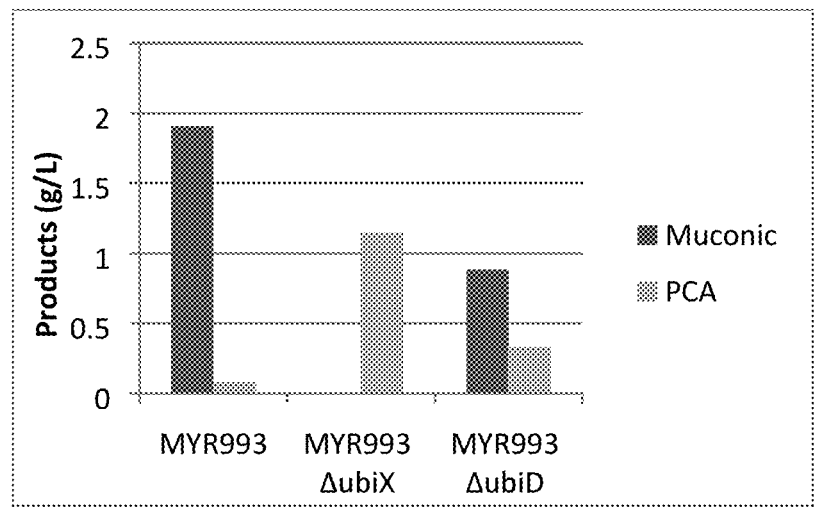
FIG. 20. Muconic acid and PCA production in the *E. coli* strain MYR993 genetically engineered to produce muconic acid and two MYR993 derivatives MYR993ΔubiX and MYR993ΔubiD. The MYR993ΔubiX *E. coli* strain was derived from MYR993 strain by means of replacing the coding region for ubiX gene with a cassette coding for kanamycin resistance. The MYR993ΔubiD *E. coli* strain was similarly derived from MYR933 strain by means of replacing the coding region for ubiD gene with a cassette coding for kanamycin resistance.

The *E. coli* strains MYR993, MYR993 ΔubiX and MYR993 ΔubiD were grown as 25 ml cultures in 250 ml shake flasks at 250 rpm at 37° C. for 48 hours in a medium comprised of 5 g $K_2HPO_4$, 3.5 g $KH_2HPO_4$, 3.5 g $(NH_4)_2HPO_4$, 1 mM $MgSO_4$, 0.1 mM $CaCl_2$, trace elements (1.6 mg $FeCl_3.6H_2O$, 0.2 mg $CoCl_2.6H_2O$, 0.1 mg $CuCl_2.2H_2O$, 0.2 mg $ZnCl_2$, 0.2 mg $Na_2MsO_4.2H_2O$, 0.05 mg $H_3BO_3$, 0.55 mg $MnCl_2.4H_2O$), and 0.2 M MOPS buffer (all per liter), using glucose as a carbon source. At the end of 48 hours of growth, the culture supernatants were analyzed for muconic acid and PCA content. As the results shown in FIG. 20 indicates, the parental strain MYR993 accumulated primarily muconic acid in the culture medium with very little PCA while the *E. coli* strain MYR993ΔubiX accumulated only PCA and muconic acid was not detectable. On the other hand, the *E. coli* strain MYR993ΔubiD showed the reduced accumulation of both muconic acid and PCA. The conclusion was that UbiX protein is needed for AroY (PCA decarboxylase) activity.

Example 19

Comparison of Activities of UbiX Homologs in an In Vitro Assay

An in vitro assay was followed to compare the activities of UbiX and four of its homologs. In this in vitro assay the lysate from an *E. coli* strain over expressing AroY protein was combined with the lysate from another *E. coli* strain expressing UbiX protein or it homolog and the combined lysate was assayed for its ability to consume PCA as a substrate. In the muconic acid producing *E. coli* strain PCA is decarboxylated by AroY protein to yield catechol which in turn is converted into muconic acid by CatA protein. The decarboxylation activity of AroY protein is expected to be enhanced by the presence of UbiX or one of tis homolog and depending on the efficiency of UbiX or its homologs, the PCA in the assay solution will be consumed at different rate.

In this in vitro assay UbiX and four of its homologs namely KpdB coded by kpdB gene of *Klebsiella pnemoniae* (kpdB) (SEQ ID 42), Elw coded by the elw gene of *E. coli* W (SEQ ID 46), Kox coded by the kox gene of *Klebsiella oxytoca* (kox) (SEQ ID 48) and Lpl coded by lpl gene of *Lactobacillus plantarum* (lpl) (SEQ ID 50). The names for the last three homologs are simply provisional names given for this disclosure. AroY, UbiX, KpdB, Elw, Kox and Lpl were expressed from the strong constitutive Lambda Phage promoter $P_R$ (SEQ ID3) on a low copy plasmid (SC101 origin of replication). The plasmids pCAT350 (SEQ ID 55) and pCP165 (SEQ ID 56) were used for gene cloning. In constructing AroY plasmid, the primers RP712 and RP714 were used to amplify the aroY gene and the primers MS461 and MS346 were used to amplify the pCAT350 plasmid backbone. The resulting PCR products were ligated to obtain a plasmid overexpressing the AroY protein. In constructing a KpdB plasmid, the primers RP731 and RP732 were used to amplify kpdB gene and the primers MS461 and MS346 were used to amplify the pCAT350 plasmid backbone. The resulting PCR products were ligated to obtain a plasmid overexpressing KpdB protein. In constructing a UbiX plasmid, the primers MS669 and MS666 were used to amplify ubiX gene and the primers MS461 and RP607 were used to amplify the pCAT350 plasmid backbone. The resulting PCR products were ligated to obtain a plasmid overexpressing UbiX protein. In constructing an Elw plasmid, the primers MS676 and MS680 were used to amplify elw gene and the primers MS461 and MS621 were used to amplify the pCP165 plasmid backbone. The resulting PCR products were ligated to obtain a plasmid overexpressing the Elw protein. In constructing a Kox plasmid, the primers MS686 and MS684 were used to amplify the kox gene and the primers MS461 and MS621 were used to amplify the pCP165 plasmid backbone. The resulting PCR products were ligated to obtain a plasmid overexpressing Kox protein. In constructing an Lpl plasmid, the primers MS692 and MS691 were used to amplify the lpl gene and the primers MS461 and MS621 were used to amplify the pCP165 plasmid backbone. The resulting PCR products were ligated to obtain a plasmid overexpressing Lpl protein. All fragments contained 20 bp of homology to enable cloning using the NEBuilder HiFi DNA Assembly Cloning Kit and cloned into NEB5α *E. coli* cells (New England Biolabs).

Figure 21:
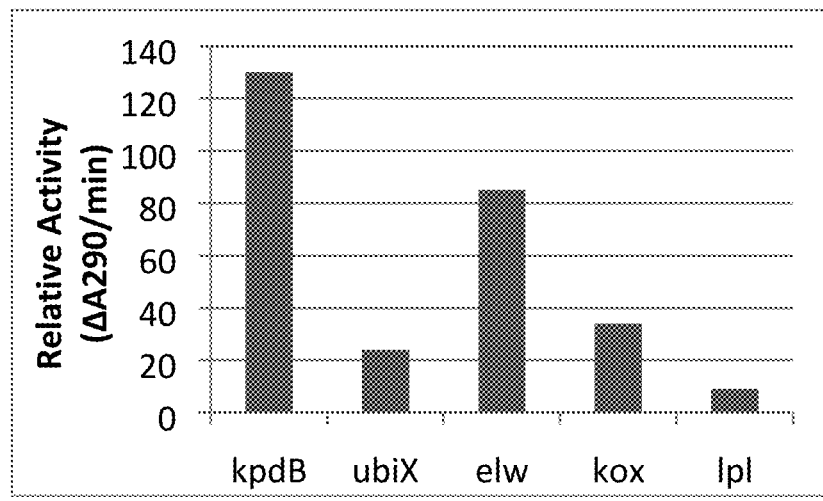
FIG. 21. Measurement of relative activity of various homologs of UbiX. Measurement of activity of UbiX homologs was carried out from the decarboxylation of PCA as measured by a decrease in the absorbance at 290 nm (A290). Five different UbiX homologs namely KpdB, UbiX, Elw, Kok and Lpl were use in this study.

Following plasmid cloning, an in vitro enzyme assay was developed to demonstrate AroY activity. 1 mL of an overnight LB grown culture was spun down and resuspended in 200 μL of Bacterial Protein Extraction Reagent (B-PER) (Thermo Fisher Scientific). After 5 minutes incubation in a rotary mixer, the cell debris was removed by centrifuging the samples at 13,000 rpm in a table top centrifuge. The clarified crude lysate supernatant was transferred to a new tube and stored on ice. 20 μL of an AroY overexpression lysate was combined with 20 μL of UbiX or a homolog lysate into a 150 μL reaction (final volume) containing 100 mM sodium phosphate buffer pH 6.4, 25 mM $MgCl_2$ and 1 mM protocatechuic acid (Sigma-Aldrich). The absorbance at 290 nm was read every minute for 60 minutes. The AroY activity was measured by monitoring disappearance of PCA at A290. The relative activities of the UbiX and its homologs are shown in FIG. 21. All UbiX homologs tested improved AroY activity, but a wide variation of enzyme activity was produced depending on the specific homolog tested. The highest AroY activity was achieved using KpdB, while the lowest activity was observed from the *Lactobacillus* homolog. The wide range of activities shown can be employed to improve muconic pathway performance, as the highest activity may not always be optimal.

Example 20

Effect of KpdB Expression Level on the Activity of AroY

Figure 22:
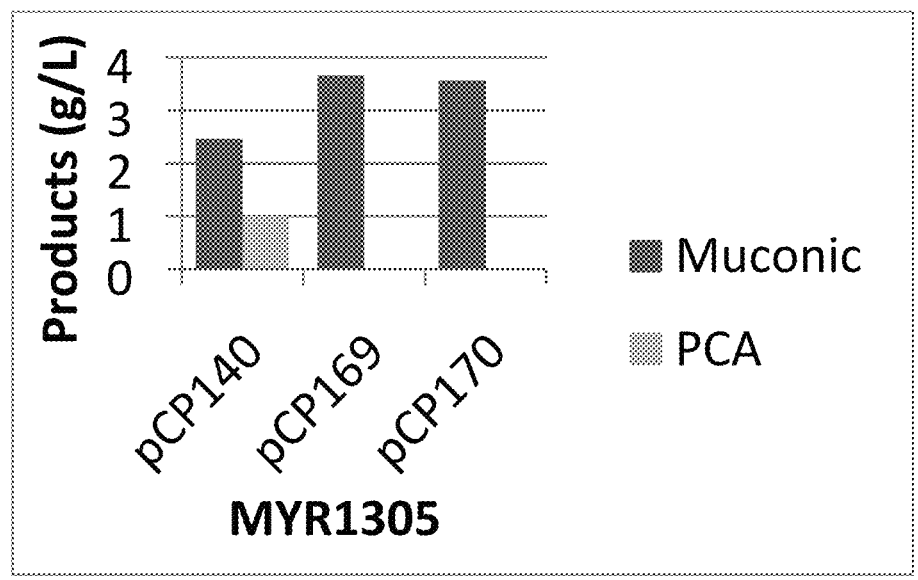
FIG. 22. Muconic acid and PCA production in *E. coli* strains having low or high level of kpdB gene expression. *E. coli* strain MYR1305 with no exogenous kpdB gene was used as the parent strain and was transformed with a low copy plasmid having the kpdB gene expressed either from the P26 promoter or the *E. coli* pgi promoter. The gene expression from the P26 promoter is expected to be at a relatively low level while the gene expression from the pgi promoter is expected to be at a relatively high level.

Having established that that the expression of KpdB protein enhance the activity of AroY protein in the in vitro assay, efforts were made to determine if the level of expression of KpdB protein within the muconic acid producing biocatalysts would affect the level of muconic acid production. In this experiment, the muconic acid production strain MYR1305 was transformed with various plasmids that express KpdB at different levels. Transformation of MYR1305 was conducted with three different plasmids. In the experimental control, MYR1305 was transformed with the control plasmid pCP140 without any genes coding for KpdB protein. The DNA sequence of pCP140 is given in SEQ ID 57. Briefly, pCP140 was constructed to express an E. coli codon-optimized catAX under the P15 promoter, E. coli tktA under native E. coli promoter, E. coli aroB under the P15 promoter, and E. coli aroD under P26 promoter (SEQ ID 2). The second plasmid pCP169 used to transform MYR1305 is a derivative of pCP140 additionally having the kpdB gene under the P26 promoter. The third plasmid pCP170 used to transform MYR1305 is a derivative of pCP140 additionally having kpdB under the E. coli pgi promoter (SEQ ID 52). Low level expression was achieved using the P26 promoter while high expression was achieved using the E. coli pgi promoter. pCP169 and pCP170 were constructed by first amplifying the pCP140 plasmid in two fragments using two sets of primers (PCR primers RP607 and RP677 for the first fragment and the PCR primers RP671 and RP664 for the second fragment). Two smaller PCR products facilitate easier plasmid construction than a single large PCR product. In constructing the plasmid pCP169, the P26 promoter was amplified using primers RP702 and RP783 and kpdB was amplified using primers RP781 and RP780. In constructing the plasmid pCP170, the pgi promoter was amplified using primers RP700 and RP784 and kpdB was amplified using primers RP779 and RP780. All PCR products had 20 bp homology overlaps to enable cloning using the NEBuilder HiFi DNA Assembly Cloning Kit. As shown in FIG. 22, strains expressing kpdB produced higher levels of muconic acid than did the control strains without any exogenous kpdB gene expression. Additionally, the PCA accumulation was eliminated in the strains expressing exogenous kpdB gene. The level of muconic acid produced did not increase with the increased expression of kpdB gene suggesting a saturating level of activity was achieved even when the exogenous kpdB gene is expressed under low level of expression.

Example 21

Complementation of a Ppc Mutant and Effect on Muconic Formation

The increased availability of PEP for muconic acid formation was investigated using the bacterial strains with the deletion of the phosphoenolpyruvate carboxylase (ppc) gene. The E. coli strain MYR1674 was genetically engineered to use as a biocatalyst for muconioc acid production. MYR1674 is able to grow in minimal medium containing glucose as a source of carbon and energy and produce muconic acid. However, when the ppc gene is deleted from MYR1674, the resulting stain MYR1674 Δppc is not able to grow in minimal medium containing glucose and is viable only on rich media such as Luria Broth (LB). The loss of the ability of MYR1674 Δppc to grow on minimal medium can be regained by means of inserting the pyc gene coding for pyruvate carboxylase at the original ppc locus in the MYR1674 Δppc strain of E. coli.

Figure 23:
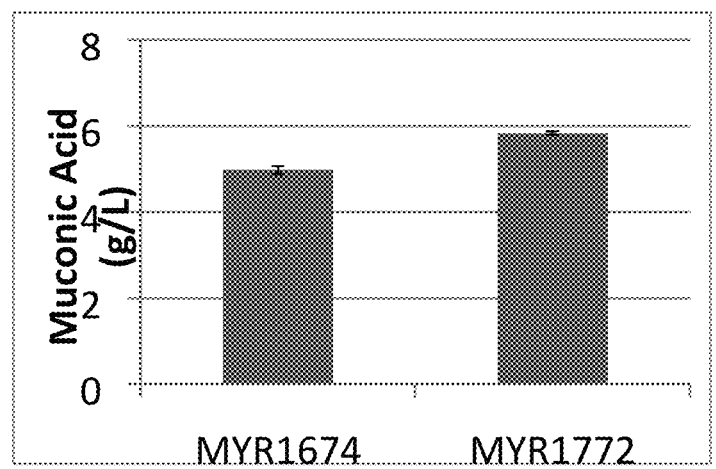
FIG. 23. Muconic acid production in the *E. coli* strain MYR1674 and its derivative MYR1772. MYR1772 was derived from MYR1674 by replacing the coding region and promoter of ppc with the $P_R$-pyc gene. $P_R$ is an abbreviation for the strong rightward promoter from the coliphage lambda.

The pyruvate carboxylase (pyc) gene from Saccharomyces cerevisiae (SEQ ID 53) was cloned using primers MS1383 and MS1384, containing flanking homology to the E. coli ppc promoter and terminator. In order to facilitate strong growth on minimal media, the strong constitutive rightward Lambda Phage promoter $P_R$ was required. The $P_R$ promoter was amplified using primers MS1429 and MS1430 and the resulting PCR product was used to replace the endogenous ppc promoter. The final nucleotide sequence for the Δppc::$P_R$-pyc locus is shown in SEQ ID 58. The S. cerevisiae pyc gene was chosen because it is not closely related to any E. coli gene, and the expected lower expression due to differing codon usage could be beneficial in preserving PEP for muconic acid production. There are many organisms that contain pyruvate carboxylase, and any homologs or analogs having pyruvate carboxylase activity could be used. New strain MYR1772 derived from MYR1674 by integrating Δppc::$P_R$-pyc at the original ppc locus was viable on a minimal medium confirming the functionality of the cloned S. cerevisiae pyc gene. MYR1772 and its parent MYR1674 strains were compared in shake flask experiments for their ability to produce muconic acid. As the results shown in FIG. 23 indicates, MYR1772 strain produced higher titer of muconic acid production than parent MYR1674, demonstrating the advantage in replacing the endogenous phosphoenolpyruvate carboxylase enzyme with the exogenous pyruvate carboxylase enzyme.

Example 22

Measuring Muconic Acid Production

The bacterial strains MYR814, MYR993, MYR1536, MYR1557, MYR1570, MYR1595, MYR1630, MYR1674 and MYR1772 were grown in shake flask cultures overnight and titer and yield for muconic acid production were determined. In addition, the growth rate was determined by measuring the absorbance at 600 nm and the relative growth of various bacterial strains are provided in Table 8. The bacterial growth represented by "+++" indicates a growth similar to the growth seen in a wild type E. coli strain. The bacterial growth represented by "+" indicates poor growth. An intermediate growth is represented by "++". When a particular strain is showing a poor growth, that strain is subjected to 5 overnight transfers to improve the growth, each transfer produces approximately 10 generations or doublings.

The bacterial strains MYR814, MYR1570, MYR1630 and MYR1674 were grown in 7 liter fermenters in a fed-batch mode and the titer and yield for muconic acid production were determined (Table 9). The bacterial strains tested for muconic acid titer and yield produced very little byproducts. For example, the bacterial strain after 72 hours of fed batch fermentation showed only 0.08 g/L of PCA and 0.07 g/L of fumarate as byproducts.

TABLE 1

Bacterial strains used in the present invention

| Bacterial strain | Genotype/Description |
| --- | --- |
| ATCC8739 | Escherichia coli "C" wild type |
| MYR34 | ATCC8739 ΔaroE |
| MYR170 | ATCC8739 ΔaroE, ΔackA::$P_{15}$aroB |
| MYR261 | ATCC8739 ΔaroE, ΔackA::$P_{15}$aroB, ΔpoxB::tktA |
| MYR305 | ATCC8739 ΔaroE, ΔackA::$P_{15}$aroB, ΔpoxB |
| MYR31 | ATCC8739 ΔptsHI, ΔgalP |
| MYR217 | ATCC8739 ΔptsHI, ΔgalP, Δtdc::glf-glk, ΔaroE |

TABLE 1-continued

Bacterial strains used in the present invention

| Bacterial strain | Genotype/Description |
|---|---|
| MYR352 | ATCC8739 ΔaroE, ΔackA::P$_{15}$aroB, ΔadhE::P$_{15}$-catAX, P$_R$-aroY, P$_{26}$-quiC |
| RY903 | ΔaroE, ΔackA::P$_{15}$aroB, pMG37, aroG*20-893 |
| RY909 | ΔaroE, ΔackA::P$_{15}$aroB, pMG37, aroG*20-899 |
| RY911 | ΔaroE, ΔackA::P$_{15}$aroB, pMG37, aroG*20-901 |
| RY912 | ΔaroE, ΔackA::P$_{15}$aroB, pMG37, aroGwt |
| RY913 | ΔaroE, ΔackA::P$_{15}$aroB, pMG37, aroG*20-893, ΔtyrR::kan |
| RY919 | ΔaroE, ΔackA::P$_{15}$aroB, pMG37, aroG*20-899, ΔtyrR::kan |
| RY921 | ΔaroE, ΔackA::P$_{15}$aroB, pMG37, aroG*20-901, ΔtyrR::kan |
| RY922 | ΔaroE, ΔackA::P$_{15}$aroB, pMG37, aroGwt, ΔtyrR::kan |

TABLE 3

Plasmids used in the present invention

| Bacterial Plasmid | Genotype/Description |
|---|---|
| YEp24 | 2μ yeast origin, URA3, Tc$^R$, pMB1 replicon, Ap$^R$ |
| pCP32AMP | 2μ yeast origin, URA3, Tc$^R$, pMB1 replicon, Ap$^R$, aroG |
| pCP14 | 2μ yeast origin, URA3, Tc$^R$, pMB1 replicon, Ap$^R$, P$_{15}$aroB |
| pCP54 | 2μ yeast origin, URA3, Tc$^R$, pMB1 replicon, Ap$^R$, P$_{15}$aroB, aroG |
| pCP50 | 2μ yeast origin, URA3, Tc$^R$, pMB1 replicon, Ap$^R$, aroG, tktA |
| pCP55 | 2μ yeast origin, URA3, Tc$^R$, pMB1 replicon, Ap$^R$, aroG, aroB, tktA |
| pCL1921 | pSC101 replicon, Spc$^R$ |
| pMG27 | pSC101 replicon, Spc$^R$, P$_R$-aroY |

TABLE 2

Bacterial used in the present invention

| Strain Name | Genotype/Description | Parent |
|---|---|---|
| MYR802 | ΔackA::P15-aroB ΔadhE::P15-catAX + P$_R$-aroY + P26-quiC ΔpflB::P15-catAX ΔtyrR aroG$^{FBR}$ ΔpoxB::tktA ΔptsHI Δtdc::P26-glf-glk ΔgalP aroE G105M | |
| MYR814 | ΔackA::P15-aroB ΔadhE::P15-catAX + P$_R$-aroY + P26-quiC ΔpflB::P15-catAX ΔtyrR aroG$^{FBR}$ ΔpoxB::tktA ΔptsHI Δtdc::P26-glf-glk ΔgalP aroE G105M [P15-catA-catX + tktA + P15-aroB + P26-aroD in pCL1921 backbone] | MYR802 |
| MYR993 | ΔackA::P15-aroB ΔadhE::P$_R$-aroY + P26-quiC ΔpflB::P$_R$-catAX ΔtyrR aroG$^{FBR}$ ΔpoxB::tktA ΔptsHI Δtdc::P26-glf-glk ΔgalP aroE G105M | MYR802 |
| MYR993 ΔubiX | ΔackA::P15-aroB ΔadhE::P$_R$-aroY + P26-quiC ΔpflB::P$_R$-catAX ΔtyrR aroG$^{FBR}$ ΔpoxB::tktA ΔptsHI Δtdc::P26-glf-glk ΔgalP aroE G105M ΔubiX::Kan$^R$ | MYR993 |
| MYR993 ΔubiD | ΔackA::P15-aroB ΔadhE::P$_R$-aroY + P26-quiC ΔpflB::P$_R$-catAX ΔtyrR aroG$^{FBR}$ ΔpoxB::tktA ΔptsHI Δtdc::P26-glf-glk ΔgalP aroE G105M ΔubiD::Kan$^R$ | MYR993 |
| MYR1305 | ΔackA::P15-aroB ΔadhE::P15-catAX + P$_R$-aroY + P26-quiC ΔpflB::P15-catAX ΔtyrR aroG$^{FBR}$ ΔpoxB::tktA ΔptsHI Δtdc::P26-glf-glk ΔgalP ΔaroE Δzwf | MYR802 |
| MYR1305 pCP140 | ΔackA::P15-aroB ΔadhE::P15-catAX + P$_R$-aroY + P26-quiC ΔpflB::P15-catAX ΔtyrR aroG$^{FBR}$ ΔpoxB::tktA ΔptsHI Δtdc::P26-glf-glk ΔgalP ΔaroE Δzwf [P$_R$-catA-catX + tktA + P15-aroB + P26-aroD in pCL1921 backbone] | MYR1305 |
| MYR1305 pCP169 | ΔackA::P15-aroB ΔadhE::P15-catAX + P$_R$-aroY + P26-quiC ΔpflB::P15-catAX ΔtyrR aroG$^{FBR}$ ΔpoxB::tktA ΔptsHI Δtdc::P26-glf-glk ΔgalP ΔaroE Δzwf [P$_R$-catA-catX + tktA + P15-aroB + P26-aroD + P26-kpdB in pCL1921 backbone] | MYR1305 |
| MYR1305 pCP170 | ΔackA::P15-aroB ΔadhE::P15-catAX + P$_R$-aroY + P26-quiC ΔpflB::P15-catAX ΔtyrR aroG$^{FBR}$ ΔpoxB::tktA ΔptsHI Δtdc::P26-glf-glk ΔgalP ΔaroE Δzwf [P$_R$-catA-catX + tktA + P15-aroB + P26-aroD + P$_{PGI}$-kpdB in pCL1921 backbone] | MYR1305 |
| MYR1536 | ΔackA::P$_{acpp}$-aroB ΔadhE::P15-qa4 ΔtyrR aroG$^{FBR}$ ΔpoxB::P$_R$-tktA Δtdc::P26-glf-glk ΔgalP::P15-ubiX ΔpflB::P$_R$-CatAX P$_{acpp}$-aroD ΔmgsA::P$_{rplU}$-qa4 ΔptsHI::P$_R$-aroY Δ0039::P$_R$-catAX | MYR802 |
| MYR1557 | ΔackA::P$_{acpp}$-aroB ΔadhE::P15-qa4 ΔtyrR aroG$^{FBR}$ ΔpoxB::P$_R$-tktA Δtdc::P26-glf-glk ΔgalP::P15-ubiX ΔpflB::P$_R$-CatAX P$_{acpp}$-aroD ΔmgsA::P$_{rplU}$-qa4 ΔptsHI::P$_R$-aroY Δ0039::P$_R$-catAX (Evolved version of MYR1536 for faster growth) | MYR1536 |
| MYR1570 | ΔackA::P$_{acpp}$-aroB ΔadhE::P15-qa4 ΔtyrR aroG$^{FBR}$ ΔpoxB::P$_R$-tktA Δtdc::P26-glf-glk ΔgalP::P15-ubiX ΔpflB::P$_R$-CatAX P$_{acpp}$-aroD ΔmgsA::P$_{rplU}$-qa4 ΔptsHI::P$_R$-aroY Δ0039::P$_R$-catAX Δzwf (Evolved version of MYR1536 for faster growth) | MYR1536 |
| MYR1595 | ΔackA::P$_{acpp}$-aroB ΔadhE::P15-qa4 ΔtyrR aroG$^{FBR}$ ΔpoxB::P$_R$-tktA Δtdc::P26-glf-glk ΔgalP::P15-ubiX ΔpflB::P$_R$-CatAX P$_{acpp}$-aroD ΔmgsA::P$_{rplU}$-qa4 ΔptsHI::P$_R$-AroY Δ0039::P$_R$-catAX Δzwf ΔpykF | MYR1557 |
| MYR1630 | ΔackA::P$_{acpp}$-aroB ΔadhE::P15-qa4 ΔtyrR aroG$^{FBR}$ ΔpoxB::P$_R$-tktA Δtdc::P26-glf-glk ΔgalP::P15-ubiX ΔpflB::P$_R$-CatAX P$_{acpp}$-aroD ΔmgsA::P$_{rplU}$-qa4 ΔptsHI::P$_R$-aroY Δ0039::P$_R$-catAX Δzwf ΔpykF Δ2160::P$_R$-aroG$^{FBR}$ | MYR1595 |
| MYR1674 | ΔackA::P$_{acpp}$-aroB ΔadhE::P15-qa4 ΔtyrR aroG$^{FBR}$ ΔpoxB::P$_R$-tktA Δtdc::P26-glf-glk ΔgalP::P15-ubiX ΔpflB::P$_R$-CatAX P$_{acpp}$-aroD ΔmgsA::P$_{rplU}$-qa4 ΔptsHI::P$_R$-aroY Δ0039::P$_R$-catAX Δzwf ΔpykF Δ2160::P$_R$-aroG$^{FBR}$ (Evolved version of MYR1630 for faster growth) | MYR1630 |
| MYR1772 | ΔackA::P$_{acpp}$-aroB ΔadhE::P15-qa4 ΔtyrR aroG$^{FBR}$ ΔpoxB::P$_R$-tktA Δtdc::P26-glf-glk ΔgalP::P15-ubiX ΔpflB::P$_R$-CatAX P$_{acpp}$-aroD ΔmgsA::P$_{rplU}$-qa4 ΔptsHI::P$_R$-aroY Δ0039::P$_R$-catAX Δzwf ΔpykF Δ2160::P$_R$-aroG$^{FBR}$ Δppc::P$_R$-pyc | MYR1674 |

TABLE 3-continued

Plasmids used in the present invention

| Bacterial Plasmid | Genotype/Description |
|---|---|
| pMG31 | pSC101 replicon, Spc$^R$, P$_{15}$-catAX |
| pMG33 | pSC101 replicon, Spc$^R$, P$_{15}$-catAX, P$_R$-aroY |
| pMG37 | pSC101 replicon, Spc$^R$, P$_{15}$-catAX-CatX, P$_R$-aroY, P$_{26}$-quiC |
| pMG39 | pSC101 replicon, Spc$^R$, P$_{26}$-quiC |
| pMG47 | pSC101 replicon, Spc$^R$, P$_{15}$-catAX, P$_R$-aroY, P$_{26}$-asbF |
| pMG70 | pSC101 replicon, Spc$^R$, P$_{15}$-catAX, P$_R$-aroY, P$_{26}$-qa-4 |

TABLE 4 aroG*mutant alleles that lead to resistance to phenylalanine feedback inhibition

| Strain | Allele number | Nucleotide mutation | Amino acid mutation |
|---|---|---|---|
| RY893 | aroG*20-893 | C449T | Pro150Leu |
| RY897 | aroG*20-897 | C449T | Pro150Leu |
| RY899 | aroG*20-899 | T538C | Ser180Pro |
| RY901 | aroG*20-901 | C438T | Pro150Ser |
| MYR450 | aroG*111 | C55T | Pro19Ser |
| MYR451 | aroG*211 | G533A | Gly178Glu |
| MYR452 | aroG*212 | C540T | Ser180Phe |
| MYR453 | aroG*311 | Deletion from base pair 36 to 44 bp | Deletion of Glu-Ile-Lys |
| MYR454 | aroG*312 | C632T | Ser211Phe |
| MYR455 | aroG*411 | T29A | Ile10Asn |
| MYR456 | aroG*412 | G533A | Gly178Glu |
| MYR457 | aroG*511 | C448T | Pro150Ser |

TABLE 5

AroG activity measurement in crude extract from various recombinant E. coli strains

| Strain | aroG* allele | Specific activity mU (One mU = one nM product made per milligram protein per minute) | % of activity resistant to phenylalanine |
|---|---|---|---|
| RY893 | aroG*20-893 | 62 | 34 |
| RY897 | aroG*20-897 | 55 | 77 |
| RY899 | aroG*20-899 | 92 | 113 |
| RY901 | aroG*20-901 | 78 | 76 |
| RY902 | aroG wild type | 38 | 6 |
| RY890 | aroG wild type | 54 | 7 |

TABLE 6

Muconic acid production in shake flasks by strains containing feedback resistant aroG* alleles

| Strain | Muconic acid titer g/l |
|---|---|
| RY913 | 3.04 |
| RY919 | 3.11 |
| RY921 | 2.99 |
| RY922 | 1.45 |

TABLE 7

Sequence Information

| No. | Name | Description |
|---|---|---|
| 1 | SEQ ID No. 1 | The P$_{15}$ promoter from *Bacillus subtilis* phage SP01, with a stem and loop added just downstream from the transcription start site. |
| 2 | SEQ ID No. 2 | The P$_{26}$ promoter from *Bacillus subtilis* phage SP01 |
| 3 | SEQ ID No. 3 | The P$_R$ promoter from *Escherichia coli* phage |
| 4 | SEQ ID No. 4 | Protein sequence of 3-dehydroshikimate dehydratase from *Neurospora crassa* encoded by the qa-4 gene. |
| 5 | SEQ ID No. 5 | Genomic DNA sequence of the qa-4 gene from *Neurospora crassa* plus surrounding sequences. |
| 6 | SEQ ID No. 6 | Protein sequence of 3dehydroshikimate dehydratase from *Aspergillus nidulans*. encoded by the qutC gene |
| 7 | SEQ ID No. 7 | Genomic DNA sequence of the qutC gene from *Aspergillus nidulans* plus surrounding sequences |
| 8 | SEQ ID No. 8 | Protein sequence of protocatechuate decarboxylase (AroY) from *Klebsiella pnemoniae* ATCC25597 |
| 9 | SEQ ID No. 9 | DNA sequence of the aroY gene of *Klebsiella pneumoniae* 342 plus 2 kilobases of surrounding DNA sequences |
| 10 | SEQ ID No. 10 | DNA sequence of the catA gene from *Acinetobacter baylyi* ADP1, including 410 bases of upstream sequence and two open reading frames downstream |
| 11 | SEQ ID No. 11 | Protein sequence of CatA (catechol 1,2-dioxygenase) from *Acinetobacter baylyi* ADP1 |
| 12 | SEQ ID No. 12 | DNA sequence of the quiC (3-dehydroshikimate dehydratase) gene from *Acinetobacter* sp. ADP1 |
| 13 | SEQ ID No. 13 | Codon-optimized DNA sequence of the quiC (3-dehydroshikimate dehydratase) gene from *Acinetobacter* sp. ADP1 |
| 14 | SEQ ID No. 14 | Protein sequence of QuiC (3-dehydroshikimate dehydrogenase from *Acinetobacter* sp. ADP1 |
| 15 | SEQ ID No. 15 | DNA sequence of the plasmid pAC21 |
| 16 | SEQ ID No. 16 | DNA sequence of the plasmid pAC19 |
| 17 | SEQ ID No. 17 | DNA sequence of the plasmid pMH17F |
| 18 | SEQ ID No. 18 | DNA sequence of the coding region of the wild type aroG gene |
| 19 | SEQ ID No. 19 | DNA sequence of the plasmid pMH28F |
| 20 | SEQ ID No. 20 | DNA sequence of the plasmid pCL1921 |
| 21 | SEQ ID No. 21 | DNA sequence of the plasmid pMG27 |
| 22 | SEQ ID No. 22 | DNA sequence of the plasmid pMG31 |
| 23 | SEQ ID No. 23 | DNA sequence of the plasmid pMG33 |
| 24 | SEQ ID No. 24 | DNA sequence of the plasmid pMG37 |
| 25 | SEQ ID No. 25 | DNA sequence of the plasmid pMG39 |

TABLE 7-continued

Sequence Information

| | | |
|---|---|---|
| 26 | SEQ ID No. 26 | DNA sequence of the plasmid pMG47 |
| 27 | SEQ ID No. 27 | DNA sequence of the plasmid pMG70 |
| 28 | SEQ ID No. 28 | DNA sequence of the plasmid pCP32AMP |
| 29 | SEQ ID No. 29 | DNA sequence of the plasmid pCP14 |
| 30 | SEQ ID No. 30 | DNA sequence of the plasmid pCP50 |
| 31 | SEQ ID No. 31 | DNA sequence of the plasmid pCP54 |
| 32 | SEQ ID No. 32 | DNA sequence of the plasmid pCP55 |
| 33 | SEQ ID No. 33 | DNA sequence of the plasmid YEP24 |
| 34 | SEQ ID No. 34 | DNA sequence of the deleted aroE region |
| 35 | SEQ ID No. 35 | DNA sequence of the integrated cassette $\Delta$ack::$P_{15}$aroB |
| 36 | SEQ ID No. 36 | DNA sequence of the $\Delta$poxB region |
| 37 | SEQ ID No. 37 | DNA sequence of the integrated cassette $\Delta$poxB::tktA |
| 38 | SEQ ID No. 38 | DNA sequence of the $\Delta$ptsHI region |
| 39 | SEQ ID No. 9 | DNA sequence of the integrated cassette $\Delta$tdc::glf-glk |
| 40 | SEQ ID No. 40 | DNA sequence of the $\Delta$galP region |
| 41 | SEQ ID No. 41 | MYR352 $\Delta$adhE::$P_{15}$-catAX, $P_R$-aroY, $P_{26}$-quiC |
| 42 | SEQ ID No. 42 | Nucleotide sequence of *Klebsiella pneumoniae* kpdB gene. |
| 43 | SEQ ID No. 43 | Amino acid sequence of KpdB protein of *Klebsiella pneumoniae* |
| 44 | SEQ ID No. 44 | Nucleotide sequence of *Escherichia coli* ubiX gene |
| 45 | SEQ ID No. 45 | Amino acid sequence of UbiX protein of *Escherichia coli*. |
| 46 | SEQ ID No. 46 | Nucleotide sequence of *Escherichia coli* Wstrain elw gene |
| 47 | SEQ ID No. 47 | Amino acid sequence of Elw protein of *Escherichia coli* W strain. |
| 48 | SEQ ID No. 48 | Nucleotide sequence of *Klebsiella oxytoca* kox gene |
| 49 | SEQ ID No. 49 | Amino acid sequence of Kox protein of *Klebsiella oxytoca*. |
| 50 | SEQ ID No. 50 | Nucleotide sequence of *Lactobacillus plantarum* lpl gene |
| 51 | SEQ ID No. 51 | Amino acid sequence of Lpl protein of *Lactobacillus plantarum*. |
| 52 | SEQ ID No. 52 | Nucleotide sequence of Pgi promoter |
| 53 | SEQ ID No. 53 | Nucleotide sequence of *Saccharomyces cerevisiae* pyc gene |
| 54 | SEQ ID No. 54 | Amino acid sequence of Pyc protein of *Saccharomyces cerevisiae*. |
| 55 | SEQ ID No. 55 | DNA sequence of the plasmid pCAT350 |
| 56 | SEQ ID No. 56 | DNA sequence of the plasmid pCP165 |
| 57 | SEQ ID No. 57 | DNA sequence of the plasmid pCP140 |
| 58 | SEQ ID No. 58 | Nucleotide sequence of $\Delta$ppc::$P_R$-pyc |
| 59 | SEQ ID No. 59 | Nucleotide sequence of acpP promoter |
| 60 | SEQ ID No. 60 | Nuclotide sequence of rplU promoter |

| SEQ ID No. | Primer Name | Sequence |
|---|---|---|
| 61 | MS604 | AACGCCGTATAATGGGCGCAGATTAAGAGGCTACAGTGGGCTTACATGGCGATAGCTAGA |
| 62 | MS605 | TGTCGGATCGATAAATAGGGCAAAACAAACGCGCATCCCGGAAAACGATTCCGAAGCCCA |
| 63 | MS608 | AAAGTCTGCCTGCAAGTCTGACAGGGCAACTATTTGTGGGCTTACATGGCGATAGCTAGA |
| 64 | MS609 | TTGCAAAATTGCCCTGAAACAGGGCAACAGCGGAGTCCCGGAAAACGATTCCGAAGCCCA |
| 65 | MS461 | GGCTATATTCCTTATCTAGATTAGT |
| 66 | MS346 | GTCTGACAGGTGCCGGATTTCATAT |
| 67 | RP712 | TCTAGATAAGGAATATAGCCATGACCGCACCGATTCAGGATCTGC |
| 68 | RP714 | AAATCCGGCACCTGTCAGACTTATTTTGCGCTACCCTGGTTTTTT |
| 69 | RP731 | CATGTACTAATCTAGATAAGGAATATAGCCATGAAACTGATTATTGGGATGACGGGGGCC |
| 70 | RP732 | GCCGGATATGAAATCCGGCACCTGTCAGACTTATTCGATCTCCTGTGCAAATTGTTCTGC |
| 71 | MS669 | TCTAGATAAGGAATATAGCCATGAAACGACTCATTGTAGGCATCA |
| 72 | MS666 | ACCGAACAGGCTTATGTCCAGATAGCAGGTATAGCGGTTGAATCG |
| 73 | RP607 | TGGACATAAGCCTGTTCGGTTCGT |
| 74 | MS621 | TTAGATTTGACTGAAATCGTACAGT |
| 75 | MS676 | TCTAGATAAGGAATATAGCCATGAAACTGATCGTCGGGATGACAG |
| 76 | MS680 | ACGATTTCAGTCAAATCTAATTATTCATTCTCCTGAGAAAAATTC |
| 77 | MS686 | TCTAGATAAGGAATATAGCCATGACGGCACGCATCATCATTGGTA |
| 78 | MS684 | ACGATTTCAGTCAAATCTAATTAATTAAAACGTAGCTCGCCTTCA |
| 79 | MS692 | TCTAGATAAGGAATATAGCCATGAAACGAATTGTTGTGGGAATCA |
| 80 | MS691 | ACGATTTCAGTCAAATCTAATTAATCCCCCTCCCAACGGCGATCA |
| 81 | RP677 | CGACGTTGTAAAACGACGGCCAGTG |
| 82 | RP671 | TTAATCGCCTTGCAGCACATCCCCC |
| 83 | RP664 | ACGAACCGAACAGGCTTATGTCCA |
| 84 | RP702 | GCCGTCGTTTTACAACGTCGGATCCGCCTACCTAGCTTCCAAGAA |
| 85 | RP783 | CCTACAATGAGTCGTTTCATTAGGTTTTCCTCAACCCGGGAGCGT |
| 86 | RP781 | CCCGGGTTGAGGAAAAACCTAATGAAACGACTCATTGTAGGCATCA |
| 87 | RP780 | ATGTGCTGCAAGGCGATTAAGATAGCAGGTATAGCGGTTGAATCG |
| 88 | RP700 | GCCGTCGTTTTACAACGTCGAGCGGGGCGGTTGTCAACGATGGGG |
| 89 | RP784 | CCTACAATGAGTCGTTTCATGGCTATATTCCTCCTCTGCATGAGA |
| 90 | RP779 | TGCAGAGGAGGAATATAGCCATGAAACGACTCATTGTAGGCATCA |
| 91 | MS1383 | GATGGGGTGTCTGGGGTAATATGTCGCAAAGAAAATTCGCCGGCT |
| 92 | MS1384 | GGGTTTGCAGAAGAGGAAGATCATGCCTTAGTTTCAACAGGAACT |
| 93 | MS1429 | ATTCCTGCTATTTATTCGTTCGTTAAATCTATCACCGCAAGGGAT |
| 94 | MS1430 | GCGAATTTTCTTTGCGACATGGCTATATTCCTTATCTAGATTAGT |

TABLE 8

Titer and yield for muconic acid production and growth of various *E. coli* strains in shake flask cultures

| Strain Name | Titer (grams muconic acid/liter) | Yield (grams muconic acid/gram glucose) | Growth |
|---|---|---|---|
| MYR814 | 2 | 0.16 | +++ |
| MYR993 | 1.9 | 0.15 | +++ |
| MYR1536 | 2.7 | 0.22 | + |
| MYR1557 | 3 | 0.25 | +++ |
| MYR1570 | 4.5 | 0.38 | ++ |
| MYR1595 | 4.5 | 0.38 | ++ |
| MYR1630 | 4.8 | 0.4 | + |
| MYR1674 | 3.8 | 0.32 | +++ |
| MYR1772 | 5 | 0.42 | +++ |

TABLE 9

Titer and yield for muconic acid production for various *E. coli* strains in fed batch cultures

| Strain Name | Titer (grams muconic acid/liter) | Yield (grams muconic acid/gram glucose) | Time (hours) |
|---|---|---|---|
| MYR814 | 30.9 | 0.20 | 48 |
| MYR1570 | 49.0 | 0.36 | 48 |
| MYR1630 | 58.3 | 0.47 | 48 |
| MYR1630 | 69.5 | 0.42 | 72 |
| MYR1674 | 81.5 | 0.43 | 72 |

REFERENCES

All the patents, patent applications, publications, sequences, and other published materials are incorporated herein are incorporated by reference.

U.S. Pat. No. 4,480,034
U.S. Pat. No. 4,535,059
U.S. Pat. No. 4,588,688
U.S. Pat. No. 4,608,338
U.S. Pat. No. 4,681,852
U.S. Pat. No. 4,753,883
U.S. Pat. No. 4,833,078
U.S. Pat. No. 4,968,612
U.S. Pat. No. 5,168,056
U.S. Pat. No. 5,272,073
U.S. Pat. No. 5,487,987
U.S. Pat. No. 5,616,496
U.S. Pat. No. 6,600,077
U.S. Pat. No. 6,180,373
U.S. Pat. No. 6,210,937
U.S. Pat. No. 6,472,169
U.S. Pat. No. 6,613,552
U.S. Pat. No. 6,962,794
U.S. Pat. No. 7,244,593
U.S. Pat. No. 7,638,312
U.S. Pat. No. 7,790,431
U.S. Pat. No. 8,871,489
U.S. Pat. No. 9,017,976
U.S. Patent Application Publication No. US 2009/0191610 A1
U.S. Patent Application Publication No. US 2010/0314243 A1
U.S. Patent Application Publication No. US 2013/0337519 A1
U.S. Patent Application Publication No. US. 2014/0234923A1
U.S. Patent Application Publication No. US 2015/0044755 A1
U.S. Patent Application Publication No. US2016/0017381 A1
European Patent Application No. 86300748.0
International Patent Application Publication No. WO 2011/017560
International Patent Application Publication No. WO 2011/085311
International Patent Application Publication No. WO 2011/123154
International Patent Application Publication No. WO2013/116244

Altschul, S. F., Gish, W., Miller, W., Myers, E. W., and Lipman, D. J. (1990) Basic local alignment search tool, *J Mol Biol* 215, 403-410.

Altschul, S. F., Madden, T. L., Schaffer, A. A., Zhang, J., Zhang, Z., Miller, W., and Lipman, D. J. (1997) Gapped BLAST and PSI-BLAST: a new generation of protein database search programs, *Nucleic Acids Res* 25, 3389-3402.

Aussel, Laurent, Fabien Pierrel, Laurent Loiseau, Murielle Lombard, Marc Fontecave, and Frédéric Barras. 2014. "Biosynthesis and Physiology of Coenzyme Q in Bacteria." *Biochimica et Biophysica Acta—Bioenergetics* 1837 (7): 1004-11.

Baba, Tomoya, Takeshi Ara, Miki Hasegawa, Yuki Takai, Yoshiko Okumura, Miki Baba, Kirill A Datsenko, Masaru Tomita, Barry L Wanner, and Hirotada Mori. 2006. "Construction of *Escherichia Coli* K-12 in-Frame, Single-Gene Knockout Mutants: The Keio Collection." *Molecular Systems Biology* 2: 2006.0008. doi:10.1038/msb4100050.

Barbe, V., Vallenet, D., Fonknechten, N., Kreimeyer, A., Oztas, S., Labarre, L., Cruveiller, S., Robert, C., Duprat, S., Wincker, P., Ornston, L. N., Weissenbach, J., Marliere, P., Cohen, G. N., and Medigue, C. (2004) Unique features revealed by the genome sequence of *Acinetobacter* sp. ADP1, a versatile and naturally transformation competent bacterium, *Nucleic Acids Res* 32, 5766-5779.

Bird, J. A. and Cain, R. B. (1968) cis-cis-muconate, the product inducer of catechol 1,2-oxygenase in *Pseudomonas aeruginosa*. *Biochem. J.* 109, 479-481.

Bongaerts, J., Kramer, M., Muller, U., Raven, L. and Wubbolts, M. (2001) Metabollic engineering for microbial producitnof aromatic acids and derived compunds. Met. Eng. 3, 289-300.

Chandran, S. S., Yi, J., Draths, K. M., von Daeniken, R., Weber, W. and Frost, J. W. (2003) Phosphoenolpyruvate availability and the biosynthesis of shikimic acid. *Biotechnol. Prog.* 19, 808-814.

Chen, R., Hatzimanikatis, V., Yap, W. M. G. J., Potma, P. W. and Bailey, J. E. (1997) Metabolic consequences of phosphotransferase (PTS) mutation in a phenylalanie-producing recombinatn *Escherichia coli*. *Biotechnol. Prog.* 13, 768-775.

Chen, K., Dou, J., Tang, S., Yang, Y., Wang, H., Fang, H. and Zhou, C. (2012) Deletion of the aroK gene is essential for high shikimic acid accumulation through the shikimate in *E. coli*. Bioresource Technol, 119, 141-147.

Choi, W. J., Lee, E. Y., Cho, M. H., and Choi, C. Y. (1997) Enhanced production of cis, cis-muconate in a cell-recycle bioreactor. *J. Fermentation and Bioengineering*. 84, 70-76.

Curran, Kathleen a., John M. Leavitt, Ashty S. Karim, and Hal S. Alper. 2013. "Metabolic Engineering of Muconic Acid Production in *Saccharomyces Cerevisiae*." *Metabolic Engineering* 15 (1): 55-66.

de Berardinis, V., Vallenet, D., Castelli, V., Besnard, M., Pinet, A., Cruaud, C., Samair, S., Lechaplais, C., Gyapay, G., Richez, C., Durot, M., Kreimeyer, A., Le Fevre, F., Schachter, V., Pezo, V., Doring, V., Scarpelli, C., Medigue, C., Cohen, G. N., Marliere, P., Salanoubat, M., and Weissenbach, J. (2008) A complete collection of single-gene deletion mutants of *Acinetobacter baylyi* ADP1, *Mol Syst Biol* 4, 174.

Draths, K. M., Pompliano, D. L., Conley, D. L., Frost, J. W., Berry, A., Disbrow, G. L., Staversky, R. J., and Lievense, J. C. (1992) Biocatalytic Synthesis of Aromatics from D-Glucose—the Role of Transketolase, *Journal of the American Chemical Society* 114, 3956-3962.

Draths, K. M., and Frost, J. W. (1995) Environmentally Compatible Synthesis of Catechol from D-Glucose, *Journal of the American Chemical Society* 117, 2395-2400.

Elsemore, D. A., and Ornston, L. N. (1995) Unusual ancestry of dehydratases associated with quinate catabolism in *Acinetobacter calcoaceticus*, *J Bacteriol* 177, 5971-5978.

Escalante, A., Calderon, R., Valdiva, A., de Anda, R., Hernandez, G., Ramirez, O. T., Gosset, G. and Boliver, F. (2010) Metabolic engineering for the production of shikimic acid in an evolved *Escherichia coli* strain lacking the phosphoenolpyrvate: carbohydrate phosphotransferase system. Microbial Cell Factories 9, 21-33.

Escalante, Adelfo, Rocio Calderon, Araceli Valdivia, Ramon de Anda, Georgina Hernández, Octavio T Ramirez, Guillermo Gosset, and Francisco Bolivar. 2010. "Metabolic Engineering for the Production of Shikimic Acid in an Evolved *Escherichia coli* Strain Lacking the Phosphoenolpyruvate: Carbohydrate Phosphotransferase System." *Microbial Cell Factories* 9 (Ccm): 21. doi:10.1186/1475-2859-9-21.

Flores, N., Xiao, J., Berry, A., Bolivar, F. and Valle, F. (1996) Pathway engineering for the production of aromatic compounds in *Escherichia coli*. *Nature Biotechn*. 14, 620-623.

Fox, D. T., Hotta, K., Kim, C. Y., and Koppisch, A. T. (2008) The missing link in petrobactin biosynthesis: asbF encodes a (−)-3-dehydroshikimate dehydratase, *Biochemistry* 47, 12251-12253.

Ger, Y., Chen, S., Chiang, H., and Shivan, D. (1994) A Single Ser-180 Mutation Desensitizes Feedback Inhibition of the Phyenylalanine-Sensitive 3-Deoxy-D-Arabino-Hepulosonate 7-Phosphate (DAHP) Synthetase in *Escherichia coli*, *J Biochem* 116, 986-990.

Grant, D. J., and Patel, J. C. (1969) The non-oxidative decarboxylation of p-hydroxybenzoic acid, gentisic acid, protocatechuic acid and gallic acid by *Klebsiella aerogenes* (*Aerobacter aerogenes*), *Antonie Van Leeuwenhoek* 35, 325-343.

Hansen, E. H., Moller, B. L., Kock, G. R., Bunner, C. M., Kristensen, C., Jensen, O. R., Okkels, F. T., Olsen, C. E., Motawia, M. S., and Hansen, J. (2009) De novo biosynthesis of vanillin in fission yeast (*Schizosaccharomyces pombe*) and baker's yeast (*Saccharomyces cerevisiae*), *Appl Environ Microbiol* 75, 2765-2774.

Horwitz, Andrew A., Jessica M. Walter, Max G. Schubert, Stephanie H. Kung, Kristy Hawkins, Darren M. Platt, Aaron D. Hernday, et al. 2015. "Efficient Multiplexed Integration of Synergistic Alleles and Metabolic Pathways in Yeasts via CRISPR-Cas." *Cell Systems*. 1(1): 88-96.

Hu, Changyun, Peihong Jiang, Jianfeng Xu, Yongqing Wu, and Weida Huang. 2003. "Mutation Analysis of the Feedback Inhibition Site of Phenylalanine-Sensitive 3-Deoxy-D-Arabino-Heptulosonate 7-Phosphate Synthase of *Escherichia Coli*." *Journal of Basic Microbiology* 43 (5): 399-406.

Hu, C., Jiang, P., Xu, J., Wu, Y., and Huang, W. (2003) Mutation analysis of the feedback inhibition site of phenylalanine-sensitive 3-deoxy-D-arabino-heptulosonate 7-phosphate synthase of *Escherichia coli*, *J Basic Microbiol* 43, 399-406.

Iwagami, S. G., Yang, K., and Davies, J. (2000) Characterization of the protocatechuic acid catabolic gene cluster from *Streptomyces* sp. strain 2065, *Appl Environ Microbiol* 66, 1499-1508.

Jantama, K., Haupt, M. J., Svoronos, S. A., Zhang, X., Moore, J. C., Shanmugam, K. T., and Ingram, L. O. (2008a) Combining metabolic engineering and metabolic evolution to develop nonrecombinant strains of *Escherichia coli* C that produce succinate and malate, *Biotechnol Bioeng* 99, 1140-1153.

Jantama, K., Zhang, X., Moore, J. C., Shanmugam, K. T., Svoronos, S. A., and Ingram, L. O. (2008b) Eliminating side products and increasing succinate yields in engineered strains of *Escherichia coli* C, *Biotechnol Bioeng* 101, 881-893.

Jiménez, Natalia, José Antonio Curiel, Ines Reverón, Blanca de las Rivas, and Rosario Munoz. 2013. "Uncovering the *Lactobacillus Plantarum* WCFS1 Gallate Decarboxylase Involved in Tannin Degradation." *Applied and Environmental Microbiology* 79 (14): 4253-63.

Johnson, C. W., Salvachua, D., Khanna, P., Peterson, D. J. and Beckham, G. (2016) Enhancing muconic acid production from glucose and lignin-derived aromatic compound via increased protocatechuate decarboxylase activity. Metabolic Engineering Communication. 3: 111-119.

Kaneko, A., Ishii, Y., and Kirimura, K. (2011) High-yield production of cis, cis-muconic acid from catechol in aqueous solution by biocatalyst. *Chem. Lett.* 40, 381-383.

Kikuchi, Y., Tsujimoto, K., and Kurahashi, 0. (1997) Mutational analysis of the feedback sites of phenylalanine-sensitive 3-deoxy-D-arabino-heptulosonate-7-phosphate synthase of *Escherichia coli*, *Appl Environ Microbiol* 63, 761-762.

Kojima, Y., Fujisawa, H., Nakazawa, A., Nakazawa, T., Kanetsuna, F., Taniuchi, H., Nozaki, M., and Hayaishi, O. (1967) Studies on pyrocatechase. I. Purification and spectral properties, *J Biol Chem* 242, 3270-3278.

Kramer, M., Bongaerts, J., Bovenberg, R., Kremer, S., Muller, U., Orf, S., Wubbolts, M. and Raeven, L. (2003) Metabolic engineering for microbial production of shikimic acid. *Metabol. Eng.* 5, 277-283.

Lerner, C. G., and Inouye, M. (1990) Low copy number plasmids for regulated low-level expression of cloned genes in *Escherichia coli* with blue/white insert screening capability, *Nucleic Acids Res* 18, 4631.

Li, K. and Frost, J. W. (1999) Microbial synthesis of 3-dehydroshikimic acid: A comparative analysis of D-xylose, L-arabinose, and D-glucose carbon sources. *Biotechnol. Prog.* 15, 876-883.

Lin, H., Ravishankar V Vadali, R. V., George N Bennett, G. N. and San, K. Y. (2004) Increasing the Acetyl-CoA Pool in the Presence of Overexpressed Phosphoenolpyruvate Carboxylase or Pyruvate Carboxylase Enhances Succinate Production in *Escherichia coli*. *Biotechnology Progress* 20 (5): 1599-1604.

Lin, Fengming, Kyle L. Ferguson, David R. Boyer, Xiaoxia Nina Lin, and E. Neil G. Marsh. 2015. "Isofunctional Enzymes PAD1 and UbiX Catalyze Formation of a Novel Cofactor Required by Ferulic Acid Decarboxylase and 4-Hydroxy-3-Polyprenylbenzoic Acid Decarboxylase." *ACS Chemical Biology* 11(4): 1137-1144.

Lu, J. L., and Liao, J. C. (1997) Metabolic engineering and control analysis for production of aromatics: Role of transaldolase, *Biotechnol Bioeng* 53, 132-138.

Lupa, Boguslaw, Delina Lyon, Moreland D. Gibbs, Rosalind a. Reeves, and Juergen Wiegel. 2005. "Distribution of Genes Encoding the Microbial Non-Oxidative Reversible Hydroxyarylic Acid Decarboxylases/phenol Carboxylases." *Genomics* 86 (3): 342-51.

Lutke-Eversloh, T., and Stephanopoulos, G. (2007) L-tyrosine production by deregulated strains of *Escherichia coli, Appl Microbiol Biotechnol* 75, 103-110.

Mizuno, S., Yoshikawa, N., Seki, M., Mikawa, T., and Imada, Y. (1988) Microbial production of cis, cis-muconic acid from benzoic acid. *Appl Microbiol Biotechnol.* 28, 20-25.

Nakazawa, A., Kojima, Y., and Taniuchi, H. (1967) Purification and properties of pyrocatechase from *Pseudomonas fluorescens, Biochim Biophys Acta* 147, 189-199.

Neidhardt, F. C., and Curtiss, R. (1996) *Escherichia coli* and *Salmonella*: cellular and molecular biology, Vol. 22nd ed., ASM Press, Washington, D.C.

Neidle, E. L., and Ornston, L. N. (1986) Cloning and expression of *Acinetobacter calcoaceticus* catechol 1,2-dioxygenase structural gene catA in *Escherichia coli*, Bacteriol 168, 815-820.

Niu, W., Draths, K. M., and Frost, J. W. (2002) Benzene-free synthesis of adipic acid, *Biotechnol Prog* 18, 201-211.

Parker, C., Barnell, W. O., Snoep, J. L., Ingram, L. O., and Conway, T. (1995) Characterization of the *Zymomonas mobilis* glucose facilitator gene product (glf) in recombinant *Escherichia coli*: examination of transport mechanism, kinetics and the role of glucokinase in glucose transport, *Mol Microbiol* 15, 795-802.

Parsek, M. R., Shinabarger, D. L., Rithmel, R. K. and Chakrabarty, A. M. (1992) Roles of CatR and cis, cis-Muconate in activation of the catBC operson, which is involved in benzoate degradationin *Pseudomonas putida. J Bacteriol.* 174, 7798-7806.

Patnaik, R. and Liao, J. C. (1994) Engineering of *Escherichia coli* central metabolism for aromatic metabolite with near theoretical yield. *App. Env. Microbiol.* 60, 3903-3908.

Payne, Karl a. P., Mark D. White, Karl Fisher, Basile Khara, Samuel S. Bailey, David Parker, Nicholas J. W. Rattray, et al. 2015. "New Cofactor Supports A,β-Unsaturated Acid Decarboxylation via 1,3-Dipolar Cycloaddition." *Nature* 522 (7557): 497-501.

Pfleger, B. F., Kim, Y., Nusca, T. D., Maltseva, N., Lee, J. Y., Rath, C. M., Scaglione, J. B., Janes, B. K., Anderson, E. C., Bergman, N. H., Hanna, P. C., Joachimiak, A., and Sherman, D. H. (2008) Structural and functional analysis of AsbF: origin of the stealth 3,4-dihydroxybenzoic acid subunit for petrobactin biosynthesis, *Proc Natl Acad Sci USA* 105, 17133-17138.

Perez-Pantoja, D., De la Iglesia, R., Pieper, D. H., and Gonzalez, B. (2008) Metabolic reconstruction of aromatic compounds degradation from the genome of the amazing pollutant-degrading bacterium *Cupriavidus necator* JMP134, *FEMS Microbiol Rev* 32, 736-794.

Perez-Pantoja, D., Donoso, R., Agullo, L., Cordova, M., Seeger, M., Pieper, D. H., and Gonzalez, B. (2011) Genomic analysis of the potential for aromatic compounds biodegradation in Burkholderiales, *Environ Microbiol.* 14.5 (2012): 1091-1117.

Pittard, J. and Wallace, B. J. (1966) Distribution and function of genes concerned with aromatic biosynthesis in *Escherichia coli. J Bacteriol.* 91, 1494-1508.

Polen, T., Spelberg, M. and Bott, M. (2013) Toward bietchnological produciton of adipic acid and precursors from biorenewables, *J. Biotechnol.* 167(2): 75-84.

Rutledge, B. J. (1984) Molecular characterization of the qa-4 gene of *Neurospora crassa, Gene* 32, 275-287.

Schirmer, F., and Hillen, W. (1998) The *Acinetobacter calcoaceticus* NCIB8250 mop operon mRNA is differentially degraded, resulting in a higher level of the 3' CatA-encoding segment than of the 5' phenolhydroxylase-encoding portion, *Mol Gen Genet* 257, 330-337.

Shumilin, I. A., Kretsinger, R. H., and Bauerle, R. H. (1999) Crystal structure of phenylalanine-regulated 3-deoxy-D-arabino-heptulosonate-7-phosphate synthase from *Escherichia coli*, Structure 7, 865-875.

Shumilin, I. A., Zhao, C., Bauerle, R., and Kretsinger, R. H. (2002) Allosteric inhibition of 3-deoxy-D-arabino-heptulosonate-7-phosphate synthase alters the coordination of both substrates, *J Mol Biol* 320, 1147-1156.

Shumilin, I. A., Bauerle, R., Wu, J., Woodard, R. W., and Kretsinger, R. H. (2004) Crystal structure of the reaction complex of 3-deoxy-D-arabino-heptulosonate-7-phosphate synthase from *Thermotoga maritima* refines the catalytic mechanism and indicates a new mechanism of allosteric regulation, *J Mol Biol* 341, 455-466.

Shumkova, E. S., Solyanikova, I. P., Plotnikova, E. G. and Golovleva, L. A. (2009) Phenol degrdation by *Rhodococcus opacus* Strain 1G. *App. Biochem. Microbiol.* 45, 43-49.

Sietmann, R., Uebe, R., Boer, E., Bode, R., Kunze, G., and Schauer, F. (2010) Novel metabolic routes during the oxidation of hydroxylated aromatic acids by the yeast *Arxula adeninivorans, J Appl Microbiol* 108, 789-799.

Smith, M. R. and Ratledge, C. (1989) Quantitative biotransformation of catechol to cis, cis-muconate. *Biotech. Lett.* 11, 105-110.

Snoep, J. L., Arfman, N., Yomano, L. P., Fliege, R. K., Conway, T., and Ingram, L. O. (1994) Reconstruction of glucose uptake and phosphorylation in a glucose-negative mutant of *Escherichia coli* by using *Zymomonas mobilis* genes encoding the glucose facilitator protein and glucokinase, *J Bacteriol* 176, 2133-2135.

Sonoki, Tomonori, Miyuki Morooka, Kimitoshi Sakamoto, Yuichiro Otsuka, Masaya Nakamura, Jody Jellison, and Barry Goodell. 2014. Enhancement of Protocatechuate Decarboxylase Activity for the Effective Production of Muconate from Lignin-Related Aromatic Compounds. *Journal of Biotechnology* 192 (Part A): 71-77.

Sprenger, G. A. (1995) Genetics of pentose-phosphate pathway enzymes of *Escherichia coli* K-12, *Arch Microbiol* 164, 324-330.

Sprenger, G. A., Schorken, U., Sprenger, G., and Sahm, H. (1995a) Transketolase A of *Escherichia coli* K12. Purification and properties of the enzyme from recombinant strains, *Eur J Biochem* 230, 525-532.

Sprenger, G. A., Schorken, U., Sprenger, G., and Sahm, H. (1995b) Transaldolase B of *Escherichia coli* K-12: cloning of its gene, talB, and characterization of the enzyme from recombinant strains, *J Bacteriol* 177, 5930-5936.

Stroman, P., Reinert, W. R., and Giles, N. H. (1978) Purification and characterization of 3-dehydroshikimate dehydratase, an enzyme in the inducible quinic acid catabolic pathway of *Neurospora crassa, J Biol Chem* 253, 4593-4598.

Tang, J., Zhu, X., Lu, J. and Liu, P. (2012) Recruiting alternative glucose utilization pathways for improving succinate production. *App Microbiol Biotechnol* DOI 10, 1007/s00253-012-434.1.

Tateoka, T., and Yasuda, I. (1995) 3-Dehydroshikimate dehydratase in mung bean cultured cells, *Plant Cell Reports* 15, 212-217.

Vemuri, G. N., M. A. Eiteman, and E. Altman. 2002. "Effects of Growth Mode and Pyruvate Carboxylase on Succinic Acid Production by Metabolically Engineered Strains of *Escherichia coli.*" Applied and Environmental Microbiology 68 (4): 1715-27.

Weaver, L. M., and Herrmann, K. M. (1990) Cloning of an aroF allele encoding a tyrosine-insensitive 3-deoxy-D-arabino-heptulosonate 7-phosphate synthase, *J Bacteriol* 172, 6581-6584.

Weber, C., Bruckner, C., Weinreb, S., Lehr, C., Essl, C. and Bole, E. (2012) Biosynthesis of cis, cis-muconic acid and its aromatic precursors catechol and proteocatechuic acid, from renewable feedstocks by *Saccharomyces cerevisiae*, *App Environ Microbiol.* 78, 8421-8430.

Wheeler, K. A., Lamb, H. K., and Hawkins, A. R. (1996) Control of metabolic flux through the quinate pathway in *Aspergillus nidulans, Biochem J* 315 (Pt 1), 195-205.

White, Mark D., Karl A. P. Payne, Karl Fisher, Stephen A. Marshall, David Parker, Nicholas J. W. Rattray, Drupad K. Trivedi, et al. 2015. "UbiX Is a Flavin Prenyltransferase Required for Bacterial Ubiquinone Biosynthesis." *Nature* 522 (7557): 502-6.

Wu, C-M., Wu, C-C., Su, C-C., Lee, S-N., Lee, Y-A. and Wu, J-Y. (2006) Microbial synthesis of cis,cis-muconic acid form benzoate by Sphingobacterium sp. Mutants. *Biochem. Eng. J.* 29, 35-40.

Xie, N., Tang, H., Feng, J., Tao, F., Ma, C. and Xu, P. (2009) Characterization of benzoate degradation by newly isolated bacterium *Pseudomonas* sp. XP-M2. *Biochem. Eng. J.* 46, 79-82.

Xie, N., Hong Liang, Ri-Bo Huang, and Ping Xu. 2014. "Biotechnological Production of Muconic Acid: Current Status and Future Prospects." *Biotechnology Advances* 32 (3): 615-22.

Yi, J., Draths, K. M., Li, K. and Frost, J. W. (2003) Altered Glucose Transport and Shikimate Pathway Product Yields in *E. coli. Biotechnol. Prog.* 2003, 19, 1450-1459.

Yoshikawa, N., Mizuno, S., Ohta, K., and Suzuki, M. (1990) Microbial production of cis, cis-muconic acid. *J. Biotechno.* 14, 203-210.

The invention claimed is:

1. A genetically engineered *Escherichia coli* microorganism that produces muconic acid from a non-aromatic carbon source comprising:
- at least one exogenous gene encoding for 3,4-dihydroxybenzoic acid decarboxylase, a ubiX gene from *Escherichia coli* encoding for UbiX protein that increases the activity of said 3,4-dihydroxybenzoic acid decarboxylase,
- at least one catAX exogenous gene encoding for catechol 1,2-dioxygenase, and
- at least one exogenous gene encoding for 3-dehydroshikimate dehydratase selected from the group consisting of aroZ, qa4, asbF and quiC.

2. The genetically engineered microorganism of claim 1, wherein the genetically engineered microorganism produces at least 60 g/L of muconic acid in 72 hours.

3. The genetically engineered microorganism of claim 1, further comprising at least one aroB exogenous gene encoding for 3-dehydroquinate synthase.

4. The genetically engineered microorganism of claim 1, further comprising at least one aroG exogenous gene encoding for deoxyarabino-heptulosonate.

5. The genetically engineered microorganism of claim 1, further comprising at least one tktA exogenous gene encoding for transketolase.

6. The genetically engineered microorganism of claim 1, further comprising at least one aroD exogenous gene encoding for 3-dehydroquinate dehydratase.

7. The genetically engineered microorganism of claim 1, further comprising a mutation or deletion in at least one gene that encodes at least one protein that function in a phosphotransferase system for sugar import.

8. The genetically engineered microorganism of claim 7, wherein the at least one gene is a ptsH gene, a ptsI gene or a combination thereof.

9. The genetically engineered microorganism of claim 1, further comprising at least one exogenous gene encoding for a protein that functions in the facilitated diffusion of a sugar.

10. The genetically engineered microorganism of claim 9, wherein the at least one exogenous gene is a glf gene encoding for the glucose facilitator.

11. The genetically engineered microorganism of claim 9, further comprising a glk exogenous gene encoding for the glucokinase.

12. The genetically engineered microorganism of claim 1, further comprising a deletion in a gene encoding for a sugar importer that functions using proton symport.

13. The genetically engineered microorganism of claim 1, further comprising at least one pyc exogenous gene encoding for pyruvate carboxylase and a mutation of ppc gene encoding for phosphoenol pyruvate carboxylase.

* * * * *

SEQUENCE LISTING

```
<160> NUMBER OF SEQ ID NOS: 99

<210> SEQ ID NO 1
<211> LENGTH: 195
<212> TYPE: DNA
<213> ORGANISM: Bacillus subtilis
<220> FEATURE:
<221> NAME/KEY: promoter
<222> LOCATION: (1)..(195)
<223> OTHER INFORMATION: The P15 promoter from Bacillus subtilis phage
      SP01, with a stem and loop added just downstream from the
      transcription start site.

<400> SEQUENCE: 1
gctattgacg acagctatgg ttcactgtcc accaaccaaa actgtgctca gtaccgccaa      60
tatttctccc ttgaggggta caaagaggtg tccctagaag agatccacgc tgtgtaaaaa     120
ttttacaaaa aggtattgac tttccctaca gggtgtgtaa taatttaatt acaggcgggg     180
gcaaccccgc ctgtt                                                      195

<210> SEQ ID NO 2
<211> LENGTH: 164
<212> TYPE: DNA
<213> ORGANISM: Bacillus subtilis
<220> FEATURE:
<221> NAME/KEY: promoter
<222> LOCATION: (1)..(164)
<223> OTHER INFORMATION: The P26 promoter from Bacillus subtilis phage
      SP01

<400> SEQUENCE: 2
gcctacctag cttccaagaa agatatccta acagcacaag agcggaaaga tgttttgttc      60
tacatccaga acaacctctg ctaaaattcc tgaaaaattt tgcaaaaagt tgttgactttt   120 atctacaagg tgtggtataa taatcttaac aacagcagga cgct                      164

<210> SEQ ID NO 3
<211> LENGTH: 91
<212> TYPE: DNA
<213> ORGANISM: Escherichia coli
```

```
<220> FEATURE:
<221> NAME/KEY: promoter
<222> LOCATION: (1)..(91)
<223> OTHER INFORMATION: The PR promoter from Escherichia coli phage

<400> SEQUENCE: 3
acgttaaatc tatcaccgca agggataaat atctaacacc gtgcgtgttg actattttac      60
ctctggcggt gataatggtt gcatgtacaa g                                    91

<210> SEQ ID NO 4
<211> LENGTH: 359
<212> TYPE: PRT
<213> ORGANISM: Neurospora crassa
<220> FEATURE:
<221> NAME/KEY: PEPTIDE
<222> LOCATION: (1)..(359)
<223> OTHER INFORMATION: Protein sequence of 3-dehydroshikimate
      dehydratase from Neurospora crassa encoded by the qa-4 gene.

<400> SEQUENCE: 4
```

Met Pro Ser Lys Leu Ala Ile Ser Ser Met Ser Leu Gly Arg Cys Phe
1               5                   10                  15

Ala Gly His Ser Leu Asp Ser Lys Leu Asp Ala Ala Gln Arg Tyr Gly
            20                  25                  30

Tyr Leu Gly Ile Glu Leu Phe Tyr Glu Asp Leu Val Asp Val Ala Glu
        35                  40                  45

His Leu Ser Asn Glu Arg Pro Ser Pro Glu Gly Pro Phe Val Glu Ala
    50                  55                  60

Gln Ile Ala Ala Ala Arg His Ile Leu Gln Met Cys Gln Ala Arg Gly
65                  70                  75                  80

Leu Glu Val Val Cys Leu Gln Pro Phe Met His Tyr Asp Gly Leu Asn
                85                  90                  95

Asp Arg Ala Glu His Glu Arg Arg Leu Glu Lys Leu Ala Leu Trp Ile
            100                 105                 110

Glu Leu Ala His Glu Leu His Thr Asp Ile Ile Gln Ile Pro Ala Asn
        115                 120                 125

Phe Leu Pro Ala Asn Gln Val Ser Asp Asn Leu Asp Leu Ile Val Ser
    130                 135                 140

Asp Leu Cys Lys Val Ala Asp Ile Gly Ala Gln Ala Leu Pro Pro Ile
145                 150                 155                 160

Arg Phe Ala Tyr Glu Ser Leu Cys Trp Ser Thr Arg Val Asp Leu Trp
                165                 170                 175

Glu Arg Cys Trp Asp Ile Val Gln Arg Val Asp Arg Pro Asn Phe Gly
            180                 185                 190

Ile Cys Leu Asp Thr Phe Asn Ile Leu Gly Arg Ile Tyr Ala Asp Pro
        195                 200                 205

Thr Ser Pro Ser Gly Arg Thr Pro Asn Ala Lys Glu Ala Val Arg Lys
    210                 215                 220

Ser Ile Ala Asn Leu Val Ser Arg Val Asp Val Ser Lys Val Phe Tyr
225                 230                 235                 240

Val Gln Val Val Asp Ala Glu Arg Leu Ser Lys Pro Leu Leu Pro Gly
                245                 250                 255

His Pro Tyr Tyr Asn Pro Glu Gln Pro Ala Arg Met Ser Trp Ser Arg
            260                 265                 270

Asn Cys Arg Leu Phe Tyr Gly Glu Thr Glu Tyr Gly Ala Tyr Leu Pro
        275                 280                 285

Val Lys Glu Val Ala Arg Ala Leu Phe His Gly Ile Gly Phe Glu Gly

```
                290                 295                 300
Trp Val Ser Leu Glu Leu Phe Asn Arg Arg Met Ser Glu Glu Gly Pro
305                 310                 315                 320

Glu Val Pro Glu Glu Leu Ala Met Arg Gly Ala Ile Ser Trp Ala Lys
                325                 330                 335

Leu Val Gln Asp Leu Arg Ile Pro Val Glu Gly Pro Leu Val Thr Met
                340                 345                 350

Pro Arg Val Ser Ala Ser Leu
        355

<210> SEQ ID NO 5
<211> LENGTH: 2160
<212> TYPE: DNA
<213> ORGANISM: Neurospora crassa
<220> FEATURE:
<221> NAME/KEY: gene
<222> LOCATION: (1)..(2160)
<223> OTHER INFORMATION: Genomic DNA sequence of the qa-4 gene from
      Neurospora crassa plus surrounding sequences.

<400> SEQUENCE: 5
gaattcggga aatggaatct tacctgggaa ccgaaatcac agtccgggta ggttatagag      60
catatagtga actgtcaaag ttctagacct ggaccagcca cttggagtcg ttgttttagt     120
tatacctaca ttcactcact gttgactttc aatcatactt acttagacgg agcaacgcgc     180
cagaatccaa attgttgcat agttgcggta tcaccaagtg gcttcccata atagtttgcc     240
attcgatgag acagctaact ggaagaccgg tactcgcagg ttgcacgatt acacggaagg     300
attcggtatt ccgtgtttca tctgtcaaag tcccttttcca tatgaatccg aggtactatg     360
actggatctc gatacaagct ggccagcgag gtgcctgcct tgacaggctg tcaactgcgg     420
gacggccggc taagtgttta acacgcaagg gtggaagatg tctcgtcccg tcatccaaga     480
ccgtcaacat tcgaggccat ctgatcgttg aagagatgct aaatcttgtg aaacgctcat     540
aggtcgctta ccttcggccc acccgttaat gctttattcc gctgagcaaa cttcggcttc     600
catcccgcgg ttcaccgttt acatcactta tcgttgcggt tattggccga ttcttcgcaa     660
accgaaacga tgacatcccg aatatctgca atacaccgcc acggccggcg tctttatcac     720
acctcctatg ggagacgaaa gtgccttgat acccctagtc atttgaagat tcaggatggg     780
agacggctgg ccgcttgcgg agttacgttc gagtcttggt cgcaggaacg cttgccgtat     840
tgaatgagac cccgagaagg tcaaatcaaa tcttggaaga ccccaactgc ttcctcattg     900
ccttcactcc ccatatcaat ggggcacatc ctgtgactac cttggtgctt tatttcctca     960
ccatttggcg atacaagctc aaggacaccg aggtgatata cagttcttca aggacactat    1020
ctcacctcaa tatcaagaac cagtctcatc atctcttatt tctccaggat ccccccacca    1080
acaacatcgg cttttttttt tcccctattc tcaagaccca tcaagacgct cacttcgctg    1140
agcctttcgc catgccgtca aagctagcca ttagttccat gtcccctaggg cgctgctttg    1200 ccggccactc tctggacagc aagcttgatg ccgctcaacg atacggctat cttggtatcg    1260
agctttttta tgaggatctg tcgacgttg cagagcattt gtcgaacgag cgtccctctc    1320
ccgaaggccc ttttgtcgaa gctcagatag ccgccgctcg tcatattctc cagatgtgtc    1380
aagccagggg gcttgaggtc gtctgcctcc agcctttcat gcactacgac ggccttaacg    1440
acagggcaga acatgagcgt cgtctggaga agctagcact atggattgag ctcgctcatg    1500
agcttcacac cgacatcatt cagatcccag ccaacttcct ccctgccaac caagtcagtg    1560
```

-continued

```
acaacctcga cctgattgtc tcagatcttt gcaaggtggc cgatattgga gctcaagctt    1620
tgccccctat ccgctttgcc tacgagagtc tttgctggag cacccgtgtc gacctctggg    1680
agcgctgctg ggacatcgta caacgcgttg accgccccaa ctttggcatt tgccttgaca    1740
ccttcaacat cctcggccgc atctatgccg accctacatc tcctagcggt aggacaccca    1800
acgcaaaaga ggcagtcagg aagtccatcg ccaacttggt ctcgcgcgtg gatgtctcca    1860
aagtcttcta cgtccaggtg gttgacgccg agaggctgag caagccacta ctgcccggtc    1920
acccgtatta caatccagag cagccggcga ggatgagctg gtcgcgcaat gtagactgt    1980 tctacggcga aacagaatat ggtgcgtatc ttcccgtgaa ggaggttgct cgagcccttt    2040
tccacggcat tggtttcgag ggctgggtca gtttggagct tttcaaccgc agaatgtctg    2100
aggagggacc tgaagtgccg gaggaacttg ccatgagagg cgctatctcg tgggccaagt    2160
```

<210> SEQ ID NO 6
<211> LENGTH: 348
<212> TYPE: PRT
<213> ORGANISM: Aspergillus niger
<220> FEATURE:
<221> NAME/KEY: PEPTIDE
<222> LOCATION: (1)..(340)
<223> OTHER INFORMATION: Protein sequence of 3dehydroshikimate
      dehydratase from Aspergillus nidulans. encoded by the qutC gene

<400> SEQUENCE: 6

```
Met Pro Ala Asn Leu Lys Ile Gly Ile Pro Thr Val Ser Leu Ser Lys
1               5                   10                  15

Pro Gly Leu His Ser Leu Asp His Lys Leu Arg Ser Ala Ala His Gly
            20                  25                  30

Phe Ala Gly Ile Glu Leu Phe Ile Asp Asp Leu Ser His Phe Ala Ser
        35                  40                  45

Ser Ser Phe Asn Gly Ser Leu Thr Gln Ala Ala Lys Tyr Ile Ser Ser
    50                  55                  60

Leu Ala Lys Gln Leu Asn Leu Thr Phe Ile Cys Leu Gln Pro Phe Gly
65                  70                  75                  80

Phe Tyr Glu Gly Leu Val Asp Thr Asn Gln Ser Thr Tyr Leu Leu Thr
                85                  90                  95

Glu Lys Leu Pro Leu Trp Phe Ala Ile Ala Arg Ile Ile Gly Thr Asp
            100                 105                 110

Leu Ile Gln Ile Pro Ala Asn Phe Leu Gln Asn Asp Pro Val Thr Gly
        115                 120                 125

Ala Ala Arg Thr Ser Gly Asp Ile Arg Leu Ile Val Ser Asp Leu Gln
    130                 135                 140

Thr Ile Ala Asp Ile Gly Val Lys Gln Gly Phe Arg Phe Val Tyr Glu
145                 150                 155                 160

Ala Leu Cys Trp Ser Thr His Val Asp Thr Trp Glu Ala Ala Trp Asn
                165                 170                 175

Val Val Lys Leu Val Asp Arg Glu Asn Phe Gly Ile Cys Leu Asp Ser
            180                 185                 190

Phe Asn Thr Arg Thr Pro Leu Pro Ser Leu Gly Arg Arg Met Leu
        195                 200                 205

Ser Lys Pro Trp Pro Ser Pro Trp Arg Arg Ser Val Leu Ser Ser Pro
    210                 215                 220

Val Glu Asn Trp Thr Ser Gly Lys Ser Ser Thr Ser Ser Leu Ser Met
225                 230                 235                 240

Ala Ser Gly Cys Arg Arg Arg Trp Thr Arg Ser Thr Pro Phe Met Trp
```

```
                    245                 250                 255
Arg Ala Asn Pro Arg Met Ser Trp Ser Arg Asn Ala Arg Leu Phe
        260                 265                 270

Pro Cys Glu Glu Arg Gly Gly Tyr Leu Pro Val Leu Glu Ile Ala
        275                 280                 285

Arg Ala Phe Phe Glu Ile Gly Phe Glu Gly Trp Val Ser Leu Glu Leu
        290                 295                 300

Phe Ser Arg Thr Cys Asn Asp Pro Asp Val Asn Thr Val Gly Glu His
305                 310                 315                 320

Ala Arg Arg Gly Met Asp Arg Arg Arg Val Val Ala Ala Leu Gly
                325                 330                 335

Leu Asp Val Glu Val Pro Ala Arg Asn Cys Glu Cys
        340                 345

<210> SEQ ID NO 7
<211> LENGTH: 3298
<212> TYPE: DNA
<213> ORGANISM: Aspergillus niger
<220> FEATURE:
<221> NAME/KEY: gene
<222> LOCATION: (1)..(3298)
<223> OTHER INFORMATION: Genomic DNA sequence of the qutC gene from
      Aspergillus nidulans plus surrounding sequences

<400> SEQUENCE: 7
aagcttggtt tcaagtgatg atatatagtt atgaggatat aatatgaacc gaaagacgat     60
gtttcttgtg aatatttacg tgatagttgt ctgtctaata tggtacagca gtagaacaac    120
tacatacggt cactacttac agccctagtc attccctccc tcgattgcct accatttata    180
cactttgaac atccacaggc ttgcctccct ccatactctc cctaacagct tgaacaactc    240
tgagcgccct caccccatct tcaacgccac agccaactcc tcgctcgcca tcctcacccct   300 ttccactaac aacatcaaca aaatatcccc actgcgcatc aaacggcctc acatcagcat    360
ccttcactga aatctgctgc atcgccaact ccgtattcca gcctttctct ttcccctgtc    420
cacaagaaac atggtcatag ctccagcgcg tcatatcagg cacactgaga ctcgctctgg    480
ttccaagaat tcgataacag tcgcttgcac tcttggaagg agcgggcgga atcgtaggat    540
tctcgcccgt tcctgtttca aagttcaacg gcgaaggcgt cgcgtcgcag atgagaaatg    600
tgcctactat cccagacgca aagcgcagcg tcacagcaca gccttcctcg gcggtatgtt    660
ccgggttctg gcgcatgcgc tgcaggagtg taccctccgc gtagacccta ctgacgggcc    720
caaacagaaa ctgcagcacg tcgatatcgt ggataagatt aatccccagc acgccgccct    780
tcttcttatc tgcgcgccaa gaaccgagcg gcggcgcgaa gtaagaggcc ggcttcagaa    840
gtgtccagag gccgttcact gcaacgacgt gccgagtgaa gtctgtctct aacaaagact    900
ttgtggtttg gatgtacgga ttgaagcggc ggtggtggcc gatctggatg ttgatcttcg    960
catccttgcc tctcttctca tctttacatt tctgttcctt gacggtagcg aggaggtgct   1020
cggccgactc cagatcgtca ctgatcggtt tctcaaggag gatattgcgg attccgttct   1080
ccagcagctg gagcgtgacg tccacgtgcg tgtgattggg cgtgctcacg atcgccgcgt   1140
ctggtttccc ggttgtctta ccgacaacgt ctaacataga cgtaatagaa tcatagcaag   1200
gaacgccaaa tgattctgcg accgggattg cagagggtga agggtcaaca aaagcgatca   1260
gctgggttcg tgggtgtcgt tgcacggatt gtgcgtgacg gggcccaata agtccggcac   1320
cgacgatgac aatgaggata ttcttgtcct tttccttgct gcagggcacc attgtgcatg   1380
```

```
tcggtggctg gaaataaaca gaacagggat atggtcaagt cggagaatcg gtgcaggata    1440
gaccggctac ttgatgtagg acgacagtcg cgatctaccg agagcgtgag attcactgtg    1500
ggactgattt atgtaatttg aggcgcagca gacttaggga cttgaaatgt ggctgtctgt    1560
ggatgcattt gcggggtatg gagtacagag tgcatacagc tgtgtatatg gagttcctta    1620
cggagagggt gacctggtat ggggagaacg ggcaaaatgc tcacccggca acctctcaaa    1680
gcgtttaccc ggtatactcc tctgatatca atatttccaa tcagcaccta tatcatcacg    1740
acgctctcct gaggattccg tagctaaccg ccctggatcc tacattaata aataagccat    1800 ttgcttttc tgctgcgagt gtgattctca atacgattac gtatcacatg cagattgcct    1860
ttacttcagc tgcatttgat cagccacagc tctaagagca acatacccct acctacctac    1920
ctacttcgcc tagggtacat aatcaccgcc atctcctcct cgatcagtct tcaactcaat    1980
cagctcattc attctattct taatataata tatacccttta gatctccagc agagacccga    2040
agagtcggca attcaaaatg cccgcaaacc tcaaaatcgg tatcccaacc gtgtccctgt    2100
caaaaccggg cctgcactct cttgaccata agctccgctc ggccgctcat ggcttcgcgg    2160
ggatcgagct gtttattgat gacctctccc atttcgcctc atcgtcattc aatggctccc    2220
tcactcaagc ggcaaagtat atctcctcgc tcgccaagca acttaacctc acatttatct    2280
gcctgcaacc attcggtttc tacgagggtc tggtggacac aaatcagtcg acgtacctgc    2340
tcactgagaa actcccgctc tggtttgcga tcgcccgcat tataggcaca gatctcatcc    2400
aaatccccgc aaatttcctc cagaatgacc ctgtcaccgg ggctgcacga acaagcggcg    2460
acataaggct tatcgtctca gatctgcaga cgatcgcaga tatcggtgta aagcagggct    2520
tccgctttgt gtacgaggcg ctctgctggt cgacgcatgt cgatacatgg gaagcagcgt    2580
ggaatgtcgt caagctggtt gatagagaga atttcgggat ctgcctggat agcttcaaca    2640
cgcggacccc gcttccgtca ctgggaagac gccggatgct gagcaagccg tggccaagtc    2700
catggagacg ctccgttctc tcgtctccag tggagaactg gacatcagga aaatcttcta    2760
catccagctt gtcgatggcg agcggttgtc ggcgccgctg gacgagaagc accccttttca    2820 tgtggagggc caaccccccga agaatgagct ggagtcgcaa tgcgcggtta ttcccctgtg    2880
aagaggagag gggtgggtat cttcctgtgt tggagatcgc gagggcgttc tttgaaatcg    2940
ggttcgaggg gtgggtgagt ctagagctgt tttcaaggac gtgtaatgat cccgatgtga    3000
acacggtggg ggagcatgcg agacgtggga tggatagaag gaggagggtt gttgcggcgc    3060
taggactcga tgttgaggtg ccagcacgta actgtgaatg ttagcatgaa cggcaaggag    3120
agggtggagg tgcaggtgca ggaggagctg gctgttcagc atcggctgta ggtagtggta    3180
tcttgaaagg acgatagggt ttgatctaga gatttttatt ttgtctaatt actggtaatg    3240
atggcctcat gcacgctgtt gaacacgctg tacaacatca ctgttgaaga tgatacct      3298
```

<210> SEQ ID NO 8
<211> LENGTH: 502
<212> TYPE: PRT
<213> ORGANISM: Klebsiella pneumoniae
<220> FEATURE:
<221> NAME/KEY: PEPTIDE
<222> LOCATION: (1)..(502)
<223> OTHER INFORMATION: Protein sequence of protocatechuate
      decarboxylase (AroY) from Klebsiella pnemoniae ATCC25597

<400> SEQUENCE: 8

```
Met Thr Ala Pro Ile Gln Asp Leu Arg Asp Ala Ile Ala Leu Leu Gln
1               5                   10                  15
```

-continued

```
Gln His Asp Asn Gln Tyr Leu Glu Thr Asp His Pro Val Asp Pro Asn
             20                  25                  30

Ala Glu Leu Ala Gly Val Tyr Arg His Ile Gly Ala Gly Gly Thr Val
         35                  40                  45

Lys Arg Pro Thr Arg Ile Gly Pro Ala Met Met Phe Asn Asn Ile Lys
 50                  55                  60

Gly Tyr Pro His Ser Arg Ile Leu Val Gly Met His Ala Ser Arg Gln
 65                  70                  75                  80

Arg Ala Ala Leu Leu Leu Gly Cys Glu Ala Ser Gln Leu Ala Leu Glu
             85                  90                  95

Val Gly Lys Ala Val Lys Pro Val Ala Pro Val Val Val Pro Ala
        100                 105                 110

Ser Ser Ala Pro Cys Gln Glu Gln Ile Phe Leu Ala Asp Asp Pro Asp
        115                 120                 125

Phe Asp Leu Arg Thr Leu Leu Pro Ala His Thr Asn Thr Pro Ile Asp
130                 135                 140

Ala Gly Pro Phe Phe Cys Leu Gly Leu Ala Leu Ala Ser Asp Pro Val
145                 150                 155                 160

Asp Ala Ser Leu Thr Asp Val Thr Ile His Arg Leu Cys Val Gln Gly
                165                 170                 175

Arg Asp Glu Leu Ser Met Phe Leu Ala Ala Gly Arg His Ile Glu Val
            180                 185                 190

Phe Arg Gln Lys Ala Glu Ala Ala Gly Lys Pro Leu Pro Ile Thr Ile
        195                 200                 205

Asn Met Gly Leu Asp Pro Ala Ile Tyr Ile Gly Ala Cys Phe Glu Ala
    210                 215                 220

Pro Thr Thr Pro Phe Gly Tyr Asn Glu Leu Gly Val Ala Gly Ala Leu
225                 230                 235                 240

Arg Gln Arg Pro Val Glu Leu Val Gln Gly Val Ser Val Pro Glu Lys
                245                 250                 255

Ala Ile Ala Arg Ala Glu Ile Val Ile Glu Gly Glu Leu Leu Pro Gly
            260                 265                 270

Val Arg Val Arg Glu Asp Gln His Thr Asn Ser Gly His Ala Met Pro
        275                 280                 285

Glu Phe Pro Gly Tyr Cys Gly Gly Ala Asn Pro Ser Leu Pro Val Ile
    290                 295                 300

Lys Val Lys Ala Val Thr Met Arg Asn Asn Ala Ile Leu Gln Thr Leu
305                 310                 315                 320

Val Gly Pro Gly Glu Glu His Thr Thr Leu Ala Gly Leu Pro Thr Glu
                325                 330                 335

Ala Ser Ile Trp Asn Ala Val Glu Ala Ala Ile Pro Gly Phe Leu Gln
            340                 345                 350

Asn Val Tyr Ala His Thr Ala Gly Gly Gly Lys Phe Leu Gly Ile Leu
        355                 360                 365

Gln Val Lys Lys Arg Gln Pro Ala Asp Glu Gly Arg Gln Gly Gln Ala
    370                 375                 380

Ala Leu Leu Ala Leu Ala Thr Tyr Ser Glu Leu Lys Asn Ile Ile Leu
385                 390                 395                 400

Val Asp Glu Asp Val Asp Ile Phe Asp Ser Asp Ile Leu Trp Ala
                405                 410                 415

Met Thr Thr Arg Met Gln Gly Asp Val Ser Ile Thr Thr Ile Pro Gly
            420                 425                 430
```

```
Ile Arg Gly His Gln Leu Asp Pro Ser Gln Thr Pro Glu Tyr Ser Pro
            435                 440                 445

Ser Ile Arg Gly Asn Gly Ile Ser Cys Lys Thr Ile Phe Asp Cys Thr
        450                 455                 460

Val Pro Trp Ala Leu Lys Ser His Phe Glu Arg Ala Pro Phe Ala Asp
465                 470                 475                 480

Val Asp Pro Arg Pro Phe Ala Pro Glu Tyr Phe Ala Arg Leu Glu Lys
                485                 490                 495

Asn Gln Gly Ser Ala Lys
            500

<210> SEQ ID NO 9
<211> LENGTH: 5502
<212> TYPE: DNA
<213> ORGANISM: Klebsiella pneumoniae
<220> FEATURE:
<221> NAME/KEY: gene
<222> LOCATION: (1)..(5502)
<223> OTHER INFORMATION: DNA sequence of the aroY gene of Klebsiella
      pneumoniae 342 plus 2 kilobases of surrounding DNA sequences

<400> SEQUENCE: 9
gcgacgccga ctgggcgatc cgtgaactgc tggcgcgtat gacccagcgt ctgcagggct      60
gtgaaaccat agaggatgtg attaaggtgg cggagctgtt cgcgccgaac atcgccccga     120
cgatccccgg taaactgtat attctggata ccgatccatg gcagatgcgc tgcgtggcgc     180
agtggctgtc gcccgccggg gagacgacgt cctttgctcc cgacgactgc tgggcgatac     240
ggcggggact cagccatccg ccggtgcagg gtgagcccga tatcacctgc tatcatctgc     300
cggaggcgca cgccggccag tcgctctgcg taccgctcat cgcccagggc gaagcgatcg     360
gtctgctgag ctttcagaac gtcaccgcca gtgacgcccc ttcccgggct tacctggagc     420
tgatggccga agcgctgggg ctggcgctcg ccaatcagcg tttacgcagc gccctgctgg     480
aaaaagcgtt gttcgattcg ctgaccggcc tgcgtaaccg ccatcatctt gatgaagcgc     540
tgcactcgca gatggcgctg cggtccata cccacacccc gctgagctgc ctgatgatcg     600
acatcgatca cttcaaagcc atcaatgacc gctacgccca tgaagccggg gatctggtga     660
ttaagagcgt cgcgaccatt gtgcagcgcg cggtgcgcga tatcggcatg gctttccgct     720
acggcggcga ggagtttta gtgctgctcc ccgggattga cgaagccggg gcgcaccagt     780
gcgccagcga gatctacacc caggtgcaca atatgacgct gcgcgatggc ctgacggaga     840
taggccaggt ggatgtgtcg attggcatcg ccagctaccc gcagcacacc caaagcgaca     900
gcctgctgcg cgcagcggac gccgcgctgt accgggcgaa agagctgggc cgttcaagga     960
ttgtcagctt tggccgcctg aagacccgct aagcgggatt attgctcagc ggcattaagc    1020
agcgagataa ctttccgcac caccgccgaa cggaaatggc ggtggtaaac catgctcagc    1080
tcactctccg ccagccgatc ctgaagatcg atatacacca cgttatcaag gcgtaaggcc    1140
ctcgccgaga ccggcaccag cgccaccccc accccggcgg agaccaggct aatcatcgag    1200
gtgacatcgt taattcgctg caccacctgc ggcgtaaaac ccgcgacgcg acaggcgtca    1260
ataaatacct gctccagtcc ggtgccctgc ggatcgtcaa gcgagatcca gttgtcagtg    1320
cgcaacgagg ccagattgag cgcccccacg cctgccagcg gatgctgttg ataaagcgcc    1380
aggcaaagtt tttcccgcac aaatggcctg accaccagcg cgtccggcgg tgacgccagc    1440
ggcgcgcgga tgatgcgat atccagacgc agatccagca gcgcttcgta gagcatttgc    1500
acatccccct gcaccagcga cagctcaatc cccggccagt cagcgcgcag ctcgcgcagg    1560
```

```
agccccggca gtttgctgtc atacatcgca ctggagacat agcccagatg caatcgcccc   1620
tgctcgcctc gtgcggtgcg ctgggcgtcc aggaccgcct gatcggccat ctccagcgcc   1680
agccgcgtct tctgcaagaa ggcctcgccc gcggcggtga gggtcaggcg ccggttagcg   1740
cgggagaaga gcaccacgcc caggcgctgc tcgagttgtt taatctgctg ctgagggcg    1800 ggctgggcga tatgtaaccg ctctgccgcc cgatgcatat gtagttcttc agcaacgacc   1860
acaaaatggc gtaacgctcg caaggacatg gccggactcc gcggagtaaa ttgataataa   1920
aaatgttatc aataaagcat gaatgatgca attgataacc attagcctgc gagcatactg   1980
tgcgcatcga cacgctaagg agaacatcat gaccgcaccg attcaggatc tgcgcgacgc   2040
tatcgcgctg ctgcaacagc atgacaatca gtacctcgaa accgatcatc cggttgaccc   2100
taacgctgag ctggccggcg tctatcgcca catcggcgcg gcggcaccg tgaagcgccc   2160 cacgcgcatc ggcccggcga tgatgtttaa caatattaag gctatccgc actcgcgcat    2220 tctggtgggc atgcacgcca gccgccagcg ggccgcgctg ctgctgggct gcgaagcctc    2280
acagctggcg ctggaggtag gcaaagcggt gaaaaaccg gtcgcgccgg tggtcgttcc    2340
ggccagcagc gcccccctgtc aggaacaggt ctttctggcc gacgatccgg attttgattt    2400
gcgcaccctg ctcccggcgc ccaccaacac cccgatcgac gccggtccct tcttctgcct    2460
gggcctggcg ctggccagcg atcccgacga cgcctcgctc accgacgtca ccatccaccg    2520
cttgtgcgtc cagggccggg atgagctgtc gatgtttctc gccgctggcc gccatatcga    2580
agtgtttcgt cagaaagccg aggccgctgg caaaccgctg ccgataacca tcaatatggg    2640
actcgatccg gctatctata tcggcgcctg ctttgaagcg ccgaccacac gtttggctat    2700
aacgaactgg gcgtcgccgg tgcgctgcgt cagcgtccgg tagagctggt acagggcgtc    2760
agcgtcccgg agaaagccat cgctcgcgcc gagatcgtta tcgaagggga actgctgccg    2820
ggggtacgcg tcagagaaga tcagcacaca cagcggcca tgcgatgccg gaatttcctg    2880
gttactgcgg cggcgccaat ccgtcgctgc cggtcattaa agtcaaagcg gtgaccatgc    2940
gaaacaatgc gattctgcag acgctggtag ggccgggcga agagcatacc accctcgccg    3000
gattgccaac ggaagccagt atctggaatg ctgtcgaggc tgctatcccg ggcttttttac    3060 aaaatgtcta cgcccacacc gcgggcggcg gtaaattcct cgggatcctg caggtgaaaa    3120
aacgccagcc cgccgacgaa gggcgtcagg gcaggccgc gttgctggcg ctggcgacct    3180
attccgagct gaaaaatatc attctggtcg atgaagatgt cgatatcttt gacagcgacg    3240
atatcctgtg ggccatgacc acccgcatgc aggggatgt cagcatcacg acgatcccag    3300
gcattcgtgg tcaccagctg gatccttccc agaccccggc ctacagcccg tcgatccgcg    3360
gagagggtat cagttgcaag acgattttcg attgcacggt gccgtgggcg ctaaaatcac    3420
acttcgagcg cgcaccgttt gccgatgtcg atccgcgtcc gtttgcgccg gagtattttg    3480
cccggctgga aaaaaccac ggtcagtaaa atcaggtgat agccgccgga gcacggcggc    3540
atcttccggg ccagcatcac ctgcagcggg tggctgacgc agggttagtt gatcgcggcg    3600
gagaggtctt ttttcacctg ctcacgctgc tcggggtca acacctggct cacgtcgaag    3660
tagtatttca cacgataata ccgcacctgc tggtccagct ggccaaaggc ggccagctgc    3720
tgtttgacct tagcgtcatc ccatttcccg gagtgaataa cgtctgccag gcaccatcc    3780 tgatagccgt tgatttaatc tggcttacat tgttttcgaa tccctgacgc agcgcctgga    3840
ttttggcgac ctgctcttca ctcagcttca ggtgctggac gaccggatcc tgcgagacag    3900
```

| | |
|---|---:|
| acggtatatc ggcggaggtc gacgcctggc tggctgccgt aaagcaggtg gtcagcgcaa | 3960 |
| tggcgagcag ggtgttacgc aagcgagtat tcacagtgaa tgatccttca aaaaagaaaa | 4020 |
| tgagaggcga ttatcactgc gctaataaag actatctgta acaaagggtt aatttaaaac | 4080 |
| tggataaaaa aaggatggta agaaacagaa atcagatccc gggtcagcag cacagaaaga | 4140 |
| tatattcatc cttccagtaa cggccctgtc caatgatatc cccggcggcg ctgattaact | 4200 |
| gttttttgctt ttggtttcaa tcccctcaac gatcacatgg ctggtcaggg tatgaataga | 4260 |
| ttgcaacagc ccgggaaaag cggggtcgtt ttctttatcc cagaagtaat ctttatccac | 4320 |
| tttgacgcaa tcgaagcgga agcgctccag cagcgggaag gacgtcgtcc gcggccaaaa | 4380 |
| tcatccagcc agaccgggca aagcgccgcc agcgtgctca gcgccgtcag ctcacgtccg | 4440 |
| gcgataaact cgtgaaagtt ctcatttatt tccagagcaa tgtgtttaca ggagcgcagg | 4500 |
| aaatcacaga gatagcgatc cgtcagaata aagtggctta ataaatcatc aatattcagc | 4560 |
| gatatcggtt tattatcgac ccgggcgaaa tcaaatacag aaagtaactc gatttgccga | 4620 |
| ataaatagag caagcttatc gcgttcggta agcgtggaga agaaaacgt cgacgcagag | 4680 |
| gtggtatttt gtgcgggtgc tataatatct ttagtaagca actcccacga gtggtagctg | 4740 |
| ccgtcatcgc taatagcggg ctccagaacg aagcgataag aggtattttt cacgttttct | 4800 |
| tcaaccattt aaaaaatacc aaaaataaga aagggttaag catgtcatat attttccgcc | 4860 |
| aacaaaaata gtttaaagtg atcgataata atcattcgat agttaaaaac tatcaagata | 4920 |
| taatttattg atcggtaaat tgaattaata taaattagcc actgccgtaa ctccctctga | 4980 |
| aaagtcaatt aaaatattgt ttcaaaccag ccagttacca gagtattctg cgtaaagcct | 5040 |
| ggtcgtctca cgctttgtgc tgccaggtaa aaaagagag gggtaataaa atgaaaaat | 5100 |
| acaagccgcc agttttagtc atatcattat gccgaatatg aataacgctg cgctgaggcg | 5160 |
| ccgcttcgcc tggcatgcca tgagtcctca acaaaaaagt gtgactcagt cgacaaaacg | 5220 |
| tcatattttc ccgctatcct gcagcgaaga agagtgaagt ggatgacagg cagtgaaaaa | 5280 |
| aataaacgtg attccgctgg ggctgatgct attcatgctc atcgccagcg catggctggg | 5340 |
| ccctgcgccg cggcacaccg gcagcatgca gtgcgtttgg tttgacgggg caatggtgag | 5400 |
| ctgcctgccg aagcaacgac tgggcgaagg ctcgccgcat catttactgg tcagacgata | 5460 |
| aaccggtact cgccgggtgg tgttgaacag attatcgctg gc | 5502 |

```
<210> SEQ ID NO 10
<211> LENGTH: 4629
<212> TYPE: DNA
<213> ORGANISM: Acinetobacter baylyi
<220> FEATURE:
<221> NAME/KEY: gene
<222> LOCATION: (1)..(4629)
<223> OTHER INFORMATION: DNA sequence of the catA gene from
      Acinetobacter baylyi ADP1, including 410 bases of upstream
      sequence and two open reading frames downstream

<400> SEQUENCE: 10
```

| | |
|---|---:|
| atctgctcga ccatagtaat gatcacatta tgagctaaat ttacttttta aaatttaaat | 60 |
| atattatata tatttgaatt ttattgtttt atttttaattt ttagcttaga agttttttatt | 120 |
| aagatttatt tttaaattag atgtcgaaaa aattagtata ccaaaaaagc atgaaaacat | 180 |
| actctcttag gaattggagt cgccatgagt ttcagataca gttgatcagt atggaaggta | 240 |
| tagaaacgac tatcgaaata aataagtttg tggtgtgtga agcaaggtaa agctcaaggc | 300 |
| tgaggcaaac caagcaaagg ttaattgaac cgatatgcac aacacattca acgatagcgt | 360 |

```
cgacagataa gtttatcaaa tgatgttttg gcgatttcaa ggagaaagcc atggaagtta    420
aaatattcaa tactcaggat gtgcaagatt ttttacgtgt tgcaagcgga cttgagcaag    480
aaggtggcaa tccgcgtgta aagcagatca tccatcgtgt gctttcagat ttatataaag    540
ccattgaaga tttgaatatc acttcagatg aatactgggc aggtgtggca tatttaaatc    600
agctaggtgc caatcaagaa gctggtttac tctcgccagg cttgggtttt gaccattacc    660
tcgatatgcg tatggatgcc gaagatgccg cactaggtat tgaaaatgcg acaccacgta    720
ccattgaagg cccgctatac gtggcaggtg cgcctgaatc ggtaggttat gcgcgcatgg    780
atgacggaag tgatccaaat ggtcataccc tgattctaca tggcacgatc tttgatgcag    840
atggaaaacc tttacccaat gccaaagttg aaatctggca tgccaatacc aaaggctttt    900
attcacactt cgacccaaca ggcgagcagc aggcgttcaa tatgcgccgt agtattatta    960
ccgatgaaaa cggtcagtat cgcgttcgta ccattttgcc tgcgggttat ggttgcccac   1020
cagaaggtcc aacgcaacag ttgctgaatc agttgggccg tcatggtaac cgccctgcgc   1080
acattcacta ttttgtttct gccgatggac accgcaaact aactacgcaa attaatgtgg   1140
ctggcgatcc gtacacctat gacgactttg cttatgcaac ccgtgaaggc ttggtggttg   1200
atgcagtgga acacaccgat cctgaagcca ttaaggccaa tgatgttgaa ggcccattcg   1260
ctgaaatggt tttcgatcta aaattgacgc gtttggttga tggtgtagat aaccaagttg   1320
ttgatcgtcc acgtctagcg gtgtaataca ccaaaatggt tcaaaattat caggcgagtg   1380
atcatgatca ctggcctgtt tttatttcag ggaagggtgg agacaattac gtggacaatc   1440
aaatcattca ggaaaccgta gataaaattt taagcgtatt gccgaatcag ctgggcaat    1500 tggcacgctt ggttcgtctg atgcagtttg cttgtgaccc caccattacc gtcattggta   1560
aatataatca tggtaaaagc cgactactca atgagctgat cgggacagat attttttctg   1620
ttgccgataa cgagagacg attcaactgg ccgaacataa acaagatcag gtgcgttggt    1680
tggatgcacc cggactcgat gcagatgttg cggcagtgga tgatcgtcat gcttttgaag   1740
cagtctggac acaggcagat attgcccttt ttgtgcattc agtccgagaa ggcgaactcg   1800
atgcaactga gcatcatctt ttacaacaac ttattgaaga tgcagaccat agccggcgcc   1860
aaaccatact ggtcttgacc cagatagatc agataccgga tcagacaatt ttaacccaga   1920
ttaaaacctc aattgcacag caggtaccca aactcgatat ttgggctgtt tcggccactc   1980
gccaccgtca gggtattgaa aatggaaaaa ccttgctgat cgaaaaaagt ggaatcggcg   2040
cgttacgaca tacacttgag caggcacttg ctcaggttcc atctgcacga acgtatgaaa   2100
agaatagatt gctgtctgac ttgcatcatc aacttaagca gttattactc gatcaaaaac   2160
atgtacttca gcaactacaa cagacacagc agcagcaatt gcatgacttt gatacaggac   2220
tcatcaacat actcgataag attcgagtag atcttgagcc cattgtaaat atagatggtc   2280
aagaccaagc actcaatcca gattcatttg ccacgatgtt taaaaataca gcagccaagc   2340
agcaacgtgc caaagtgcag attgcttact cacgtgcctg tatcgagatc aatagccatc   2400
tcatacgtca cggtgtggtg ggtttacccg cagagcaaca aaccacgata aaaagtattg   2460
atacggtcat tgttgcggtt tttggaattt cagtgaaatt tcgcgatcag ctacgtgcat   2520
tgttttatac cgataccgaa cgacaacgct tgcaaagaga gtttcgattt tattttgaaa   2580
agtcagcagg ccgaatgatt ttagctgcca agattgagca gacaatgcgg cagcaagggt   2640
gtattcaaaa tgcaatgatg gcgttgcaac agatggagag tgcagcatga ccagcggcgg   2700
```

```
acacattcaa ttgtttatcg aacacacccg gcagattgcg actgcccaag gggatataca    2760
gttggcattg caatcgatgc agcaatggcg cgaagcattt gctacagcat aaaacaaaa     2820 tacctttgat ttaacgggct ggtcaccgca gacaaagatc gccaatcaac tcaagcaatt    2880
taaccataag cttacaacgc atgtatcgaa ttgggatacc gaatggcata cttttagtgc    2940
tgctcaatcg gttgcagaag tatttcatga tcgggtgatg ttgcttgtat tcggtaagtt    3000
taatgccgga aagagttcat tgtgtaactt actggccgaa tgctttcgtt ctcacgaaca    3060
aaccgtgcaa tattttcatg ttcaaaatga acagatattt tataccgaat ctcacttacg    3120
cgaaggtgca accgagacga cagcgcaact acagggcgta tgtctgggtg aaaaacttat    3180
tttgctagat acaccaggtt tgcattctgg tactcagaaa aatgcagcgc tcacacaaaa    3240
atttatcgac agtgcagatg gtgtgctgtg gctcagtagc gcaacttcac cgggtcaggt    3300
gcaagagcta gatgcactgg ggcgcgagtt aaagcgtcat aaacctttat ttcctgttat    3360
tacccgaagc gatttgtcg aagaagatga aattgatggt gagctatgta cagtgctttg     3420
caataaaaat tcagaacaac gtgcgttgca agagtctgat gtattgatgc gtgcgaaaga    3480
aaaactgcac atatgcaagt ggatgtgagt ttattaaagc cgcccgtgtc cgtttcaact    3540
caaatggcgc gtgaagcaga tatgaaccca caagccatga acgaggctgg ttttgagcga    3600
ttatttgcag cacttttggc tcttattgag cctgctttgc gctataagca gcgtaaacct    3660
gccgaagtat tgttgcattt tttgcaagaa catatcattg aaggtttaag gttttacctg    3720
caacccgatc tagagcaaat acaacaggac ctcaaacagg ctcaagatga tttacgacag    3780
ctacacaccg atttagccga ggcagtctgg cgtagcgtat tgcctgagct accacaactt    3840
cttgagcaac atgcaagtac acaaaatatt gatgccgtag tgaacagttt gaacgagtgg    3900
ataaacgtcg cattcgaaca acagcttgca attcagcttg atgcttatgg tttaaatttg    3960
gattcgctta gcaagatcga aaaaaccgaa aaaatgcagt atgaacgcat tgcgggaatg    4020
gtggtgcatg atggcttgta cacgactctc acgcagcaga ttcaacaagc tgtcaaagct    4080
tctacgagtg aattgattga tcagtgtcag gctcaacttg agcagtcaat caaacatgtt    4140
caaacactcg atgaaaccct catcgattac agcgcagcac tcgatcaact cagccaagcg    4200
ctacgcattg aataaagagc agtaaatttt tcagacatat tttattcgat gagtggcctg    4260
atatggtgcg ttgcaaacac ctcctgtaca caggcgagaa ttttaggaat gtaattactg    4320
tggtccatat ttcgcaccgc gagtgaaatt gggctatagg catcatcatc taaaattgga    4380
atataaagta gattcttcac cccaatatcc atggcagacg ccggtacgat gcagacgcct    4440
tcacctgctg ccaccaagcc gagtgccagt tgaatttctc gaatttcggt gagtttggat    4500
ggtactaggc ctagttcggt aaagagtgac tgaataaagg tcgcaaaatt gggcttttga    4560
gagactgggt acagcagcat cggttcatca ataatttgag agagatgaac ccctgttgct    4620
gcaaactga                                                           4629
```

<210> SEQ ID NO 11
<211> LENGTH: 311
<212> TYPE: PRT
<213> ORGANISM: Acinetobacter baylyi
<220> FEATURE:
<221> NAME/KEY: PEPTIDE
<222> LOCATION: (1)..(311)
<223> OTHER INFORMATION: Protein sequence of CatA (catechol 1,2-
      dioxygenase) from Acinetobacter baylyi ADP1

<400> SEQUENCE: 11

Met Glu Val Lys Ile Phe Asn Thr Gln Asp Val Gln Asp Phe Leu Arg
1               5                   10                  15

Val Ala Ser Gly Leu Glu Gln Glu Gly Gly Asn Pro Arg Val Lys Gln
            20                  25                  30

Ile Ile His Arg Val Leu Ser Asp Leu Tyr Lys Ala Ile Glu Asp Leu
        35                  40                  45

Asn Ile Thr Ser Asp Glu Tyr Trp Ala Gly Val Ala Tyr Leu Asn Gln
    50                  55                  60

Leu Gly Ala Asn Gln Glu Ala Gly Leu Leu Ser Pro Gly Leu Gly Phe
65              70                  75                  80

Asp His Tyr Leu Asp Met Arg Met Asp Ala Glu Asp Ala Ala Leu Gly
                85                  90                  95

Ile Glu Asn Ala Thr Pro Arg Thr Ile Glu Gly Pro Leu Tyr Val Ala
            100                 105                 110

Gly Ala Pro Glu Ser Val Gly Tyr Ala Arg Met Asp Asp Gly Ser Asp
        115                 120                 125

Pro Asn Gly His Thr Leu Ile Leu His Gly Thr Ile Phe Asp Ala Asp
    130                 135                 140

Gly Lys Pro Leu Pro Asn Ala Lys Val Glu Ile Trp His Ala Asn Thr
145                 150                 155                 160

Lys Gly Phe Tyr Ser His Phe Asp Pro Thr Gly Glu Gln Gln Ala Phe
                165                 170                 175

Asn Met Arg Arg Ser Ile Ile Thr Asp Glu Asn Gly Gln Tyr Arg Val
            180                 185                 190

Arg Thr Ile Leu Pro Ala Gly Tyr Gly Cys Pro Pro Glu Gly Pro Thr
        195                 200                 205

Gln Gln Leu Leu Asn Gln Leu Gly Arg His Gly Asn Arg Pro Ala His
    210                 215                 220

Ile His Tyr Phe Val Ser Ala Asp Gly His Arg Lys Leu Thr Thr Gln
225                 230                 235                 240

Ile Asn Val Ala Gly Asp Pro Tyr Thr Tyr Asp Phe Ala Tyr Ala
                245                 250                 255

Thr Arg Glu Gly Leu Val Val Asp Ala Val Glu His Thr Asp Pro Glu
        260                 265                 270

Ala Ile Lys Ala Asn Asp Val Glu Gly Pro Phe Ala Glu Met Val Phe
    275                 280                 285

Asp Leu Lys Leu Thr Arg Leu Val Asp Gly Val Asp Asn Gln Val Val
290                 295                 300

Asp Arg Pro Arg Leu Ala Val
305             310

<210> SEQ ID NO 12
<211> LENGTH: 1461
<212> TYPE: DNA
<213> ORGANISM: Acinetobacter sp. ADP1
<220> FEATURE:
<221> NAME/KEY: gene
<222> LOCATION: (1)..(1461)
<223> OTHER INFORMATION: DNA sequence of the quiC (3-dehydroshikimate
      dehydratase)gene from Acinetobacter sp. ADP1

<400> SEQUENCE: 12
atgaaattaa cttctttacg cgtatcttta ttggcgctgg gcttggtaac atcaggtttt      60
gctgcggcag aaacttatac tgtagatcgt tatcaggatg atagtgaaaa aggctctttg     120
cgttgggcaa ttgaacaatc taatgcaaat agcgcacaag agaatcagat tctgattcag     180

```
gctgttggta aggcaccttta tgtgatcaag gtggataaac cgttaccacc gattaaatca    240
tctgtaaaaa ttattggtac agaatgggat aaaacgggcg aatttattgc gattgatggt    300
tcaaactata tcaagggcga aggcgaaaaa gcatgtccag gtgcaaatcc aggacaatat    360
ggtaccaatg ttcgtaccat gactttacca ggtttggttc tacaagatgt caatggtgtg    420
accctgaaag gtcttgatgt tcatcgcttc tgtattggtg tactggtaaa tcgttcaagc    480
aataatttga ttcagcataa ccgtatttca ataattacg gtggcgctgg tgtcatgatc    540
acgggtgatg atggtaaagg taacccaacg tctaccacca ccaataacaa caaagtattg    600
gataatgtgt ttattgacaa tggcgatggt cttgaactga cgcgtggagc agcattcaac    660
ctgattgcta acaatctgtt tacatcgacc aaagccaatc cagagccgtc tcaaggcatt    720
gaaattcttt gggggaatga caatgcagtg gtgggtaaca aatttgaaaa ctattcagat    780
ggtctacaaa tcaactgggg taaacgtaat tacatcgctt ataacgaatt gaccaataac    840
tctttgggtt tcaatcttac aggtgatgga aacatcttcg atagtaacaa agtgcatggc    900
aatcgtattg gtatcgcaat tcgttctgaa aaagatgcaa atgcacgtat cacacttacc    960
aaaaatcaga tttgggataa tggtaaagat atcaaacgct gtgaggctgg tggttcatgt   1020
gttccaaacc aacgtttagg tgcaattgta tttggtgttc ctgcgcttga gcatgaaggt   1080
tttgtaggct ctcgtggtgg cggtgtagtc attgaacctg caaaattaca aaaaacatgt   1140
acacagccaa atcaacaaaa ctgtaatgcc attccgaacc aaggtattca ggcacctaaa   1200
ctgactgtca gtaaaaaaca acttacagtt gaagttaaag gaacaccaaa ccagcgttac   1260
aacgtagaat tttttggaaa tcgtaatgca tcttcttccg aagctgagca atatttaggt   1320
tcaattgttg tagtgacaga tcatcaaggt cttgcaaaag caaactgggc accaaaagtc   1380
agcatgccat ctgttactgc gaatgtaact gatcacttgg gcgccacttc agagttaagt   1440
tctgcagtga aaatgagata a                                             1461
```

<210> SEQ ID NO 13  
<211> LENGTH: 1461  
<212> TYPE: DNA  
<213> ORGANISM: Acinetobacter sp. arc5  
<220> FEATURE:  
<221> NAME/KEY: gene  
<222> LOCATION: (1)..(1461)  
<223> OTHER INFORMATION: Codon-optimized DNA sequence of the quiC (3-dehydroshikimate dehydratase) gene from Acinetobacter sp. ADP1

<400> SEQUENCE: 13

```
atgaaactga ccagcctgcg tgttagcctg ctggcactgg gtctggttac cagcggtttt     60
gcagcagcag aaacctatac cgttgatcgt tatcaggatg atagcgaaaa aggtagcctg    120
cgttgggcaa ttgaacagag caatgcaaat agcgcacaag aaaaccagat tctgattcag    180
gcagttggta agcaccgta tgttatcaaa gttgataaac cgctgcctcc gattaaaagc    240
agcgttaaaa tcattggcac cgagtgggat aaaaccggtg aatttattgc aattgatggc    300
agcaactata tcaaggcga aggtgaaaaa gcatgtccgg gtgcaaatcc gggtcagtat    360
ggcaccaatg ttcgtaccat gaccctgcct ggtctggttc tgcaagatgt taatggtgtt    420
accctgaaag gtctggatgt tcatcgtttt tgtattggtg ttctggttaa tcgcagcagc    480
aataacctga ttcagcataa tcgtatcagc aacaattatg gtggtgccgg tgttatgatt    540
accggtgatg atggtaaagg taatccgacc agcaccacca ccaataataa caaagttctg    600
gataacgtgt tcatcgataa tggtgatggt ctggaactga cccgtggtgc agcatttaat    660
```

```
ctgattgcaa ataacctgtt taccagcaca aaagccaatc cggaaccgag ccagggtatt      720
gaaattctgt ggggtaatga taatgccgtg gtgggtaaca aattcgaaaa ctattcagat      780
ggcctgcaaa tcaattgggg taaacgtaac tatatcgcct ataacgaact gaccaataac      840
agcctgggtt tcaatctgac aggtgatggt aacattttcg acagcaataa agtgcatggt      900
aaccgtattg gtattgccat tcgtagtgaa aaagatgcca atgcacgtat taccctgacc      960
aaaaatcaga tttgggataa cggcaaagat atcaaacgtt gtgaagccgg tggtagctgt     1020
gttccgaatc agcgtctggg tgcaattgtt tttggtgttc cggcactgga acatgaaggt     1080
tttgttggta gccgtggcgg tggtgttgtt attgaaccgg caaaactgca aaaaacctgc     1140
acccagccga accagcagaa ttgtaatgca attcctaatc agggtattca ggcaccgaaa     1200
ctgacagtta gcaaaaaaca gctgaccgtt gaagttaaag gcaccccgaa tcagcgttat     1260
aatgtggaat ttttggcaa tcgtaatgcc agcagcagcg aagcagaaca gtatctgggt     1320
agcattgttg ttgttaccga tcatcagggt ctggcaaaag caaattgggc tccgaaagtt     1380
agcatgccga gcgttaccgc aaatgtgaca gatcatctgg gtgcgaccag cgaactgagc     1440
agcgcagtta aaatgcgtta a                                                1461
```

<210> SEQ ID NO 14
<211> LENGTH: 486
<212> TYPE: PRT
<213> ORGANISM: Acinetobacter sp. arc5
<220> FEATURE:
<221> NAME/KEY: PEPTIDE
<222> LOCATION: (1)..(486)
<223> OTHER INFORMATION: Protein sequence of QuiC (3-dehydroshikimate dehydrogenase from Acinetobacter sp. ADP1

<400> SEQUENCE: 14

```
Met Lys Leu Thr Ser Leu Arg Val Ser Leu Leu Ala Leu Gly Leu Val
1               5                   10                  15

Thr Ser Gly Phe Ala Ala Ala Glu Thr Tyr Thr Val Asp Arg Tyr Gln
            20                  25                  30

Asp Asp Ser Glu Lys Gly Ser Leu Arg Trp Ala Ile Glu Gln Ser Asn
        35                  40                  45

Ala Asn Ser Ala Gln Glu Asn Gln Ile Leu Ile Gln Ala Val Gly Lys
    50                  55                  60

Ala Pro Tyr Val Ile Lys Val Asp Lys Pro Leu Pro Ile Lys Ser
65                  70                  75                  80

Ser Val Lys Ile Ile Gly Thr Glu Trp Asp Lys Thr Gly Glu Phe Ile
                85                  90                  95

Ala Ile Asp Gly Ser Asn Tyr Ile Lys Gly Glu Gly Lys Ala Cys
            100                 105                 110

Pro Gly Ala Asn Pro Gly Gln Tyr Gly Thr Asn Val Arg Thr Met Thr
        115                 120                 125

Leu Pro Gly Leu Val Leu Gln Asp Val Asn Gly Val Thr Leu Lys Gly
    130                 135                 140

Leu Asp Val His Arg Phe Cys Ile Gly Val Leu Val Asn Arg Ser Ser
145                 150                 155                 160

Asn Asn Leu Ile Gln His Asn Arg Ile Ser Asn Tyr Gly Gly Ala
                165                 170                 175

Gly Val Met Ile Thr Gly Asp Asp Gly Lys Gly Asn Pro Thr Ser Thr
            180                 185                 190

Thr Thr Asn Asn Asn Lys Val Leu Asp Asn Val Phe Ile Asp Asn Gly
        195                 200                 205
```

Asp Gly Leu Glu Leu Thr Arg Gly Ala Ala Phe Asn Leu Ile Ala Asn
            210                 215                 220

Asn Leu Phe Thr Ser Thr Lys Ala Asn Pro Glu Pro Ser Gln Gly Ile
225                 230                 235                 240

Glu Ile Leu Trp Gly Asn Asp Asn Ala Val Val Gly Asn Lys Phe Glu
                245                 250                 255

Asn Tyr Ser Asp Gly Leu Gln Ile Asn Trp Gly Lys Arg Asn Tyr Ile
            260                 265                 270

Ala Tyr Asn Glu Leu Thr Asn Asn Ser Leu Gly Phe Asn Leu Thr Gly
        275                 280                 285

Asp Gly Asn Ile Phe Asp Ser Asn Lys Val His Gly Asn Arg Ile Gly
        290                 295                 300

Ile Ala Ile Arg Ser Glu Lys Asp Ala Asn Ala Arg Ile Thr Leu Thr
305                 310                 315                 320

Lys Asn Gln Ile Trp Asp Asn Gly Lys Asp Ile Lys Arg Cys Glu Ala
                325                 330                 335

Gly Gly Ser Cys Val Pro Asn Gln Arg Leu Gly Ala Ile Val Phe Gly
            340                 345                 350

Val Pro Ala Leu Glu His Glu Gly Phe Val Gly Ser Arg Gly Gly Gly
        355                 360                 365

Val Val Ile Glu Pro Ala Lys Leu Gln Lys Thr Cys Thr Gln Pro Asn
370                 375                 380

Gln Gln Asn Cys Asn Ala Ile Pro Asn Gln Gly Ile Gln Ala Pro Lys
385                 390                 395                 400

Leu Thr Val Ser Lys Lys Gln Leu Thr Val Glu Val Lys Gly Thr Pro
                405                 410                 415

Asn Gln Arg Tyr Asn Val Glu Phe Phe Gly Asn Arg Asn Ala Ser Ser
            420                 425                 430

Ser Glu Ala Glu Gln Tyr Leu Gly Ser Ile Val Val Thr Asp His
        435                 440                 445

Gln Gly Leu Ala Lys Ala Asn Trp Ala Pro Lys Val Ser Met Pro Ser
    450                 455                 460

Val Thr Ala Asn Val Thr Asp His Leu Gly Ala Thr Ser Glu Leu Ser
465                 470                 475                 480

Ser Ala Val Lys Met Arg
                485

<210> SEQ ID NO 15
<211> LENGTH: 9462
<212> TYPE: DNA
<213> ORGANISM: Escherichia coli
<220> FEATURE:
<221> NAME/KEY: misc_feature
<222> LOCATION: (1)..(9462)
<223> OTHER INFORMATION: DNA sequence of the plasmid pAC21
<220> FEATURE:
<221> NAME/KEY: misc_feature
<222> LOCATION: (5924)..(5924)
<223> OTHER INFORMATION: n is a, c, g, or t

<400> SEQUENCE: 15
gttgacagta agacgggtaa gcctgttgat gataccgctg ccttactggg tgcattagcc      60
agtctgaatg acctgtcacg ggataatccg aagtggtcag actggaaaat cagagggcag    120
gaactgctga acagcaaaaa gtcagatagc accacatagc agacccgcca taaacgccc     180 tgagaagccc gtgacgggct tttcttgtat tatgggtagt ttccttgcat gaatccataa    240

```
aaggcgcctg tagtgccatt taccccatt cactgccaga gccgtgagcg cagcgaactg      300
aatgtcacga aaagacagc gactcaggtg cctgatggtc ggagacaaaa ggaatattca      360
gcgatttgcc cgagcttgcg agggtgctac ttaagccttt agggttttaa ggtctgtttt      420
gtagaggagc aaacagcgtt tgcgacatcc ttttgtaata ctgcggaact gactaaagta      480
gtgagttata cacagggctg ggatctattc tttttatctt tttttattct ttctttattc      540
tataaattat aaccacttga atataaacaa aaaaaacaca caaaggtcta gcggaattta      600
cagagggtct agcagaattt acaagttttc cagcaaaggt ctagcagaat ttacagatac      660
ccacaactca aaggaaaagg actagtaatt atcattgact agcccatctc aattggtata      720
gtgattaaaa tcacctagac caattgagat gtatgtctga attagttgtt ttcaaagcaa      780
atgaactagc gattagtcgc tatgacttaa cggagcatga aaccaagcta attttatgct      840
gtgtggcact actcaacccc acgattgaaa accctacaag gaagaacgg acggtatcgt       900 tcacttataa ccaatacgct cagatgatga acatcagtag ggaaaatgct tatggtgtat      960
tagctaaagc aaccagagag ctgatgacga gaactgtgga aatcaggaat cctttggtta     1020
aaggctttga gattttccag tggacaaact atgccaagtt ctcaagcgaa aaattagaat     1080 tagttttag tgaagagata ttgccttatc ttttccagtt aaaaaaattc ataaaatata      1140
atctggaaca tgttaagtct tttgaaaaca aatactctat gaggatttat gagtggttat     1200
taaaagaact aacacaaaag aaaactcaca aggcaaatat agagattagc cttgatgaat     1260
ttaagttcat gttaatgctt gaaaataact accatgagtt taaaaggctt aaccaatggg     1320
ttttgaaacc aataagtaaa gatttaaaca cttacagcaa tatgaaattg gtggttgata     1380
agcgaggccg cccgactgat acgttgattt tccaagttga actagataga caaatggatc     1440
tcgtaaccga acttgagaac aaccagataa aaatgaatgg tgacaaaata ccaacaacca     1500
ttacatcaga ttcctaccta cgtaacggac taagaaaaac actacacgat gctttaactg     1560
caaaaattca gctcaccagt tttgaggcaa aattttttgag tgacatgcaa agtaagcatg     1620
atctcaatgg ttcgttctca tggctcacgc aaaaacaacg aaccacacta gagaacatac     1680
tggctaaata cggaaggatc tgaggttctt atggctcttg tatctatcag tgaagcatca     1740
agactaacaa acaaaagtag aacaactgtt caccgttaga tatcaaaggg aaaactgtcc     1800
atatgcacag atgaaaacgg tgtaaaaaag atagatacat cagagctttt acgagttttt     1860
ggtgcattta agctgttca ccatgaacag atcgacaatg taacagatga acagcatgta      1920
acacctaata gaacaggtga aaccagtaaa acaaagcaac tagaacatga aattgaacac     1980
ctgagacaac ttgttacagc tcaacagtca cacatagaca gcctgaaaca ggcgatgctg     2040
cttatcgaat caaagctgcc gacaacacgg gagccagtga cgcctcccgt ggggaaaaaa     2100
tcatggcaat tctggaagaa atagcgcttt cagccggcaa acctgaagcc ggatctgcga     2160
ttctgataac aaactagcaa caccagaaca gcccgtttgc gggcagcaaa acccgttatg     2220
cttgtaaacc gttttgtgaa aaaattttta aaataaaaaa ggggacctct agggtcccca     2280
attaattagt aatataatct attaaaggtc attcaaaagg tcatccaccg gatcaattcc     2340
cctgctcgcg caggctgggt gccaagctct cgggtaacat caaggcccga tccttggagc     2400
ccttgccctc ccgcacgatg atcgtgccgt gatcgaaatc cagatccttg acccgcagtt     2460
gcaaaccctc actgatccgc atgcccgttc catacagaag ctgggcgaac aaacgatgct     2520
cgccttccag aaaaccgagg atgcgaacca cttcatccgg ggtcagcacc accggcaagc     2580
gccgcgacgg ccgaggtctt ccgatctcct gaagccaggg cagatccgtg cacagcacct     2640
```

```
tgccgtagaa gaacagcaag gccgccaatg cctgacgatg cgtggagacc gaaaccttgc    2700
gctcgttcgc cagccaggac agaaatgcct cgacttcgct gctgcccaag gttgccgggt    2760
gacgcacacc gtggaaacgg atgaaggcac gaacccagtg gacataagcc tgttcggttc    2820
gtaagctgta atgcaagtag cgtatgcgct cacgcaactg gtccagaacc ttgaccgaac    2880
gcagcggtgg taacggcgca gtggcggttt tcatggcttg ttatgactgt ttttttgggg    2940
tacagtctat gcctcgggca tccaagcagc aagcgcgtta cgccgtgggt cgatgtttga    3000
tgttatggag cagcaacgat gttacgcagc agggcagtcg ccctaaaaca aagttaaaca    3060
tcatgaggga agcggtgatc gccgaagtat cgactcaact atcagaggta gttggcgtca    3120
tcgagcgcca tctcgaaccg acgttgctgg ccgtacattt gtacggctcc gcagtggatg    3180
gcggcctgaa gccacacagt gatattgatt tgctggttac ggtgaccgta aggcttgatg    3240
aaacaacgcg gcgagctttg atcaacgacc ttttggaaac ttcggcttcc cctggagaga    3300
gcgagattct ccgcgctgta gaagtcacca ttgttgtgca cgacgacatc attccgtggc    3360
gttatccagc taagcgcgaa ctgcaatttg gagaatggca gcgcaatgac attcttgcag    3420
gtatcttcga gccagccacg atcgacattg atctggctat cttgctgaca aaagcaagag    3480
aacatagcgt tgccttggta ggtccagcgg cggaggaact ctttgatccg gttcctgaac    3540
aggatctatt tgaggcgcta aatgaaacct aacgctatg gaactcgccg cccgactggg    3600
ctggcgatga gcgaaatgta gtgcttacgt tgtcccgcat ttggtacagc gcagtaaccg    3660
gcaaaatcgc gccgaaggat gtcgctgccg actgggcaat ggagcgcctg ccggcccagt    3720
atcagcccgt catacttgaa gctagacagg cttatcttgg acaagaagaa gatcgcttgg    3780
cctcgcgcgc agatcagttg gaagaatttg tccactacgt gaaaggcgag atcaccaagg    3840
tagtcggcaa ataatgtcta acaattcgtt caagccgacg ccgcttcgcg gcgcggctta    3900
actcaagcgt tagatgcact aagcacataa ttgctcacag ccaaactatc aggtcaagtc    3960
tgcttttatt attttaagc gtgcataata agccctacac aaattgggag atatatcatg    4020
aaaggctggc ttttcttgt tatcgcaata gttggcgaag taatcgcaac atccgcatta    4080
aaatctagcg agggctttac taagctgatc cggtggatga ccttttgaat gacctttaat    4140
agattatatt actaattaat tggggaccct agaggtcccc ttttttattt taaaaatttt    4200
ttcacaaaac ggtttacaag catacgttgg ccgattcatt aatgcagctg gcacgacagg    4260
tttcccgact ggaaagcggg cagtgagcgc aacgcaatta atgtgagtta gctcactcat    4320
taggcacccc aggctttaca ctttatgctt ccggctcgta tgttgtgtgg aattgtgagc    4380
ggataacaat ttcacacagg aaacagctat gaccatgatt acgccaagct tgcatgcctg    4440
caggtcgact ctagaggatc cccccgcg ccgacagagt aataggtttt acttaatagc    4500
tcttcctgtc ccttccaggc agtgatccgc attccgttct catggcgagg caacatttcg    4560
ggatggaaga taatgttctt tgctacagga aaatcaacaa tatgcgcacc agatgccact    4620
ggcagccgcc cgctgcgcgt tactaactct ataaatgcag ggatctcatc aatgacaaca    4680
tcctgcggac tgtttcctgc cagtcccatg atgatggcga catccgtggc atggcctttg    4740
cccgtcagtg acaacgaccc gtacagatcg accacaatat ggctcgtcgc ggttaataag    4800
ccgctacttt ccagccgatc aataaaactt tttccggcat tcattggccc cacggtatgc    4860
gaactggagg gaccaatccc aattttgaaa atatcgaatg cactaatcat gtgacgaag    4920 atcacttcgc agaataaata aatcctggtg tccctgttga taccgggaag ccctgggcca    4980
```

```
acttttggcg aaaatgagac gttgatcggc acgtaagagg ttccaactttt caccataatg    5040 aaataagatc actaccgggc gtattttttg agttatcgag attttcagga gctaaggaag    5100
ctaaaatgga gaaaaaaatc actggatata ccaccgttga tatatcccaa tggcatcgta    5160
aagaacattt tgaggcattt cagtcagttg ctcaatgtac ctataaccag accgttcagc    5220
tggatattac ggcctttta aagaccgtaa agaaaaataa gcacaagttt tatccggcct    5280
ttattcacat tcttgcccgc ctgatgaatg ctcatccgga attccgtatg gcaatgaaag    5340
acggtgagct ggtgatatgg gatagtgttc acccttgtta caccgttttc catgagcaaa    5400
ctgaaacgtt ttcatcgctc tggagtgaat accacgacga tttccggcag tttctacaca    5460
tatattcgca agatgtggcg tgttacggtg aaaacctggc ctatttccct aaagggttta    5520
ttgagaatat gttttcgtc tcagccaatc cctgggtgag tttcaccagt tttgatttaa    5580
acgtggccaa tatggacaac ttcttcgccc ccgttttcac catgggcaaa tattatacgc    5640
aaggcgacaa ggtgctgatg ccgctggcga ttcaggttca tcatgccgtt tgtgatggct    5700
tccatgtcgg cagaatgctt aatgaattac aacagtactg cgatgagtgg cagggcgggg    5760
cgtaattttt ttaaggcagt tattggtgcc cttaaacgcc tggtgctacg cctgaataag    5820
tgataataag cggatgaatg gcagaaattc gaaagcaaat tcgacccggt cgtcggttca    5880 ggcagggtc gttaaatagc cgcttatgtc tattgctggt ttantcggta cccggggatc    5940
gcggccgcgg accggatccc atcacatata cctgccgttc actattattt agtgaaatga    6000
gatattatga tattttctga attgtgatta aaaaggcaac tttatgccca tgcaacagaa    6060
actataaaaa atacagagaa tgaaaagaaa cagatagatt ttttagttct ttaggcccgt    6120
agtctgcaaa tccttttatg attttctatc aaacaaaaga ggaaaataga ccagttgcaa    6180
tccaaacgag agtctaatag aatgaggtcg aaaagtaaat cgcgcgggtt tgttactgat    6240
aaagcaggca agacctaaaa tgtgtaaagg gcaaagtgta tactttggcg tcaccccta    6300 catatttag gtcttttttt attgtgcgta actaacttgc catcttcaaa caggagggct    6360
ggaagaagca gaccgctaac acagtacata aaaaggaga catgaacgat gaacatcaaa    6420
aagtttgcaa acaagcaac agtattaacc tttactaccg cactgctggc aggaggcgca    6480
actcaagcgt ttgcgaaaga acgaaccaa aagccatata aggaaacata cggcatttcc    6540
catattacac gccatgatat gctgcaaatc cctgaacagc aaaaaaatga aaatatcaa    6600 gttcctgaat tcgattcgtc cacaattaaa aatatctctt ctgcaaaagg cctggacgtt    6660
tgggacagct ggcccattaca aaacgctgac ggcactgtcg caaactatca cggctaccac    6720
atcgtctttg cattagccgg agatcctaaa aatgcggatg acacatcgat ttacatgttc    6780
tatcaaaaag tcggcgaaac ttctattgac agctggaaaa acgctggccg cgtcttaaa    6840 gacagcgaca aattcgatgc aaatgattct atcctaaaag accaaacaca agaatggtca    6900
ggttcagcca catttacatc tgacggaaaa atccgtttat tctacactga tttctccggt    6960
aaacattacg gcaaacaaac actgacaact gcacaagtta acgtatcagc atcagacagc    7020 tcttttgaaca tcaacggtgt agaggattat aaaatcaatct ttgacggtga cggaaaaacg    7080
tatcaaaatg tacagcagtt catcgatgaa ggcaactaca gctcaggcga caaccatacg    7140
ctgagagatc ctcactacgt agaagataaa ggccacaaat acttagtatt tgaagcaaac    7200
actggaactg aagatggcta ccaaggcgaa gaatctttat ttaacaaagc atactatggc    7260
aaaagcacat cattcttccg tcaagaaagt caaaaacttc tgcaaagcga taaaaaacgc    7320
acggctgagt tagcaaacgg cgctctcggt atgattgagc taaacgatga ttacacactg    7380
```

```
aaaaaagtga tgaaaccgct gattgcatct aacacagtaa cagatgaaat tgaacgcgcg    7440
aacgtcttta aaatgaacgg caaatggtac ctgttcactg actcccgcgg atcaaaaatg    7500
acgattgacg gcattacgtc taacgatatt tacatgcttg gttatgtttc taattcttta    7560
actggcccat acaagccgct gaacaaaact ggccttgtgt taaaaatgga tcttgatcct    7620
aacgatgtaa cctttactta ctcacacttc gctgtacctc aagcgaaagg aaacaatgtc    7680
gtgattacaa gctatatgac aaacagagga ttctacgcag acaaacaatc aacgtttgcg    7740
ccgagcttcc tgctgaacat caaaggcaag aaaacatctg ttgtcaaaga cagcatcctt    7800
gaacaaggac aattaacagt taacaaataa aaacgcaaaa gaaaatgcca atatcctatt    7860
ggcattttct tttatttctt ccatttaaat ggatgcatgc gctagcggag tgtatactgg    7920
cttactatgt tggcactgat gagggtgtca gtgaagtgct tcagcctcgt gagcgggacg    7980
gtcgtaaggt cgttccgctc cacttcactg aacggcaatc cgagggtgtg atccaatta    8040
aggccacgct gtcatttaaa ttccgttttt ccagttcaaa tgcaattgcc ttcaatgcac    8100
cttcgtagct gtggtgagcc agcggtgctg gctctccccc atttacggat aagaatgcat    8160
tttccgagtt aataccgtcg gcaataccctg acattaatac ttcacagtcg ctggcatcga    8220
gtacggaaaa cttaatcgaa gacgaaccac agttaataac caaaacaacc ggaaattcat    8280
tcatctcttt tctcatcctg agttacggat taaaacagtt tgtatacgat gttcaggatg    8340
gtcagcagac caatcacggt aacaaacacg ttatccagac gaccacggta tttcgccaga    8400
gacggcgctt tacggatggc atacatcggc aacaggcaca gcaggatgc gataatcggt    8460
gcgcccatgg cttcaatcag gtcgaggatg ttcggttgg cgtaggcaac aacccaggtg    8520
gagcccatga tgaagatcat gctgagagta ttcagtttac ccagcgacac tttggttttg    8580
tcacctttat aaccgaactt cagaatcaga ccattcaagc cttccagcgt ccccagatag    8640
tgaccgaaga aagatttgaa gatagccacg agtgcgatga tggaagccgc atattccagt    8700
gtaatcgcga acgttgtttt ggtaccggtc atggacgcaa agtggttagc cagataagaa    8760
agcactggaa tattctgcgc tttggcttcc gccatgttgg ccggagacag agtaaacagg    8820
cagctaaagg caaagaacat caccactgca accatcagca tgctggcacg agaaatgatt    8880
tgggaacatt tacgttcggt gaagtcgcga ccgaagtctt tctcatactc ttcacgttta    8940
gaaaccacga aggaagagac gattggcgag aagttaaagg agaaaccat gatggaaatc    9000
cccagccaga cagtgatcag gataccgtca tgaccggtta acgacagcga accgaggtca    9060
acctggtcga taactgcaga gttccagtaa gggatcagcg acaaagaaat cagcaccagg    9120
ctggcgataa acggccatac caggtagctc agggtaccga gctcgaattc actggccgtc    9180
gttttacaac gtcgtgactg ggaaaaccct ggcgttaccc aacttaatcg ccttgcagca    9240
catccccctt tcgccagctg gcgtaatagc gaagaggccc gcaccgatcg cccttcccaa    9300
cagttgcgca gcctgaatgg cgaatggcgc ctgatgcggt attttctcct tacgcatctg    9360
tgcggtattt cacaccgcat atggtgcact ctcagtacaa tctgctctga tgccgcatag    9420
ttaagccagc cccgacaccc gccaacaccc gctgacgaat tc                       9462
```

<210> SEQ ID NO 16
<211> LENGTH: 9430
<212> TYPE: DNA
<213> ORGANISM: Escherichia coli
<220> FEATURE:
<221> NAME/KEY: misc_feature
<222> LOCATION: (1)..(9430)

<223> OTHER INFORMATION: DNA sequence of the plasmid pAC19

<400> SEQUENCE: 16

```
gttgacagta agacgggtaa gcctgttgat gataccgctg ccttactggg tgcattagcc      60
agtctgaatg acctgtcacg ggataatccg aagtggtcag actggaaaat cagagggcag     120
gaactgctga acagcaaaaa gtcagatagc accacatagc agacccgcca taaaacgccc     180
tgagaagccc gtgacgggct tttcttgtat tatgggtagt ttccttgcat gaatccataa     240
aaggcgcctg tagtgccatt tacccccatt cactgccaga gccgtgagcg cagcgaactg     300
aatgtcacga aaagacagc gactcaggtg cctgatggtc ggagacaaaa ggaatattca      360
gcgatttgcc cgagcttgcg agggtgctac ttaagccttt agggttttaa ggtctgtttt     420
gtagaggagc aaacagcgtt tgcgacatcc ttttgtaata ctgcggaact gactaaagta     480
gtgagttata cacagggctg ggatctattc ttttttatctt tttttattct ttctttattc    540
tataaattat aaccacttga atataaacaa aaaaaacaca caaaggtcta gcggaattta     600
cagagggtct agcagaattt acaagttttc cagcaaaggt ctagcagaat ttacagatac     660
ccacaactca aaggaaaagg actagtaatt atcattgact agcccatctc aattggtata     720
gtgattaaaa tcacctagac caattgagat gtatgtctga attagttgtt ttcaaagcaa     780
atgaactagc gattagtcgc tatgacttaa cggagcatga aaccaagcta attttatgct     840
gtgtggcact actcaacccc acgattgaaa accctacaag gaaagaacgg acggtatcgt     900
tcacttataa ccaatacgct cagatgatga acatcagtag ggaaaatgct tatggtgtat     960
tagctaaagc aaccagagag ctgatgacga gaactgtgga aatcaggaat cctttggtta    1020
aaggctttga gattttccag tggacaaact atgccaagtt ctcaagcgaa aaattagaat    1080
tagttttttag tgaagagata ttgccttatc ttttccagtt aaaaaaattc ataaaatata    1140
atctggaaca tgttaagtct tttgaaaaca atactctat gaggatttat gagtggttat     1200
taaaagaact aacacaaaag aaaactcaca aggcaaatat agagattagc cttgatgaat    1260
ttaagttcat gttaatgctt gaaaataact accatgagtt taaaaggctt aaccaatggg    1320
ttttgaaaacc aataagtaaa gatttaaaca cttacagcaa tatgaaattg gtggttgata    1380
agcgaggccg cccgactgat acgttgattt tccaagttga actagataga caaatggatc    1440
tcgtaaccga acttgagaac aaccagataa aaatgaatgg tgacaaaata ccaacaacca    1500
ttacatcaga ttcctaccta cgtaacggac taagaaaaac actacacgat gctttaactg    1560
caaaaattca gctcaccagt tttgaggcaa aattttttgag tgacatgcaa agtaagcatg    1620
atctcaatgg ttcgttctca tggctcacgc aaaaacaacg aaccacacta gagaacatac    1680
tggctaaata cggaaggatc tgaggttctt atggctcttg tatctatcag tgaagcatca    1740
agactaacaa acaaaagtag aacaactgtt caccgttaga tatcaaaggg aaaactgtcc    1800
atatgcacag atgaaaacgg tgtaaaaaag atagatacat cagagctttt acgagttttt    1860
ggtgcattta aagctgttca ccatgaacag atcgacaatg taacagatga acagcatgta    1920
acacctaata gaacaggtga aaccagtaaa acaaagcaac tagaacatga aattgaacac    1980
ctgagacaac ttgttacagc tcaacagtca cacatagaca gcctgaaaca ggcgatgctg    2040
cttatcgaat caaagctgcc gacaacacgg gagccagtga cgcctcccgt ggggaaaaaa    2100
tcatggcaat tctggaagaa atagcgcttt cagccggcaa acctgaagcc ggatctgcga    2160
ttctgataac aaactagcaa caccagaaca gcccgtttgc gggcagcaaa acccgttatg    2220
cttgtaaacc gttttgtgaa aaaattttta aaataaaaaa ggggacctct agggtcccca    2280
```

```
attaattagt aatataatct attaaaggtc attcaaaagg tcatccaccg gatcaattcc    2340
cctgctcgcg caggctgggt gccaagctct cgggtaacat caaggcccga tccttggagc    2400
ccttgccctc ccgcacgatg atcgtgccgt gatcgaaatc cagatccttg acccgcagtt    2460
gcaaaccctc actgatccgc atgcccgttc catacagaag ctgggcgaac aaacgatgct    2520
cgccttccag aaaaccgagg atgcgaacca cttcatccgg ggtcagcacc accggcaagc    2580
gccgcgacgg ccgaggtctt ccgatctcct gaagccaggg cagatccgtg cacagcacct    2640
tgccgtagaa gaacagcaag gccgccaatg cctgacgatg cgtggagacc gaaaccttgc    2700
gctcgttcgc cagccaggac agaaatgcct cgacttcgct gctgcccaag gttgccgggt    2760
gacgcacacc gtggaaacgg atgaaggcac gaacccagtg gacataagcc tgttcggttc    2820
gtaagctgta atgcaagtag cgtatgcgct cacgcaactg gtccagaacc ttgaccgaac    2880
gcagcggtgg taacggcgca gtggcggttt tcatggcttg ttatgactgt ttttttgggg    2940
tacagtctat gcctcgggca tccaagcagc aagcgcgtta cgccgtgggt cgatgtttga    3000
tgttatggag cagcaacgat gttacgcagc agggcagtcg ccctaaaaca aagttaaaca    3060
tcatgaggga agcggtgatc gccgaagtat cgactcaact atcagaggta gttggcgtca    3120
tcgagcgcca tctcgaaccg acgttgctgg ccgtacattt gtacggctcc gcagtggatg    3180
gcggcctgaa gccacacagt gatattgatt tgctggttac ggtgaccgta aggcttgatg    3240
aaacaacgcg gcgagctttg atcaacgacc ttttggaaac ttcggcttcc cctggagaga    3300
gcgagattct ccgcgctgta gaagtcacca ttgttgtgca cgacgacatc attccgtggc    3360
gttatccagc taagcgcgaa ctgcaatttg gagaatggca gcgcaatgac attcttgcag    3420
gtatcttcga gccagccacg atcgacattg atctggctat cttgctgaca aaagcaagag    3480
aacatagcgt tgccttggta ggtccagcgg cggaggaact ctttgatccg gttcctgaac    3540
aggatctatt tgaggcgcta aatgaaacct aacgctatg gaactcgccg cccgactggg    3600
ctggcgatga gcgaaatgta gtgcttacgt tgtcccgcat ttggtacagc gcagtaaccg    3660
gcaaaatcgc gccgaaggat gtcgctgccg actgggcaat ggagcgcctg ccggcccagt    3720
atcagcccgt catacttgaa gctagacagg cttatcttgg acaagaagaa gatcgcttgg    3780
cctcgcgcgc agatcagttg gaagaatttg tccactacgt gaaaggcgag atcaccaagg    3840
tagtcggcaa ataatgtcta acaattcgtt caagccgacg ccgcttcgcg gcgcggctta    3900
actcaagcgt tagatgcact aagcacataa ttgctcacag ccaaactatc aggtcaagtc    3960
tgcttttatt attttttaagc gtgcataata agccctacac aaattgggag atatatcatg    4020
aaaggctggc ttttttcttgt tatcgcaata gttggcgaag taatcgcaac atccgcatta    4080
aaatctagcg agggctttac taagctgatc cggtggatga ccttttgaat gacctttaat    4140
agattatatt actaattaat tggggaccct agaggtcccc ttttttattt taaaattttt    4200
ttcacaaaac ggtttacaag catacgttgg ccgattcatt aatgcagctg gcacgacagg    4260
tttcccgact ggaaagcggg cagtgagcgc aacgcaatta atgtgagtta gctcactcat    4320
taggcacccc aggctttaca ctttatgctt ccggctcgta tgttgtgtgg aattgtgagc    4380
ggataacaat ttcacacagg aaacagctat gaccatgatt acgccaagct tgcatgcctg    4440
caggtcgact ctagaggatc cccccgccg ccgacagagt aataggtttt acttaatagc    4500
tcttcctgtc ccttccaggc agtgatccgc attccgttct catggcgagg caacatttcg    4560
ggatggaaga taatgttctt tgctacagga aaatcaacaa tatgcgcacc agatgccact    4620
```

```
ggcagccgcc cgctgcgcgt tactaactct ataaatgcag ggatctcatc aatgacaaca    4680
tcctgcggac tgtttcctgc cagtcccatg atgatggcga catccgtggc atggcctttg    4740
cccgtcagtg acaacgaccc gtacagatcg accacaatat ggctcgtcgc ggttaataag    4800
ccgctacttt ccagccgatc aataaaactt tttccggcat tcattggccc cacggtatgc    4860
gaactggagg gaccaatccc aattttgaaa atatcgaatg cactaatcat atccacaccc    4920
tcggattgcc gttcagtgaa gtggagcgga acgaccttac gaccgtcccg ctcacgaggc    4980
tttacgcact acgtactgcg atggcttcaa tttccagcgg gagggcggat ccactaatac    5040
aaaatatatc aaaagttaat aataatatta ttcttactta agactttttt gtcttcattt    5100
tttagtaaaa aatataaaaa aggccacctc ccgatttat cggaaggcag cctcttaaat     5160
tcagttcata atattaaaaa atattattca acttcagaat atttgttggc ataggcagct    5220
gccgcaccca acagtccagg ctgcggataa gtaatcaact taaccggaat cttggacatg    5280
acgcgttcaa agcgtccttt tgaaacaaag cgctgacgga aaccagattc tggcaaatgg    5340
gaagcgatac gaagaccgac accaccgcca ataacaacac tggttgcacc ctgtgccaaa    5400
gcaagatcac cagcgatagc gccaaggctc aagcagaagc gatccaaagc ggcttcagca    5460
aggttgtctt taccttccaa agccatctgc cataatttaa tatcatccag caagctgaac    5520
ggaacgcctt caatggcagc cagtgcttcg tagatattac caagacccgg gccagaaata    5580
atgcgttcga tagaaacgcg gcggaaacgt tcacgtaaac gtgccagaat tttgtcttca    5640
agtctgtcaa gcggagcaaa gtcgatatga ccgccttcag tttcgatgac gaaataacgg    5700
ccttcagtcc gcaacagatg ggcaacaccc aagcccgttc ccggaccaag aatagtgata    5760
acaccatcgc taggaagcgc ttcatcagga ccacaaatat gatccagata agaagaatcc    5820
atatgcgcaa ccgcgtgggc aaccgcgccg aagtcattga tcagaacatg cgtatcgatg    5880
tccagctttt cattcagagt agctggtctt aatacccaag ggttattggt aagttttaaa    5940
acttcaccat gaaccgggcc agcccatgca atagctgcgg cacgtggcag aggacgaccc    6000
agttttcac cgaaacgttc ccaagctaac tgcaagctag catgttctgc cgttttaaaa      6060
gttgtttctt ctccaagaga aagaacccga ccattgctta cttccgcaat agagaaacgc    6120
gcatgcgttc caccgatgtc aatcgcaaca atttccataa taattccttt ctgaaatcag    6180
aaggctaccc aacaggtaaa ataagtccgc ccgctttata ccatcgttgt aaacaaaaag    6240
tataattggt taagacttat ctaaaaaaga caaaaggatt cagccaaagc aagtttaact    6300
acttctggga gcgccacatc tcctcgattt catccaggct ccgacctttg gtttccggca    6360
cgaagcgagc aacaatcaag ccacctaaga tacttaatgc tgcgaaaacg agataggaga    6420
aaccgtggtt gaaagtctga ttcaatgctg gagaaccatc ggcaaccttta aacaggaagt    6480
taaccaagat attagctaac cattgtccgg taacagcgat aggcatagct gcgcccttga    6540
tggaactcgg gaacatttct gacagaacaa cccagcagac agggcccat gacataccaa     6600
agactgcaat ataagaagc acagaagcca aggcaaaac accaccgact ttgaaccaga      6660
aacagcagcc taaaacagcc atcattgcag ccataccgag agcaccccaa ataagcagag    6720
gtttacggcc gaagcggtca acaacacggg aagcaatcat ggtgaagatg aagttcacaa    6780
caccgataga gatggtctgc aataatgccg tatcagctcc aaaacctaaa ttctggaaca    6840
tctgcggtgc ataatacagc acggcgttaa taccgactaa ctgctggaag gcagcaacgg    6900
atacaccggc aaaaacaacg gtgataccaa agcaaacaa acctgcgctg cttttgtcca    6960
tggctttatc aaagccagct ttaatctttt gaatcgtcag attaggatcg gcttgcggtt    7020
```

```
ccagacgagc aaggattttg ctagcctcgg aatgacgtcc cttcatcacc aaccaatgcg   7080
gcgtatccgg tgcggttaac agcagcaata agaaggcaat accgatcagg ccttctgaag   7140
ccggagacca gcaccaacca ctggcattaa cccaatcgat agaaccgaaa tgagccagta   7200
accaggtaaa gatataaccg gttaaagcac ccgtcacaat ggccatctgc tgaccagaaa   7260
ccatctgacc acgtttgtct ggcggagcaa tttcagcaat ataggttggg gtcaaggttg   7320
aaacgacacc gatacctaaa ccggcaagaa accggaaaaa gcaaaaaatt tgtaaagccg   7380
aaccaccggt tccaaataat ttttcggtta acgcagcacc aaaaccggcg gcgacgaaac   7440
aaatggaact catcaacaat ccgccgcgac gaccgaagcg aataccaatc cagccagaca   7500
gcaaagaacc ggtaacacaa ccgaccaaaa cagcaacaac gaccatccca gaaagggaag   7560
ccgcagccgt agcagacagg tgacgagggg caataaaatg gatatcaacc ggtgtaccga   7620
ttgcagcgat aaccgctgaa tcgtaaccga aaagcaagcc gcctatagca gcgattaggg   7680
ctagtcgcgt gactagaccc tgactacttt cagaactcat ggcgattcct ctccctctag   7740
agcgtcctgc tgttgttaag attattatac cacaccttgt agataaagtc aacaactttt   7800
tgcaaaattt ttcaggaatt ttagcagagg ttgttctgga tgtagaacaa acatctttc    7860 cgctcttgtg ctgttaggat atctttcttg gaagctaggt aggcctcgag ttatggcagt   7920
tggttaaaag gaaacaaaaa gaccgttttc acacaaaacg gtcttttttcg atttctttt    7980 acagtcacag ccacttttgc accaattaag gccacgctgt catttaaact ccgttttttcc   8040 agttcaaatg caattgcctt caatgcacct tcgtagctgt ggtgagccag cggtgctggc   8100
tctcccccat ttacggataa gaatgcattt tccgagttaa taccgtcggc aatacctgac   8160
attaatactt cacagtcgct ggcatcgagt acggaaaact taatcgaaga cgaaccacag   8220
ttaataacca aaacaaccgg aaattcattc atctcttttc tcatcctgag ttacggatta   8280
aaacagtttg tatacgatgt tcaggatggt cagcagacca atcacggtaa caaacacgtt   8340
atccagacga ccacggtatt tcgccagaga cggcgcttta cggatggcat acatcggcaa   8400
caggcacagc agggatgcga taatcggtgc gcccatggct tcaatcaggt cgaggatgtt   8460
cgggttggcg taggcaacaa cccaggtgga gcccatgatg aagatcatgc tgagagtatt   8520
cagtttaccc agcgacactt tggttttgtc acctttataa ccgaacttca gaatcagacc   8580
attcaagcct tccagcgtcc ccagatagtg accgaagaaa gatttgaaga tagccacgag   8640
tgcgatgatg gaagccgcat attccagtgt aatcgcgaac gttgttttgg taccggtcat   8700
ggacgcaaag tggttagcca gataagaaag cactggaata ttctgcgctt tggcttccgc   8760
catgttggcc ggagacagag taaacaggca gctaaaggca agaacatca ccactgcaac    8820 catcagcatg ctggcacgag aaatgatttg gaacattta cgttcggtga agtcgcgacc    8880
gaagtctttc tcatactctt cacgtttaga aaccacgaag gaagagacga ttggcgagaa   8940
gttaaaggag aaaaccatga tggaaatccc cagccagaca gtgatcagga taccgtcatg   9000
accggttaac gacagcgaac cgaggtcaac ctggtcgata actgcagagt tccagtaagg   9060
gatcagcgac aaagaaatca gcaccaggct ggcgataaac ggccatacca ggtagctcag   9120
ggtaccgagc tcgaattcac tggccgtcgt tttacaacgt cgtgactggg aaaaccctgg   9180
cgttacccaa cttaatcgcc ttgcagcaca tccccctttc gccagctggc gtaatagcga   9240
agaggcccgc accgatcgcc cttcccaaca gttgcgcagc ctgaatggcg aatggcgcct   9300
gatgcggtat tttctcctta cgcatctgtg cggtatttca caccgcatat ggtgcactct   9360
```

```
cagtacaatc tgctctgatg ccgcatagtt aagccagccc cgacacccgc caacacccgc    9420
tgacgaattc                                                           9430

<210> SEQ ID NO 17
<211> LENGTH: 5768
<212> TYPE: DNA
<213> ORGANISM: Escherichia coli
<220> FEATURE:
<221> NAME/KEY: misc_feature
<222> LOCATION: (1)..(5768)
<223> OTHER INFORMATION: DNA sequence of the plasmid pMH17F

<400> SEQUENCE: 17
gttgacagta agacgggtaa gcctgttgat gataccgctg ccttactggg tgcattagcc      60
agtctgaatg acctgtcacg ggataatccg aagtggtcag actggaaaat cagagggcag     120
gaactgctga acagcaaaaa gtcagatagc accacatagc agacccgcca taaaacgccc     180
tgagaagccc gtgacgggct tttcttgtat tatgggtagt ttccttgcat gaatccataa     240
aaggcgcctg tagtgccatt taccccatt cactgccaga gccgtgagcg cagcgaactg     300
aatgtcacga aaagacagc gactcaggtg cctgatggtc ggagacaaaa ggaatattca     360
gcgatttgcc cgagcttgcg agggtgctac ttaagccttt agggttttaa ggtctgtttt     420
gtagaggagc aaacagcgtt tgcgacatcc ttttgtaata ctgcggaact gactaaagta     480
gtgagttata cacagggctg ggatctattc tttttatctt tttttattct ttctttattc     540
tataaattat aaccacttga atataaacaa aaaaaacaca caaaggtcta gcggaattta     600
cagagggtct agcagaattt acaagttttc cagcaaaggt ctagcagaat ttacagatac     660
ccacaactca aggaaaagg actagtaatt atcattgact agcccatctc aattggtata     720
gtgattaaaa tcacctagac caattgagat gtatgtctga attagttgtt ttcaaagcaa     780
atgaactagc gattagtcgc tatgacttaa cggagcatga accaagcta atttatgct     840 gtgtggcact actcaacccc acgattgaaa accctacaag gaaagaacgg acggtatcgt     900
tcacttataa ccaatacgct cagatgatga acatcagtag ggaaaatgct tatggtgtat     960
tagctaaagc aaccagagag ctgatgacga gaactgtgga aatcaggaat cctttggtta    1020
aaggctttga gattttccag tggacaaact atgccaagtt ctcaagcgaa aaattagaat    1080 tagttttag tgaagagata ttgccttatc ttttccagtt aaaaaaattc ataaaatata    1140
atctggaaca tgttaagtct tttgaaaaca aatactctat gaggatttat gagtggttat    1200
taaaagaact aacacaaaag aaaactcaca aggcaaatat agagattagc cttgatgaat    1260
ttaagttcat gttaatgctt gaaaataact accatgagtt taaaaggctt aaccaatggg    1320
ttttgaaacc aataagtaaa gatttaaaca cttacagcaa tatgaaattg gtggttgata    1380
agcgaggccg cccgactgat acgttgattt tccaagttga actagataga caaatggatc    1440
tcgtaaccga acttgagaac aaccagataa aaatgaatgg tgacaaaata ccaacaacca    1500
ttacatcaga ttcctaccta cgtaacggac taagaaaaac actacgcgat gctttaactg    1560
caaaaattca gctcaccagt tttgaggcaa aattttttgag tgacatgcaa agtaagcatg    1620
atctcaatgg ttcgttctca tggctcacgc aaaaacaacg aaccacacta gagaacatac    1680 tggctaaaata cggaaggatc tgaggttctt atggctcttg tatctatcag tgaagcatca    1740
agactaacaa acaaaagtag aacaactgtt caccgttaga tatcaaaggg aaaactgtcc    1800
atatgcacag atgaaaacgg tgtaaaaaag atagatacat cagagctttt acgagttttt    1860
ggtgcattta agctgttca ccatgaacag atcgacaatg taacagatga acagcatgta    1920
```

```
acacctaata gaacaggtga aaccagtaaa acaaagcaac tagaacatga aattgaacac    1980
ctgagacaac ttgttacagc tcaacagtca cacatagaca gcctgaaaca ggcgatgctg    2040
cttatcgaat caaagctgcc gacaacacgg gagccagtga cgcctcccgt ggggaaaaaa    2100
tcatggcaat tctggaagaa atagcgcttt cagccggcaa acctgaagcc ggatctgcga    2160
ttctgataac aaactagcaa caccagaaca gcccgtttgc gggcagcaaa acccgttatg    2220
cttgtaaacc gttttgtgaa aaattttta aaataaaaaa ggggacctct agggtcccca    2280
attaattagt aatataatct attaaaggtc attcaaaagg tcatccaccg gatcaattcc    2340
cctgctcgcg caggctgggt gccaagctct cgggtaacat caaggcccga tccttggagc    2400
ccttgccctc ccgcacgatg atcgtgccgt gatcgaaatc cagatccttg acccgcagtt    2460
gcaaaccctc actgatccgc atgcccgttc catacagaag ctgggcgaac aaacgatgct    2520
cgccttccag aaaaccgagg atgcgaacca cttcatccgg ggtcagcacc accggcaagc    2580
gccgcgacgg ccgaggtctt ccgatctcct gaagccaggg cagatccgtg cacagcacct    2640
tgccgtagaa gaacagcaag gccgccaatg cctgacgatg cgtggagacc gaaaccttgc    2700
gctcgttcgc cagccaggac agaaatgcct cgacttcgct gctgcccaag gttgccgggt    2760
gacgcacacc gtggaaacgg atgaaggcac gaacccagtg gacataagcc tgttcggttc    2820
gtaagctgta atgcaagtag cgtatgcgct cacgcaactg gtccagaacc ttgaccgaac    2880
gcagcggtgg taacggcgca gtggcggttt tcatggcttg ttatgactgt tttttggg    2940 tacagtctat gcctcgggca tccaagcagc aagcgcgtta cgccgtgggt cgatgtttga    3000
tgttatggag cagcaacgat gttacgcagc agggcagtcg ccctaaaaca aagttaaaca    3060
tcatgaggga agcggtgatc gccgaagtat cgactcaact atcagaggta gttggcgtca    3120
tcgagcgcca tctcgaaccg acgttgctgg ccgtacattt gtacggctcc gcagtggatg    3180
gcggcctgaa gccacacagt gatattgatt tgctggttac ggtgaccgta aggcttgatg    3240
aaacaacgcg gcgagctttg atcaacgacc ttttggaaac ttcggcttcc cctggagaga    3300
gcgagattct ccgcgctgta gaagtcacca ttgttgtgca cgacgacatc attccgtggc    3360
gttatccagc taagcgcgaa ctgcaatttg gagaatggca gcgcaatgac attcttgcag    3420
gtatcttcga gccagccacg atcgacattg atctggctat cttgctgaca aaagcaagag    3480
aacatagcgt tgccttggta ggtccagcgg cggaggaact ctttgatccg gttcctgaac    3540
aggatctatt tgaggcgcta aatgaaacct taacgctatg gaactcgccg cccgactggg    3600
ctggcgatga gcgaaatgta gtgcttacgt tgtcccgcat ttggtacagc gcagtaaccg    3660
gcaaaatcgc gccgaaggat gtcgctgccg actgggcaat ggagcgcctg ccggcccagt    3720
atcagcccgt catacttgaa gctagacagg cttatcttgg acaagaagaa gatcgcttgg    3780
cctcgcgcgc agatcagttg gaagaatttg tccactacgt gaaaggcgag atcaccaagg    3840
tagtcggcaa ataatgtcta acaattcgtt caagccgacg ccgcttcgcg gcgcggctta    3900
actcaagcgt tagatgcact aagcacataa ttgctcacag ccaaactatc aggtcaagtc    3960
tgcttttatt attttaagc gtgcataata agccctacac aaattgggag atatatcatg    4020
aaaggctggc ttttcttgt tatcgcaata gttggcgaag taatcgcaac atccgcatta    4080
aaatctagcg agggctttac taagctgatc cggtggatga ccttttgaat gacctttaat    4140
agattatatt actaattaat tggggaccct agaggtcccc ttttttattt taaaatttt    4200 ttcacaaaac ggtttacaag catacgttgg ccgattcatt aatgcagctg gcacgacagg    4260
```

```
tttcccgact ggaaagcggg cagtgagcgc aacgcaatta atgtgagtta gctcactcat    4320
taggcacccc aggctttaca ctttatgctt ccggctcgta tgttgtgtgg aattgtgagt    4380
tacctagaga gggtgagaat tgccgaacat gcgcataagt ttcccggaca gatttcaggt    4440
ggtcagcagc aacgcgttgc cattgcgcgt tcgctgtgta tgaagccgaa aattatgttg    4500
tttgatgagc aacgtcggc gctcgatcct gagatggtga agaggtgct ggatacgatg    4560 attgggctgg cgcagtcggg tatgacaatg ttgtgtgtaa cacatgagat ggggtttgca    4620
cgaaccgtcg ctgaccgggt aattttatg gatcgtgggg aaatagtgga gcaagctgca    4680
cctgatgaat ttttgcgca tcctaaatca gagcgtacga gggcattttt atcgcaggta    4740
atccattaat tgaatgttag ttcgaaaagc aaaaaggcca tcctttcgga tggcctttcg    4800
cttgatttga tgtctggcag tttatggcgg gcgtcctgcc cgccaccctc cgggccgttg    4860
cttcgcaacg ttcaaatccg ctcccggcgg atttgtccta ctcgggagag tgttcaccga    4920
caaacaacag ataaaacaaa agcccagtc ttccgactga ccttttgtt ttatttgatg    4980 tctggcagtt ccctactctc gcatggggag acccacact accatcggcg ctacggcggt    5040
ttcacttctg agttcggcat ggggtcaggt gggaccaccg cgctactgcc gccagacaaa    5100
ttcttttcta atctgccgaa cttaacctaa aaagtggtg ctgatacccca gagtcgaact    5160 ggggacctca cccttaccaa gggtgcgctc taccaactga gccatatcag cacgctaaat    5220
ttgatgcctg gcagttccct actctcgcat ggggagaccc cacactacca tcggcgctac    5280
ggcgtttcac ttctgagttc ggcatggggt caggtgggac caccgcgcta cggccgccag    5340
gcaaattctg ttttatcaga ccgcttctgc gttctgattt aatctgtatc aggctgaaaa    5400
tcttctctca tccggataac aatttcacac aggaaacagc tatgaccatg attacgccaa    5460
gctcgagctc gaattcactg gccgtcgttt tacaacgtcg tgactgggaa aaccctggcg    5520
ttacccaact taatcgcctt gcagcacatc ccccttcgc cagctggcgt aatagcgaag    5580
aggcccgcac cgatcgccct tcccaacagt tgcgcagcct gaatggcgaa tggcgcctga    5640
tgcggtattt tctccttacg catctgtgcg gtatttcaca ccgcatatgg tgcactctca    5700
gtacaatctg ctctgatgcc gcatagttaa gccagccccg acaccgcca acaccgctg    5760 acgaattc                                                            5768
```

<210> SEQ ID NO 18
<211> LENGTH: 1053
<212> TYPE: DNA
<213> ORGANISM: Escherichia coli
<220> FEATURE:
<221> NAME/KEY: gene
<222> LOCATION: (1)..(1053)
<223> OTHER INFORMATION: DNA sequence of the coding region of the wild
      type aroG gene

<400> SEQUENCE: 18

```
atgaattatc agaacgacga tttacgcatc aaagaaatca agagttact tcctcctgtc     60 gcattgctgg aaaaattccc cgctactgaa atgccgcgaa atacggttgc ccatgccga    120 aaagcgatcc ataagatcct gaaaggtaat gatgatcgcc tgttggttgt gattggccca    180
tgctcaattc atgatcctgt cgcggcaaaa gagtatgcca ctcgcttgct ggcgctgcgt    240
gaagagctga agatgagct ggaaatcgta atgcgcgtct attttgaaaa gccgcgtacc    300
acggtgggct ggaaagggct gattaacgat ccgcatatgg ataatagctt ccagatcaac    360
gacggtctgc gtatagcccg taaattgctg cttgatatta cgacagcgg tctgccagcg    420
```

-continued

| | |
|---|---|
| gcaggtgagt ttctcgatat gatcacccca caatatctcg ctgacctgat gagctgggcc | 480 |
| gcaattggcg cacgtaccac cgaatcgcag gtgcaccgcg aactggcatc agggctttct | 540 |
| tgtccggtcg gcttcaaaaa tggcaccgac ggtacgatta aagtggctat cgatgccatt | 600 |
| aatgccgccg gtgcgccgca ctgcttcctg tccgtaacga atgggggca ttcggcgatt | 660 |
| gtgaatacca gcggtaacgg cgattgccat atcattctgc gcggcggtaa agagcctaac | 720 |
| tacagcgcga agcacgttgc tgaagtgaaa gaagggctga caaagcagg cctgccagca | 780 |
| caggtgatga tcgatttcag ccatgctaac tcgtccaaac aattcaaaaa gcagatggat | 840 |
| gtttgtgctg acgtttgcca gcagattgcc ggtggcgaaa aggccattat tggcgtgatg | 900 |
| gtggaaagcc atctggtgga aggcaatcag agcctcgaga gcggggagcc gctggcctac | 960 |
| ggtaagagca tcaccgatgc ctgcatcggc tgggaagata ccgatgctct gttacgtcaa | 1020 |
| ctggcgaatg cagtaaaagc gcgtcgcggg taa | 1053 |

<210> SEQ ID NO 19
<211> LENGTH: 8820
<212> TYPE: DNA
<213> ORGANISM: Escherichia coli
<220> FEATURE:
<221> NAME/KEY: misc_feature
<222> LOCATION: (1)..(8820)
<223> OTHER INFORMATION: DNA sequence of the plasmid pMH28F
<220> FEATURE:
<221> NAME/KEY: misc_feature
<222> LOCATION: (5894)..(5894)
<223> OTHER INFORMATION: n is a, c, g, or t

<400> SEQUENCE: 19

| | |
|---|---|
| gttgacagta agacgggtaa gcctgttgat gataccgctg ccttactggg tgcattagcc | 60 |
| agtctgaatg acctgtcacg ggataatccg aagtggtcag actggaaaat cagagggcag | 120 |
| gaactgctga acagcaaaaa gtcagatagc accacatagc agacccgcca taaaacgccc | 180 |
| tgagaagccc gtgacgggct tttcttgtat tatgggtagt ttccttgcat gaatccataa | 240 |
| aaggcgcctg tagtgccatt taccccattt cactgccaga gccgtgagcg cagcgaactg | 300 |
| aatgtcacga aaaagacagc gactcaggtg cctgatggtc ggagacaaaa ggaatattca | 360 |
| gcgatttgcc cgagcttgcg agggtgctac ttaagccttt agggttttaa ggtctgtttt | 420 |
| gtagaggagc aaacagcgtt tgcgacatcc ttttgtaata ctgcggaact gactaaagta | 480 |
| gtgagttata cacagggctg ggatctattc ttttttatctt ttttttattct ttctttattc | 540 |
| tataaattat aaccacttga atataaacaa aaaaaacaca caaaggtcta gcggaattta | 600 |
| cagagggtct agcagaattt acaagttttc cagcaaaggt ctagcagaat ttacagatac | 660 |
| ccacaactca aaggaaaagg actagtaatt atcattgact agcccatctc aattggtata | 720 |
| gtgattaaaa tcacctagac caattgagat gtatgtctga attagttgtt ttcaaagcaa | 780 |
| atgaactagc gattagtcgc tatgacttaa cggagcatga accaagcta atttatgct | 840 |
| gtgtggcact actcaacccc acgattgaaa accctacaag gaaagaacgg acggtatcgt | 900 |
| tcacttataa ccaatacgct cagatgatga acatcagtag ggaaaatgct tatggtgtat | 960 |
| tagctaaagc aaccagagag ctgatgacga gaactgtgga atcaggaat cctttggtta | 1020 |
| aaggctttga gattttccag tggacaaact atgccaagtt ctcaagcgaa aaattagaat | 1080 |
| tagtttttag tgaagagata ttgccttatc ttttccagtt aaaaaaattc ataaaatata | 1140 |
| atctggaaca tgttaagtct tttgaaaaca aatactctat gaggatttat gagtggttat | 1200 |
| taaaagaact aacacaaaag aaaactcaca aggcaaatat agagattagc cttgatgaat | 1260 |

```
ttaagttcat gttaatgctt gaaaataact accatgagtt taaaaggctt aaccaatggg    1320 tttttgaaacc aataagtaaa gatttaaaca cttacagcaa tatgaaattg gtggttgata    1380
agcgaggccg cccgactgat acgttgattt tccaagttga actagataga caaatggatc    1440
tcgtaaccga acttgagaac aaccagataa aaatgaatgg tgacaaaata ccaacaacca    1500
ttacatcaga ttcctaccta cgtaacggac taagaaaaac actacacgat gctttaactg    1560
caaaaattca gctcaccagt tttgaggcaa aatttttgag tgacatgcaa agtaagcatg    1620
atctcaatgg ttcgttctca tggctcacgc aaaaacaacg aaccacacta gagaacatac    1680
tggctaaata cggaaggatc tgaggttctt atggctcttg tatctatcag tgaagcatca    1740
agactaacaa acaaaagtag aacaactgtt caccgttaga tatcaaaggg aaaactgtcc    1800
atatgcacag atgaaaacgg tgtaaaaaag atagatacat cagagctttt acgagttttt    1860
ggtgcattta agctgttca ccatgaacag atcgacaatg taacagatga acagcatgta    1920
acacctaata gaacaggtga aaccagtaaa acaaagcaac tagaacatga aattgaacac    1980
ctgagacaac ttgttacagc tcaacagtca cacatagaca gcctgaaaca ggcgatgctg    2040
cttatcgaat caaagctgcc gacaacacgg gagccagtga cgcctcccgt ggggaaaaaa    2100
tcatggcaat tctggaagaa atagcgcttt cagccggcaa acctgaagcc ggatctgcga    2160
ttctgataac aaactagcaa caccagaaca gcccgtttgc gggcagcaaa acccgttatg    2220
cttgtaaacc gttttgtgaa aaaattttta aataaaaaa ggggacctct agggtcccca    2280
attaattagt aatataatct attaaaggtc attcaaaagg tcatccaccg gatcaattcc    2340
cctgctcgcg caggctgggt gccaagctct cgggtaacat caaggcccga tccttggagc    2400
ccttgccctc ccgcacgatg atcgtgccgt gatcgaaatc cagatccttg acccgcagtt    2460
gcaaaccctc actgatccgc atgcccgttc catacagaag ctgggcgaac aaacgatgct    2520
cgccttccag aaaaccgagg atgcgaacca cttcatccgg ggtcagcacc accggcaagc    2580
gccgcgacgg ccgaggtctt ccgatctcct gaagccaggg cagatccgtg cacagcacct    2640
tgccgtagaa gaacagcaag gccgccaatg cctgacgatg cgtggagacc gaaaccttgc    2700
gctcgttcgc cagccaggac agaaatgcct cgacttcgct gctgcccaag gttgccgggt    2760
gacgcacacc gtggaaacgg atgaaggcac gaacccagtg gacataagcc tgttcggttc    2820
gtaagctgta atgcaagtag cgtatgcgct cacgcaactg gtccagaacc ttgaccgaac    2880
gcagcggtgg taacggcgca gtggcggttt tcatggcttg ttatgactgt ttttttgggg    2940
tacagtctat gcctcgggca tccaagcagc aagcgcgtta cgccgtgggt cgatgtttga    3000
tgttatggag cagcaacgat gttacgcagc agggcagtcg ccctaaaaca aagttaaaca    3060
tcatgaggga agcggtgatc gccgaagtat cgactcaact atcagaggta gttggcgtca    3120
tcgagcgcca tctcgaaccg acgttgctgg ccgtacattt gtacggctcc gcagtggatg    3180
gcggcctgaa gccacacagt gatattgatt tgctggttac ggtgaccgta aggcttgatg    3240
aaacaacgcg gcgagctttg atcaacgacc ttttggaaac ttcggcttcc cctggagaga    3300
gcgagattct ccgcgctgta gaagtcacca ttgttgtgca cgacgacatc attccgtggc    3360
gttatccagc taagcgcgaa ctgcaatttg gagaatggca gcgcaatgac attcttgcag    3420
gtatcttcga gccagccacg atcgacattg atctggctat cttgctgaca aaagcaagag    3480
aacatagcgt tgccttggta ggtccagcgg cggaggaact ctttgatccg gttcctgaac    3540
aggatctatt tgaggcgcta aatgaaacct taacgctatg gaactcgccg cccgactggg    3600
```

```
ctggcgatga gcgaaatgta gtgcttacgt tgtcccgcat ttggtacagc gcagtaaccg    3660
gcaaaatcgc gccgaaggat gtcgctgccg actgggcaat ggagcgcctg ccggcccagt    3720
atcagcccgt catacttgaa gctagacagg cttatcttgg acaagaagaa gatcgcttgg    3780
cctcgcgcgc agatcagttg gaagaatttg tccactacgt gaaaggcgag atcaccaagg    3840
tagtcggcaa ataatgtcta acaattcgtt caagccgacg ccgcttcgcg gcgcggctta    3900
actcaagcgt tagatgcact aagcacataa ttgctcacag ccaaactatc aggtcaagtc    3960
tgcttttatt atttttaagc gtgcataata agccctacac aaattgggag atatatcatg    4020
aaaggctggc ttttttcttgt tatcgcaata gttggcgaag taatcgcaac atccgcatta    4080
aaatctagcg agggctttac taagctgatc cggtggatga ccttttgaat gacctttaat    4140
agattatatt actaattaat tgggaccct agaggtcccc ttttttattt taaaaatttt    4200
ttcacaaaac ggtttacaag catacgttgg ccgattcatt aatgcagctg gcacgacagg    4260
tttcccgact ggaaagcggg cagtgagcgc aacgcaatta atgtgagtta gctcactcat    4320
taggcacccc aggctttaca ctttatgctt ccggctcgta tgttgtgtgg aattgtgagt    4380
tacctagaga gggtgagaat tgccgaacat gcgcataagt ttcccggaca gatttcaggt    4440
ggtcagcagc aacgcgttgc cattgcgcgt tcgctgtgta tgaagccgaa aattatgttg    4500
tttgatgagc caacgtcggc gctcgatcct gagatggtga agaggtgct ggatacgatg    4560 attgggctgg cgcagtcggg tatgacaatg ttgtgtgtaa cacatgagat ggggtttgca    4620
cgaaccgtcg ctgaccgggt aattttatg gatcgtgggg aaatagtgga gcaagctgca    4680
cctgatgaat ttttgcgca tcctaaatca gagcgtacga gggcattttt atcgcaggta    4740
atccattaat tgaatgttag ttcgaaaagc aaaaaggcca tcctttcgga tggccttttcg    4800 cttgatttga tgtctggcag tttatggcgg gcgtcctgcc cgccaccctc cgggccgttg    4860
cttcgcaacg ttcaaatccg gtgacggaag atcacttcgc agaataaata atcctggtg    4920 tccctgttga taccgggaag ccctgggcca acttttggcg aaaatgagac gttgatcggc    4980
acgtaagagg ttccaacttt caccataatg aaataagatc actaccgggc gtattttttg    5040
agttatcgag attttcagga gctaaggaag ctaaaatgga gaaaaaatc actggatata    5100 ccaccgttga tatatcccaa tggcatcgta aagaacattt tgaggcattt cagtcagttg    5160
ctcaatgtac ctataaccag accgttcagc tggatattac ggcctttta aagaccgtaa    5220 agaaaaataa gcacaagttt tatccggcct ttattcacat tcttgcccgc ctgatgaatg    5280
ctcatccgga attccgtatg gcaatgaaag acggtgagct ggtgatatgg gatagtgttc    5340
acccttgtta caccgtttc catgagcaaa ctgaaacgtt ttcatcgctc tggagtgaat    5400
accacgacga tttccggcag tttctacaca tatattcgca agatgtggcg tgttacggtg    5460
aaaacctggc ctatttccct aaagggttta ttgagaatat gttttttcgtc tcagccaatc    5520 cctgggtgag tttcaccagt tttgatttaa acgtggccaa tatggacaac ttcttcgccc    5580
ccgttttcac catgggcaaa tattatacgc aaggcgacaa ggtgctgatg ccgctggcga    5640
ttcaggttca tcatgccgtt tgtgatggct tccatgtcgg cagaatgctt aatgaattac    5700
aacagtactg cgatgagtgg cagggcgggg cgtaattttt ttaaggcagt tattggtgcc    5760
cttaaacgcc tggtgctacg cctgaataag tgataataag cggatgaatg gcagaaattc    5820
gaaagcaaat tcgacccggt cgtcggttca gggcagggtc gttaaatagc cgcttatgtc    5880
tattgctggt ttantcggta cccggggatc gcggccgcgg accggatccc atcacatata    5940
cctgccgttc actattattt agtgaaatga gatattatga tatttctga attgtgatta    6000
```

```
aaaaggcaac tttatgccca tgcaacagaa actataaaaa atacagagaa tgaaaagaaa    6060
cagatagatt ttttagttct ttaggcccgt agtctgcaaa tccttttatg attttctatc    6120
aaacaaaaga ggaaaataga ccagttgcaa tccaaacgag agtctaatag aatgaggtcg    6180
aaaagtaaat cgcgcgggtt tgttactgat aaagcaggca agacctaaaa tgtgtaaagg    6240
gcaaagtgta tactttggcg tcacccctta catattttag gtctttttt attgtgcgta     6300 actaacttgc catcttcaaa caggagggct ggaagaagca gaccgctaac acagtacata    6360
aaaaaggaga catgaacgat gaacatcaaa aagtttgcaa aacaagcaac agtattaacc    6420
tttactaccg cactgctggc aggaggcgca actcaagcgt ttgcgaaaga aacgaaccaa    6480
aagccatata aggaaacata cggcatttcc catattacac gccatgatat gctgcaaatc    6540
cctgaacagc aaaaaaatga aaaatatcaa gttcctgaat tcgattcgtc cacaattaaa    6600
aatatctctt ctgcaaaagg cctggacgtt tgggacagct ggccattaca aaacgctgac    6660
ggcactgtcg caaactatca cggctaccac atcgtctttg cattagccgg agatcctaaa    6720
aatgcggatg acacatcgat ttacatgttc tatcaaaaag tcggcgaaac ttctattgac    6780
agctggaaaa acgctggccg cgtctttaaa gacagcgaca aattcgatgc aaatgattct    6840
atcctaaaag accaaacaca agaatggtca ggttcagcca catttacatc tgacggaaaa    6900
atccgtttat tctacactga tttctccggt aaacattacg gcaaacaaac actgacaact    6960
gcacaagtta acgtatcagc atcagacagc tctttgaaca tcaacggtgt agaggattat    7020
aaatcaatct ttgacggtga cggaaaaacg tatcaaaatg tacagcagtt catcgatgaa    7080
ggcaactaca gctcaggcga caaccatacg ctgagagatc ctcactacgt agaagataaa    7140
ggccacaaat acttagtatt tgaagcaaac actggaactg aagatggcta ccaaggcgaa    7200
gaatctttat ttaacaaagc atactatggc aaaagcacat cattcttccg tcaagaaagt    7260
caaaaacttc tgcaaagcga taaaaaacgc acggctgagt tagcaaacgg cgctctcggt    7320
atgattgagc taaacgatga ttacacactg aaaaaagtga tgaaaccgct gattgcatct    7380
aacacagtaa cagatgaaat tgaacgcgcg aacgtcttta aaatgaacgg caaatggtac    7440
ctgttcactg actcccgcgg atcaaaaatg acgattgacg gcattacgtc taacgatatt    7500
tacatgcttg gttatgtttc taattctta actggcccat acaagccgct gaacaaaact    7560
ggccttgtgt taaaaatgga tcttgatcct aacgatgtaa cctttactta ctcacacttc    7620
gctgtacctc aagcgaaagg aaacaatgtc gtgattacaa gctatatgac aaacagagga    7680
ttctacgcag acaaacaatc aacgtttgcg ccgagcttcc tgctgaacat caaaggcaag    7740
aaaacatctg ttgtcaaaga cagcatcctt gaacaaggac aattaacagt taacaaataa    7800
aaacgcaaaa gaaaatgcca atatcctatt ggcattttct tttatttctt ccatttaaat    7860
ggatgcatgc gctagcggag tgtatactgg cttactatgt tggcactgat gagggtgtca    7920
gtgaagtgct tcctcccggc ggatttgtcc tactcgggag agtgttcacc gacaaacaac    7980
agataaaaca aaaggcccag tcttccgact gagccttttg ttttatttga tgtctggcag    8040
ttccctactc tcgcatgggg agaccccaca ctaccatcgg cgctacggcg gtttcacttc    8100
tgagttcggc atggggtcag gtgggaccac gcgctactg ccgccagaca aattctttc     8160 taatctgccg aactttaacc taaaagtgg tgctgatacc cagagtcgaa ctggggacct    8220 caccccttacc aagggtgcgc tctaccaact gagccataatc agcacgctaa atttgatgcc   8280
tggcagttcc ctactctcgc atggggagac cccacactac catcggcgct acggcgtttc    8340
```

-continued

| | |
|---|---:|
| acttctgagt tcggcatggg gtcaggtggg accaccgcgc tacggccgcc aggcaaattc | 8400 |
| tgttttatca gaccgcttct gcgttctgat ttaatctgta tcaggctgaa aatcttctct | 8460 |
| catccggata acaatttcac acaggaaaca gctatgacca tgattacgcc aagctcgagc | 8520 |
| tcgaattcac tggccgtcgt tttacaacgt cgtgactggg aaaaccctgg cgttacccaa | 8580 |
| cttaatcgcc ttgcagcaca tcccccttc gccagctggc gtaatagcga gaggcccgc | 8640 |
| accgatcgcc cttcccaaca gttgcgcagc ctgaatggcg aatggcgcct gatgcggtat | 8700 |
| tttctcctta cgcatctgtg cggtatttca caccgcatat ggtgcactct cagtacaatc | 8760 |
| tgctctgatg ccgcatagtt aagccagccc cgacacccgc caacacccgc tgacgaattc | 8820 |

<210> SEQ ID NO 20
<211> LENGTH: 4774
<212> TYPE: DNA
<213> ORGANISM: Escherichia coli
<220> FEATURE:
<221> NAME/KEY: misc_feature
<222> LOCATION: (1)..(4774)

<400> SEQUENCE: 20

| | |
|---|---:|
| gttgacagta agacgggtaa gcctgttgat gataccgctg ccttactggg tgcattagcc | 60 |
| agtctgaatg acctgtcacg ggataatccg aagtggtcag actggaaaat cagagggcag | 120 |
| gaactgctga acagcaaaaa gtcagatagc accacatagc agaccgcca taaaacgccc | 180 |
| tgagaagccc gtgacgggct tttcttgtat tatgggtagt ttccttgcat gaatccataa | 240 |
| aaggcgcctg tagtgccatt taccccatt cactgccaga gccgtgagcg cagcgaactg | 300 |
| aatgtcacga aaagacagc gactcaggtg cctgatggtc ggagacaaaa ggaatattca | 360 |
| gcgatttgcc cgagcttgcg agggtgctac ttaagccttt agggttttaa ggtctgtttt | 420 |
| gtagaggagc aaacagcgtt tgcgacatcc ttttgtaata ctgcggaact gactaaagta | 480 |
| gtgagttata cacagggctg ggatctattc ttttttatctt ttttttattct ttctttattc | 540 |
| tataaattat aaccacttga atataaacaa aaaaaacaca caaaggtcta gcggaattta | 600 |
| cagagggtct agcagaattt acaagttttc cagcaaaggt ctagcagaat ttacagatac | 660 |
| ccacaactca aaggaaaagg actagtaatt atcattgact agcccatctc aattggtata | 720 |
| gtgattaaaa tcacctagac caattgagat gtatgtctga attagttgtt ttcaaagcaa | 780 |
| atgaactagc gattagtcgc tatgacttaa cggagcatga aaccaagcta atttatgct | 840 |
| gtgtggcact actcaacccc acgattgaaa accctacaag gaaagaacgg acggtatcgt | 900 |
| tcacttataa ccaatacgct cagatgatga acatcagtag ggaaaatgct tatggtgtat | 960 |
| tagctaaagc aaccagagag ctgatgacga gaactgtgga atcaggaat cctttggtta | 1020 |
| aaggctttga gattttccag tggacaaact atgccaagtt ctcaagcgaa aaattagaat | 1080 |
| tagttttag tgaagagata ttgccttatc ttttccagtt aaaaaaattc ataaaatata | 1140 |
| atctggaaca tgttaagtct tttgaaaaca aatactctat gaggatttat gagtggttat | 1200 |
| taaaagaact aacacaaaag aaaactcaca aggcaaatat agagattagc cttgatgaat | 1260 |
| ttaagttcat gttaatgctt gaaaataact accatgagtt taaaaggctt aaccaatggg | 1320 |
| ttttgaaacc aataagtaaa gatttaaaca cttacagcaa tatgaaattg gtggttgata | 1380 |
| agcgaggccg cccgactgat acgttgattt tccaagttga actagataga caaatggatc | 1440 |
| tcgtaaccga acttgagaac aaccagataa aaatgaatgg tgacaaaata ccaacaacca | 1500 |
| ttacatcaga ttcctaccta cgtaacggac taagaaaaac actacacgat gctttaactg | 1560 |

```
caaaaattca gctcaccagt tttgaggcaa aattttttgag tgacatgcaa agtaagcatg   1620
atctcaatgg ttcgttctca tggctcacgc aaaaacaacg aaccacacta gagaacatac   1680
tggctaaata cggaaggatc tgaggttctt atggctcttg tatctatcag tgaagcatca   1740
agactaacaa acaaaagtag aacaactgtt caccgttaga tatcaaaggg aaaactgtcc   1800
atatgcacag atgaaaacgg tgtaaaaaag atagatacat cagagctttt acgagttttt   1860
ggtgcattta agctgttca ccatgaacag atcgacaatg taacagatga acagcatgta   1920
acacctaata gaacaggtga aaccagtaaa acaaagcaac tagaacatga aattgaacac   1980
ctgagacaac ttgttacagc tcaacagtca cacatagaca gcctgaaaca ggcgatgctg   2040
cttatcgaat caaagctgcc gacaacacgg gagccagtga cgcctcccgt ggggaaaaaa   2100
tcatggcaat tctggaagaa atagcgcttt cagccggcaa acctgaagcc ggatctgcga   2160
ttctgataac aaactagcaa caccagaaca gcccgtttgc gggcagcaaa accgttatg   2220 cttgtaaacc gttttgtgaa aaatttta aataaaaaa ggggacctct agggtcccca   2280
attaattagt aatataatct attaaaggtc attcaaaagg tcatccaccg gatcaattcc   2340
cctgctcgcg caggctgggt gccaagctct cgggtaacat caaggcccga tccttggagc   2400
ccttgccctc ccgcacgatg atcgtgccgt gatcgaaatc cagatccttg acccgcagtt   2460
gcaaaccctc actgatccgc atgcccgttc catacagaag ctgggcgaac aaacgatgct   2520
cgccttccag aaaaccgagg atgcgaacca cttcatccgg ggtcagcacc accggcaagc   2580
gccgcgacgg ccgaggtctt ccgatctcct gaagccaggg cagatccgtg cacagcacct   2640
tgccgtagaa gaacagcaag gccgccaatg cctgacgatg cgtggagacc gaaaccttgc   2700
gctcgttcgc cagccaggac agaaatgcct cgacttcgct gctgcccaag gttgccgggt   2760
gacgcacacc gtggaaacgg atgaaggcac gaacccagtg gacataagcc tgttcggttc   2820
gtaagctgta atgcaagtag cgtatgcgct cacgcaactg gtccagaacc ttgaccgaac   2880
gcagcggtgg taacgcgca gtggcggttt tcatggcttg ttatgactgt tttttttggg   2940
tacagtctat gcctcgggca tccaagcagc aagcgcgtta cgccgtgggt cgatgtttga   3000
tgttatggag cagcaacgat gttacgcagc agggcagtcg ccctaaaaca aagttaaaca   3060
tcatgaggga agcggtgatc gccgaagtat cgactcaact atcagaggta gttggcgtca   3120
tcgagcgcca tctcgaaccg acgttgctgg ccgtacattt gtacggctcc gcagtggatg   3180
gcggcctgaa gccacacagt gatattgatt tgctggttac ggtgaccgta aggcttgatg   3240
aaacaacgcg gcgagctttg atcaacgacc ttttggaaac ttcggcttcc cctggagaga   3300
gcgagattct ccgcgctgta gaagtcacca ttgttgtgca cgacgacatc attccgtggc   3360
gttatccagc taagcgcgaa ctgcaatttg gagaatggca gcgcaatgac attcttgcag   3420
gtatcttcga gccagccacg atcgacattg atctggctat cttgctgaca aaagcaagag   3480
aacatagcgt tgccttggta ggtccagcgg cggaggaact ctttgatccg gttcctgaac   3540
aggatctatt tgaggcgcta atgaaaccct aacgctatg gaactcgccg cccgactggg   3600
ctggcgatga gcgaaatgta gtgcttacgt tgtcccgcat ttggtacagc gcagtaaccg   3660
gcaaaatcgc gccgaaggat gtcgctgccg actgggcaat ggagcgcctg ccggcccagt   3720
atcagcccgt catacttgaa gctagacagg cttatcttgg acaagaagaa gatcgcttgg   3780
cctcgcgcgc agatcagttg gaagaatttt tccactacgt gaaaggcgag atcaccaagg   3840
tagtcggcaa ataatgtcta acaattcgtt caagccgacg ccgcttcgcg gcgcggctta   3900
actcaagcgt tagatgcact aagcacataa ttgctcacag ccaaactatc aggtcaagtc   3960
```

```
tgcttttatt attttttaagc gtgcataata agccctacac aaattgggag atatatcatg   4020
aaaggctggc tttttcttgt tatcgcaata gttggcgaag taatcgcaac atccgcatta   4080
aaatctagcg agggctttac taagctgatc cggtggatga cctttttgaat gacctttaat   4140 agattatatt actaattaat tggggaccct agaggtcccc ttttttattt taaaaatttt   4200
ttcacaaaac ggtttacaag catacgttgg ccgattcatt aatgcagctg cacgacagg    4260 tttcccgact ggaaagcggg cagtgagcgc aacgcaatta atgtgagtta gctcactcat   4320
taggcacccc aggctttaca ctttatgctt ccggctcgta tgttgtgtgg aattgtgagc   4380
ggataacaat ttcacacagg aaacagctat gaccatgatt acgccaagct tgcatgcctg   4440
caggtcgact ctagaggatc cccgggtacc gagctcgaat tcactggccg tcgttttaca   4500
acgtcgtgac tgggaaaacc ctggcgttac ccaacttaat cgccttgcag cacatccccc   4560
tttcgccagc tggcgtaata gcgaagaggc ccgcaccgat cgcccttccc aacagttgcg   4620
cagcctgaat ggcgaatggc gcctgatgcg gtattttctc cttacgcatc tgtgcggtat   4680
ttcacaccgc atatggtgca ctctcagtac aatctgctct gatgccgcat agttaagcca   4740
gccccgacac ccgccaacac ccgctgacga attc                               4774
```

<210> SEQ ID NO 21
<211> LENGTH: 6432
<212> TYPE: DNA
<213> ORGANISM: Escherichia coli
<220> FEATURE:
<221> NAME/KEY: misc_feature
<222> LOCATION: (1)..(6432)
<223> OTHER INFORMATION: DNA sequence of the plasmid pMG27

<400> SEQUENCE: 21

```
gttgacagta agacgggtaa gcctgttgat gataccgctg ccttactggg tgcattagcc     60
agtctgaatg acctgtcacg ggataatccg aagtggtcag actggaaaat cagagggcag    120
gaactgctga acagcaaaaa gtcagatagc accacatagc agacccgcca taaaacgccc    180
tgagaagccc gtgacgggct tttcttgtat tatgggtagt ttccttgcat gaatccataa    240
aaggcgcctg tagtgccatt tacccccatt cactgccaga gccgtgagcg cagcgaactg    300
aatgtcacga aaagacagc gactcaggtg cctgatggtc ggagacaaaa ggaatattca    360
gcgatttgcc cgagcttgcg agggtgctac ttaagccttt agggttttaa ggtctgtttt    420
gtagaggagc aaacagcgtt tgcgacatcc ttttgtaata ctgcggaact gactaaagta    480
gtgagttata cacagggctg ggatctattc tttttatctt ttttttattct ttctttattc   540 tataaattat aaccacttga atataaacaa aaaaacaca caaaggtcta gcggaattta   600
cagggggtct agcagaattt acaagttttc cagcaaaggt ctagcagaat ttacagatac   660
ccacaactca aggaaaagg actagtaatt atcattgact agcccatctc aattggtata   720
gtgattaaaa tcacctagac caattgagat gtatgtctga attagttgtt tcaaagcaa    780 atgaactagc gattagtcgc tatgacttaa cggagcatga accaagcta tttttatgct    840 gtgtggcact actcaacccc acgattgaaa accctacaag gaaagaacgg acggtatcgt    900
tcacttataa ccaatacgct cagatgatga acatcagtag ggaaaatgct tatggtgtat    960
tagctaaagc aaccagagag ctgatgacga gaactgtgga aatcaggaat cctttggtta   1020
aaggctttga gattttccag tggacaaact atgccaagtt ctcaagcgaa aaattagaat   1080 tagttttttag tgaagagata ttgccttatc tttttccagtt aaaaaaattc ataaaatata   1140
```

-continued

```
atctggaaca tgttaagtct tttgaaaaca aatactctat gaggatttat gagtggttat      1200
taaaagaact aacacaaaag aaaactcaca aggcaaatat agagattagc cttgatgaat      1260
ttaagttcat gttaatgctt gaaaataact accatgagtt taaaaggctt aaccaatggg      1320
ttttgaaacc aataagtaaa gatttaaaca cttacagcaa tatgaaattg gtggttgata      1380
agcgaggccg cccgactgat acgttgattt ccaagttga actagataga caaatggatc       1440
tcgtaaccga acttgagaac aaccagataa aaatgaatgg tgacaaaata ccaacaacca      1500
ttacatcaga ttcctaccta cgtaacggac taagaaaaac actacacgat gctttaactg      1560
caaaaattca gctcaccagt tttgaggcaa aattttttgag tgacatgcaa agtaagcatg     1620
atctcaatgg ttcgttctca tggctcacgc aaaaacaacg aaccacacta gagaacatac     1680
tggctaaata cggaaggatc tgaggttctt atggctcttg tatctatcag tgaagcatca     1740
agactaacaa acaaaagtag aacaactgtt caccgttaga tatcaaaggg aaaactgtcc     1800
atatgcacag atgaaaacgg tgtaaaaaag atagatacat cagagctttt acgagttttt      1860
ggtgcattta aagctgttca ccatgaacag atcgacaatg taacagatga acagcatgta     1920
acacctaata aacaggtga aaccagtaaa acaaagcaac tagaacatga aattgaacac      1980
ctgagacaac ttgttacagc tcaacagtca cacatagaca gcctgaaaca ggcgatgctg     2040
cttatcgaat caaagctgcc gacaacacgg gagccagtga cgcctcccgt ggggaaaaaa    2100
tcatggcaat tctggaagaa atagcgcttt cagccggcaa acctgaagcc ggatctgcga    2160
ttctgataac aaactagcaa caccagaaca gcccgtttgc gggcagcaaa acccgttatg     2220
cttgtaaacc gttttgtgaa aaaatttta aaataaaaaa ggggacctct agggtcccca     2280
attaattagt aatataatct attaaaggtc attcaaaagg tcatccaccg gatcaattcc    2340
cctgctcgcg caggctgggt gccaagctct cgggtaacat caaggcccga tccttggagc    2400
ccttgccctc ccgcacgatg atcgtgccgt gatcgaaatc cagatccttg acccgcagtt    2460
gcaaaccctc actgatccgc atgcccgttc catacagaag ctgggcgaac aaacgatgct    2520
cgccttccag aaaaccgagg atgcgaacca cttcatccgg ggtcagcacc accggcaagc    2580
gccgcgacgg ccgaggtctt ccgatctcct gaagccaggg cagatccgtg cacagcacct    2640
tgccgtagaa gaacagcaag gccgccaatg cctgacgatg cgtggagacc gaaaccttgc    2700
gctcgttcgc cagccaggac agaaatgcct cgacttcgct gctgcccaag gttgccgggt    2760
gacgcacacc gtggaaacgg atgaaggcac gaacccagtg gacataagcc tgttcggttc    2820
gtaagctgta atgcaagtag cgtatgcgct cacgcaactg gtccagaacc ttgaccgaac    2880
gcagcggtgg taacggcgca gtggcggttt tcatggcttg ttatgactgt tttttttgggg   2940 tacagtctat gcctcgggca tccaagcagc aagcgcgtta cgccgtgggt cgatgtttga    3000
tgttatggag cagcaacgat gttacgcagc agggcagtcg ccctaaaaca aagttaaaca    3060
tcatgaggga agcggtgatc gccgaagtat cgactcaact atcagaggta gttggcgtca    3120
tcgagcgcca tctcgaaccg acgttgctgg ccgtacattt gtacggctcc gcagtggatg    3180
gcggcctgaa gccacacagt gatattgatt tgctggttac ggtgaccgta aggcttgatg    3240
aaacaacgcg gcgagctttg atcaacgacc ttttggaaac ttcggcttcc cctggagaga    3300
gcgagattct ccgcgctgta aagtcacca ttgttgtgca cgacgacatc attccgtggc     3360
gttatccagc taagcgcgaa ctgcaatttg gagaatggca gcgcaatgac attcttgcag    3420
gtatcttcga gccagccacg atcgacattg atctggctat cttgctgaca aaagcaagag    3480
aacatagcgt tgccttggta ggtccagcgg cggaggaact cttttgatccg gttcctgaac    3540
```

```
aggatctatt tgaggcgcta aatgaaacct taacgctatg gaactcgccg cccgactggg    3600
ctggcgatga gcgaaatgta gtgcttacgt tgtcccgcat ttggtacagc gcagtaaccg    3660
gcaaaatcgc gccgaaggat gtcgctgccg actgggcaat ggagcgcctg ccggcccagt    3720
atcagcccgt catacttgaa gctagacagg cttatcttgg acaagaagaa gatcgcttgg    3780
cctcgcgcgc agatcagttg gaagaatttg tccactacgt gaaaggcgag atcaccaagg    3840
tagtcggcaa ataatgtcta acaattcgtt caagccgacg ccgcttcgcg gcgcggctta    3900
actcaagcgt tagatgcact aagcacataa ttgctcacag ccaaactatc aggtcaagtc    3960
tgcttttatt attttttaagc gtgcataata agccctacac aaattgggag atatatcatg    4020
aaaggctggc ttttcttgt tatcgcaata gttggcgaag taatcgcaac atccgcatta     4080
aaatctagcg agggctttac taagctgatc cggtggatga cctttgaat gacctttaat      4140 agattatatt actaattaat tggggaccct agaggtcccc ttttttattt taaaaatttt     4200
ttcacaaaac ggtttacaag catacgttgg ccgattcatt aatgcagctg gcacgacagg    4260
tttcccgact ggaaagcggg cagtgagcgc aacgcaatta atgtgagtta gctcactcat    4320
taggcacccc aggctttaca ctttatgctt ccggctcgta tgttgtgtgg aattgtgagc    4380
ggataacaat ttcacacagg aaacagctat gaccatgatt acgccaagct tgcatgcctg    4440
caggtcgacc gttaaatcta tcaccgcaag ggataaatat ctaacaccgt gcgtgttgac    4500
tattttacct ctggcggtga taatggttgc atgtactaat ctagataagg aatatagcca    4560
tgaccgcacc gattcaggat ctgcgtgatg caattgccct gctgcaacag catgataatc    4620
agtatctgga aaccgatcat ccggttgatc cgaatgcaga actggcaggc gtttatcgtc    4680
atattggtgc cggtggcacc gttaaacgtc cgacccgtat tggtccggca atgatgttta    4740
ataacattaa aggttatccg cacagccgta ttctggttgg tatgcatgca agccgtcagc    4800
gtgcagcact gctgctgggt tgtgaagcaa gtcagctggc actggaagtt ggtaaagcag    4860
ttaaaaaacc ggttgcaccg gtggttgttc cggcaagcag cgcaccgtgt caagagcaga    4920
tttttctggc agatgatccg gattttgatc tgcgtaccct gctgcctgca cataccaata    4980
ccccgattga tgcaggtccg ttttttttgtc tgggtctggc cctggcaagc gatccggtgg    5040
atgcaagcct gaccgatgtt accattcatc gtctgtgtgt tcagggtcgt gatgaactga    5100
gcatgttcct ggcagcaggt cgccatattg aagttttcg tcagaaagca gaagcagcag    5160
gtaaaccgct gccgattacc attaatatgg gtctggaccc agcaatctat attggcgcat    5220
gttttgaagc accgaccacc ccgtttggtt ataatgaact gggtgttgcc ggtgcactgc    5280
gtcagcgtcc ggttgaactg gttcagggtg ttagcgttcc ggaaaaagca attgcacgtg    5340
ccgaaattgt tattgaaggt gaactgctgc ctggtgttgc tgttcgtgaa gatcagcata    5400
ccaattcagg tcatgcaatg ccggaatttc cgggttattg tggtggtgca atccgagcc    5460 tgccggttat taaagttaaa gccgttacca tgccgcaataa cgcaattctg caaaccctgg    5520
ttggtccggg tgaagaacat accaccctgg caggtctgcc gaccgaagca agcatttgga    5580
atgcagttga agcagcaatt ccgggttttc tgcaaaatgt ttatgcccat accgcaggcg    5640
gtggtaaatt tctgggtatt ctgcaagtga aaaacgtca gcctgccgat gaaggtcgtc    5700
agggtcaggc agccctgctg gcgctggcaa cctatagcga actgaaaaat atcattctgg    5760
tggatgagga tgtggacatt tttgatagtg atgatattct gtgggcaatg accacccgta    5820
tgcagggtga tgttagcatt accaccattc cgggtattcg cggtcatcag ctggacccga    5880
```

| | |
|---|---|
| gccagacacc ggaatattca ccgagcattc gtggtaatgg tattagctgc aaaaccatct | 5940 |
| ttgattgtac cgttccgtgg gcactgaaaa gccattttga acgtgcaccg tttgcagatg | 6000 |
| ttgatccgcg tccgtttgca cctgaatatt ttgcacgtct ggaaaaaaat cagggcagcg | 6060 |
| caaaataagc taataacagg cctgctggta atcgcaggaa ttttttatttg gatggatccc | 6120 |
| cgggtaccga gctcgaattc actggccgtc gttttacaac gtcgtgactg gaaaaccct | 6180 |
| ggcgttaccc aacttaatcg ccttgcagca catcccctt tcgccagctg gcgtaatagc | 6240 |
| gaagaggccc gcaccgatcg cccttcccaa cagttgcgca gcctgaatgg cgaatggcgc | 6300 |
| ctgatgcggt attttctcct tacgcatctg tgcggtattt cacaccgcat atggtgcact | 6360 |
| ctcagtacaa tctgctctga tgccgcatag ttaagccagc cccgacaccc gccaacaccc | 6420 |
| gctgacgaat tc | 6432 |

<210> SEQ ID NO 22
<211> LENGTH: 7294
<212> TYPE: DNA
<213> ORGANISM: Escherichia coli
<220> FEATURE:
<221> NAME/KEY: misc_feature
<222> LOCATION: (1)..(7294)
<223> OTHER INFORMATION: DNA sequence of the plasmid pMG31

<400> SEQUENCE: 22

| | |
|---|---|
| gttgacagta agacgggtaa gcctgttgat gataccgctg ccttactggg tgcattagcc | 60 |
| agtctgaatg acctgtcacg ggataatccg aagtggtcag actggaaaat cagagggcag | 120 |
| gaactgctga acagcaaaaa gtcagatagc accacatagc agacccgcca taaaacgccc | 180 |
| tgagaagccc gtgacgggct tttcttgtat tatgggtagt ttccttgcat gaatccataa | 240 |
| aaggcgcctg tagtgccatt taccccatt cactgccaga gccgtgagcg cagcgaactg | 300 |
| aatgtcacga aaagacagc gactcaggtg cctgatggtc ggagacaaaa ggaatattca | 360 |
| gcgatttgcc cgagcttgcg agggtgctac ttaagccttt agggttttaa ggtctgtttt | 420 |
| gtagaggagc aaacagcgtt tgcgacatcc ttttgtaata ctgcggaact gactaaagta | 480 |
| gtgagttata cacagggctg ggatctattc tttttatctt tttttattct ttctttattc | 540 |
| tataaattat aaccacttga atataaacaa aaaaaacaca caaaggtcta gcggaattta | 600 |
| cagagggtct agcagaattt acaagttttc cagcaaaggt ctagcagaat ttacagatac | 660 |
| ccacaactca aaggaaaagg actagtaatt atcattgact agcccatctc aattggtata | 720 |
| gtgattaaaa tcacctagac caattgagat gtatgtctga attagttgtt ttcaaagcaa | 780 |
| atgaactagc gattagtcgc tatgacttaa cggagcatga accaagcta attttatgct | 840 |
| gtgtggcact actcaacccc acgattgaaa accctacaag gaaagaacgg acggtatcgt | 900 |
| tcacttataa ccaatacgct cagatgatga acatcagtag ggaaaatgct tatggtgtat | 960 |
| tagctaaagc aaccagagag ctgatgacga gaactgtgga atcaggaat cctttggtta | 1020 |
| aaggctttga gattttccag tggacaaact atgccaagtt ctcaagcgaa aaattagaat | 1080 |
| tagttttag tgaagagata ttgccttatc ttttccagtt aaaaaaattc ataaaatata | 1140 |
| atctggaaca tgttaagtct tttgaaaaca aatactctat gaggatttat gagtggttat | 1200 |
| taaaagaact aacacaaaag aaaactcaca aggcaaatat agagattagc cttgatgaat | 1260 |
| ttaagttcat gttaatgctt gaaaataact accatgagtt taaaggctt aaccaatggg | 1320 |
| ttttgaaacc aataagtaaa gatttaaaca cttacagcaa tatgaaattg gtggttgata | 1380 |
| agcgaggccg cccgactgat acgttgattt tccaagttga actagataga caaatggatc | 1440 |

```
tcgtaaccga acttgagaac aaccagataa aaatgaatgg tgacaaaata ccaacaacca    1500
ttacatcaga ttcctaccta cgtaacggac taagaaaaac actacacgat gctttaactg    1560
caaaaattca gctcaccagt tttgaggcaa aattttttgag tgacatgcaa agtaagcatg    1620
atctcaatgg ttcgttctca tggctcacgc aaaaacaacg aaccacacta gagaacatac    1680
tggctaaata cggaaggatc tgaggttctt atggctcttg tatctatcag tgaagcatca    1740
agactaacaa acaaaagtag aacaactgtt caccgttaga tatcaaaggg aaaactgtcc    1800
atatgcacag atgaaaacgg tgtaaaaaag atagatacat cagagctttt acgagttttt    1860
ggtgcattta aagctgttca ccatgaacag atcgacaatg taacagatga acagcatgta    1920
acacctaata gaacaggtga aaccagtaaa acaaagcaac tagaacatga aattgaacac    1980
ctgagacaac ttgttacagc tcaacagtca cacatagaca gcctgaaaca ggcgatgctg    2040
cttatcgaat caaagctgcc gacaacacgg gagccagtga cgcctcccgt ggggaaaaaa    2100
tcatggcaat tctggaagaa atagcgcttt cagccggcaa acctgaagcc ggatctgcga    2160
ttctgataac aaactagcaa caccagaaca gcccgtttgc gggcagcaaa accgttatg    2220 cttgtaaacc gttttgtgaa aaatttttta aataaaaaa ggggacctct agggtcccca    2280
attaattagt aatataatct attaaaggtc attcaaaagg tcatccaccg gatcaattcc    2340
cctgctcgcg caggctgggt gccaagctct cgggtaacat caaggcccga tccttggagc    2400
ccttgccctc ccgcacgatg atcgtgccgt gatcgaaatc cagatccttg acccgcagtt    2460
gcaaaccctc actgatccgc atgcccgttc catacagaag ctgggcgaac aaacgatgct    2520
cgccttccag aaaaccgagg atgcgaacca cttcatccgg ggtcagcacc accggcaagc    2580
gccgcgacgg ccgaggtctt ccgatctcct gaagccaggg cagatccgtg cacagcacct    2640
tgccgtagaa gaacagcaag gccgccaatg cctgacgatg cgtggagacc gaaaccttgc    2700
gctcgttcgc cagccaggac agaaatgcct cgacttcgct gctgcccaag gttgccgggt    2760
gacgcacacc gtggaaacgg atgaaggcac gaacccagtg gacataagcc tgttcggttc    2820
gtaagctgta atgcaagtag cgtatgcgct cacgcaactg gtccagaacc ttgaccgaac    2880
gcagcggtgg taacggcgca gtggcggttt tcatggcttg ttatgactgt ttttttgggg    2940
tacagtctat gcctcgggca tccaagcagc aagcgcgtta cgccgtgggt cgatgtttga    3000
tgttatggag cagcaacgat gttacgcagc agggcagtcg ccctaaaaca aagttaaaca    3060
tcatgaggga agcggtgatc gccgaagtat cgactcaact atcagaggta gttggcgtca    3120
tcgagcgcca tctcgaaccg acgttgctgg ccgtacattt gtacggctcc gcagtggatg    3180
gcggcctgaa gccacacagt gatattgatt tgctggttac ggtgaccgta aggcttgatg    3240
aaacaacgcg gcgagctttg atcaacgacc ttttggaaac ttcggcttcc cctggagaga    3300
gcgagattct ccgcgctgta gaagtcacca ttgttgtgca cgacgacatc attccgtggc    3360
gttatccagc taagcgcgaa ctgcaatttg gagaatggca gcgcaatgac attcttgcag    3420
gtatcttcga gccagccacg atcgacattg atctggctat cttgctgaca aaagcaagag    3480
aacatagcgt tgccttggta ggtccagcgg cggaggaact cttttgatccg gttcctgaac    3540 aggatctatt tgaggcgcta aatgaaacct taacgctatg gaactcgccg cccgactggg    3600
ctggcgatga gcgaaatgta gtgcttacgt tgtcccgcat ttggtacagc gcagtaaccg    3660
gcaaaatcgc gccgaaggat gtcgctgccg actgggcaat ggagcgcctg ccggcccagt    3720
atcagcccgt catacttgaa gctagacagg cttatcttgg acaagaagaa gatcgcttgg    3780
```

```
cctcgcgcgc agatcagttg gaagaatttg tccactacgt gaaaggcgag atcaccaagg   3840
tagtcggcaa ataatgtcta acaattcgtt caagccgacg ccgcttcgcg gcgcggctta   3900
actcaagcgt tagatgcact aagcacataa ttgctcacag ccaaactatc aggtcaagtc   3960
tgcttttatt attttttaagc gtgcataata agccctacac aaattgggag atatatcatg   4020
aaaggctggc ttttcttgt tatcgcaata gttggcgaag taatcgcaac atccgcatta    4080
aaatctagcg agggctttac taagctgatc cggtggatga cctttgaat gacctttaat    4140
agattatatt actaattaat tggggaccct agaggtcccc ttttttattt taaaaatttt   4200
ttcacaaaac ggtttacaag catacgttgg ccgattcatt aatgcagctg gcacgacagg    4260
tttcccgact ggaaagcggg cagtgagcgc aacgcaatta atgtgagtta gctcactcat   4320
taggcacccc aggctttaca ctttatgctt ccggctcgta tgttgtgtgg aattgtgagc   4380
ggataacaat ttcacacagg aaacagctat gaccatgatt acgccaagct tgctattgac   4440
gacagctatg gttcactgtc caccaaccaa aactgtgctc agtaccgcca atatttctcc   4500
cttgaggggt acaaagaggt gtccctagaa gagatccacg ctgtgtaaaa attttacaaa   4560
aaggtattga cttccctac agggtgtgta ataatttaat tacaggcggg ggcaaccccg     4620
cctgttctgc agaggaggaa tatagccatg gaagtgaaaa tcttcaacac ccaggatgtt   4680
caggattttc tgcgtgttgc aagcggtctg gaacaagagg gtggtaatcc gcgtgttaaa    4740
caaattattc atcgtgttct gagcgacctg tataaagcaa ttgaagatct gaatatcacc   4800
agcgacgaat attgggcagg cgttgcatat ctgaatcagc tgggtgcaaa tcaagaagca   4860
ggtctgctga gtccgggtct gggttttgat cattatctgg atatgcgtat ggatgcagaa    4920
gatgcagcac tgggtattga aaatgcaaca ccgcgtacca ttgaaggtcc gctgtatgtt   4980
gcgggtgcac cggaaagcgt tggttatgca cgcatggatg atggtagcga tccgaatggt   5040
catacccctga ttctgcatgg caccattttt gatgcagatg gtaaaccgct gccgaatgca    5100
aaagttgaaa tttggcatgc aaacaccaaa ggctttttata gccattttga tccgaccggt   5160
gaacagcagg cctttaatat gcgtcgtagc attattaccg atgagaatgg tcagtatcgt   5220
gttcgtacca ttctgcctgc cggttatggt tgtcctccgg aaggtccgac ccagcaactg    5280
ctgaaccaac tgggtcgtca tggtaatcgt ccggcacata ttcattattt tgttagcgca   5340
gatggtcacc gtaaactgac cacccagatt aatgttgccg gtgatccgta tacctatgat   5400
gattttgcat atgccacccg tgaaggtctg gttgttgatg cagttgaaca taccgatccg   5460
gaagcaatta aagccaatga tgtggaaggt ccttttgccg aaatggtgtt tgatctgaaa    5520
ctgacccgtc tggttgatgg tgttgataat caggttgtgg atcgtccgcg tctggcagtt    5580
taatacacca aaatggttca aaattatcag gcgagtgatc atgatcactg gcctgttttt    5640
atttcaggga agggtggaga caattacgtg ataatcaga tcatccaaga aaccgtggat    5700
aaaattctga gcgttctgcc gaatcaggca ggtcagctgg cacgtctggt gcgtctgatg   5760
caatttgcat gcgatccgac cattaccgtt attggcaaat ataaccatgg taaaagccgt   5820
ctgctgaatg aactgattgg caccgatatc tttagcgttg cagataaacg tgaaaccatt   5880
cagctggccg aacataaaca ggatcaggtt cgttggctgg atgcacctgg tctggatgcc    5940
gatgttgcag cagttgatga tcgtcatgca tttgaagcag tttggaccca ggcagatatt   6000
cgtctgtttg ttcatagcgt tcgtgaaggt gaactggatg caaccgaaca ccatctgctg   6060
caacagctga ttgaagatgc cgatcatagc cgtcgtcaga ccattctggt tctgacccag   6120
attgatcaga ttccggatca gaccatcctg acacagatta aaaccagcat tgcacagcag   6180
```

```
gttccgaaac tggatatttg ggcagttagc gcaacccgtc atcgtcaggg cattgaaaac    6240
ggtaaaaccc tgctgatcga aaaaagcggt attggtgcac tgcgccatac cctggaacag    6300
gcactggcac aggtgccgag cgcacgtacc tatgaaaaaa atcgtctgct gtcagatctg    6360
caccatcagc tgaaacaact gctgctggat cagaaacatg ttctgcaaca actgcaacag    6420
acacagcaac agcagctgca tgattttgat accggtctga ttaacattct ggacaaaatt    6480
cgtgttgatc tggaaccgat tgtgaatatt gatggtcagg atcaagcact gaatccggat    6540
agctttgcaa ccatgtttaa aaacaccgca gcaaacagc agcgtgccaa agttcagatt     6600
gcatatagcc gtgcatgcat tgaaatcaac agccatctga ttcgccatgg tgttgttggt    6660
ctgcctgcgg aacagcagac caccattaaa agcattgata ccgtgattgt tgccgtgttt    6720
ggtatcagcg ttaaatttcg tgatcagctg cgtgccctgt tttataccga taccgaacgt    6780
cagcgtctgc aacgtgaatt tcgtttctat tttgaaaaaa gtgccggtcg catgattctg    6840
gcagcaaaaa ttgaacagac catgcgtcag cagggctgta ttcagaatgc catgatggca    6900
ctgcaacaaa tggaaagcgc agcataaaaa cacggacgcc gcaaacggcg tccgaatttc    6960
ttggtcgact ctagaggatc cccgggtacc gagctcgaat tcactggccg tcgttttaca    7020
acgtcgtgac tgggaaaacc ctggcgttac ccaacttaat cgccttgcag cacatccccc    7080
tttcgccagc tggcgtaata gcgaagaggc ccgcaccgat cgcccttccc aacagttgcg    7140
cagcctgaat ggcgaatggc gcctgatgcg gtattttctc cttacgcatc tgtgcggtat    7200
ttcacaccgc atatggtgca ctctcagtac aatctgctct gatgccgcat agttaagcca    7260
gccccgacac ccgccaacac ccgctgacga attc                                 7294

<210> SEQ ID NO 23
<211> LENGTH: 8952
<212> TYPE: DNA
<213> ORGANISM: Escherichia coli
<220> FEATURE:
<221> NAME/KEY: misc_feature
<222> LOCATION: (1)..(8952)
<223> OTHER INFORMATION: DNA sequence of the plasmid pMG33

<400> SEQUENCE: 23
gttgacagta agacgggtaa gcctgttgat gataccgctg ccttactggg tgcattagcc      60
agtctgaatg acctgtcacg ggataatccg aagtggtcag actggaaaat cagagggcag     120
gaactgctga acagcaaaaa gtcagatagc accacatagc agacccgcca taaaacgccc     180
tgagaagccc gtgacgggct tttcttgtat tatgggtagt ttccttgcat gaatccataa     240
aaggcgcctg tagtgccatt taccccatt cactgccaga gccgtgagcg cagcgaactg      300
aatgtcacga aaagacagc gactcaggtg cctgatggtc ggagacaaaa ggaatattca      360
gcgatttgcc cgagcttgcg agggtgctac ttaagccttt agggttttaa ggtctgtttt     420
gtagaggagc aaacagcgtt tgcgacatcc ttttgtaata ctgcggaact gactaaagta     480
gtgagttata cacagggctg ggatctattc ttttttatctt tttttattct ttctttattc    540
tataaattat aaccacttga atataaacaa aaaaaacaca caaaggtcta gcggaattta     600
cagagggtct agcagaattt acaagttttc cagcaaaggt ctagcagaat ttacagatac     660
ccacaactca aggaaaagg actagtaatt atcattgact agcccatctc aattggtata     720
gtgattaaaa tcacctagac caattgagat gtatgtctga ttagttgtt tcaaagcaa      780 atgaactagc gattagtcgc tatgacttaa cggagcatga aaccaagcta atttttatgct    840
```

```
gtgtggcact actcaacccc acgattgaaa accctacaag gaaagaacgg acggtatcgt      900
tcacttataa ccaatacgct cagatgatga acatcagtag ggaaaatgct tatggtgtat      960
tagctaaagc aaccagagag ctgatgacga gaactgtgga aatcaggaat cctttggtta     1020
aaggctttga gattttccag tggacaaact atgccaagtt ctcaagcgaa aaattagaat     1080
tagtttttag tgaagagata ttgccttatc ttttccagtt aaaaaaattc ataaaatata     1140
atctggaaca tgttaagtct tttgaaaaca aatactctat gaggatttat gagtggttat     1200
taaaagaact aacacaaaag aaaactcaca aggcaaatat agagattagc cttgatgaat     1260
ttaagttcat gttaatgctt gaaaataact accatgagtt taaaaggctt aaccaatggg     1320
ttttgaaacc aataagtaaa gatttaaaca cttacagcaa tatgaaattg gtggttgata     1380
agcgaggccg cccgactgat acgttgattt ccaagttga actagataga caaatggatc     1440
tcgtaaccga acttgagaac aaccagataa aaatgaatgg tgacaaaata ccaacaacca     1500
ttacatcaga ttcctaccta cgtaacggac taagaaaaac actacacgat gctttaactg     1560
caaaaattca gctcaccagt tttgaggcaa aattttgag tgcatgcaa agtaagcatg       1620 atctcaatgg ttcgttctca tggctcacgc aaaaacaacg aaccacacta gagaacatac     1680
tggctaaata cggaaggatc tgaggttctt atggctcttg tatctatcag tgaagcatca     1740
agactaacaa acaaaagtag aacaactgtt caccgttaga tatcaaaggg aaaactgtcc     1800
atatgcacag atgaaaacgg tgtaaaaaag atagatacat cagagctttt acgagttttt     1860
ggtgcattta agctgttca ccatgaacag atcgacaatg taacagatga acagcatgta     1920
acacctaata gaacaggtga aaccagtaaa acaaagcaac tagaacatga aattgaacac     1980
ctgagacaac ttgttacagc tcaacagtca cacatagaca gcctgaaaca ggcgatgctg     2040
cttatcgaat caaagctgcc gacaacacgg gagccagtga cgcctcccgt ggggaaaaaa     2100
tcatggcaat tctggaagaa atagcgcttt cagccggcaa acctgaagcc ggatctgcga     2160
ttctgataac aaactagcaa caccagaaca gcccgtttgc gggcagcaaa acccgttatg     2220
cttgtaaacc gttttgtgaa aaaattttta aaataaaaaa ggggacctct agggtcccca     2280
attaattagt aatataatct attaaaggtc attcaaaagg tcatccaccg gatcaattcc     2340
cctgctcgcg caggctgggt gccaagctct cgggtaacat caaggcccga tccttggagc     2400
ccttgccctc ccgcacgatg atcgtgccgt gatcgaaatc cagatccttg acccgcagtt     2460
gcaaaccctc actgatccgc atgcccgttc catacagaag ctgggcgaac aaacgatgct     2520
cgccttccag aaaaccgagg atgcgaacca cttcatccgg ggtcagcacc accggcaagc     2580
gccgcgacgg ccgaggtctt ccgatctcct gaagccaggg cagatccgtg cacagcacct     2640
tgccgtagaa gaacagcaag gccgccaatg cctgacgatg cgtggagacc gaaaccttgc     2700
gctcgttcgc cagccaggac agaaatgcct cgacttcgct gctgcccaag gttgccgggt     2760
gacgcacacc gtggaaacgg atgaaggcac gaacccagtg gacataagcc tgttcggttc     2820
gtaagctgta atgcaagtag cgtatgcgct cacgcaactg gtccagaacc ttgaccgaac     2880
gcagcggtgg taacggcgca gtggcggttt tcatggcttg ttatgactgt ttttttgggg     2940
tacagtctat gcctcgggca tccaagcagc aagcgcgtta cgccgtgggt cgatgtttga     3000
tgttatggag cagcaacgat gttacgcagc agggcagtcg ccctaaaaca aagttaaaca     3060
tcatgaggga agcggtgatc gccgaagtat cgactcaact atcagaggta gttggcgtca     3120
tcgagcgcca tctcgaaccg acgttgctgg ccgtacattt gtacggctcc gcagtggatg     3180
gcggcctgaa gccacacagt gatattgatt tgctggttac ggtgaccgta aggcttgatg     3240
```

```
aaacaacgcg gcgagctttg atcaacgacc ttttggaaac ttcggcttcc cctggagaga   3300
gcgagattct ccgcgctgta gaagtcacca ttgttgtgca cgacgacatc attccgtggc   3360
gttatccagc taagcgcgaa ctgcaatttg gagaatggca gcgcaatgac attcttgcag   3420
gtatcttcga gccagccacg atcgacattg atctggctat cttgctgaca aaagcaagag   3480
aacatagcgt tgccttggta ggtccagcgg cggaggaact ctttgatccg gttcctgaac   3540
aggatctatt tgaggcgcta aatgaaacct taacgctatg gaactcgccg cccgactggg   3600
ctggcgatga gcgaaatgta gtgcttacgt tgtcccgcat ttggtacagc gcagtaaccg   3660
gcaaaatcgc gccgaaggat gtcgctgccg actgggcaat ggagcgcctg ccggcccagt   3720
atcagcccgt catacttgaa gctagacagg cttatcttgg acaagaagaa gatcgcttgg   3780
cctcgcgcgc agatcagttg gaagaatttg tccactacgt gaaaggcgag atcaccaagg   3840
tagtcggcaa ataatgtcta acaattcgtt caagccgacg ccgcttcgcg gcgcggctta   3900
actcaagcgt tagatgcact aagcacataa ttgctcacag ccaaactatc aggtcaagtc   3960
tgcttttatt attttttaagc gtgcataata agccctacac aaattgggag atatatcatg   4020
aaaggctggc tttttcttgt tatcgcaata gttggcgaag taatcgcaac atccgcatta   4080
aaatctagcg agggctttac taagctgatc cggtggatga ccttttgaat gacctttaat   4140
agattatatt actaattaat tggggaccct agaggtcccc tttttatttt taaaaatttt   4200
ttcacaaaac ggtttacaag catacgttgg ccgattcatt aatgcagctg gcacgacagg   4260
tttcccgact ggaaagcggg cagtgagcgc aacgcaatta atgtgagtta gctcactcat   4320
taggcacccc aggctttaca ctttatgctt ccggctcgta tgttgtgtgg aattgtgagc   4380
ggataacaat ttcacacagg aaacagctat gaccatgatt acgccaagct tgctattgac   4440
gacagctatg gttcactgtc caccaaccaa aactgtgctc agtaccgcca atatttctcc   4500 cttgagggt acaagagggt gtccctagaa gagatccacg ctgtgtaaaa attttacaaa   4560
aaggtattga ctttccctac agggtgtgta ataatttaat tacaggcggg ggcaaccccg   4620
cctgttctgc agaggaggaa tatagccatg gaagtgaaaa tcttcaacac ccaggatgtt   4680
caggattttc tgcgtgttgc aagcggtctg gaacaagagg gtggtaatcc gcgtgttaaa   4740
caaattattc atcgtgttct gagcgacctg tataaagcaa ttgaagatct gaatatcacc   4800
agcgacgaat attgggcagg cgttgcatat ctgaatcagc tgggtgcaaa tcaagaagca   4860
ggtctgctga gtccgggtct gggttttgat cattatctgg atatgcgtat ggatgcagaa   4920
gatgcagcac tgggtattga aaatgcaaca ccgcgtacca ttgaaggtcc gctgtatgtt   4980
gcgggtgcac cggaaagcgt tggttatgca cgcatggatg atggtagcga tccgaatggt   5040
cataccctga ttctgcatgg caccattttt gatgcagatg gtaaaccgct gccgaatgca   5100
aaagttgaaa tttggcatgc aaacaccaaa ggctttata gccattttga tccgaccggt   5160
gaacagcagg cctttaatat gcgtcgtagc attattaccg atgagaatgg tcagtatcgt   5220
gttcgtacca ttctgcctgc cggttatggt tgtcctccgg aaggtccgac ccagcaactg   5280
ctgaaccaac tgggtcgtca tggtaatcgt ccggcacata ttcattattt tgttagcgca   5340
gatggtcacc gtaaactgac cacccagatt aatgttgccg gtgatccgta tacctatgat   5400
gattttgcat atgccacccg tgaaggtctg gttgttgatg cagttgaaca taccgatccg   5460
gaagcaatta aagccaatga tgtggaaggt ccttttgccg aaatggtgtt tgatctgaaa   5520
ctgacccgtc tggttgatgg tgttgataat caggttgtgg atcgtccgcg tctggcagtt   5580
```

```
taatacacca aaatggttca aaattatcag gcgagtgatc atgatcactg gcctgttttt   5640
atttcaggga agggtggaga caattacgtg gataatcaga tcatccaaga aaccgtggat   5700
aaaattctga gcgttctgcc gaatcaggca ggtcagctgg cacgtctggt gcgtctgatg   5760
caatttgcat gcgatccgac cattaccgtt attggcaaat ataaccatgg taaaagccgt   5820
ctgctgaatg aactgattgg caccgatatc tttagcgttg cagataaacg tgaaaccatt   5880
cagctggccg aacataaaca ggatcaggtt cgttggctgg atgcacctgg tctggatgcc   5940
gatgttgcag cagttgatga tcgtcatgca tttgaagcag tttggaccca ggcagatatt   6000
cgtctgtttg ttcatagcgt tcgtgaaggt gaactggatg caaccgaaca ccatctgctg   6060
caacagctga ttgaagatgc cgatcatagc cgtcgtcaga ccattctggt tctgacccag   6120
attgatcaga ttccggatca gaccatcctg acacagatta aaaccagcat tgcacagcag   6180
gttccgaaac tggatatttg gcagttagc gcaacccgtc atcgtcaggg cattgaaaac   6240
ggtaaaaccc tgctgatcga aaaagcggt attggtgcac tgcgccatac cctggaacag   6300
gcactggcac aggtgccgag cgcacgtacc tatgaaaaaa atcgtctgct gtcagatctg   6360
caccatcagc tgaaacaact gctgctggat cagaaacatg ttctgcaaca actgcaacag   6420
acacagcaac agcagctgca tgattttgat accggtctga ttaacattct ggacaaaatt   6480
cgtgttgatc tggaaccgat tgtgaatatt gatggtcagg atcaagcact gaatccggat   6540
agctttgcaa ccatgtttaa aaacaccgca gcaaaacagc agcgtgccaa agttcagatt   6600
gcatatagcc gtgcatgcat tgaaatcaac agccatctga ttcgccatgg tgttgttggt   6660
ctgcctgcgg aacagcagac caccattaaa agcattgata ccgtgattgt tgccgtgttt   6720
ggtatcagcg ttaaatttcg tgatcagctg cgtgccctgt tttataccga taccgaacgt   6780
cagcgtctgc aacgtgaatt tcgtttctat tttgaaaaaa gtgccggtcg catgattctg   6840
gcagcaaaaa ttgaacagac catgcgtcag cagggctgta ttcagaatgc catgatggca   6900
ctgcaacaaa tggaaagcgc agcataaaaa cacggacgcc gcaaacggcg tccgaatttc   6960
ttggtcgacc gttaaatcta tcaccgcaag ggataaatat ctaacaccgt gcgtgttgac   7020
tattttacct ctggcggtga taatggttgc atgtactaat ctagataagg aatatagcca   7080
tgaccgcacc gattcaggat ctgcgtgatg caattgccct gctgcaacag catgataatc   7140
agtatctgga aaccgatcat ccggttgatc cgaatgcaga actggcaggc gtttatcgtc   7200
atattggtgc cggtggcacc gttaaacgtc cgacccgtat tggtccggca atgatgttta   7260
ataacattaa aggttatccg cacagccgta ttctggttgg tatgcatgca agccgtcagc   7320
gtgcagcact gctgctgggt tgtgaagcaa gtcagctggc actggaagtt ggtaaagcag   7380
ttaaaaaacc ggttgcaccg gtggttgttc cggcaagcag cgcaccgtgt caagagcaga   7440
tttttctggc agatgatccg gattttgatc tgcgtaccct gctgcctgca cataccaata   7500
ccccgattga tgcaggtccg tttttttgtc tgggtctggc cctggcaagc gatccggtgg   7560
atgcaagcct gaccgatgtt accattcatc gtctgtgtgt tcagggtcgt gatgaactga   7620
gcatgttcct ggcagcaggt cgccatattg aagttttttcg tcagaaagca gaagcagcag   7680
gtaaaccgct gccgattacc attaatatgg gtctggaccc agcaatctat attggcgcat   7740
gttttgaagc accgaccacc ccgtttggtt ataatgaact gggtgttgcc ggtgcactgc   7800
gtcagcgtcc ggttgaactg gttcagggtg ttagcgttcc ggaaaaagca attgcacgtg   7860
ccgaaattgt tattgaaggt gaactgctgc ctggtgttcg tgttcgtgaa gatcagcata   7920
ccaattcagg tcatgcaatg ccggaatttc cgggttattg tggtggtgca aatccgagcc   7980
```

```
tgccggttat taaagttaaa gccgttacca tgcgcaataa cgcaattctg caaaccctgg    8040
ttggtccggg tgaagaacat accaccctgg caggtctgcc gaccgaagca agcatttgga    8100
atgcagttga agcagcaatt ccgggttttc tgcaaaatgt ttatgcccat accgcaggcg    8160
gtggtaaatt tctgggtatt ctgcaagtga aaaaacgtca gcctgccgat gaaggtcgtc    8220
agggtcaggc agccctgctg gcgctggcaa cctatagcga actgaaaaat atcattctgg    8280
tggatgagga tgtggacatt tttgatagtg atgatattct gtgggcaatg accacccgta    8340
tgcagggtga tgttagcatt accaccattc cgggtattcg cggtcatcag ctggacccga    8400
gccagacacc ggaatattca ccgagcattc gtggtaatgg tattagctgc aaaaccatct    8460
ttgattgtac cgttccgtgg gcactgaaaa gccattttga acgtgcaccg tttgcagatg    8520
ttgatccgcg tccgtttgca cctgaatatt ttgcacgtct ggaaaaaaat cagggcagcg    8580
caaaataagc taataacagg cctgctggta atcgcaggaa ttttattttg gatggatccc    8640
cgggtaccga gctcgaattc actggccgtc gttttacaac gtcgtgactg ggaaaaccct    8700
ggcgttaccc aacttaatcg ccttgcagca catccccctt cgccagctg gcgtaatagc    8760 gaagaggccc gcaccgatcg cccttcccaa cagttgcgca gcctgaatgg cgaatggcgc    8820
ctgatgcggt attttctcct tacgcatctg tgcggtattt cacaccgcat atggtgcact    8880
ctcagtacaa tctgctctga tgccgcatag ttaagccagc cccgacaccc gccaacaccc    8940
gctgacgaat tc                                                       8952
```

<210> SEQ ID NO 24
<211> LENGTH: 10630
<212> TYPE: DNA
<213> ORGANISM: Escherichia coli
<220> FEATURE:
<221> NAME/KEY: misc_feature
<222> LOCATION: (1)..(10630)
<223> OTHER INFORMATION: DNA sequence of the plasmid pMG37

<400> SEQUENCE: 24

```
gttgacagta agacgggtaa gcctgttgat gataccgctg ccttactggg tgcattagcc      60
agtctgaatg acctgtcacg ggataatccg aagtggtcag actggaaaat cagagggcag    120
gaactgctga acagcaaaaa gtcagatagc accacatagc agacccgcca taaaacgccc    180
tgagaagccc gtgacgggct tttcttgtat tatgggtagt ttccttgcat gaatccataa    240
aaggcgcctg tagtgccatt tacccccatt cactgccaga gccgtgagcg cagcgaactg    300
aatgtcacga aaagacagc gactcaggtg cctgatggtc ggagacaaaa ggaatattca    360
gcgatttgcc cgagcttgcg agggtgctac ttaagccttt agggttttaa ggtctgtttt    420
gtagaggagc aaacagcgtt tgcgacatcc ttttgtaata ctgcggaact gactaaagta    480
gtgagttata cacagggctg gatctattc tttttatctt tttttattct ttctttattc    540
tataaattat aaccacttga atataaacaa aaaaaacaca caaaggtcta gcggaattta    600
cagagggtct agcagaattt acaagttttc cagcaaaggt ctagcagaat ttacagatac    660
ccacaactca aaggaaaagg actagtaatt atcattgact agcccatctc aattggtata    720
gtgattaaaa tcacctagac caattgagat gtatgtctga attagttgtt ttcaaagcaa    780
atgaactagc gattagtcgc tatgacttaa cggagcatga accaagcta attttatgct    840 gtgtggcact actcaacccc acgattgaaa accctacaag gaaagaacgg acggtatcgt    900
tcacttataa ccaatacgct cagatgatga acatcagtag ggaaaatgct tatggtgtat    960
```

```
tagctaaagc aaccagagag ctgatgacga gaactgtgga aatcaggaat cctttggtta    1020
aaggctttga gattttccag tggacaaact atgccaagtt ctcaagcgaa aaattagaat    1080 tagttttag  tgaagagata ttgccttatc ttttccagtt aaaaaaattc ataaaatata    1140
atctggaaca tgttaagtct tttgaaaaca aatactctat gaggatttat gagtggttat    1200
taaaagaact aacacaaaag aaaactcaca aggcaaatat agagattagc cttgatgaat    1260
ttaagttcat gttaatgctt gaaaataact accatgagtt taaaaggctt aaccaatggg    1320
ttttgaaacc aataagtaaa gatttaaaca cttacagcaa tatgaaattg gtggttgata    1380
agcgaggccg cccgactgat acgttgattt ccaagttgga actagataga caaatggatc    1440
tcgtaaccga acttgagaac aaccagataa aaatgaatgg tgacaaaata ccaacaacca    1500
ttacatcaga ttcctaccta cgtaacggac taagaaaaac actacacgat gctttaactg    1560
caaaaattca gctcaccagt tttgaggcaa aattttgag  tgacatgcaa agtaagcatg    1620
atctcaatgg ttcgttctca tggctcacgc aaaaacaacg aaccacacta gagaacatac    1680
tggctaaata cggaaggatc tgaggttctt atggctcttg tatctatcag tgaagcatca    1740
agactaacaa acaaaagtag aacaactgtt caccgttaga tatcaaaggg aaaactgtcc    1800
atatgcacag atgaaaacgg tgtaaaaaag atagatacat cagagctttt acgagttttt    1860
ggtgcattta aagctgttca ccatgaacag atcgacaatg taacagatga acagcatgta    1920
acacctaata gaacaggtga aaccagtaaa acaaagcaac tagaacatga aattgaacac    1980
ctgagacaac ttgttacagc tcaacagtca cacatagaca gcctgaaaca ggcgatgctg    2040
cttatcgaat caaagctgcc gacaacacgg gagccagtga cgcctcccgt ggggaaaaaa    2100
tcatggcaat tctggaagaa atagcgcttt cagccggcaa acctgaagcc ggatctgcga    2160
ttctgataac aaactagcaa caccagaaca gcccgtttgc gggcagcaaa acccgttatg    2220
cttgtaaacc gttttgtgaa aaaattttta aaataaaaaa ggggacctct agggtcccca    2280
attaattagt aatataatct attaaaggtc attcaaaagg tcatccaccg gatcaattcc    2340
cctgctcgcg caggctgggt gccaagctct cgggtaacat caaggcccga tccttggagc    2400
ccttgccctc ccgcacgatg atcgtgccgt gatcgaaatc cagatccttg acccgcagtt    2460
gcaaaccctc actgatccgc atgcccgttc catacagaag ctgggcgaac aaacgatgct    2520
cgccttccag aaaaccgagg atgcgaacca cttcatccgg ggtcagcacc accggcaagc    2580
gccgcgacgg ccgaggtctt ccgatctcct gaagccaggg cagatccgtg cacagcacct    2640
tgccgtagaa gaacagcaag gccgccaatg cctgacgatg cgtggagacc gaaaccttgc    2700
gctcgttcgc cagccaggac agaaatgcct cgacttcgct gctgcccaag gttgccgggt    2760
gacgcacacc gtggaaacgg atgaaggcac gaacccagtg gacataagcc tgttcggttc    2820
gtaagctgta atgcaagtag cgtatgcgct cacgcaactg gtccagaacc ttgaccgaac    2880
gcagcggtgg taacgcgca  gtggcggttt tcatggcttg ttatgactgt ttttttgggg    2940
tacagtctat gcctcgggca tccaagcagc aagcgcgtta cgccgtgggt cgatgtttga    3000
tgttatggag cagcaacgat gttacgcagc agggcagtcg ccctaaaaca aagttaaaca    3060
tcatgaggga agcggtgatc gccgaagtat cgactcaact atcagaggta gttggcgtca    3120
tcgagcgcca tctcgaaccg acgttgctgg ccgtacattt gtacggctcc gcagtggatg    3180
gcggcctgaa gccacacagt gatattgatt tgctggttac ggtgaccgta aggcttgatg    3240
aaacaacgcg gcgagctttg atcaacgacc ttttggaaac ttcggcttcc cctggagaga    3300
gcgagattct ccgcgctgta gaagtcacca ttgttgtgca cgacgacatc attccgtggc    3360
```

```
gttatccagc taagcgcgaa ctgcaatttg gagaatggca gcgcaatgac attcttgcag    3420
gtatcttcga gccagccacg atcgacattg atctggctat cttgctgaca aaagcaagag    3480
aacatagcgt tgccttggta ggtccagcgg cggaggaact ctttgatccg gttcctgaac    3540
aggatctatt tgaggcgcta aatgaaacct taacgctatg gaactcgccg cccgactggg    3600
ctggcgatga gcgaaatgta gtgcttacgt tgtcccgcat ttggtacagc gcagtaaccg    3660
gcaaaatcgc gccgaaggat gtcgctgccg actgggcaat ggagcgcctg ccggcccagt    3720
atcagcccgt catacttgaa gctagacagg cttatcttgg acaagaagaa gatcgcttgg    3780
cctcgcgcgc agatcagttg gaagaatttg tccactacgt gaaaggcgag atcaccaagg    3840
tagtcggcaa ataatgtcta acaattcgtt caagccgacg ccgcttcgcg gcgcggctta    3900
actcaagcgt tagatgcact aagcacataa ttgctcacag ccaaactatc aggtcaagtc    3960
tgcttttatt attttaagc gtgcataata agccctacac aaattgggag atatatcatg    4020
aaaggctggc ttttcttgt tatcgcaata gttggcgaag taatcgcaac atccgcatta    4080
aaatctagcg agggctttac taagctgatc cggtggatga ccttttgaat gacctttaat    4140
agattatatt actaattaat tggggaccct agaggtcccc ttttttattt taaaaatttt    4200
ttcacaaaac ggtttacaag catacgttgg ccgattcatt aatgcagctg gcacgacagg    4260
tttcccgact ggaaagcggg cagtgagcgc aacgcaatta atgtgagtta gctcactcat    4320
taggcacccc aggctttaca ctttatgctt ccggctcgta tgttgtgtgg aattgtgagc    4380
ggataacaat ttcacacagg aaacagctat gaccatgatt acgccaagct tgctattgac    4440
gacagctatg gttcactgtc caccaaccaa aactgtgctc agtaccgcca atatttctcc    4500 cttgagggt acaagaggt gtccctagaa gagatccacg ctgtgtaaaa attttacaaa    4560
aaggtattga ctttccctac agggtgtgta ataatttaat tacaggcggg ggcaaccccg    4620
cctgttctgc agaggaggaa tatagccatg gaagtgaaaa tcttcaacac ccaggatgtt    4680
caggattttc tgcgtgttgc aagcggtctg gaacaagagg gtggtaatcc gcgtgttaaa    4740
caaattattc atcgtgttct gagcgacctg tataaagcaa ttgaagatct gaatatcacc    4800
agcgacgaat attgggcagg cgttgcatat ctgaatcagc tgggtgcaaa tcaagaagca    4860
ggtctgctga gtccgggtct gggttttgat cattatctgg atatgcgtat ggatgcagaa    4920
gatgcagcac tgggtattga aaatgcaaca ccgcgtacca ttgaaggtcc gctgtatgtt    4980
gcgggtgcac cggaaagcgt tggttatgca cgcatggatg atggtagcga tccgaatggt    5040 catacccctga ttctgcatgg caccattttt gatgcagatg gtaaaccgct gccgaatgca    5100
aaagttgaaa tttggcatgc aaacaccaaa ggcttttata gccatttga tccgaccggt    5160 gaacagcagg ccttttaatat gcgtcgtagc attattaccg atgagaatgg tcagtatcgt    5220
gttcgtacca ttctgcctgc cggttatggt tgtcctccgg aaggtccgac ccagcaactg    5280
ctgaaccaac tgggtcgtca tggtaatcgt ccggcacata ttcattattt tgttagcgca    5340
gatggtcacc gtaaactgac cacccagatt aatgttgccg gtgatccgta tacctatgat    5400
gattttgcat atgccacccg tgaaggtctg gttgttgatg cagttgaaca taccgatccg    5460
gaagcaatta aagccaatga tgtggaaggt ccttttgccg aaatggtgtt tgatctgaaa    5520
ctgacccgtc tggttgatgg tgttgataat caggttgtgg atcgtccgcg tctggcagtt    5580
taatacacca aaatgttca aaattatcag gcgagtgatc atgatcactg gcctgttttt    5640
atttcaggga agggtggaga caattacgtg ataatcaga tcatccaaga aaccgtggat    5700
```

```
aaaattctga gcgttctgcc gaatcaggca ggtcagctgg cacgtctggt gcgtctgatg   5760
caatttgcat gcgatccgac cattaccgtt attggcaaat ataaccatgg taaaagccgt   5820
ctgctgaatg aactgattgg caccgatatc tttagcgttg cagataaacg tgaaaccatt   5880
cagctggccg aacataaaca ggatcaggtt cgttggctgg atgcacctgg tctggatgcc   5940
gatgttgcag cagttgatga tcgtcatgca tttgaagcag tttggaccca ggcagatatt   6000
cgtctgtttg ttcatagcgt tcgtgaaggt gaactggatg caaccgaaca ccatctgctg   6060
caacagctga ttgaagatgc cgatcatagc cgtcgtcaga ccattctggt tctgacccag   6120
attgatcaga ttccggatca gaccatcctg acacagatta aaaccagcat tgcacagcag   6180
gttccgaaac tggatatttg gcagttagc gcaacccgtc atcgtcaggg cattgaaaac   6240
ggtaaaaccc tgctgatcga aaaagcggt attggtgcac tgcgccatac cctggaacag   6300
gcactggcac aggtgccgag cgcacgtacc tatgaaaaaa atcgtctgct gtcagatctg   6360
caccatcagc tgaaacaact gctgctggat cagaaacatg ttctgcaaca actgcaacag   6420
acacagcaac agcagctgca tgattttgat accggtctga ttaacattct ggacaaaatt   6480
cgtgttgatc tggaaccgat tgtgaatatt gatggtcagg atcaagcact gaatccggat   6540
agctttgcaa ccatgtttaa aaacaccgca gcaaaacagc agcgtgccaa agttcagatt   6600
gcatatagcc gtgcatgcat tgaaatcaac agccatctga ttcgccatgg tgttgttggt   6660
ctgcctgcgg aacagcagac caccattaaa agcattgata ccgtgattgt tgccgtgttt   6720
ggtatcagcg ttaaatttcg tgatcagctg cgtgccctgt tttataccga taccgaacgt   6780
cagcgtctgc aacgtgaatt tcgtttctat tttgaaaaaa gtgccggtcg catgattctg   6840
gcagcaaaaa ttgaacagac catgcgtcag cagggctgta ttcagaatgc catgatggca   6900
ctgcaacaaa tggaaagcgc agcataaaaa cacggacgcc gcaaacggcg tccgaatttc   6960
ttggtcgacc gttaaatcta tcaccgcaag ggataaatat ctaacaccgt gcgtgttgac   7020
tattttacct ctggcggtga taatggttgc atgtactaat ctagataagg aatatagcca   7080
tgaccgcacc gattcaggat ctgcgtgatg caattgccct gctgcaacag catgataatc   7140
agtatctgga aaccgatcat ccggttgatc cgaatgcaga actggcaggc gtttatcgtc   7200
atattggtgc cggtggcacc gttaaacgtc cgacccgtat tggtccggca atgatgttta   7260
ataacattaa aggttatccg cacagccgta ttctggttgg tatgcatgca agccgtcagc   7320
gtgcagcact gctgctgggt tgtgaagcaa gtcagctggc actggaagtt ggtaaagcag   7380
ttaaaaaacc ggttgcaccg gtggttgttc cggcaagcag cgcaccgtgt caagagcaga   7440
tttttctggc agatgatccg gattttgatc tgcgtaccct gctgcctgca cataccaata   7500
ccccgattga tgcaggtccg tttttttgtc tgggtctggc cctggcaagc gatccggtgg   7560
atgcaagcct gaccgatgtt accattcatc gtctgtgtgt tcagggtcgt gatgaactga   7620
gcatgttcct ggcagcaggt cgccatattg aagtttttcg tcagaaagca gaagcagcag   7680
gtaaaccgct gccgattacc attaatatgg gtctggaccc agcaatctat attggcgcat   7740
gttttgaagc accgaccacc ccgtttggtt ataatgaact gggtgttgcc ggtgcactgc   7800
gtcagcgtcc ggttgaactg gttcaggtgt ttagcgttcc ggaaaaagca attgcacgtg   7860
ccgaaattgt tattgaaggt gaactgctgc ctggtgttcg tgttcgtgaa gatcagcata   7920
ccaattcagg tcatgcaatg ccggaatttc cgggttattg tggtggtgca aatccgagcc   7980
tgccggttat taaagttaaa gccgttacca tgcgcaataa cgcaattctg caaaccctgg   8040
ttggtccggg tgaagaacat accacccctgg caggtctgcc gaccgaagca agcatttgga   8100
```

```
atgcagttga agcagcaatt ccgggttttc tgcaaaatgt ttatgcccat accgcaggcg   8160
gtggtaaatt tctgggtatt ctgcaagtga aaaaacgtca gcctgccgat gaaggtcgtc   8220
agggtcaggc agccctgctg gcgctggcaa cctatagcga actgaaaaat atcattctgg   8280
tggatgagga tgtggacatt tttgatagtg atgatattct gtgggcaatg accacccgta   8340
tgcagggtga tgttagcatt accaccattc cgggtattcg cggtcatcag ctggacccga   8400
gccagacacc ggaatattca ccgagcattc gtggtaatgg tattagctgc aaaaccatct   8460
ttgattgtac cgttccgtgg gcactgaaaa gccattttga acgtgcaccg tttgcagatg   8520
ttgatccgcg tccgtttgca cctgaatatt ttgcacgtct ggaaaaaaat cagggcagcg   8580
caaaataagc taataacagg cctgctggta atcgcaggaa ttttatttg gatggatccg   8640
cctacctagc ttccaagaaa gatatcctaa cagcacaaga gcggaaagat gttttgttct   8700
acatccagaa caacctctgc taaaattcct gaaaaatttt gcaaaagtt gttgacttta   8760
tctacaaggt gtggtataat aatcttaaca acagcaggac gctcccgggt tgaggaaaac   8820
ctaatgaaac tgaccagcct gcgtgttagc ctgctggcac tgggtctggt taccagcggt   8880
tttgcagcag cagaaaccta ccgttgat cgttatcagg atgatagcga aaaaggtagc   8940
ctgcgttggg caattgaaca gagcaatgca aatagcgcac aagaaaacca gattctgatt   9000
caggcagttg gtaaagcacc gtatgttatc aaagttgata accgctgcc tccgattaaa   9060
agcagcgtta aaatcattgg caccgagtgg gataaaaccg gtgaatttat tgcaattgat   9120
ggcagcaact atatcaaagg cgaaggtgaa aaagcatgtc cgggtgcaaa tccgggtcag   9180
tatggcacca atgttcgtac catgaccctg cctggtctgg ttctgcaaga tgttaatggt   9240
gttaccctga aggtctgga tgttcatcgt ttttgtattg gtgttctggt taatcgcagc   9300
agcaataacc tgattcagca taatcgtatc agcaacaatt atggtggtgc cggtgttatg   9360
attaccggtg atgatggtaa aggtaatccg accagcacca ccaccaataa taacaaagtt   9420
ctggataacg tgttcatcga taatggtgat ggtctggaac tgacccgtgg tgcagcattt   9480
aatctgattg caaataaccct gtttaccagc acaaaagcca atccggaacc gagccagggt   9540
attgaaattc tgtggggtaa tgataatgcc gtggtgggta acaaattcga aaactattca   9600
gatggcctgc aaatcaattg gggtaaaacgt aactatatcg cctataacga actgaccaat   9660
aacagcctgg gtttcaatct gacaggtgat ggtaacattt tcgacagcaa taaagtgcat   9720
ggtaaccgta ttggtattgc cattcgtagt gaaaaagatg ccaatgcacg tattaccctg   9780
accaaaaatc agatttggga taacggcaaa gatatcaaac gttgtgaagc cggtggtagc   9840
tgtgttccga atcagcgtct gggtgcaatt gttttggtg ttccggcact ggaacatgaa   9900
ggttttgttg gtagccgtgg cggtggtgtt gttattgaac cggcaaaact gcaaaaaacc   9960
tgcacccagc cgaaccagca gaattgtaat gcaattccta atcagggtat tcaggcaccg  10020
aaactgacag ttagcaaaaa acagctgacc gttgaagtta aaggcacccc taatcagcgt  10080
tataatgtgg aattttttgg caatcgtaat gccagcagca gcgaagcaga acagtatctg  10140
ggtagcattg ttgttgttac cgatcatcag ggtctggcaa aagcaaattg ggctccgaaa  10200
gttagcatgc cgagcgttac cgcaaatgtg acagatcatc tgggtgcgac cagcgaactg  10260
agcagcgcag ttaaaatgcg ttaaatgcat gcgcgccgcg ttcgcgcggc gcttttttt  10320
ggtaccgagc tcgaattcac tggccgtcgt tttacaacgt cgtgactggg aaaaccctgg  10380
cgttacccaa cttaatcgcc ttgcagcaca tcccccttt gccagctggc gtaatagcga  10440
```

-continued

```
agaggcccgc accgatcgcc cttcccaaca gttgcgcagc ctgaatggcg aatggcgcct      10500
gatgcggtat tttctcctta cgcatctgtg cggtatttca caccgcatat ggtgcactct      10560
cagtacaatc tgctctgatg ccgcatagtt aagccagccc cgacacccgc aacacccgc       10620 tgacgaattc                                                             10630
```

<210> SEQ ID NO 25
<211> LENGTH: 6452
<212> TYPE: DNA
<213> ORGANISM: Escherichia coli
<220> FEATURE:
<221> NAME/KEY: misc_feature
<222> LOCATION: (1)..(6452)
<223> OTHER INFORMATION: DNA sequence of the plasmid pMG39

<400> SEQUENCE: 25

```
gttgacagta agacgggtaa gcctgttgat gataccgctg ccttactggg tgcattagcc        60
agtctgaatg acctgtcacg ggataatccg aagtggtcag actggaaaat cagagggcag       120
gaactgctga acagcaaaaa gtcagatagc accacatagc agacccgcca taaaacgccc       180
tgagaagccc gtgacgggct tttcttgtat tatgggtagt ttccttgcat gaatccataa       240
aaggcgcctg tagtgccatt tacccccatt cactgccaga gccgtgagcg cagcgaactg       300
aatgtcacga aaagacagc gactcaggtg cctgatggtc ggagacaaaa ggaatattca       360
gcgatttgcc cgagcttgcg agggtgctac ttaagccttt agggttttaa ggtctgtttt       420
gtagaggagc aaacagcgtt tgcgacatcc ttttgtaata ctgcggaact gactaaagta       480
gtgagttata cacagggctg ggatctattc tttttatctt ttttttattct ttctttattc      540 tataaattat aaccacttga atataaacaa aaaaaacaca caaggtctaa gcggaattta      600
cagagggtct agcagaattt acaagttttc cagcaaaggt ctagcagaat ttacagatac      660
ccacaactca aggaaaagg actagtaatt atcattgact agcccatctc aattggtata       720
gtgattaaaa tcacctagac caattgagat gtatgtctga attagttgtt ttcaaagcaa       780
atgaactagc gattagtcgc tatgacttaa cggagcatga aaccaagcta attttatgct       840
gtgtggcact actcaacccc acgattgaaa accctacaag gaaagaacgg acggtatcgt       900
tcacttataa ccaatacgct cagatgatga acatcagtag ggaaaatgct tatggtgtat       960
tagctaaagc aaccagagag ctgatgacga gaactgtgga atcaggaat cctttggtta      1020 aaggctttga gattttccag tggacaaact atgccaagtt ctcaagcgaa aaattagaat      1080
tagtttttag tgaagagata ttgccttatc ttttccagtt aaaaaaattc ataaaatata      1140
atctggaaca tgttaagtct tttgaaaaca aatactctat gaggatttat gagtggttat      1200
taaaagaact aacacaaaag aaaactcaca aggcaaatat agagattagc cttgatgaat      1260
ttaagttcat gttaatgctt gaaaataact accatgagtt taaaaggctt aaccaatggg      1320
ttttgaaacc aataagtaaa gatttaaaca cttacagcaa tatgaaattg gtggttgata      1380
agcgaggccg cccgactgat acgttgattt ccaagttga actagataga caaatggatc      1440
tcgtaaccga acttgagaac aaccagataa aaatgaatgg tgacaaaata ccaacaacca      1500
ttacatcaga ttcctaccta cgtaacggac taagaaaaac actacacgat gctttaactg      1560
caaaaattca gctcaccagt tttgaggcaa aatttttgag tgacatgcaa agtaagcatg      1620
atctcaatgg ttcgttctca tggctcacgc aaaaacaacg aaccacacta gagaacatac      1680
tggctaaata cggaaggatc tgaggttctt atggctcttg tatctatcag tgaagcatca      1740
agactaacaa acaaaagtag aacaactgtt caccgttaga tatcaaaggg aaaactgtcc      1800
```

```
atatgcacag atgaaaacgg tgtaaaaaag atagatacat cagagctttt acgagttttt     1860
ggtgcattta aagctgttca ccatgaacag atcgacaatg taacagatga acagcatgta     1920
acacctaata gaacaggtga aaccagtaaa acaaagcaac tagaacatga aattgaacac     1980
ctgagacaac ttgttacagc tcaacagtca cacatagaca gcctgaaaca ggcgatgctg     2040
cttatcgaat caaagctgcc gacaacacgg gagccagtga cgcctcccgt ggggaaaaaa     2100
tcatggcaat tctggaagaa atagcgcttt cagccggcaa acctgaagcc ggatctgcga     2160
ttctgataac aaactagcaa caccagaaca gcccgtttgc gggcagcaaa acccgttatg     2220
cttgtaaacc gttttgtgaa aaaatttta aaataaaaaa ggggacctct agggtcccca     2280
attaattagt aatataatct attaaaggtc attcaaaagg tcatccaccg gatcaattcc     2340
cctgctcgcg caggctgggt gccaagctct cgggtaacat caaggcccga tccttggagc     2400
ccttgccctc ccgcacgatg atcgtgccgt gatcgaaatc cagatccttg acccgcagtt     2460
gcaaaccctc actgatccgc atgcccgttc catacagaag ctgggcgaac aaacgatgct     2520
cgccttccag aaaaccgagg atgcgaacca cttcatccgg ggtcagcacc accggcaagc     2580
gccgcgacgg ccgaggtctt ccgatctcct gaagccaggg cagatccgtg cacagcacct     2640
tgccgtagaa gaacagcaag gccgccaatg cctgacgatg cgtggagacc gaaaccttgc     2700
gctcgttcgc cagccaggac agaaatgcct cgacttcgct gctgcccaag gttgccgggt     2760
gacgcacacc gtggaaacgg atgaaggcac gaacccagtg gacataagcc tgttcggttc     2820
gtaagctgta atgcaagtag cgtatgcgct cacgcaactg gtccagaacc ttgaccgaac     2880
gcagcggtgg taacggcgca gtggcggttt tcatggcttg ttatgactgt tttttggggg     2940
tacagtctat gcctcgggca tccaagcagc aagcgcgtta cgccgtgggt cgatgtttga     3000
tgttatggag cagcaacgat gttacgcagc agggcagtcg ccctaaaaca aagttaaaca     3060
tcatgaggga agcggtgatc gccgaagtat cgactcaact atcagaggta gttggcgtca     3120
tcgagcgcca tctcgaaccg acgttgctgg ccgtacattt gtacggctcc gcagtggatg     3180
gcggcctgaa gccacacagt gatattgatt tgctggttac ggtgaccgta aggcttgatg     3240
aaacaacgcg gcgagctttg atcaacgacc ttttggaaac ttcggcttcc cctggagaga     3300
gcgagattct ccgcgctgta gaagtcacca ttgttgtgca cgacgacatc attccgtggc     3360
gttatccagc taagcgcgaa ctgcaatttg gagaatggca gcgcaatgac attcttgcag     3420
gtatcttcga gccagccacg atcgacattg atctggctat cttgctgaca aaagcaagag     3480
aacatagcgt tgccttggta ggtccagcgg cggaggaact ctttgatccg gttcctgaac     3540
aggatctatt tgaggcgcta aatgaaacct aacgctatg gaactcgccg cccgactggg     3600
ctggcgatga gcgaaatgta gtgcttacgt tgtcccgcat ttggtacagc gcagtaaccg     3660
gcaaaatcgc gccgaaggat gtcgctgccg actgggcaat ggagcgcctg ccggcccagt     3720
atcagcccgt catacttgaa gctagacagg cttatcttgg acaagaagaa gatcgcttgg     3780
cctcgcgcgc agatcagttg gaagaatttg tccactacgt gaaaggcgag atcaccaagg     3840
tagtcggcaa ataatgtcta acaattcgtt caagccgacg ccgcttcgcg gcgcggctta     3900
actcaagcgt tagatgcact aagcacataa ttgctcacag ccaaactatc aggtcaagtc     3960
tgcttttatt attttttaagc gtgcataata agccctacac aaattgggag atatatcatg     4020
aaaggctggc ttttcttgt tatcgcaata gttggcgaag taatcgcaac atccgcatta     4080
aaatctagcg agggctttac taagctgatc cggtggatga ccttttgaat gacctttaat     4140
```

```
agattatatt actaattaat tggggaccct agaggtcccc tttttatttt taaaaatttt    4200
ttcacaaaac ggtttacaag catacgttgg ccgattcatt aatgcagctg cacgacagg     4260
tttcccgact ggaaagcggg cagtgagcgc aacgcaatta atgtgagtta gctcactcat    4320
taggcacccc aggctttaca ctttatgctt ccggctcgta tgttgtgtgg aattgtgagc    4380
ggataacaat ttcacacagg aaacagctat gaccatgatt acgccaagct tgcatgcctg    4440
caggtcgact ctagaggatc cgcctaccta gcttccaaga agatatcct aacagcacaa     4500
gagcggaaag atgttttgtt ctacatccag aacaacctct gctaaaattc ctgaaaaatt    4560
ttgcaaaaag ttgttgactt tatctacaag gtgtggtata ataatcttaa caacagcagg    4620
acgctcccgg gttgaggaaa acctaatgaa actgaccagc ctgcgtgtta gcctgctggc    4680
actgggtctg gttaccagcg ttttgcagc agcagaaacc tataccgttg atcgttatca     4740
ggatgatagc gaaaaggta gcctgcgttg ggcaattgaa cagagcaatg caaatagcgc     4800
acaagaaaac cagattctga ttcaggcagt tggtaaagca ccgtatgtta tcaaagttga    4860
taaaccgctg cctccgatta aaagcagcgt taaaatcatt ggcaccgagt gggataaaac    4920
cggtgaattt attgcaattg atggcagcaa ctatatcaaa ggcgaaggtg aaaaagcatg    4980
tccgggtgca aatccgggtc agtatggcac caatgttcgt accatgaccc tgcctggtct    5040
ggttctgcaa gatgttaatg tgttacccct gaaaggtctg gatgttcatc gttttgtat     5100
tggtgttctg gttaatcgca gcagcaataa cctgattcag cataatcgta tcagcaacaa    5160
ttatggtggt gccggtgtta tgattaccgg tgatgatggt aaaggtaatc gaccagcac     5220
caccaccaat aataacaaag ttctggataa cgtgttcatc gataatggtg atggtctgga    5280
actgacccgt ggtgcagcat ttaatctgat tgcaaataac ctgtttacca gcacaaaagc    5340
caatccggaa ccgagccagg gtattgaaat tctgtggggt aatgataatg ccgtggtggg    5400
taacaaattc gaaaactatt cagatggcct gcaaatcaat tggggtaaac gtaactatat    5460
cgcctataac gaactgacca ataacagcct gggtttcaat ctgacaggtg atggtaacat    5520
tttcgacagc aataaagtgc atggtaaccg tattggtatt gccattcgta gtgaaaaaga    5580
tgccaatgca cgtattaccc tgaccaaaaa tcagatttgg gataacggca agatatcaa     5640
acgttgtgaa gccggtggta gctgtgttcc gaatcagcgt ctgggtgcaa ttgttttgg     5700
tgttccggca ctggaacatg aaggttttgt tggtagccgt ggcggtggtg ttgttattga    5760
accggcaaaa ctgcaaaaaa cctgcaccca gccgaaccag cagaattgta atgcaattcc    5820
taatcagggt attcaggcac cgaaactgac agttagcaaa aaacagctga ccgttgaagt    5880
taaaggcacc cctaatcagc gttataatgt ggaattttt ggcaatcgta atgccagcag     5940
cagcgaagca aacagtatc tgggtagcat tgttgttgtt accgatcatc agggtctggc     6000
aaaagcaaat tgggctccga agttagcat gccgagcgtt accgcaaatg tgacagatca    6060
tctgggtgcg accagcgaac tgagcagcgc agttaaaatg cgttaaatgc atgcgcgccg    6120
cgttcgcgcg gcgcttttt ttggtaccga gctcgaattc actggccgtc gttttacaac    6180
gtcgtgactg ggaaaaccct ggcgttaccc aacttaatcg ccttgcagca catccccctt    6240
tcgccagctg gcgtaatagc gaagaggccc gcaccgatcg cccttcccaa cagttgcgca    6300
gcctgaatgg cgaatggcgc ctgatgcggt attttctcct tacgcatctg tgcggtattt    6360
cacaccgcat atggtgcact ctcagtacaa tctgctctga tgccgcatag ttaagccagc    6420
cccgacaccc gccaacaccc gctgacgaat tc                                  6452
```

<210> SEQ ID NO 26
<211> LENGTH: 10012
<212> TYPE: DNA
<213> ORGANISM: Escherichia coli
<220> FEATURE:
<221> NAME/KEY: misc_feature
<222> LOCATION: (1)..(10012)
<223> OTHER INFORMATION: DNA sequence of the plasmid pMG47

<400> SEQUENCE: 26

```
gttgacagta agacgggtaa gcctgttgat gataccgctg ccttactggg tgcattagcc      60
agtctgaatg acctgtcacg ggataatccg aagtggtcag actggaaaat cagagggcag     120
gaactgctga acagcaaaaa gtcagatagc accacatagc agacccgcca taaaacgccc     180
tgagaagccc gtgacgggct tttcttgtat tatgggtagt ttccttgcat gaatccataa     240
aaggcgcctg tagtgccatt taccccatt cactgccaga gccgtgagcg cagcgaactg      300
aatgtcacga aaagacagc gactcaggtg cctgatggtc ggagacaaaa ggaatattca     360
gcgatttgcc cgagcttgcg agggtgctac ttaagccttt agggttttaa ggtctgtttt     420
gtagaggagc aaacagcgtt tgcgacatcc ttttgtaata ctgcggaact gactaaagta     480
gtgagttata cacagggctg ggatctattc tttttatctt tttttattct ttctttattc     540
tataaattat aaccacttga atataaacaa aaaaaacaca caaggtctga gcggaattta     600
cagagggtct agcagaattt acaagttttc agcaaaggt ctagcagaat ttacagatac      660
ccacaactca aaggaaaagg actagtaatt atcattgact agcccatctc aattggtata     720
gtgattaaaa tcacctagac caattgagat gtatgtctga attagttgtt ttcaaagcaa     780
atgaactagc gattagtcgc tatgacttaa cggagcatga accaagcta attttatgct      840
gtgtggcact actcaacccc acgattgaaa accctacaag gaagaacgg acggtatcgt      900
tcacttataa ccaatacgct cagatgatga acatcagtag ggaaaatgct tatggtgtat     960
tagctaaagc aaccagagag ctgatgacga gaactgtgga atcaggaat ccttggtta      1020
aaggctttga gattttccag tggacaaact atgccaagtt ctcaagcgaa aaattagaat    1080
tagttttttag tgaagagata ttgccttatc ttttccagtt aaaaaaattc ataaaatata    1140
atctggaaca tgttaagtct tttgaaaaca atactctat gaggatttat gagtggttat     1200
taaaagaact aacacaaaag aaaactcaca aggcaaatat agagattagc cttgatgaat    1260
ttaagttcat gttaatgctt gaaaataact accatgagtt taaaaggctt aaccaatggg    1320
ttttgaaacc aataagtaaa gatttaaaca cttacagcaa tatgaaattg gtggttgata    1380
agcgaggccg cccgactgat acgttgattt tccaagttga actagataga caaatggatc    1440
tcgtaaccga acttgagaac aaccagataa aaatgaatgg tgacaaaata ccaacaacca    1500
ttacatcaga ttcctaccta cgtaacggac taagaaaaac actacacgat gctttaactg    1560
caaaaattca gctcaccagt tttgaggcaa aatttttgag tgacatgcaa agtaagcatg    1620
atctcaatgg ttcgttctca tggctcacgc aaaaacaacg aaccacacta gagaacatac    1680
tggctaaata cggaaggatc tgaggttctt atggctcttg tatctatcag tgaagcatca    1740
agactaacaa acaaaagtag aacaactgtt caccgttaga tatcaagggg aaaactgtcc    1800
atatgcacag atgaaaacgg tgtaaaaaag atagatacat cagagctttt acgagttttt    1860
ggtgcattta agctgttca ccatgaacag atcgacaatg taacagatga acagcatgta    1920
acacctaata gaacaggtga aaccagtaaa acaaagcaac tagaacatga aattgaacac    1980
ctgagacaac ttgttacagc tcaacagtca cacatagaca gcctgaaaca ggcgatgctg    2040
```

```
cttatcgaat caaagctgcc gacaacacgg gagccagtga cgcctcccgt ggggaaaaaa    2100
tcatggcaat tctggaagaa atagcgcttt cagccggcaa acctgaagcc ggatctgcga    2160
ttctgataac aaactagcaa caccagaaca gcccgtttgc gggcagcaaa accgttatg    2220 cttgtaaacc gttttgtgaa aaattttta aataaaaaa ggggacctct agggtcccca     2280
attaattagt aatataatct attaaaggtc attcaaaagg tcatccaccg gatcaattcc    2340
cctgctcgcg caggctgggt gccaagctct cgggtaacat caaggcccga tccttggagc    2400
ccttgccctc ccgcacgatg atcgtgccgt gatcgaaatc cagatccttg acccgcagtt    2460
gcaaaccctc actgatccgc atgcccgttc catacagaag ctgggcgaac aaacgatgct    2520
cgccttccag aaaaccgagg atgcgaacca cttcatccgg ggtcagcacc accggcaagc    2580
gccgcgacgg ccgaggtctt ccgatctcct gaagccaggg cagatccgtg cacagcacct    2640
tgccgtagaa gaacagcaag gccgccaatg cctgacgatg cgtggagacc gaaaccttgc    2700
gctcgttcgc cagccaggac agaaatgcct cgacttcgct gctgcccaag gttgccgggt    2760
gacgcacacc gtggaaacgg atgaaggcac gaacccagtg gacataagcc tgttcggttc    2820
gtaagctgta atgcaagtag cgtatgcgct cacgcaactg gtccagaacc ttgaccgaac    2880
gcagcggtgg taacggcgca gtggcggttt tcatggcttg ttatgactgt tttttgggg     2940 tacagtctat gcctcgggca tccaagcagc aagcgcgtta cgccgtgggt cgatgtttga    3000
tgttatggag cagcaacgat gttacgcagc agggcagtcg ccctaaaaca aagttaaaca    3060
tcatgaggga agcggtgatc gccgaagtat cgactcaact atcagaggta gttggcgtca    3120
tcgagcgcca tctcgaaccg acgttgctgg ccgtacattt gtacggctcc gcagtggatg    3180
gcggcctgaa gccacacagt gatattgatt tgctggttac ggtgaccgta aggcttgatg    3240
aaacaacgcg gcgagctttg atcaacgacc ttttggaaac ttcggcttcc cctggagaga    3300
gcgagattct ccgcgctgta gaagtcacca ttgttgtgca cgacgacatc attccgtggc    3360
gttatccagc taagcgcgaa ctgcaatttg gagaatggca gcgcaatgac attcttgcag    3420
gtatcttcga gccagccacg atcgacattg atctggctat cttgctgaca aaagcaagag    3480
aacatagcgt tgccttggta ggtccagcgg cggaggaact cttttgatccg gttcctgaac    3540 aggatctatt tgaggcgcta atgaaaacct aacgctatg gaactcgccg cccgactggg    3600
ctggcgatga gcgaaatgta gtgcttacgt tgtcccgcat ttggtacagc gcagtaaccg    3660
gcaaaatcgc gccgaaggat gtcgctgccg actgggcaat ggagcgcctg ccggcccagt    3720
atcagcccgt catacttgaa gctagacagg cttatcttgg acaagaagaa gatcgcttgg    3780
cctcgcgcgc agatcagttg gaagaatttg tccactacgt gaaaggcgag atcaccaagg    3840
tagtcggcaa ataatgtcta acaattcgtt caagccgacg ccgcttcgcg gcgcggctta    3900
actcaagcgt tagatgcact aagcacataa ttgctcacag ccaaactatc aggtcaagtc    3960
tgcttttatt atttttaagc gtgcataata agccctacac aaattgggag atatatcatg    4020
aaaggctggc tttttcttgt tatcgcaata gttggcgaag taatcgcaac atccgcatta    4080
aaatctagcg agggctttac taagctgatc cggtggatga ccttttgaat gacctttaat    4140
agattatatt actaattaat tggggaccct agaggtcccc ttttttattt taaaaatttt    4200
ttcacaaaac ggtttacaag catacgttgg ccgattcatt aatgcagctg gcacgacagg    4260
tttcccgact ggaaagcggg cagtgagcgc aacgcaatta atgtgagtta gctcactcat    4320
taggcacccc aggctttaca ctttatgctt ccggctcgta tgttgtgtgg aattgtgagc    4380
ggataacaat ttcacacagg aaacagctat gaccatgatt acgccaagct tgctattgac    4440
```

```
gacagctatg gttcactgtc caccaaccaa aactgtgctc agtaccgcca atatttctcc    4500 cttgagggt  acaaagaggt gtccctagaa gagatccacg ctgtgtaaaa attttacaaa    4560
aaggtattga ctttccctac agggtgtgta ataatttaat tacaggcggg ggcaaccccg    4620
cctgttctgc agaggaggaa tatagccatg gaagtgaaaa tcttcaacac ccaggatgtt    4680
caggattttc tgcgtgttgc aagcggtctg gaacaagagg gtggtaatcc gcgtgttaaa    4740
caaattattc atcgtgttct gagcgacctg tataaagcaa ttgaagatct gaatatcacc    4800
agcgacgaat attgggcagg cgttgcatat ctgaatcagc tgggtgcaaa tcaagaagca    4860
ggtctgctga gtccgggtct gggttttgat cattatctgg atatgcgtat ggatgcagaa    4920
gatgcagcac tgggtattga aaatgcaaca ccgcgtacca ttgaaggtcc gctgtatgtt    4980
gcgggtgcac cggaaagcgt tggttatgca cgcatggatg atggtagcga tccgaatggt    5040 catacccctga ttctgcatgg caccattttt gatgcagatg gtaaaccgct gccgaatgca    5100
aaagttgaaa tttggcatgc aaacaccaaa ggcttttata gccatttga tccgaccggt    5160 gaacagcagg cctttaatat gcgtcgtagc attattaccg atgagaatgg tcagtatcgt    5220
gttcgtacca ttctgcctgc cggttatggt tgtcctccgg aaggtccgac ccagcaactg    5280
ctgaaccaac tgggtcgtca tggtaatcgt ccggcacata ttcattattt tgttagcgca    5340
gatggtcacc gtaaactgac cacccagatt aatgttgccg gtgatccgta tacctatgat    5400
gattttgcat atgccacccg tgaaggtctg gttgttgatg cagttgaaca taccgatccg    5460
gaagcaatta aagccaatga tgtggaaggt ccttttgccg aaatggtgtt tgatctgaaa    5520
ctgacccgtc tggttgatgg tgttgataat caggttgtgg atcgtccgcg tctggcagtt    5580
taatacacca aaatggttca aaattatcag gcgagtgatc atgatcactg gcctgttttt    5640
atttcaggga agggtggaga caattacgtg gataatcaga tcatccaaga aaccgtggat    5700
aaaattctga gcgttctgcc gaatcaggca ggtcagctgg cacgtctggt gcgtctgatg    5760
caatttgcat gcgatccgac cattaccgtt attggcaaat ataaccatgg taaaagccgt    5820
ctgctgaatg aactgattgg caccgatatc tttagcgttg cagataaacg tgaaaccatt    5880
cagctggccg aacataaaca ggatcaggtt cgttggctgg atgcacctgg tctggatgcc    5940
gatgttgcag cagttgatga tcgtcatgca tttgaagcag tttggaccca ggcagatatt    6000
cgtctgtttg ttcatagcgt tcgtgaaggt gaactggatg caaccgaaca ccatctgctg    6060
caacagctga ttgaagatgc cgatcatagc cgtcgtcaga ccattctggt tctgacccag    6120
attgatcaga ttccggatca gaccatcctg acacagatta aaaccagcat tgcacagcag    6180
gttccgaaac tggatatttg ggcagttagc gcaacccgtc atcgtcaggg cattgaaaac    6240
ggtaaaaccc tgctgatcga aaaagcggt  attggtgcac tgcgccatac cctggaacag    6300
gcactggcac aggtgccgag cgcacgtacc tatgaaaaaa atcgtctgct gtcagatctg    6360
caccatcagc tgaaacaact gctgctggat cagaaacatg ttctgcaaca actgcaacag    6420
acacagcaac agcagctgca tgattttgat accggtctga ttaacattct ggacaaaatt    6480
cgtgttgatc tggaaccgat tgtgaatatt gatggtcagg atcaagcact gaatccggat    6540
agctttgcaa ccatgtttaa aaacaccgca gcaaacagc  agcgtgccaa agttcagatt    6600
gcatatagcc gtgcatgcat tgaaatcaac agccatctga ttcgccatgg tgttgttggt    6660
ctgcctgcgg aacagcagac caccattaaa agcattgata ccgtgattgt tgccgtgttt    6720
ggtatcagcg ttaaatttcg tgatcagctg cgtgccctgt tttataccga taccgaacgt    6780
```

```
cagcgtctgc aacgtgaatt tcgtttctat tttgaaaaaa gtgccggtcg catgattctg    6840
gcagcaaaaa ttgaacagac catgcgtcag cagggctgta ttcagaatgc catgatggca    6900
ctgcaacaaa tggaaagcgc agcataaaaa cacggacgcc gcaaacggcg tccgaatttc    6960
ttggtcgacc gttaaatcta tcaccgcaag ggataaatat ctaacaccgt gcgtgttgac    7020
tattttacct ctggcggtga taatggttgc atgtactaat ctagataagg aatatagcca    7080
tgaccgcacc gattcaggat ctgcgtgatg caattgccct gctgcaacag catgataatc    7140
agtatctgga aaccgatcat ccggttgatc cgaatgcaga actggcaggc gtttatcgtc    7200
atattggtgc cggtggcacc gttaaacgtc cgacccgtat tggtccggca atgatgttta    7260
ataacattaa aggttatccg cacagccgta ttctggttgg tatgcatgca agccgtcagc    7320
gtgcagcact gctgctgggt tgtgaagcaa gtcagctggc actggaagtt ggtaaagcag    7380
ttaaaaaacc ggttgcaccg gtggttgttc cggcaagcag cgcaccgtgt caagagcaga    7440
tttttctggc agatgatccg gattttgatc tgcgtaccct gctgcctgca cataccaata    7500
ccccgattga tgcaggtccg ttttttttgtc tgggtctggc cctggcaagc gatccggtgg    7560
atgcaagcct gaccgatgtt accattcatc gtctgtgtgt tcagggtcgt gatgaactga    7620
gcatgttcct ggcagcaggt cgccatattg aagttttcg tcagaaagca gaagcagcag    7680
gtaaaccgct gccgattacc attaatatgg gtctggaccc agcaatctat attggcgcat    7740
gttttgaagc accgaccacc ccgtttggtt ataatgaact gggtgttgcc ggtgcactgc    7800
gtcagcgtcc ggttgaactg gttcagggtg ttagcgttcc ggaaaaagca attgcacgtg    7860
ccgaaattgt tattgaaggt gaactgctgc ctggtgttcg tgttcgtgaa gatcagcata    7920
ccaattcagg tcatgcaatg ccggaatttc cgggttattg tggtggtgca aatccgagcc    7980
tgccggttat taaagttaaa gccgttacca tgcgcaataa cgcaattctg caaaccctgg    8040
ttggtccggg tgaagaacat accaccctgg caggtctgcc gaccgaagca agcatttgga    8100
atgcagttga agcagcaatt ccgggttttc tgcaaaatgt ttatgcccat accgcaggcg    8160
gtggtaaatt tctgggtatt ctgcaagtga aaaaacgtca gcctgccgat gaaggtcgtc    8220 agggtcagge agcccctgctg gcgctggcaa cctatagcga actgaaaaat atcattctgg    8280
tggatgagga tgtggacatt tttgatagtg atgatattct gtgggcaatg accacccgta    8340
tgcagggtga tgttagcatt accaccattc cgggtattcg cggtcatcag ctggacccga    8400
gccagacacc ggaatattca ccgagcattc gtggtaatgg tattagctgc aaaaccatct    8460
ttgattgtac cgttccgtgg gcactgaaaa gccattttga acgtgcaccg tttgcagatg    8520
ttgatccgcg tccgtttgca cctgaatatt ttgcacgtct ggaaaaaaat cagggcagcg    8580
caaaataagc taataacagg cctgctggta atcgcaggaa ttttttatttg gatggatccg    8640 cctacctagc ttccaagaaa gatatcctaa cagcacaaga gcggaaagat gttttgttct    8700
acatccagaa caacctctgc taaaattcct gaaaatttt gcaaaagtt gttgacttta    8760 tctacaaggt gtggtataat aatcttaaca acagcaggac gctcccgggt tgaggaaaac    8820
ctaatgaaat atagcctgtg caccattagc tttcgtcacc agctgattag ctttaccgat    8880
attgttcagt ttgcctatga aaacggcttt gaaggtattg aactgtgggg cacccatgca    8940
cagaatctgt atatgcaaga atatgaaacc accgaacgtg aactgaattg cctgaaagat    9000 aaaccctgg aaattaccat gatcagcgat tatctggata ttagcctgag cgcagatttt    9060
gaaaaaacca tcgaaaaatg tgaacagctg gcaattctgg ccaattggtt taaaacgaac    9120
aaaattcgta cctttgccgg tcagaaaggt agtgcagatt ttagccagca agaacgtcaa    9180
```

| | | | |
|---|---|---|---|
| gagtatgtga | atcgtattcg | catgatttgt gaactgtttg cccagcataa tatgtatgtt | 9240 |
| ctgctggaaa | cccatccgaa | taccctgacc gataccctgc cgagcaccct ggaactgctg | 9300 |
| ggtgaagttg | atcatccgaa | tctgaaaatc aacctggatt ttctgcatat ctgggaaagc | 9360 |
| ggtgcagatc | cggttgatag | ctttcagcag ctgcgtccgt ggattcagca ttatcacttt | 9420 |
| aaaaacatta | gcagcgcaga | ctatctgcat gtgtttgaac cgaataatgt ttatgcagca | 9480 |
| gcaggtaatc | gtaccggtat | ggttccgctg tttgaaggca ttgttaacta tgatgaaatc | 9540 |
| atccaagaag | tgcgcgatac | cgatcatttt gcaagcctgg aatggtttgg tcataacgca | 9600 |
| aaagatattc | tgaaagccga | aatgaaagtg ctgaccaatc gtaatctgga agttgttacc | 9660 |
| agctaaatgc | atgcgcgccg | cgttcgcgcg gcgctttttt ttggtaccga gctcgaattc | 9720 |
| actggccgtc | gttttacaac | gtcgtgactg ggaaaaccct ggcgttaccc aacttaatcg | 9780 |
| ccttgcagca | catccccctt | tcgccagctg gcgtaatagc gaagaggccc gcaccgatcg | 9840 |
| cccttcccaa | cagttgcgca | gcctgaatgg cgaatgcgc ctgatgcggt attttctcct | 9900 |
| tacgcatctg | tgcggtattt | cacaccgcat atggtgcact ctcagtacaa tctgctctga | 9960 |
| tgccgcatag | ttaagccagc | cccgacaccc gccaacaccc gctgacgaat tc | 10012 |

<210> SEQ ID NO 27
<211> LENGTH: 10249
<212> TYPE: DNA
<213> ORGANISM: Escherichia coli
<220> FEATURE:
<221> NAME/KEY: misc_feature
<222> LOCATION: (1)..(10249)
<223> OTHER INFORMATION: DNA sequence of the plasmid pMG70

<400> SEQUENCE: 27

| | | | |
|---|---|---|---|
| gttgacagta | agacgggtaa | gcctgttgat gataccgctg ccttactggg tgcattagcc | 60 |
| agtctgaatg | acctgtcacg | ggataatccg aagtggtcag actggaaaat cagagggcag | 120 |
| gaactgctga | acagcaaaaa | gtcagatagc accacatagc agacccgcca taaaacgccc | 180 |
| tgagaagccc | gtgacgggct | tttcttgtat tatgggtagt ttccttgcat gaatccataa | 240 |
| aaggcgcctg | tagtgccatt | taccccccatt cactgccaga gccgtgagcg cagcgaactg | 300 |
| aatgtcacga | aaagacagc | gactcaggtg cctgatggtc ggagacaaaa ggaatattca | 360 |
| gcgatttgcc | cgagcttgcg | agggtgctac ttaagccttt agggttttaa ggtctgtttt | 420 |
| gtagaggagc | aaacagcgtt | tgcgacatcc ttttgtaata ctgcggaact gactaaagta | 480 |
| gtgagttata | cacagggctg | ggatctattc tttttatctt ttttattct ttctttattc | 540 |
| tataaattat | aaccacttga | atataaacaa aaaaaacaca caaaggtcta gcggaattta | 600 |
| cagggggtct | agcagaattt | acaagttttc cagcaaaggt ctagcagaat ttacagatac | 660 |
| ccacaactca | aaggaaaagg | actagtaatt atcattgact agcccatctc aattggtata | 720 |
| gtgattaaaa | tcacctagac | caattgagat gtatgtctga attagttgtt ttcaaagcaa | 780 |
| atgaactagc | gattagtcgc | tatgacttaa cggagcatga accaagcta atttatgct | 840 |
| gtgtggcact | actcaacccc | acgattgaaa accctacaag gaaagaacgg acggtatcgt | 900 |
| tcacttataa | ccaatacgct | cagatgatga acatcagtag ggaaaatgct tatggtgtat | 960 |
| tagctaaagc | aaccagagag | ctgatgacga gaactgtgga aatcaggaat cctttggtta | 1020 |
| aaggctttga | gattttccag | tggacaaact atgccaagtt ctcaagcgaa aaattagaat | 1080 |
| tagttttag | tgaagagata | ttgccttatc ttttccagtt aaaaaaattc ataaaatata | 1140 |

-continued

```
atctggaaca tgttaagtct tttgaaaaca aatactctat gaggatttat gagtggttat    1200
taaaagaact aacacaaaag aaaactcaca aggcaaatat agagattagc cttgatgaat    1260
ttaagttcat gttaatgctt gaaaataact accatgagtt aaaaggctt aaccaatggg    1320 ttttgaaacc aataagtaaa gatttaaaca cttacagcaa tatgaaattg gtggttgata    1380
agcgaggccg cccgactgat acgttgattt tccaagttga actagataga caaatggatc    1440
tcgtaaccga acttgagaac aaccagataa aaatgaatgg tgacaaaata ccaacaacca    1500
ttacatcaga ttcctaccta cgtaacggac taagaaaaac actacacgat gctttaactg    1560
caaaaattca gctcaccagt tttgaggcaa aattttttgag tgacatgcaa agtaagcatg    1620
atctcaatgg ttcgttctca tggctcacgc aaaaacaacg aaccacacta gagaacatac    1680
tggctaaata cggaaggatc tgaggttctt atggctcttg tatctatcag tgaagcatca    1740
agactaacaa acaaaagtag aacaactgtt caccgttaga tatcaaaggg aaaactgtcc    1800
atatgcacag atgaaaacgg tgtaaaaaag atagatacat cagagctttt acgagttttt    1860
ggtgcattta aagctgttca ccatgaacag atcgacaatg taacagatga acagcatgta    1920
acacctaata gaacaggtga aaccagtaaa acaaagcaac tagaacatga aattgaacac    1980
ctgagacaac ttgttacagc tcaacagtca cacatagaca gcctgaaaca ggcgatgctg    2040
cttatcgaat caaagctgcc gacaacacgg gagccagtga cgcctcccgt ggggaaaaaa    2100
tcatggcaat tctggaagaa atagcgcttt cagccggcaa acctgaagcc ggatctgcga    2160
ttctgataac aaactagcaa caccagaaca gcccgtttgc gggcagcaaa acccgttatg    2220
cttgtaaacc gttttgtgaa aaaatttta aaataaaaaa ggggacctct agggtcccca    2280
attaattagt aatataatct attaaaggtc attcaaaagg tcatccaccg gatcaattcc    2340
cctgctcgcg caggctgggt gccaagctct cgggtaacat caaggcccga tccttggagc    2400
ccttgccctc ccgcacgatg atcgtgccgt gatcgaaatc cagatccttg acccgcagtt    2460
gcaaaccctc actgatccgc atgcccgttc catacagaag ctgggcgaac aaacgatgct    2520
cgccttccag aaaaccgagg atgcgaacca cttcatccgg ggtcagcacc accggcaagc    2580
gccgcgacgg ccgaggtctt ccgatctcct gaagccaggg cagatccgtg cacagcacct    2640
tgccgtagaa gaacagcaag gccgccaatg cctgacgatg cgtggagacc gaaaccttgc    2700
gctcgttcgc cagccaggac agaaatgcct cgacttcgct gctgcccaag gttgccgggt    2760
gacgcacacc gtggaaacgg atgaaggcac gaacccagtg gacataagcc tgttcggttc    2820
gtaagctgta atgcaagtag cgtatgcgct cacgcaactg gtccagaacc ttgaccgaac    2880
gcagcggtgg taacggcgca gtggcggttt tcatggcttg ttatgactgt ttttttgggg    2940
tacagtctat gcctcgggca tccaagcagc aagcgcgtta cgccgtgggt cgatgtttga    3000
tgttatggag cagcaacgat gttacgcagc agggcagtcg ccctaaaaca aagttaaaca    3060
tcatgaggga agcggtgatc gccgaagtat cgactcaact atcagaggta gttggcgtca    3120
tcgagcgcca tctcgaaccg acgttgctgg ccgtacattt gtacggctcc gcagtggatg    3180
gcggcctgaa gccacacagt gatattgatt tgctggttac ggtgaccgta aggcttgatg    3240
aaacaacgcg gcgagctttg atcaacgacc ttttggaaac ttcggcttcc cctggagaga    3300
gcgagattct ccgcgctgta gaagtcacca ttgttgtgca cgacgacatc attccgtggc    3360
gttatccagc taagcgcgaa ctgcaatttg gagaatggca gcgcaatgac attcttgcag    3420
gtatcttcga gccagccacg atcgacattg atctggctat cttgctgaca aaagcaagag    3480
aacatagcgt tgccttggta ggtccagcgg cggaggaact cttttgatccg gttcctgaac    3540
```

-continued

```
aggatctatt tgaggcgcta aatgaaacct taacgctatg gaactcgccg cccgactggg    3600
ctggcgatga gcgaaatgta gtgcttacgt tgtcccgcat ttggtacagc gcagtaaccg    3660
gcaaaatcgc gccgaaggat gtcgctgccg actgggcaat ggagcgcctg ccggcccagt    3720
atcagcccgt catacttgaa gctagacagg cttatcttgg acaagaagaa gatcgcttgg    3780
cctcgcgcgc agatcagttg gaagaatttg tccactacgt gaaaggcgag atcaccaagg    3840
tagtcggcaa ataatgtcta acaattcgtt caagccgacg ccgcttcgcg gcgcggctta    3900
actcaagcgt tagatgcact aagcacataa ttgctcacag ccaaactatc aggtcaagtc    3960
tgcttttatt attttttaagc gtgcataata agccctacac aaatttgggag atatatcatg   4020 aaaggctggc tttttcttgt tatcgcaata gttggcgaag taatcgcaac atccgcatta    4080
aaatctagcg agggctttac taagctgatc cggtggatga ccttttgaat gacctttaat    4140
agattatatt actaattaat tggggaccct agaggtcccc ttttttattt taaaaatttt    4200
ttcacaaaac ggtttacaag catacgttgg ccgattcatt aatgcagctg gcacgacagg    4260
tttcccgact ggaaagcggg cagtgagcgc aacgcaatta atgtgagtta gctcactcat    4320
taggcacccc aggctttaca ctttatgctt ccggctcgta tgttgtgtgg aattgtgagc    4380
ggataacaat ttcacacagg aaacagctat gaccatgatt acgccaagct tgctattgac    4440
gacagctatg gttcactgtc caccaaccaa aactgtgctc agtaccgcca atatttctcc    4500
cttgaggggt acaagaggt gtccctagaa gagatccacg ctgtgtaaaa attttacaaa     4560
aaggtattga ctttccctac agggtgtgta ataatttaat tacaggcggg ggcaaccccg    4620
cctgttctgc agaggaggaa tatagccatg gaagtgaaaa tcttcaacac ccaggatgtt    4680
caggattttc tgcgtgttgc aagcggtctg gaacaagagg gtggtaatcc gcgtgttaaa    4740
caaattattc atcgtgttct gagcgacctg tataaagcaa ttgaagatct gaatatcacc    4800
agcgacgaat attgggcagg cgttgcatat ctgaatcagc tgggtgcaaa tcaagaagca    4860
ggtctgctga gtccgggtct gggttttgat cattatctgg atatgcgtat ggatgcagaa    4920
gatgcagcac tgggtattga aaatgcaaca ccgcgtacca ttgaaggtcc gctgtatgtt    4980
gcgggtgcac cggaaagcgt tggttatgca cgcatggatg atggtagcga tccgaatggt    5040 catacccctga ttctgcatgg caccattttt gatgcagatg gtaaaccgct gccgaatgca   5100
aaagttgaaa tttggcatgc aaacaccaaa ggcttttata gccattttga tccgaccggt    5160
gaacagcagg ccttaatat gcgtcgtagc attattaccg atgagaatgg tcagtatcgt     5220
gttcgtacca ttctgcctgc cggttatggt tgtcctccgg aaggtccgac ccagcaactg    5280
ctgaaccaac tgggtcgtca tggtaatcgt ccggcacata ttcattattt tgttagcgca    5340
gatggtcacc gtaaactgac cacccagatt aatgttgccg gtgatccgta tacctatgat    5400
gattttgcat atgccacccg tgaaggtctg gttgttgatg cagttgaaca taccgatccg    5460
gaagcaatta aagccaatga tgtggaaggt ccttttgccg aaatggtgtt tgatctgaaa    5520
ctgacccgtc tggttgatgg tgttgataat caggttgtgg atcgtccgcg tctggcagtt    5580
taatacacca aaatggttca aaattatcag gcgagtgatc atgatcactg gcctgttttt    5640
atttcaggga agggtggaga caattacgtg gataatcaga tcatccaaga aaccgtggat    5700
aaaattctga gcgttctgcc gaatcaggca ggtcagctgg cacgtctggt gcgtctgatg    5760
caatttgcat gcgatccgac cattaccgtt attggcaaat ataaccatgg taaaagccgt    5820
ctgctgaatg aactgattgg caccgatatc tttagcgttg cagataaacg tgaaaccatt    5880
```

| | |
|---|---|
| cagctggccg aacataaaca ggatcaggtt cgttggctgg atgcacctgg tctggatgcc | 5940 |
| gatgttgcag cagttgatga tcgtcatgca tttgaagcag tttggaccca ggcagatatt | 6000 |
| cgtctgtttg ttcatagcgt tcgtgaaggt gaactggatg caaccgaaca ccatctgctg | 6060 |
| caacagctga ttgaagatgc cgatcatagc cgtcgtcaga ccattctggt tctgacccag | 6120 |
| attgatcaga ttccggatca gaccatcctg acacagatta aaaccagcat tgcacagcag | 6180 |
| gttccgaaac tggatatttg gcagttagc gcaacccgtc atcgtcaggg cattgaaaac | 6240 |
| ggtaaaaccc tgctgatcga aaaaagcggt attggtgcac tgcgccatac cctggaacag | 6300 |
| gcactggcac aggtgccgag cgcacgtacc tatgaaaaaa atcgtctgct gtcagatctg | 6360 |
| caccatcagc tgaaacaact gctgctggat cagaaacatg ttctgcaaca actgcaacag | 6420 |
| acacagcaac agcagctgca tgattttgat accggtctga ttaacattct ggacaaaatt | 6480 |
| cgtgttgatc tggaaccgat tgtgaatatt gatggtcagg atcaagcact gaatccggat | 6540 |
| agctttgcaa ccatgtttaa aaacaccgca gcaaaacagc agcgtgccaa agttcagatt | 6600 |
| gcatatagcc gtgcatgcat tgaaatcaac agccatctga ttcgccatgg tgttgttggt | 6660 |
| ctgcctgcgg aacagcagac caccattaaa agcattgata ccgtgattgt tgccgtgttt | 6720 |
| ggtatcagcg ttaaatttcg tgatcagctg cgtgccctgt tttataccga taccgaacgt | 6780 |
| cagcgtctgc aacgtgaatt tcgtttctat tttgaaaaaa gtgccggtcg catgattctg | 6840 |
| gcagcaaaaa ttgaacagac catgcgtcag cagggctgta ttcagaatgc catgatggca | 6900 |
| ctgcaacaaa tggaaagcgc agcataaaaa cacggacgcc gcaaacggcg tccgaatttc | 6960 |
| ttggtcgacc gttaaatcta tcaccgcaag ggataaatat ctaacaccgt gcgtgttgac | 7020 |
| tattttacct ctggcggtga taatggttgc atgtactaat ctagataagg aatatagcca | 7080 |
| tgaccgcacc gattcaggat ctgcgtgatg caattgccct gctgcaacag catgataatc | 7140 |
| agtatctgga aaccgatcat ccggttgatc cgaatgcaga actggcaggc gtttatcgtc | 7200 |
| atattggtgc cggtggcacc gttaaacgtc cgacccgtat tggtccggca atgatgttta | 7260 |
| ataacattaa aggttatccg cacagccgta ttctggttgg tatgcatgca agccgtcagc | 7320 |
| gtgcagcact gctgctgggt tgtgaagcaa gtcagctggc actggaagtt ggtaaagcag | 7380 |
| ttaaaaaacc ggttgcaccg gtggttgttc cggcaagcag cgcaccgtgt caagagcaga | 7440 |
| tttttctggc agatgatccg gattttgatc tgcgtaccct gctgcctgca cataccaata | 7500 |
| ccccgattga tgcaggtccg ttttttttgtc tgggtctggc cctggcaagc gatccggtgg | 7560 |
| atgcaagcct gaccgatgtt accattcatc gtctgtgtgt tcagggtcgt gatgaactga | 7620 |
| gcatgttcct ggcagcaggt cgccatattg aagttttttcg tcagaaagca gaagcagcag | 7680 |
| gtaaaccgct gccgattacc attaatatgg gtctggaccc agcaatctat attggcgcat | 7740 |
| gttttgaagc accgaccacc ccgtttggtt ataatgaact gggtgttgcc ggtgcactgc | 7800 |
| gtcagcgtcc ggttgaactg gttcagggtg ttagcgttcc ggaaaaagca attgcacgtg | 7860 |
| ccgaaattgt tattgaaggt gaactgctgc ctggtgttcg tgttcgtgaa gatcagcata | 7920 |
| ccaattcagg tcatgcaatg ccggaatttc gggttattg tggtggtgca atccgagcc | 7980 |
| tgccggttat taaagttaaa gccgttacca tgcgcaataa cgcaattctg caaaccctgg | 8040 |
| ttggtccggg tgaagaacat accaccctgg caggtctgcc gaccgaagca agcatttgga | 8100 |
| atgcagttga agcagcaatt ccgggttttc tgcaaaatgt ttatgcccat accgcaggcg | 8160 |
| gtggtaaatt tctgggtatt ctgcaagtga aaaacgtca gcctgccgat gaaggtcgtc | 8220 |
| agggtcaggc agccctgctg gcgctggcaa cctatagcga actgaaaaat atcattctgg | 8280 |

-continued

```
tggatgagga tgtggacatt tttgatagtg atgatattct gtgggcaatg accacccgta    8340
tgcagggtga tgttagcatt accaccattc cgggtattcg cggtcatcag ctggacccga    8400
gccagacacc ggaatattca ccgagcattc gtggtaatgg tattagctgc aaaaccatct    8460
ttgattgtac cgttccgtgg gcactgaaaa gccattttga acgtgcaccg tttgcagatg    8520
ttgatccgcg tccgtttgca cctgaatatt ttgcacgtct ggaaaaaaat cagggcagcg    8580
caaaataagc taataacagg cctgctggta atcgcaggaa ttttatttg gatggatccg    8640 cctacctagc ttccaagaaa gatatcctaa cagcacaaga gcggaaagat gttttgttct    8700
acatccagaa caacctctgc taaaattcct gaaaaatttt gcaaaagtt gttgacttta    8760 tctacaaggt gtggtataat aatcttaaca acagcaggac gctcccgggt tgaggaaaac    8820
ctaatgccga gcaaactggc aattagcagc atgagcctgg tcgttgttt tgcaggtcat    8880 agcctggata gtaaactgga tgcagcacag cgttatggtt atctgggtat tgaactgttt    8940
tatgaggatc tggttgatgt tgcagaacat ctgagcaatg aacgtccgag tccggaaggt    9000
ccgtttgttg aagcacagat tgcagcagca cgtcatattc tgcaaatgtg tcaggcacgt    9060
ggtctggaag ttgtttgtct gcaaccgttt atgcattatg atggtctgaa tgatcgtgcc    9120
gaacatgaac gtcgtctgga aaaactggca ctgtggattg aactggcaca tgaactgcat    9180
accgatatta ttcagattcc ggcaaatttt ctgcctgcaa atcaggttag cgataatctg    9240
gatctgattg ttagcgatct gtgtaaagtt gcagatattg gtgcacaggc actgcctccg    9300
attcgttttg catatgaaag cctgtgttgg agcacccgtg ttgatctgtg ggaacgttgt    9360
tgggatattg ttcagcgtgt ggatcgtccg aattttggta tttgtctgga tacctttaac    9420
atcctgggtc gcatttatgc agatccgacc agcccgagcg gtcgtacccc gaatgcaaaa    9480
gaagcagttc gtaaaagcat tgccaatctg gttagccgtg tggatgttag caaagttttt    9540
tatgttcagg ttgtggatgc cgaacgtctg agtaaaccgc tgctgcctgg tcatccgtat    9600
tataacccgg aacagcctgc acgtatgagc tggtcacgta attgtcgtct gttctatggt    9660
gaaaccgaat atggtgcata tctgccggtt aaagaagttg cacgcgcact gtttcatggt    9720
attggttttg aaggttgggt tagcctggaa ctgtttaatc gtcgtatgag cgaagaaggt    9780
ccggaagttc ctgaagaact ggccatgcgt ggtgcaatta gctgggcaaa actggttcag    9840
gatctgcgta ttccggttga aggtccgctg gttaccatgc ctcgtgttag cgcaagcctg    9900
taaatgcatg cgcgccgcgt tcgcgcggcg cttttttttg gtaccgagct cgaattcact    9960
ggccgtcgtt ttacaacgtc gtgactggga aaaccctggc gttacccaac ttaatcgcct    10020
tgcagcacat ccccctttcg ccagctggcg taatagcgaa gaggcccgca ccgatcgccc    10080
ttcccaacag ttgcgcagcc tgaatggcga atggcgcctg atgcggtatt ttctccttac    10140
gcatctgtgc ggtatttcac accgcatatg gtgcactctc agtacaatct gctctgatgc    10200
cgcatagtta agccagcccc gacacccgcc aacacccgct gacgaattc                10249
```

<210> SEQ ID NO 28
<211> LENGTH: 7623
<212> TYPE: DNA
<213> ORGANISM: Escherichia coli
<220> FEATURE:
<221> NAME/KEY: misc_feature
<222> LOCATION: (1)..(7623)
<223> OTHER INFORMATION: DNA sequence of the plasmid pCP32AMP

<400> SEQUENCE: 28

-continued

```
acatgaatgg tcttcggttt ccgtgtttcg taaagtctgg aaacgcggaa gtcagcgccc    60
tgcaccatta tgttccggat ctgcatcgca ggatgctgct ggctaccctg tggaacacct   120
acatctgtat taacgaagcg ctggcattga ccctgagtga ttttctctg gtcccgccgc    180
atccataccg ccagttgttt accctcacaa cgttccagta accgggcatg ttcatcatca   240
gtaacccgta tcgtgagcat cctctctcgt ttcatcggta tcattacccc catgaacaga   300
aattccccct tacacggagg catcaagtga ccaaacagga aaaaccgcc cttaacatgg    360
cccgctttat cagaagccag acattaacgc ttctggagaa actcaacgag ctggacgcgg   420
atgaacaggc agacatctgt gaatcgcttc acgaccacgc tgatgagctt taccgcagct   480
gcctcgcgcg tttcggtgat gacggtgaaa acctctgaca catgcagctc ccggagacgg   540
tcacagcttg tctgtaagcg gatgccggga gcagacaagc ccgtcagggc gcgtcagcgg   600
gtgttggcgg gtgtcggggc gcagccatga cccagtcacg tagcgatagc ggagtgtata   660
ctggcttaac tatgcggcat cagagcagat tgtactgaga gtgcaccata tgcggtgtga   720
aataccgcac agatgcgtaa ggagaaaata ccgcatcagg cgctcttccg cttcctcgct   780
cactgactcg ctgcgctcgg tcgttcggct gcggcgagcg gtatcagctc actcaaaggc   840
ggtaatacgg ttatccacag aatcagggga taacgcagga agaacatgt gagcaaaagg    900
ccagcaaaag gccaggaacc gtaaaaaggc cgcgttgctg gcgttttcc ataggctccg    960
cccccctgac gagcatcaca aaatcgacg ctcaagtcag aggtggcgaa acccgacagg   1020
actataaaga taccaggcgt ttccccctgg aagctccctc gtgcgctctc ctgttccgac   1080
cctgccgctt accggatacc tgtccgcctt tctcccttcg ggaagcgtgg cgctttctca   1140
tagctcacgc tgtaggtatc tcagttcggt gtaggtcgtt cgctccaagc tgggctgtgt   1200
gcacgaaccc cccgttcagc ccgaccgctg cgccttatcc ggtaactatc gtcttgagtc   1260
caacccggta agacacgact tatcgccact ggcagcagcc actggtaaca ggattagcag   1320
agcgaggtat gtaggcggtg ctacagagtt cttgaagtgg tggcctaact acggctacac   1380
tagaaggaca gtatttggta tctgcgctct gctgaagcca gttaccttcg gaaaaagagt   1440
tggtagctct tgatccggca aacaaaccac cgctggtagc ggtggttttt tgtttgcaa    1500
gcagcagatt acgcgcagaa aaaaggatc tcaagaagat cctttgatct tttctacggg   1560
gtctgacgct cagtggaacg aaaactcacg ttaagggatt ttggtcatga gattatcaaa   1620
aaggatcttc acctagatcc ttttaaatta aaatgaagt tttaaatcaa tctaaagtat   1680
atatgagtaa acttggtctg acagttacca atgcttaatc agtgaggcac ctatctcagc   1740
gatctgtcta tttcgttcat ccatagttgc ctgactcccc gtcgtgtaga taactacgat   1800
acgggagggc ttaccatctg gccccagtgc tgcaatgata ccgcgagacc cacgctcacc   1860
ggctccagat ttatcagcaa taaccagcc agccggaagg gccgagcgca gaagtggtcc   1920
tgcaacttta tccgcctcca tccagtctat taattgttgc cgggaagcta agtaagtag    1980
ttcgccagtt aatagtttgc gcaacgttgt tgccattgct gcaggcatcg tggtgtcacg   2040
ctcgtcgttt ggtatggctt cattcagctc cggttcccaa cgatcaaggc gagttacatg   2100
atcccccatg ttgtgcaaaa aagcggttag ctccttcggt cctccgatcg ttgtcagaag   2160
taagttggcc gcagtgttat cactcatggt tatggcagca ctgcataatt ctcttactgt   2220
catgccatcc gtaagatgct tttctgtgac tggtgagtac tcaaccaagt cattctgaga   2280
atagtgtatg cggcgaccga gttgctcttg cccggcgtca acacgggata ataccgcgcc   2340
acatagcaga actttaaaag tgctcatcat tggaaaacgt tcttcggggc gaaaactctc   2400
```

```
aaggatctta ccgctgttga gatccagttc gatgtaaccc actcgtgcac ccaactgatc    2460
ttcagcatct tttactttca ccagcgtttc tgggtgagca aaaacaggaa ggcaaaatgc    2520
cgcaaaaaag ggaataaggg cgacacggaa atgttgaata ctcatactct tccttttca    2580 atattattga agcatttatc agggttattg tctcatgagc ggatacatat ttgaatgtat    2640
ttagaaaaat aaacaaatag gggttccgcg cacatttccc cgaaaagtgc cacctgacgt    2700
ctaagaaacc attattatca tgacattaac ctataaaaat aggcgtatca cgaggccctt    2760
tcgtcttcaa gaattctgaa ccagtcctaa acgagtaaa taggaccggc aattcttcaa     2820
gcaataaaca ggaataccaa ttattaaaag ataacttagt cagatcgtac aataaagctt    2880
tgaagaaaaa tgcgccttat tcaatctttg ctataaaaaa tggcccaaaa tctcacattg    2940
gaagacattt gatgacctca tttctttcaa tgaagggcct aacggagttg actaatgttg    3000
tgggaaattg gagcgataag cgtgcttctg ccgtggccag gacaacgtat actcatcaga    3060
taacagcaat acctgatcac tacttcgcac tagtttctcg gtactatgca tatgatccaa    3120
tatcaaagga aatgatagca ttgaaggatg agactaatcc aattgaggag tggcagcata    3180
tagaacagct aaagggtagt gctgaaggaa gcatacgata ccccgcatgg aatgggataa    3240
tatcacagga ggtactagac tacctttcat cctacataaa tagacgcata aagtacgca     3300 tttaagcata aacacgcact atgccgttct tctcatgtat atatatatac aggcaacacg    3360
cagatatagg tgcgacgtga acagtgagct gtatgtgcgc agctcgcgtt gcattttcgg    3420
aagcgctcgt tttcggaaac gctttgaagt tcctattccg aagttcctat tctctagaaa    3480
gtataggaac ttcagagcgc ttttgaaaac caaaagcgct ctgaagacgc actttcaaaa    3540
aaccaaaaac gcaccggact gtaacgagct actaaaatat tgcgaatacc gcttccacaa    3600
acattgctca aaagtatctc tttgctatat atctctgtgc tatatcccta tataacctac    3660
ccatccacct ttcgctcctt gaacttgcat ctaaactcga cctctacatt ttttatgttt    3720
atctctagta ttactcttta gacaaaaaaa ttgtagtaag aactattcat agagtgaatc    3780
gaaaacaata cgaaaatgta aacatttcct atacgtagta tatagagaca aaatagaaga    3840
aaccgttcat aatttctga ccaatgaaga atcatcaacg ctatcacttt ctgttcacaa     3900
agtatgcgca atccacatcg gtatagaata taatcgggga tgcctttatc ttgaaaaaat    3960
gcacccgcag cttcgctagt aatcagtaaa cgcgggaagt ggagtcaggc ttttttatg     4020 gaagagaaaa tagacaccaa agtagccttc ttctaacctt aacggaccta cagtgcaaaa    4080
agttatcaag agactgcatt atagagcgca caaggagaa aaaagtaat ctaagatgct      4140 ttgttagaaa aatagcgctc tcgggatgca ttttgtaga acaaaaaga agtatagatt      4200 ctttgttggt aaaatagcgc tctcgcgttg catttctgtt ctgtaaaaat gcagctcaga    4260
ttctttgttt gaaaaattag cgctctcgcg ttgcattttt gttttacaaa aatgaagcac    4320
agattcttcg ttggtaaaat agcgctttcg cgttgcattt ctgttctgta aaatgcagc    4380 tcagattctt tgtttgaaaa attagcgctc tcgcgttgca ttttgttct acaaatgaa     4440 gcacagatgc ttcgttaaca aagatatgct attgaagtgc aagatggaaa cgcagaaaat    4500
gaaccgggga tgcgacgtgc aagattacct atgcaataga tgcaatagtt tctccaggaa    4560
ccgaaataca tacattgtct tccgtaaagc gctagactat atattattat acaggttcaa    4620
atatactatc tgtttcaggg aaaactccca ggttcggatg ttcaaaattc aatgatgggt    4680
aacaagtacg atcgtaaatc tgtaaaacag tttgtcggat attaggctgt atctcctcaa    4740
```

```
agcgtattcg aatatcattg agaagctgca gcgtcacatc ggataataat gatggcagcc    4800
attgtagaag tgccttttgc atttctagtc tctttctcgg tctagctagt tttactacat    4860
cgcgaagata gaatcttaga tcacactgcc tttgctgagc tggatcaata gagtaacaaa    4920
agagtggtaa ggcctcgtta aaggacaagg acctgagcgg aagtgtatcg tacagtagac    4980
ggagtatact agtatagtct atagtccgtg gaattctcat gtttgacagc ttatcatcga    5040
taagcttttc aattcaattc atcattttt ttttattctt ttttttgatt tcggtttctt    5100 tgaaatttt ttgattcggt aatctccgaa cagaaggaag aacgaaggaa ggagcacaga    5160
cttagattgg tatatatacg catatgtagt gttgaagaaa catgaaattg cccagtattc    5220
ttaacccaac tgcacagaac aaaaacctgc aggaaacgaa gataaatcat gtcgaaagct    5280
acatataagg aacgtgctgc tactcatcct agtcctgttg ctgccaagct atttaatatc    5340
atgcacgaaa agcaaacaaa cttgtgtgct tcattggatg ttcgtaccac caaggaatta    5400
ctggagttag ttgaagcatt aggtcccaaa atttgtttac taaaaacaca tgtggatatc    5460
ttgactgatt tttccatgga gggcacagtt aagccgctaa aggcattatc cgccaagtac    5520
aattttttac tcttcgaaga cagaaaattt gctgacattg gtaatacagt caaattgcag    5580
tactctgcgg gtgtatacag aatagcagaa tgggcagaca ttacgaatgc acacggtgtg    5640
gtgggcccag gtattgttag cggttttgaag caggcggcag aagaagtaac aaaggaacct    5700
agaggccttt tgatgttagc agaattgtca tgcaagggct ccctatctac tggagaatat    5760
actaagggta ctgttgacat tgcgaagagc gacaaagatt tgttatcgg ctttattgct    5820 caaagagaca tgggtggaag agatgaaggt tacgattggt tgattatgac acccggtgtg    5880
ggtttagatg acaagggaga cgcattgggt caacagtata gaaccgtgga tgatgtggtc    5940
tctacaggat ctgacattat tattgttgga agaggactat ttgcaaaggg aagggatgct    6000
aaggtagagg gtgaacgtta cagaaaagca ggctgggaag catatttgag aagatgcggc    6060
cagcaaaact aaaaaactgt attataagta aatgcatgta tactaaactc acaaattaga    6120
gcttcaattt aattatatca gttattaccc gggaatctcg gtcgtaatga cttgaaataa    6180
ttaacaaaca aaggagttac agttagaaat tgtaggagag atctcgtttt tcgcgacaat    6240
ctggcgtttt tcttgctaat tccaggatta atccgttcat agtgtaaaac cccgtttaca    6300
cattctgacg gaagatatag attggaagta ttgcattcac taagataagt atggcaacac    6360
tggaacagac atgaattatc agaacgacga tttacgcatc aaagaaatca aagagttact    6420
tcctcctgtc gcattgctgg aaaaattccc cgctactgaa aatgccgcga atacggttgc    6480
ccatgcccga aaagcgatcc ataagatcct gaaaggtaat gatgatcgcc tgttggttgt    6540
gattggccca tgctcaattc atgatcctgt cgcggcaaaa gagtatgcca ctcgcttgct    6600
ggcgctgcgt gaagagctga agatgagct ggaaatcgta atgcgcgtct attttgaaaa    6660
gccgcgtacc acggtgggct ggaaagggct gattaacgat ccgcatatgg ataatagctt    6720
ccagatcaac gacggtctgc gtatagcccg taaattgctg cttgatatta acgacagcgg    6780
tctgccagcg gcaggtgagt ttctcgatat gatcaccccca caatatctcg ctgacctgat    6840
gagctggggc gcaattggcg cacgtaccac cgaatcgcag gtgcaccgcg aactggcatc    6900
agggctttct tgtccggtcg gcttcaaaaa tggcaccgac ggtacgatta agtggctat    6960 cgatgccatt aatgccgccg gtgcgccgca ctgcttcctg tccgtaacga atgggggca    7020 ttcggcgatt gtgaatacca gcggtaacgg cgattgccat atcattctgc gcggcggtaa    7080
agagcctaac tacagcgcga agcacgttgc tgaagtgaaa gaagggctga acaaagcagg    7140
```

```
cctgccagca caggtgatga tcgatttcag ccatgctaac tcgtccaaac aattcaaaaa    7200
gcagatggat gtttgtgctg acgtttgcca gcagattgcc ggtggcgaaa aggccattat    7260
tggcgtgatg gtggaaagcc atctggtgga aggcaatcag agcctcgaga gcggggagcc    7320
gctggcctac ggtaagagca tcaccgatgc ctgcatcggc tgggaagata ccgatgctct    7380
gttacgtcaa ctggcgaatg cagtaaaagc gcgtcgcggg taaggtttaa ttgtcggatg    7440
cgccgtcaga gtgcgtatc cgatgaatca ccacaggcct gataagtcgc gcagcgtcgc     7500
atcaggcaat gtgctccatt gttagcaaca aaaagccga ctcacttgca gtcggctttc     7560
tcattttaaa cgaatgacgt ttacttcgct ttaccctggt ttgcaaccgc cgctgctttc    7620
gct                                                                  7623

<210> SEQ ID NO 29
<211> LENGTH: 7630
<212> TYPE: DNA
<213> ORGANISM: Escherichia coli
<220> FEATURE:
<221> NAME/KEY: misc_feature
<222> LOCATION: (1)..(7630)
<223> OTHER INFORMATION: DNA sequence of the plasmid pCP14

<400> SEQUENCE: 29
ctcgaggcta ttgacgacag ctatggttca ctgtccacca accaaaactg tgctcagtac      60
cgccaatatt tctcccttga ggggtacaaa gaggtgtccc tagaagagat ccacgctgtg    120
taaaaatttt acaaaaaggt attgactttc cctacaggt gtgtaataat ttaattacag     180
gcgggggcaa ccccgcctgt tctagaggag gaggaatcgc catggagagg attgtcgtta    240
ctctcgggga acgtagttac ccaattacca tcgcatctgg tttgttaat gaaccagctt      300 cattcttacc gctgaaatcg ggcgagcagg tcatgttggt caccaacgaa accctggctc    360
ctctgtatct cgataaggtc cgcggcgtac ttgaacaggc gggtgttaac gtcgatagcg    420
ttatcctccc tgacggcgag cagtatataaaa gcctggctgt actcgatacc gtctttacgg   480
cgttgttaca aaagccgcat ggtcgcgata ctacgctggt ggcgcttggc ggcggcgtag    540
tgggcgatct gaccggcttc gcggcggcga gttatcagcg cggtgttcgt ttcattcaag    600
tcccgacgac gttactgtcg caggtcgatt cctccgttgg cggcaaaact gcggtcaacc    660
atcccctcgg taaaaacatg attggcgcgt tctaccagcc tgcttcagtg gtggtggatc    720
tcgactgtct gaaaacgctt cccccgcgtg agttagcgtc ggggctggca gaagtcatca    780
aatacggcat tattcttgac ggtgcgtttt tcaactggct ggaagagaat ctggatgcgt    840
tgttgcgtct ggacggtccg gcaatggcgt actgtattcg ccgttgttgt gaactgaagg    900
cagaagttgt cgccgccgac gagcgcgaaa ccgggttacg tgctttactg aatctgggac    960
acacctttgg tcatgccatt gaagctgaaa tggggtatgg caattggtta catggtgaag   1020
cggtcgctgc gggtatggtg atggcggcgc ggacgtcgga acgtctcggg cagtttagtt   1080
ctgccgaaac gcagcgtatt ataaccctgc tcacgcgggc tgggttaccg gtcaatgggc   1140
cgcgcgaaat gtccgcgcag gcgtatttac cgcatatgct gcgtgacaag aaagtccttg   1200
cgggagagat gcgcttaatt cttccgttgg caattggtaa gagtgaagtt cgcagcggcg   1260
tttcgcacga gcttgttctt aacgccattg ccgattgtca atcagcgtaa tcatcgttca   1320
tgcctgatgc cgctatgtag gccggataag gcgttcacgc cgcatccggc aaccgatgcc   1380
tgatgcgacg cggtcgcgtc ttatcaggcc tacaggtcga tgccgatatg tacatcgtat   1440
```

```
tcggcaatta atacatagca acatgaatgg tcttcggttt ccgtgtttcg taaagtctgg    1500
aaacgcggaa gtcagcgccc tgcaccatta tgttccggat ctgcatcgca ggatgctgct    1560
ggctaccctg tggaacacct acatctgtat taacgaagcg ctggcattga ccctgagtga    1620
tttttctctg gtcccgccgc atccataccg ccagttgttt accctcacaa cgttccagta    1680
accgggcatg ttcatcatca gtaacccgta tcgtgagcat cctctctcgt ttcatcggta    1740
tcattacccc catgaacaga aattcccect tacacggagg catcaagtga ccaaacagga    1800
aaaaaccgcc cttaacatgg cccgctttat cagaagccag acattaacgc ttctggagaa    1860
actcaacgag ctggacgcgg atgaacaggc agacatctgt gaatcgcttc acgaccacgc    1920
tgatgagctt taccgcagct gcctcgcgcg tttcggtgat gacggtgaaa acctctgaca    1980
catgcagctc ccgagacggg tcacagcttg tctgtaagcg gatgccggga gcagacaagc    2040
ccgtcagggc gcgtcagcgg gtgttggcgg gtgtcggggc gcagccatga cccagtcacg    2100
tagcgatagc ggagtgtata ctggcttaac tatgcggcat cagagcagat tgtactgaga    2160
gtgcaccata tgcggtgtga ataccgcac agatgcgtaa ggagaaaata ccgcatcagg    2220
cgctcttccg cttcctcgct cactgactcg ctgcgctcgg tcgttcggct gcggcgagcg    2280
gtatcagctc actcaaaggc ggtaatacgg ttatccacag aatcagggga taacgcagga    2340
aagaacatgt gagcaaaagg ccagcaaaag gccaggaacc gtaaaaaggc cgcgttgctg    2400
gcgtttttcc ataggctccg ccccctgac gagcatcaca aaaatcgacg ctcaagtcag    2460
aggtggcgaa acccgacagg actataaaga taccaggcgt ttccccctgg aagctccctc    2520
gtgcgctctc ctgttccgac cctgccgctt accggatacc tgtccgcctt tctcccttcg    2580
ggaagcgtgg cgctttctca tagctcacgc tgtaggtatc tcagttcggt gtaggtcgtt    2640
cgctccaagc tgggctgtgt gcacgaaccc cccgttcagc ccgaccgctg cgccttatcc    2700
ggtaactatc gtcttgagtc caacccggta agacacgact tatcgccact ggcagcagcc    2760
actggtaaca ggattagcag agcgaggtat gtaggcggtg ctacagagtt cttgaagtgg    2820
tggcctaact acggctacac tagaaggaca gtatttggta tctgcgctct gctgaagcca    2880
gttaccttcg gaaaaagagt tggtagctct tgatccggca aacaaaccac cgctggtagc    2940
ggtggttttt ttgtttgcaa gcagcagatt acgcgcagaa aaaaaggatc tcaagaagat    3000
cctttgatct tttctacggg gtctgacgct cagtggaacg aaaactcacg ttaagggatt    3060
ttggtcatga gattatcaaa aaggatcttc acctagatcc ttttaaatta aaaatgaagt    3120
tttaaatcaa tctaaagtat atatgagtaa acttggtctg acagttacca atgcttaatc    3180
agtgaggcac ctatctcagc gatctgtcta tttcgttcat ccatagttgc ctgactcccc    3240
gtcgtgtaga taactacgat acgggagggc ttaccatctg gccccagtgc tgcaatgata    3300
ccgcgagacc cacgctcacc ggctccagat ttatcagcaa taaaccagcc agccggaagg    3360
gccgagcgca gaagtggtcc tgcaacttta tccgcctcca tccagtctat taattgttgc    3420
cgggaagcta gagtaagtag ttcgccagtt aatagtttgc gcaacgttgt tgccattgct    3480
gcaggcatcg tggtgtcacg ctcgtcgttt ggtatggctt cattcagctc cggttcccaa    3540
cgatcaaggc gagttacatg atcccccatg ttgtgcaaaa aagcggttag ctccttcggt    3600
cctccgatcg ttgtcagaag taagttggcc gcagtgttat cactcatggt tatggcagca    3660
ctgcataatt ctcttactgt catgccatcc gtaagatgct tttctgtgac tggtgagtac    3720
tcaaccaagt cattctgaga atagtgtatg cggcgaccga gttgctcttg cccggcgtca    3780
acacgggata ataccgcgcc acatagcaga actttaaaag tgctcatcat tggaaaacgt    3840
```

```
tcttcggggc gaaaactctc aaggatctta ccgctgttga gatccagttc gatgtaaccc   3900
actcgtgcac ccaactgatc ttcagcatct tttactttca ccagcgtttc tgggtgagca   3960
aaaacaggaa ggcaaaatgc cgcaaaaaag ggaataaggg cgacacggaa atgttgaata   4020
ctcatactct tccttttttca atattattga agcatttatc agggttattg tctcatgagc   4080
ggatacatat ttgaatgtat ttagaaaaat aaacaaatag gggttccgcg cacatttccc   4140
cgaaaagtgc cacctgacgt ctaagaaacc attattatca tgacattaac ctataaaaat   4200
aggcgtatca cgaggccctt tcgtcttcaa gaattctgaa ccagtcctaa aacgagtaaa   4260
taggaccggc aattcttcaa gcaataaaca ggaataccaa ttattaaaag ataacttagt   4320
cagatcgtac aataaagctt tgaagaaaaa tgcgccttat tcaatctttg ctataaaaaa   4380
tggcccaaaa tctcacattg gaagacattt gatgacctca tttctttcaa tgaagggcct   4440
aacggagttg actaatgttg tgggaaattg gagcgataag cgtgcttctg ccgtggccag   4500
gacaacgtat actcatcaga taacagcaat acctgatcac tacttcgcac tagtttctcg   4560
gtactatgca tatgatccaa tatcaaagga aatgatagca ttgaaggatg agactaatcc   4620
aattgaggag tggcagcata tagaacagct aaagggtagt gctgaaggaa gcatacgata   4680
ccccgcatgg aatgggataa tatcacagga ggtactagac tacctttcat cctacataaa   4740
tagacgcata taagtacgca tttaagcata aacacgcact atgccgttct tctcatgtat   4800
atatatatac aggcaacacg cagatatagg tgcgacgtga acagtgagct gtatgtgcgc   4860
agctcgcgtt gcattttcgg aagcgctcgt tttcggaaac gctttgaagt tcctattccg   4920
aagttcctat tctctagaaa gtataggaac ttcagagcgc ttttgaaaac caaaagcgct   4980
ctgaagacgc actttcaaaa aaccaaaaac gcaccggact gtaacgagct actaaaatat   5040
tgcgaatacc gcttccacaa acattgctca aaagtatctc tttgctatat atctctgtgc   5100
tatatcccta tataacctac ccatccacct ttcgctcctt gaacttgcat ctaaactcga   5160
cctctacatt ttttatgttt atctctagta ttactcttta gacaaaaaaa ttgtagtaag   5220
aactattcat agagtgaatc gaaaacaata cgaaaatgta aacatttcct atacgtagta   5280
tatagagaca aaatagaaga aaccgttcat aattttctga ccaatgaaga atcatcaacg   5340
ctatcacttt ctgttcacaa agtatgcgca atccacatcg gtatagaata taatcgggga   5400
tgcctttatc ttgaaaaaat gcacccgcag cttcgctagt aatcagtaaa cgcgggaagt   5460
ggagtcaggc ttttttttatg gaagagaaaa tagacaccaa agtagccttc ttctaacctt   5520
aacggaccta cagtgcaaaa agttatcaag agactgcatt atagagcgca caaggagaa   5580 aaaaagtaat ctaagatgct ttgttagaaa aatagcgctc tcgggatgca tttttgtaga   5640
acaaaaaaga agtatagatt ctttgttggt aaaatagcgc tctcgcgttg catttctgtt   5700
ctgtaaaaat gcagctcaga ttctttgttt gaaaaattag cgctctcgcg ttgcattttt   5760
gttttacaaa aatgaagcac agattcttcg ttggtaaaat agcgctttcg cgttgcattt   5820
ctgttctgta aaaatgcagc tcagattctt tgtttgaaaa attagcgctc tcgcgttgca   5880
tttttgttct acaaaatgaa gcacagatgc ttcgttaaca aagatatgct attgaagtgc   5940
aagatggaaa cgcagaaaat gaaccgggga tgcgacgtgc aagattacct atgcaataga   6000
tgcaatagtt tctccaggaa ccgaaataca tacattgtct tccgtaaagc gctagactat   6060
atattattat acaggttcaa atatactatc tgtttcaggg aaaactccca ggttcggatg   6120
ttcaaaattc aatgatgggt aacaagtacg atcgtaaatc tgtaaaacag tttgtcggat   6180
```

```
attaggctgt atctcctcaa agcgtattcg aatatcattg agaagctgca gcgtcacatc    6240
ggataataat gatggcagcc attgtagaag tgccttttgc atttctagtc tctttctcgg    6300
tctagctagt tttactacat cgcgaagata gaatcttaga tcacactgcc tttgctgagc    6360
tggatcaata gagtaacaaa agagtggtaa ggcctcgtta aggacaagg acctgagcgg    6420 aagtgtatcg tacagtagac ggagtatact agtatagtct atagtccgtg gaattctcat    6480
gtttgacagc ttatcatcga taagcttttc aattcaattc atcattttt ttttattctt    6540 tttttgatt tcggtttctt tgaaattttt ttgattcggt aatctccgaa cagaaggaag    6600
aacgaaggaa ggagcacaga cttagattgg tatatatacg catatgtagt gttgaagaaa    6660
catgaaattg cccagtattc ttaacccaac tgcacagaac aaaaacctgc aggaaacgaa    6720
gataaatcat gtcgaaagct acatataagg aacgtgctgc tactcatcct agtcctgttg    6780
ctgccaagct atttaatatc atgcacgaaa agcaaacaaa cttgtgtgct tcattggatg    6840
ttcgtaccac caaggaatta ctggagttag ttgaagcatt aggtcccaaa atttgtttac    6900
taaaaacaca tgtggatatc ttgactgatt tttccatgga gggcacagtt aagccgctaa    6960
aggcattatc cgccaagtac aattttttac tcttcgaaga cagaaaattt gctgacattg    7020
gtaatacagt caaattgcag tactctgcgg gtgtatacag aatagcagaa tgggcagaca    7080
ttacgaatgc acacggtgtg gtgggcccag gtattgttag cggtttgaag caggcggcag    7140
aagaagtaac aaaggaacct agaggccttt tgatgttagc agaattgtca tgcaagggct    7200
ccctatctac tggagaatat actaagggta ctgttgacat tgcgaagagc gacaaagatt    7260
ttgttatcgg cttttattgct caaagagaca tgggtggaag agatgaaggt tacgattggt    7320
tgattatgac acccggtgtg ggtttagatg acaagggaga cgcattgggt caacagtata    7380
gaaccgtgga tgatgtggtc tctacaggat ctgacattat tattgttgga agaggactat    7440
ttgcaaaggg aagggatgct aaggtagagg gtgaacgtta cagaaaagca ggctgggaag    7500
catatttgag aagatgcggc cagcaaaact aaaaaactgt attataagta aatgcatgta    7560
tactaaactc acaaattaga gcttcaattt aattatatca gttattaccc gggaatctcg    7620
gtcgtaatga                                                          7630
```

<210> SEQ ID NO 30
<211> LENGTH: 10015
<212> TYPE: DNA
<213> ORGANISM: Escherichia coli
<220> FEATURE:
<221> NAME/KEY: misc_feature
<222> LOCATION: (1)..(10015)
<223> OTHER INFORMATION: DNA sequence of the plasmid pCP50

<400> SEQUENCE: 30

```
cttgaaataa ttaacaaaca aaggagttac agttagaaat tgtaggagag atctcgtttt      60
tcgcgacaat ctggcgtttt tcttgctaat tccaggatta atccgttcat agtgtaaaac     120
cccgtttaca cattctgacg gaagatatag attggaagta ttgcattcac taagataagt     180
atggcaacac tggaacagac atgaattatc agaacgacga tttacgcatc aaagaaatca     240
aagagttact tcctcctgtc gcattgctgg aaaaattccc cgctactgaa atgccgcga     300 atacggttgc ccatgcccga aaagcgatcc ataagatcct gaaggtaat gatgatcgcc     360 tgttggttgt gattggccca tgctcaattc atgatcctgt cgcggcaaaa gagtatgcca     420
ctcgcttgct ggcgctgcgt gaagagctga agatgagctg ggaaatcgta atgcgcgtct     480
attttgaaaa gccgcgtacc acggtgggct ggaaagggct gattaacgat ccgcatatgg     540
```

```
ataatagctt ccagatcaac gacggtctgc gtatagcccg taaattgctg cttgatatta    600
acgacagcgg tctgccagcg gcaggtgagt ttctcgatat gatcacccca caatatctcg    660
ctgacctgat gagctggggc gcaattggcg cacgtaccac cgaatcgcag gtgcaccgcg    720
aactggcatc agggctttct tgtccggtcg gcttcaaaaa tggcaccgac ggtacgatta    780
aagtggctat cgatgccatt aatgccgccg gtgcgccgca ctgcttcctg tccgtaacga    840
aatgggggca ttcggcgatt gtgaatacca gcggtaacgg cgattgccat atcattctgc    900
gcggcggtaa agagcctaac tacagcgcga agcacgttgc tgaagtgaaa aagggctga    960 acaaagcagg cctgccagca caggtgatga tcgatttcag ccatgctaac tcgtccaaac   1020
aattcaaaaa gcagatggat gtttgtgctg acgtttgcca gcagattgcc ggtggcgaaa   1080
aggccattat tggcgtgatg gtggaaagcc atctggtgga aggcaatcag agcctcgaga   1140
gcggggagcc gctggcctac ggtaagagca tcaccgatgc ctgcatcggc tgggaagata   1200
ccgatgctct gttacgtcaa ctggcgaatg cagtaaaagc gcgtcgcggg taaggtttaa   1260
ttgtcggatg cgccgtcaga gtggcgtatc cgatgaatca ccacaggcct gataagtcgc   1320
gcagcgtcgc atcaggcaat gtgctccatt gttagcaaca aaaaagccga ctcacttgca   1380
gtcggctttc tcattttaaa cgaatgacgt ttacttcgct ttaccctggt ttgcaaccgc   1440
cgctgctttc gctacatgaa tggtcttcgg tttccgtgtt tcgtaaagtc tggaaacgcg   1500
gaagtcagcg ccctgcacca ttatgttccg gatctgcatc gcaggatgct gctggctacc   1560
ctgtggaaca cctacatctg tattaacgaa gcgctggcat tgaccctgag tgatttttct   1620
ctggtcccgc cgcatccata ccgccagttg tttaccctca caacgttcca gtaaccgggc   1680
atgttcatca tcagtaaccc gtatcgtgag catcctctct cgtttcatcg gtatcattac   1740
ccccatgaac agaaattccc ccttacacgg aggcatcaag tgaccaaaca ggaaaaaacc   1800
gcccttaaca tggcccgctt tatcagaagc cagacattaa cgcttctgga gaaactcaac   1860
gagctggacg cggatgaaca ggcagacatc tgtgaatcgc ttcacgacca cgctgatgag   1920
ctttaccgca gctgcctcgc gcgtttcggt gatgacggtg aaaacctctg acacatgcag   1980
ctcccggaga cggtcacagc ttgtctgtaa gcggatgccg ggagcagaca gcccgtcag   2040 ggcgcgtcag cgggtgttgg cgggtgtcgg ggcgcagcca tgacccagtc acgtagcgat   2100
agcggagtgt atactggctt aactatgcgg catcagagca gattgtactg agagtgcacc   2160
atatgcggtg tgaaataccg cacagatgcg taaggagaaa ataccgcatc aggcgctctt   2220
ccgcttcctc gctcactgac tcgctgcgct cggtcgttcg gctgcggcga gcggtatcag   2280
ctcactcaaa ggcggtaata cggttatcca cagaatcagg ggataacgca ggaaagaaca   2340
tgtgagcaaa aggccagcaa aaggccagga accgtaaaaa ggccgcgttg ctggcgtttt   2400
tccataggct ccgcccccct gacgagcatc acaaaaatcg acgctcaagt cagaggtggc   2460
gaaacccgac aggactataa agataccagg cgtttccccc tggaagctcc ctcgtgcgct   2520
ctcctgttcc gaccctgccg cttaccggat acctgtccgc ctttctccct cgggaagcg   2580 tggcgctttc tcatagctca cgctgtaggt atctcagttc ggtgtaggtc gttcgctcca   2640
agctgggctg tgtgcacgaa ccccccgttc agcccgaccg ctgcgcctta tccggtaact   2700
atcgtcttga gtccaacccg gtaagacacg acttatcgcc actggcagca gccactggta   2760
acaggattag cagagcgagg tatgtaggcg gtgctacaga gttcttgaag tggtggccta   2820
actacggcta cactagaagg acagtatttg gtatctgcgc tctgctgaag ccagttacct   2880
```

```
tcggaaaaag agttggtagc tcttgatccg gcaaacaaac caccgctggt agcggtggtt    2940
tttttgtttg caagcagcag attacgcgca gaaaaaaagg atctcaagaa gatcctttga    3000
tcttttctac ggggtctgac gctcagtgga acgaaaactc acgttaaggg attttggtca    3060
tgagattatc aaaaaggatc ttcacctaga tccttttaaa ttaaaaatga gttttaaat    3120 caatctaaag tatatatgag taaacttggt ctgacagtta ccaatgctta atcagtgagg    3180
cacctatctc agcgatctgt ctatttcgtt catccatagt tgcctgactc cccgtcgtgt    3240
agataactac gatacgggag ggcttaccat ctggccccag tgctgcaatg ataccgcgag    3300
acccacgctc accggctcca gatttatcag caataaacca gccagccgga agggccgagc    3360
gcagaagtgg tcctgcaact ttatccgcct ccatccagtc tattaattgt tgccgggaag    3420
ctagagtaag tagttcgcca gttaatagtt tgcgcaacgt tgttgccatt gctgcaggca    3480
tcgtggtgtc acgctcgtcg tttggtatgg cttcattcag ctccggttcc caacgatcaa    3540
ggcgagttac atgatccccc atgttgtgca aaaaagcggt tagctccttc ggtcctccga    3600
tcgttgtcag aagtaagttg gccgcagtgt tatcactcat ggttatggca gcactgcata    3660
attctcttac tgtcatgcca tccgtaagat gcttttctgt gactggtgag tactcaacca    3720
agtcattctg agaatagtgt atgcggcgac cgagttgctc ttgcccggcg tcaacacggg    3780
ataataccgc gccacatagc agaactttaa aagtgctcat cattggaaaa cgttcttcgg    3840
ggcgaaaact ctcaaggatc ttaccgctgt tgagatccag ttcgatgtaa cccactcgtg    3900
cacccaactg atcttcagca tcttttactt tcaccagcgt ttctgggtga gcaaaaacag    3960
gaaggcaaaa tgccgcaaaa aagggaataa gggcgacacg gaaatgttga atactcatac    4020
tcttcctttt tcaatattat tgaagcattt atcagggtta ttgtctcatg agcggataca    4080
tatttgaatg tatttagaaa aataaacaaa taggggttcc gcgcacattt ccccgaaaag    4140
tgccacctga cgtctaagaa accattatta tcatgacatt aacctataaa aataggcgta    4200
tcacgaggcc ctttcgtctt caagaattct gaaccagtcc taaaacgagt aaataggacc    4260
ggcaattctt caagcaataa acaggaatac caattattaa aagataactt agtcagatcg    4320
tacaataaag ctttgaagaa aaatgcgcct tattcaatct ttgctataaa aaatggccca    4380
aaatctcaca ttggaagaca tttgatgacc tcatttcttt caatgaaggg cctaacggag    4440
ttgactaatg ttgtgggaaa ttggagcgat aagcgtgctt ctgccgtggc caggacaacg    4500
tatactcatc agataacagc aatacctgat cactacttcg cactagtttc tcggtactat    4560
gcatatgatc caatatcaaa ggaaatgata gcattgaagg atgagactaa tccaattgag    4620
gagtggcagc atatagaaca gctaaagggt agtgctgaag gaagcatacg ataccccgca    4680
tggaatggga taatatcaca ggaggtacta gactaccttt catcctacat aaatagacgc    4740
atataagtac gcatttaagc ataaacacgc actatgccgt tcttctcatg tatatatata    4800
tacaggcaac acgcagatat aggtgcgacg tgaacagtga gctgtatgtg cgcagctcgc    4860
gttgcatttt cggaagcgct cgttttcgga aacgctttga agttcctatt ccgaagttcc    4920
tattctctag aaagtatagg aacttcagag cgcttttgaa aaccaaaagc gctctgaaga    4980
cgcactttca aaaaccaaa acgcaccgg actgtaacga gctactaaaa tattgcgaat    5040
accgcttcca caaacattgc tcaaaagtat ctctttgcta tatatctctg tgctatatcc    5100
ctatataacc tacccatcca cctttcgctc cttgaacttg catctaaact cgacctctac    5160 atttttatg tttatctcta gtattactct ttagacaaaa aaattgtagt aagaactatt    5220 catgagtga atcgaaaaca atacgaaaat gtaaacattt cctatacgta gtatatagag    5280
```

```
acaaaataga  agaaaccgtt  cataatttc   tgaccaatga  agaatcatca  acgctatcac  5340
tttctgttca  caaagtatgc  gcaatccaca  tcggtataga  atataatcgg  ggatgccttt  5400
atcttgaaaa  aatgcacccg  cagcttcgct  agtaatcagt  aaacgcggga  agtggagtca  5460
ggcttttttt  atggaagaga  aaatagacac  caaagtagcc  ttcttctaac  cttaacggac  5520
ctacagtgca  aaaagttatc  aagagactgc  attatagagc  gcacaaagga  gaaaaaagt   5580 aatctaagat  gctttgttag  aaaaatagcg  ctctcgggat  gcatttttgt  agaacaaaaa  5640
agaagtatag  attctttgtt  ggtaaaatag  cgctctcgcg  ttgcatttct  gttctgtaaa  5700
aatgcagctc  agattctttg  tttgaaaaat  tagcgctctc  gcgttgcatt  tttgttttac  5760
aaaaatgaag  cacagattct  tcgttggtaa  aatagcgctt  tcgcgttgca  tttctgttct  5820
gtaaaaatgc  agctcagatt  ctttgtttga  aaaattagcg  ctctcgcgtt  gcattttgt   5880 tctacaaaat  gaagcacaga  tgcttcgtta  acaaagatat  gctattgaag  tgcaagatgg  5940
aaacgcagaa  aatgaaccgg  ggatgcgacg  tgcaagatta  cctatgcaat  agatgcaata  6000
gtttctccag  gaaccgaaat  acatacattg  tcttccgtaa  agcgctagac  tatatattat  6060
tatacaggtt  caaatatact  atctgtttca  gggaaaactc  ccaggttcgg  atgttcaaaa  6120
ttcaatgatg  ggtaacaagt  acgatcgtaa  atctgtaaaa  cagtttgtcg  gatattaggc  6180
tgtatctcct  caaagcgtat  tcgaatatca  ttgagaagct  gcagcgtcac  atcggataat  6240
aatgatggca  gccattgtag  aagtgccttt  tgcatttcta  gtctcttct   cggtctagct  6300 agtttaacta  catcgcgaag  atagaatctt  agatcacact  gcctttgctg  agctggatca  6360
atagagtaac  aaaagagtgg  taaggcctcg  ttaaaggaca  aggacctgag  cggaagtgta  6420
tcgtacagta  gacggagtat  actagtatag  tctatagtcc  gtggaattct  catgtttgac  6480
agcttatcat  cgataagctt  ttcaattcaa  ttcatcattt  tttttttatt  cttttttttg  6540
atttcggttt  ctttgaaatt  tttttgattc  ggtaatctcc  gaacagaagg  aagaacgaag  6600
gaaggagcac  agacttagat  tggtatatat  acgcatatgt  agtgttgaag  aaacatgaaa  6660
ttgcccagta  ttcttaaccc  aactgcacag  aacaaaaacc  tgcaggaaac  gaagataaat  6720
catgtcgaaa  gctacatata  aggaacgtgc  tgctactcat  cctagtcctg  ttgctgccaa  6780
gctatttaat  atcatgcacg  aaaagcaaac  aaacttgtgt  gcttcattgg  atgttcgtac  6840
caccaaggaa  ttactggagt  tagttgaagc  attaggtccc  aaaatttgtt  tactaaaaac  6900
acatgtggat  atcttgactg  attttttccat ggagggcaca  gttaagccgc  taaaggcatt  6960
atccgccaag  tacaatttt   tactcttcga  agacagaaaa  tttgctgaca  ttggtaatac  7020
agtcaaattg  cagtactctg  cgggtgtata  cagaatagca  gaatgggcag  acattacgaa  7080
tgcacacggt  gtggtgggcc  caggtattgt  tagcggtttg  aagcaggcgg  cagaagaagt  7140
aacaaaggaa  cctagaggcc  ttttgatgtt  agcagaattg  tcatgcaagg  gctccctatc  7200
tactggagaa  tatactaagg  gtactgttga  cattgcgaag  agcgacaaag  attttgttat  7260
cggctttatt  gctcaaagag  acatgggtgg  aagagatgaa  ggttacgatt  ggttgattat  7320
gacacccggt  gtgggtttag  atgacaaggg  agacgcattg  ggtcaacagt  atagaaccgt  7380
ggatgatgtg  gtctctacag  gatctgacat  tattattgtt  ggaagaggac  tatttgcaaa  7440
gggaagggat  gctaaggtag  agggtgaacg  ttacagaaaa  gcaggctggg  aagcatattt  7500
gagaagatgc  ggccagcaaa  actaaaaaac  tgtattataa  gtaaatgcat  gtatactaaa  7560
ctcacaaatt  agagcttcaa  tttaattata  tcagttatta  cccgggaatc  tcggtcgtaa  7620
```

```
tgaaaggaaa agcgcaacgg acgggcgagt agattgcgca acatgcgagc atgatccaga    7680
gatttctgaa gcagcaaaag gatgttccat gtacatgacg cgcggcttgc ggtaaattgt    7740
tggcaaattt tccggcgtag cccaaaacgc gctgtcgtca agtcgttaag ggcgtgccct    7800
tcatcatccg atctggagtc aaaatgtcct cacgtaaaga gcttgccaat gctattcgtg    7860
cgctgagcat ggacgcagta cagaaagcca atccggtca cccgggtgcc cctatgggta     7920
tggctgacat tgccgaagtc ctgtggcgtg atttcctgaa acacaacccg cagaatccgt    7980
cctgggctga ccgtgaccgc ttcgtgctgt ccaacggcca cggctccatg ctgatctaca    8040
gcctgctgca cctcaccggt tacgatctgc cgatggaaga actgaaaaac ttccgtcagc    8100
tgcactctaa aactccgggc cacccggaag taggttatac cgctggtgtg gaaaccacca    8160
ccggtccgct gggtcagggt attgccaacg cagtcggtat ggcgattgca gaaaaaacgc    8220
tggcggcgca gtttaaccgt ccaggtcacg acattgtcga ccactacacc tacgccttca    8280
tgggcgacgg ctgcatgatg gaaggcatct cccacgaagt ttgctctctg gcgggtacgc    8340
tgaagctggg taaactgatt gcgttctacg atgacaacgg tatctcaatc gatggtcacg    8400
ttgaaggctg gttcactgac gacaccgcaa tgcgtttcga agcttacggc tggcacgtta    8460
ttcgcgacat cgacggtcat gacgcggcat ccatcaaacg cgcagtagaa gaagcgcgcg    8520
cagtgactga caaaccgtcc ctgctgatgt gcaaaaccat catcggtttc ggttccccga    8580
acaaagccgg tacccacgac tcccacggtg cgccgctggg cgacgctgaa attgccctga    8640
cccgcgaaca gctgggctgg aaatacgcgc cgttcgaaat cccgtctgaa atctatgctc    8700
agtgggatgc gaaagaagca ggccaggcga agaatctgc atggaatgag aagtttgcgg     8760
cttacgcgaa agcttatccg caggaagcgg ctgaatttac cgccgtatg aaaggcgaaa     8820 tgccgtctga cttcgacgcc aaagcgaaag agtttatcgc taaactgcag gctaatccgg    8880
cgaaaatcgc cagccgtaaa gcgtcgcaga atgctatcga agcgttcggc ccgctgttgc    8940
ctgaattcct cggcggctct gctgacctgg caccgtctaa cctgacctg tggtctggtt     9000 ctaaagcaat caacgaagat gctgcaggta actacatcca ctacggtgtt cgcgagttcg    9060
gtatgaccgc gattgctaac ggtatctccc tgcacggtgg tttcctgccg tacacctcca    9120
ccttcctgat gttcgtggaa tacgcacgta acgccgtacg tatggctgcg ctgatgaaac    9180
agcgtcaggt gatggtttac acccacgact ccatcggtct gggcgaagat ggcccgactc    9240
accagccggt tgagcaggtc gcttctctgc gcgtgacccc gaacatgtct acatggcgtc    9300
cgtgtgacca ggttgaatcc gcggtcgcgt ggaaatacgg cgttgagcgt caggacggcc    9360
cgactgcgct tatcctctcc cgtcagaacc tggcgcagca ggaacgaact gaagagcaac    9420
tggcaaacat cgcgcgcgt ggttatgtgc tgaaagactg cgccggtcag ccggaactga    9480
ttttcatcgc taccggttca gaagttgaac tggctgttgc tgcctacgaa aaactgactg    9540
ccgaaggcgt gaaagcgcgc gtggtgtcca tgccgtctac cgacgcattt gacaagcagg    9600
atgctgctta ccgtgaatcc gtactgccga aagcggttac tgcacgcgtt gctgtagaag    9660
cgggtattgc tgactactgg tacaagtatg ttggcctgaa cggtgctatc gtcggtatga    9720
ccaccttcgg tgaatctgct ccggcagagc tgctgtttga agagttcggc ttcactgttg    9780
ataacgttgt tgcgaaagca aaagaactgc tgtaattagc atttcgggta aaaaggtcgc    9840
ttcggcgacc tttttttatta ccttgatatg tccgttgcg gacaagcaat agataaagcg     9900
tgttgtagat cacaaatatt tatatgcaat aaatatcaat tatgtaatat gcatcacgat    9960
atgcgtattg acatttgttg ttataactat aactcaatgt tatataagaa attaa         10015
```

<210> SEQ ID NO 31
<211> LENGTH: 9065
<212> TYPE: DNA
<213> ORGANISM: Escherichia coli
<220> FEATURE:
<221> NAME/KEY: misc_feature
<222> LOCATION: (1)..(9065)
<223> OTHER INFORMATION: DNA sequence of the plasmid pCP54

<400> SEQUENCE: 31

```
acatgaatgg tcttcggttt ccgtgtttcg taaagtctgg aaacgcggaa gtcagcgccc      60
tgcaccatta tgttccggat ctgcatcgca ggatgctgct ggctaccctg tggaacacct     120
acatctgtat taacgaagcg ctggcattga ccctgagtga tttttctctg gtcccgccgc     180
atccataccg ccagttgttt accctcacaa cgttccagta accgggcatg ttcatcatca     240
gtaacccgta tcgtgagcat cctctctcgt ttcatcggta tcattacccc catgaacaga     300
aattcccccct tacacggagg catcaagtga ccaaacagga aaaaaccgcc cttaacatgg     360
cccgctttat cagaagccag acattaacgc ttctggagaa actcaacgag ctggacgcgg     420
atgaacaggc agacatctgt gaatcgcttc acgaccacgc tgatgagctt taccgcagct     480
gcctcgcgcg tttcggtgat gacggtgaaa acctctgaca catgcagctc ccggagacgg     540
tcacagcttg tctgtaagcg gatgccggga gcagacaagc ccgtcagggc gcgtcagcgg     600
gtgttggcgg gtgtcggggc gcagccatga cccagtcacg tagcgatagc ggagtgtata     660
ctggcttaac tatgcggcat cagagcagat tgtactgaga gtgcaccata tgcggtgtga     720
aataccgcac agatgcgtaa ggagaaaata ccgcatcagg cgctcttccg cttcctcgct     780
cactgactcg ctgcgctcgg tcgttcggct gcggcgagcg gtatcagctc actcaaaggc     840
ggtaatacgg ttatccacag aatcagggga taacgcagga agaacatgt gagcaaaagg     900
ccagcaaaag gccaggaacc gtaaaaaggc cgcgttgctg gcgtttttcc ataggctccg     960
cccccctgac gagcatcaca aaaatcgacg ctcaagtcag aggtggcgaa acccgacagg    1020
actataaaga taccaggcgt ttccccctgg aagctccctc gtgcgctctc ctgttccgac    1080
cctgccgctt accggatacc tgtccgcctt tctcccttcg ggaagcgtgg cgctttctca    1140
tagctcacgc tgtaggtatc tcagttcggt gtaggtcgtt cgctccaagc tgggctgtgt    1200
gcacgaaccc cccgttcagc ccgaccgctg cgccttatcc ggtaactatc gtcttgagtc    1260
caacccggta agacacgact tatcgccact ggcagcagcc actggtaaca ggattagcag    1320
agcgaggtat gtaggcggtg ctacagagtt cttgaagtgg tggcctaact acggctacac    1380
tagaaggaca gtatttggta tctgcgctct gctgaagcca gttaccttcg gaaaaagagt    1440
tggtagctct tgatccggca acaaaccac cgctggtagc ggtggttttt ttgtttgcaa    1500
gcagcagatt acgcgcagaa aaaaggatc tcaagaagat cctttgatct tttctacggg    1560
gtctgacgct cagtggaacg aaaactcacg ttaagggatt ttggtcatga gattatcaaa    1620
aaggatcttc acctagatcc ttttaaatta aaaatgaagt tttaaatcaa tctaaagtat    1680
atatgagtaa acttggtctg agtggcggtt tcatggctt gttatgactg ttttttgggg    1740
gtacagtcta tgcctcgggc atccaagcag caagcgcgtt acgccgtggg tcgatgtttg    1800
atgttatgga gcagcaacga tgttacgcag cagggcagtc gccctaaaac aaagttaaac    1860
atcatgaggg aagcggtgat cgccgaagta tcgactcaac tatcagaggt agttggcgtc    1920
atcgagcgcc atctcgaacc gacgttgctg gccgtacatt tgtacggctc cgcagtggat    1980
```

```
ggcggcctga agccacacag tgatattgat ttgctggtta cggtgaccgt aaggcttgat    2040
gaaacaacgc ggcgagcttt gatcaacgac cttttggaaa cttcggcttc ccctggagag    2100
agcgagattc tccgcgctgt agaagtcacc attgttgtgc acgacgacat cattccgtgg    2160
cgttatccag ctaagcgcga actgcaattt ggagaatggc agcgcaatga cattcttgca    2220
ggtatcttcg agccagccac gatcgacatt gatctggcta tcttgctgac aaaagcaaga    2280
gaacatagcg ttgccttggt aggtccagcg gcggaggaac tctttgatcc ggttcctgaa    2340
caggatctat ttgaggcgct aaatgaaacc ttaacgctat ggaactcgcc gcccgactgg    2400
gctggcgatg agcgaaatgt agtgcttacg ttgtcccgca tttggtacag cgcagtaacc    2460
ggcaaaatcg cgccgaagga tgtcgctgcc gactgggcaa tggagcgcct gccggcccag    2520
tatcagcccg tcatacttga agctagacag gcttatcttg acaagaaga agatcgcttg    2580 gcctcgcgcg cagatcagtt ggaagaattt gtccactacg tgaaaggcga gatcaccaag    2640
gtagtcggca ataatgtctc aacaattcgt tcaagccgac gccgcttcgc ggcgcggctt    2700
aactcaagcg ttagatgcac taagcacata attgctcaca gccaaactat cagaattctg    2760
aaccagtcct aaaacgagta aataggaccg gcaattcttc aagcaataaa caggaatacc    2820
aattattaaa agataactta gtcagatcgt acaataaagc tttgaagaaa aatgcgcctt    2880
attcaatctt tgctataaaa aatggcccaa aatctcacat tggaagacat ttgatgacct    2940
catttctttc aatgaagggc ctaacggagt tgactaatgt tgtgggaaat tggagcgata    3000
agcgtgcttc tgccgtggcc aggacaacgt atactcatca gataacagca atacctgatc    3060
actacttcgc actagtttct cggtactatg catatgatcc aatatcaaag gaatgatag    3120 cattgaagga tgagactaat ccaattgagg agtggcagca tatagaacag ctaaagggta    3180
gtgctgaagg aagcatacga taccccgcat ggaatgggat aatatcacag gaggtactag    3240
actacctttc atcctacata aatagacgca tataagtacg catttaagca taaacacgca    3300
ctatgccgtt cttctcatgt atatatatat acaggcaaca cgcagatata ggtgcgacgt    3360
gaacagtgag ctgtatgtgc gcagctcgcg ttgcatttc ggaagcgctc gttttcggaa    3420
acgctttgaa gttcctattc cgaagttcct attctctaga aagtatagga acttcagagc    3480
gcttttgaaa accaaaagcg ctctgaagac gcactttcaa aaaaccaaaa acgcaccgga    3540
ctgtaacgag ctactaaaat attgcgaata ccgcttccac aaacattgct caaaagtatc    3600
tctttgctat atatctctgt gctatatccc tatataacct acccatccac ctttcgctcc    3660
ttgaacttgc atctaaactc gacctctaca ttttttatgt ttatctctag tattactctt    3720
tagacaaaaa aattgtagta agaactattc atagagtgaa tcgaaaacaa tacgaaaatg    3780
taaacatttc ctatacgtag tatatagaga caaaatagaa gaaaccgttc ataattttct    3840
gaccaatgaa gaatcatcaa cgctatcact ttctgttcac aaagtatgcg caatccacat    3900
cggtatagaa tataatcggg gatgccttta tcttgaaaaa atgcaccgc agcttcgcta    3960 gtaatcagta aacgcgggaa gtggagtcag gcttttttta tggaagagaa aatagacacc    4020
aaagtagcct tcttctaacc ttaacggacc tacagtgcaa aaagttatca agagactgca    4080
ttatagagcg cacaaaggag aaaaaagta atctaagatg ctttgttaga aaaatagcgc    4140
tctcgggatg cattttgta gaacaaaaaa gaagtataga ttctttgttg gtaaaatagc    4200
gctctcgcgt tgcatttctg ttctgtaaaa atgcagctca gattcttgt ttgaaaaatt    4260 agcgctctcg cgttgcattt ttgttttaca aaaatgaagc acagattctt cgttggtaaa    4320
atagcgcttt cgcgttgcat ttctgttctg taaaaatgca gctcagattc tttgtttgaa    4380
```

-continued

```
aaattagcgc tctcgcgttg catttttgtt ctacaaaatg aagcacagat gcttcgttaa   4440
caaagatatg ctattgaagt gcaagatgga aacgcagaaa atgaaccggg gatgcgacgt   4500
gcaagattac ctatgcaata gatgcaaatag tttctccagg aaccgaaata catacattgt   4560
cttccgtaaa gcgctagact atatattatt atacaggttc aaatatacta tctgtttcag   4620
ggaaaactcc caggttcgga tgttcaaaat tcaatgatgg gtaacaagta cgatcgtaaa   4680
tctgtaaaac agtttgtcgg atattaggct gtatctcctc aaagcgtatt cgaatatcat   4740
tgagaagctg cagcgtcaca tcggataata atgatggcag ccattgtaga agtgcctttt   4800
gcatttctag tctctttctc ggtctagcta gttttactac atcgcgaaga tagaatctta   4860
gatcacactg cctttgctga gctggatcaa tagagtaaca aaagagtggt aaggcctcgt   4920
taaaggacaa ggacctgagc ggaagtgtat cgtacagtag acggagtata ctagtatagt   4980
ctatagtccg tggaattctc atgtttgaca gcttatcatc gataagcttt tcaattcaat   5040
tcatcatttt tttttattc tttttttga tttcggtttc tttgaaattt ttttgattcg      5100
gtaatctccg aacagaagga agaacgaagg aaggagcaca gacttagatt ggtatatata   5160
cgcatatgta gtgttgaaga aacatgaaat tgcccagtat tcttaaccca actgcacaga   5220
acaaaaacct gcaggaaacg aagataaatc atgtcgaaag ctacatataa ggaacgtgct   5280
gctactcatc ctagtcctgt tgctgccaag ctatttaata tcatgcacga aaagcaaaca   5340
aacttgtgtg cttcattgga tgttcgtacc accaaggaat tactggagtt agttgaagca   5400
ttaggtccca aaatttgttt actaaaaaca catgtggata tcttgactga tttttccatg   5460
gagggcacag ttaagccgct aaaggcatta tccgccaagt acaattttt actcttcgaa    5520 gacagaaaat ttgctgacat tggtaataca gtcaaattgc agtactctgc gggtgtatac   5580
agaatagcag aatgggcaga cattacgaat gcacacggtg tggtgggccc aggtattgtt   5640
agcggtttga agcaggcggc agaagaagta acaaaggaac ctagaggcct tttgatgtta   5700
gcagaattgt catgcaaggg ctccctatct actggagaat atactaaggg tactgttgac   5760
attgcgaaga gcgacaaaga ttttgttatc ggctttattg ctcaaagaga catgggtgga   5820
agagatgaag gttacgattg gttgattatg cacccggtg tgggtttaga tgacaaggga    5880
gacgcattgg gtcaacagta tagaaccgtg gatgatgtgg tctctacagg atctgacatt   5940
attattgttg gaagaggact atttgcaaag ggaagggatg ctaaggtaga gggtgaacgt   6000
tacagaaaag caggctggga agcatatttg agaagatgcg gccagcaaaa ctaaaaaact   6060
gtattataag taaatgcatg tatactaaac tcacaaatta gagcttcaat ttaattatat   6120
cagttattac ccgggaatct cggtcgtaat gacttgaaat aattaacaaa caaaggagtt   6180
acagttagaa attgtaggag agatctcgtt tttcgcgaca atctggcgtt tttcttgcta   6240
attccaggat taatccgttc atagtgtaaa accccgttta cacattctga cggaagatat   6300
agattggaag tattgcattc actaagataa gtatggcaac actggaacag acatgaatta   6360
tcagaacgac gatttacgca tcaaagaaat caaagagtta cttcctcctg tcgcattgct   6420
ggaaaaattc cccgctactg aaaatgccgc gaatacggtt gcccatgccc gaaaagcgat   6480
ccataagatc ctgaaaggta atgatgatcg cctgttggtt gtgattggcc catgctcaat   6540
tcatgatcct gtcgcggcaa aagagtatgc cactcgcttg ctggcgctgc gtgaagagct   6600
gaaagatgag ctgaaaatcg taatgcgcgt ctattttgaa aagccgcgta ccacggtggg   6660
ctggaaaggg ctgattaacg atccgcatat ggataatagc ttccagatca acgacggtct   6720
```

```
gcgtatagcc cgtaaattgc tgcttgatat taacgacagc ggtctgccag cggcaggtga    6780
gtttctcgat atgatcaccc cacaatatct cgctgacctg atgagctggg gcgcaattgg    6840
cgcacgtacc accgaatcgc aggtgcaccg cgaactggca tcagggcttt cttgtccggt    6900
cggcttcaaa aatggcaccg acggtacgat taaagtggct atcgatgcca ttaatgccgc    6960
cggtgcgccg cactgcttcc tgtccgtaac gaaatggggg cattcggcga ttgtgaatac    7020
cagcggtaac ggcgattgcc atatcattct gcgcggcggt aaagagccta actacagcgc    7080
gaagcacgtt gctgaagtga agaagggct gaacaaagca ggcctgccag cacaggtgat     7140
gatcgatttc agccatgcta actcgtccaa acaattcaaa aagcagatgg atgtttgtgc    7200
tgacgtttgc cagcagattg ccggtggcga aaaggccatt attggcgtga tggtggaaag    7260
ccatctggtg gaaggcaatc agagcctcga gagcggggag ccgctggcct acggtaagag    7320
catcaccgat gcctgcatcg gctgggaaga taccgatgct ctgttacgtc aactggcgaa    7380
tgcagtaaaa gcgcgtcgcg ggtaaggttt aattgtcgga tgcgccgtca gagtggcgta    7440
tccgatgaat caccacaggc ctgataagtc gcgcagcgtc gcatcaggca atgtgctcca    7500
ttgttagcaa caaaaaagcc gactcacttg cagtcggctt tctcatttta aacgaatgac    7560
gtttacttcg ctttaccctg gtttgcaacc gccgctgctt cgctctcga ggctattgac     7620
gacagctatg gttcactgtc caccaaccaa aactgtgctc agtaccgcca atatttctcc    7680
cttgaggggt acaagaggt gtccctagaa gagatccacg ctgtgtaaaa attttacaaa     7740
aaggtattga ctttccctac agggtgtgta ataatttaat tacaggcggg ggcaaccccg    7800
cctgttctag aggaggagga atcgccatgg agaggattgt cgttactctc ggggaacgta    7860
gttaccaat taccatcgca tctggtttgt ttaatgaacc agcttcattc ttaccgctga     7920
aatcgggcga gcaggtcatg ttggtcacca acgaaaccct ggctcctctg tatctcgata    7980
aggtccgcgg cgtacttgaa caggcgggtg ttaacgtcga tagcgttatc ctccctgacg    8040
gcgagcagta taaaagcctg gctgtactcg ataccgtctt tacggcgttg ttacaaaagc    8100
cgcatggtcg cgatactacg ctggtggcgc ttggcggcgg cgtagtgggc gatctgaccg    8160
gcttcgcggc ggcgagttat cagcgcgtg ttcgtttcat tcaagtcccg acgacgttac     8220
tgtcgcaggt cgattcctcc gttggcggca aaactgcggt caaccatccc ctcggtaaaa    8280
acatgattgg cgcgttctac cagcctgctt cagtggtggt ggatctcgac tgtctgaaaa    8340
cgcttccccc gcgtgagtta gcgtcggggc tggcagaagt catcaaatac ggcattattc    8400
ttgacggtgc gttttcaac tggctggaag agaatctgga tgcgttgttg cgtctggacg     8460
gtccggcaat ggcgtactgt attcgccgtt gttgtgaact gaaggcagaa gttgtcgccg    8520
ccgacgagcg cgaaaccggg ttacgtgctt tactgaatct gggacacacc tttggtcatg    8580
ccattgaagc tgaaatgggg tatggcaatt ggttacatgg tgaagcggtc gctgcgggta    8640
tggtgatggc ggcgcggacg tcggaacgtc tcggcagtt tagttctgcc gaaacgcagc     8700
gtattataac cctgctcacg cgggctgggt taccggtcaa tgggccgcgc gaaatgtccg    8760
cgcaggcgta tttaccgcat atgctgcgtg acaagaaagt ccttgcggga gagatgcgct    8820
taattcttcc gttggcaatt ggtaagagtg aagttcgcag cggcgtttcg cacgagcttg    8880
ttcttaacgc cattgccgat tgtcaatcag cgtaatcatc gttcatgcct gatgccgcta    8940
tgtaggccgg ataaggcgtt cacgccgcat ccggcaaccg atgcctgatg cgacgcggtc    9000
gcgtcttatc aggcctacag gtcgatgccg atatgtacat cgtattcggc aattaataca    9060
tagca                                                                9065
```

<210> SEQ ID NO 32
<211> LENGTH: 11475
<212> TYPE: DNA
<213> ORGANISM: Escherichia coli
<220> FEATURE:
<221> NAME/KEY: misc_feature
<222> LOCATION: (1)..(11475)
<223> OTHER INFORMATION: DNA sequence of the plasmid pCP55

<400> SEQUENCE: 32

| | | | | | |
|---|---|---|---|---|---|
| acatgaatgg | tcttcggttt | ccgtgtttcg | taaagtctgg | aaacgcggaa gtcagcgccc | 60 |
| tgcaccatta | tgttccggat | ctgcatcgca | ggatgctgct | ggctaccctg tggaacacct | 120 |
| acatctgtat | taacgaagcg | ctggcattga | ccctgagtga | ttttctctg gtcccgccgc | 180 |
| atccataccg | ccagttgttt | accctcacaa | cgttccagta | accgggcatg ttcatcatca | 240 |
| gtaacccgta | tcgtgagcat | cctctctcgt | ttcatcggta | tcattacccc catgaacaga | 300 |
| aattcccct | tacacggagg | catcaagtga | ccaaacagga | aaaaaccgcc cttaacatgg | 360 |
| cccgctttat | cagaagccag | acattaacgc | ttctggagaa | actcaacgag ctggacgcgg | 420 |
| atgaacaggc | agacatctgt | gaatcgcttc | acgaccacgc | tgatgagctt taccgcagct | 480 |
| gcctcgcgcg | tttcggtgat | gacggtgaaa | acctctgaca | catgcagctc ccggagacgg | 540 |
| tcacagcttg | tctgtaagcg | gatgccggga | gcagacaagc | ccgtcagggc gcgtcagcgg | 600 |
| gtgttggcgg | gtgtcgggc | gcagccatga | cccagtcacg | tagcgatagc ggagtgtata | 660 |
| ctggcttaac | tatgcggcat | cagagcagat | tgtactgaga | gtgcaccata tgcggtgtga | 720 |
| aataccgcac | agatgcgtaa | ggagaaaata | ccgcatcagg | cgctcttccg cttcctcgct | 780 |
| cactgactcg | ctgcgctcgg | tcgttcggct | gcggcgagcg | gtatcagctc actcaaaggc | 840 |
| ggtaatacgg | ttatccacag | aatcagggga | taacgcagga | agaacatgt gagcaaaagg | 900 |
| ccagcaaaag | gccaggaacc | gtaaaaaggc | cgcgttgctg | gcgttttcc ataggctccg | 960 |
| cccccctgac | gagcatcaca | aaaatcgacg | ctcaagtcag | aggtggcgaa acccgacagg | 1020 |
| actataaaga | taccaggcgt | ttccccctgg | aagctccctc | gtgcgctctc ctgttccgac | 1080 |
| cctgccgctt | accggatacc | tgtccgcctt | tctcccttcg | ggaagcgtgg cgctttctca | 1140 |
| tagctcacgc | tgtaggtatc | tcagttcggt | gtaggtcgtt | cgctccaagc tgggctgtgt | 1200 |
| gcacgaaccc | cccgttcagc | ccgaccgctg | cgccttatcc | ggtaactatc gtcttgagtc | 1260 |
| caacccggta | agacacgact | tatcgccact | ggcagcagcc | actggtaaca ggattagcag | 1320 |
| agcgaggtat | gtaggcggtg | ctacagagtt | cttgaagtgg | tggcctaact acggctacac | 1380 |
| tagaaggaca | gtatttggta | tctgcgctct | gctgaagcca | gttaccttcg gaaaaagagt | 1440 |
| tggtagctct | tgatccggca | aacaaaccac | cgctggtagc | ggtggttttt ttgtttgcaa | 1500 |
| gcagcagatt | acgcgcagaa | aaaaggatc | tcaagaagat | cctttgatct tttctacggg | 1560 |
| gtctgacgct | cagtggaacg | aaaactcacg | ttaagggatt | ttggtcatga gattatcaaa | 1620 |
| aaggatcttc | acctagatcc | ttttaaatta | aaaatgaagt | tttaaatcaa tctaaagtat | 1680 |
| atatgagtaa | acttggtctg | acagttacca | atgcttaatc | agtgaggcac ctatctcagc | 1740 |
| gatctgtcta | tttcgttcat | ccatagttgc | ctgactcccc | gtcgtgtaga taactacgat | 1800 |
| acgggagggc | ttaccatctg | gccccagtgc | tgcaatgata | ccgcgagacc cacgctcacc | 1860 |
| ggctccagat | ttatcagcaa | taaaccagc | agccggaagg | gccgagcgca gaagtggtcc | 1920 |
| tgcaacttta | tccgcctcca | tccagtctat | taattgttgc | cgggaagcta gagtaagtag | 1980 |

```
ttcgccagtt aatagtttgc gcaacgttgt tgccattgct gcaggcatcg tggtgtcacg    2040
ctcgtcgttt ggtatggctt cattcagctc cggttcccaa cgatcaaggc gagttacatg    2100
atcccccatg ttgtgcaaaa aagcggttag ctccttcggt cctccgatcg ttgtcagaag    2160
taagttggcc gcagtgttat cactcatggt tatggcagca ctgcataatt ctcttactgt    2220
catgccatcc gtaagatgct tttctgtgac tggtgagtac tcaaccaagt cattctgaga    2280
atagtgtatg cggcgaccga gttgctcttg cccggcgtca acacgggata ataccgcgcc    2340
acatagcaga actttaaaag tgctcatcat tggaaaacgt tcttcggggc gaaaactctc    2400
aaggatctta ccgctgttga gatccagttc gatgtaaccc actcgtgcac ccaactgatc    2460
ttcagcatct tttactttca ccagcgtttc tgggtgagca aaaacaggaa ggcaaaatgc    2520
cgcaaaaaag ggaataaggg cgacacggaa atgttgaata ctcatactct ccttttttca    2580
atattattga agcatttatc agggttattg tctcatgagc ggatacatat ttgaatgtat    2640
ttagaaaaat aaacaaatag gggttccgcg cacatttccc cgaaaagtgc cacctgacgt    2700
ctaagaaacc attattatca tgacattaac ctataaaaat aggcgtatca cgaggccctt    2760
tcgtcttcaa gaattctgaa ccagtcctaa acgagtaaa taggaccggc aattcttcaa    2820
gcaataaaca ggaataccaa ttattaaaag ataacttagt cagatcgtac aataaagctt    2880
tgaagaaaaa tgcgccttat tcaatctttg ctataaaaaa tggcccaaaa tctcacattg    2940
gaagacattt gatgacctca tttctttcaa tgaagggcct aacggagttg actaatgttg    3000
tgggaaattg gagcgataag cgtgcttctg ccgtggccag acaacgtat actcatcaga    3060 taacagcaat acctgatcac tacttcgcac tagtttctcg gtactatgca tatgatccaa    3120
tatcaaagga aatgatagca ttgaaggatg agactaatcc aattgaggag tggcagcata    3180
tagaacagct aaagggtagt gctgaaggaa gcatacgata ccccgcatgg aatgggataa    3240
tatcacagga ggtactagac tacctttcat cctacataaa tagacgcata taagtacgca    3300
tttaagcata aacacgcact atgccgttct tctcatgtat atatatatac aggcaacacg    3360
cagatatagg tgcgacgtga acagtgagct gtatgtgcgc agctcgcgtt gcattttcgg    3420
aagcgctcgt tttcggaaac gctttgaagt tcctattccg aagttcctat tctctagaaa    3480
gtataggaac ttcagagcgc ttttgaaaac caaaagcgct ctgaagacgc actttcaaaa    3540
aaccaaaaac gcaccggact gtaacgagct actaaaatat tgcgaatacc gcttccacaa    3600
acattgctca aaagtatctc tttgctatat atctctgtgc tatatcccta tataacctac    3660
ccatccacct ttcgctcctt gaacttgcat ctaaactcga cctctacatt ttttatgttt    3720
atctctagta ttactcttta gacaaaaaaa ttgtagtaag aactattcat agagtgaatc    3780
gaaaacaata cgaaaatgta aacatttcct atacgtagta tatagagaca aaatagaaga    3840
aaccgttcat aattttctga ccaatgaaga atcatcaacg ctatcacttt ctgttcacaa    3900
agtatgcgca atccacatcg gtatagaata taatcgggga tgcctttatc ttgaaaaaat    3960
gcacccgcag cttcgctagt aatcagtaaa cgcgggaagt ggagtcaggc ttttttatg    4020 gaagagaaaa tagacaccaa agtagccttc ttctaacctt aacggaccta cagtgcaaaa    4080
agttatcaag agactgcatt atagagcgca caaggagaa aaaagtaat ctaagatgct    4140 ttgttagaaa aatagcgctc tcgggatgca tttttgtaga acaaaaaga agtatagatt    4200 ctttgttggt aaaatagcgc tctcgcgttg catttctgtt ctgtaaaaat gcagctcaga    4260
ttctttgttt gaaaaattag cgctctcgcg ttgcatttt gttttacaaa aatgaagcac    4320
agattcttcg ttggtaaaat agcgctttcg cgttgcattt ctgttctgta aaaatgcagc    4380
```

```
tcagattctt tgtttgaaaa attagcgctc tcgcgttgca ttttgttct acaaaatgaa    4440 gcacagatgc ttcgttaaca aagatatgct attgaagtgc aagatggaaa cgcagaaaat    4500
gaaccgggga tgcgacgtgc aagattacct atgcaataga tgcaatagtt tctccaggaa    4560
ccgaaataca tacattgtct tccgtaaagc gctagactat atattattat acaggttcaa    4620
atatactatc tgtttcaggg aaaactccca ggttcggatg ttcaaaattc aatgatgggt    4680
aacaagtacg atcgtaaatc tgtaaaacag tttgtcggat attaggctgt atctcctcaa    4740
agcgtattcg aatatcattg agaagctgca gcgtcacatc ggataataat gatggcagcc    4800
attgtagaag tgccttttgc atttctagtc tctttctcgg tctagctagt tttactacat    4860
cgcgaagata gaatcttaga tcacactgcc tttgctgagc tggatcaata gagtaacaaa    4920
agagtggtaa ggcctcgtta aaggacaagg acctgagcgg aagtgtatcg tacagtagac    4980
ggagtatact agtatagtct atagtccgtg gaattctcat gtttgacagc ttatcatcga    5040
taagcttttc aattcaattc atcatttttt ttttattctt tttttgatt tcggtttctt    5100 tgaaattttt ttgattcggt aatctccgaa cagaaggaag aacgaaggaa ggagcacaga    5160
cttagattgg tatatatacg catatgtagt gttgaagaaa catgaaattg cccagtattc    5220
ttaacccaac tgcacagaac aaaaacctgc aggaaacgaa gataaatcat gtcgaaagct    5280
acatataagg aacgtgctgc tactcatcct agtcctgttg ctgccaagct atttaatatc    5340
atgcacgaaa agcaaacaaa cttgtgtgct tcattggatg ttcgtaccac caaggaatta    5400
ctggagttag ttgaagcatt aggtcccaaa atttgtttac taaaaacaca tgtggatatc    5460
ttgactgatt tttccatgga gggcacagtt aagccgctaa aggcattatc cgccaagtac    5520
aattttttac tcttcgaaga cagaaaattt gctgacattg gtaatacagt caaattgcag    5580
tactctgcgg gtgtatacag aatagcagaa tgggcagaca ttacgaatgc acacggtgtg    5640
gtgggcccag gtattgttag cggtttgaag caggcggcag aagaagtaac aaaggaacct    5700
agaggccttt tgatgttagc agaattgtca tgcaagggct ccctatctac tggagaatat    5760
actaagggta ctgttgacat tgcgaagagc gacaaagatt tgttatcgg ctttattgct    5820 caaagagaca tgggtggaag agatgaaggt tacgattggt tgattatgac acccggtgtg    5880
ggtttagatg acaagggaga cgcattgggt caacagtata gaaccgtgga tgatgtggtc    5940
tctacaggat ctgacattat tattgttgga agaggactat ttgcaaaggg aagggatgct    6000
aaggtagagg gtgaacgtta cagaaaagca ggctgggaag catatttgag aagatgcggc    6060
cagcaaaact aaaaaactgt attataagta aatgcatgta tactaaactc acaaattaga    6120
gcttcaattt aattatatca gttattaccc gggaatctcg gtcgtaatga aaggaaaagc    6180
gcaacggacg ggcgagtaga ttgcgcaaca tgcgagcatg atccagagat ttctgaagca    6240
gcaaaaggat gttccatgta catgacgcgc ggcttgcggt aaattgttgg caaattttcc    6300
ggcgtagccc aaaacgcgct gtcgtcaagt cgttaagggc gtgcccttca tcatccgatc    6360
tggagtcaaa atgtcctcac gtaaagagct tgccaatgct attcgtgcgc tgagcatgga    6420
cgcagtacag aaagccaaat ccggtcaccc gggtgcccct atgggtatgg ctgacattgc    6480
cgaagtcctg tggcgtgatt tcctgaaaca caacccgcag aatccgtcct gggctgaccg    6540
tgaccgcttc gtgctgtcca acggccacgg ctccatgctg atctacagcc tgctgcacct    6600
caccggttac gatctgccga tggaagaact gaaaaacttc cgtcagctgc actctaaaac    6660
tccgggccac ccggaagtag ttataccgc tggtgtggaa accaccaccg gtccgctggg    6720
```

```
tcagggtatt gccaacgcag tcggtatggc gattgcagaa aaaacgctgg cggcgcagtt      6780
taaccgtcca ggtcacgaca ttgtcgacca ctacacctac gccttcatgg gcgacggctg      6840
catgatggaa ggcatctccc acgaagtttg ctctctggcg ggtacgctga agctgggtaa      6900
actgattgcg ttctacgatg acaacggtat ctcaatcgat ggtcacgttg aaggctggtt      6960
cactgacgac accgcaatgc gtttcgaagc ttacggctgg cacgttattc gcgacatcga      7020
cggtcatgac gcggcatcca tcaaacgcgc agtagaagaa gcgcgcgcag tgactgacaa      7080
accgtccctg ctgatgtgca aaccatcat cggtttcggt tccccgaaca aagccggtac       7140
ccacgactcc cacggtgcgc cgctgggcga cgctgaaatt gccctgaccc gcaacagct       7200 gggctggaaa tacgcgccgt tcgaaatccc gtctgaaatc tatgctcagt gggatgcgaa      7260
agaagcaggc caggcgaaag aatctgcatg gaatgagaag tttgcggctt acgcgaaagc      7320
ttatccgcag gaagcggctg aatttacccg ccgtatgaaa ggcgaaatgc cgtctgactt      7380
cgacgccaaa gcgaaagagt ttatcgctaa actgcaggct aatccggcga aaatcgccag      7440
ccgtaaagcg tcgcagaatg ctatcgaagc gttcggcccg ctgttgcctg aattcctcgg      7500
cggctctgct gacctggcac cgtctaacct gaccctgtgg tctggttcta aagcaatcaa      7560
cgaagatgct gcaggtaact acatccacta cggtgttcgc gagttcggta tgaccgcgat      7620
tgctaacggt atctccctgc acggtggttt cctgccgtac acctccacct tcctgatgtt      7680
cgtggaatac gcacgtaacg ccgtacgtat ggctgcgctg atgaaacagc gtcaggtgat      7740
ggtttacacc cacgactcca tcggtctggg cgaagatggc ccgactcacc agccggttga      7800
gcaggtcgct tctctgcgcg tgaccccgaa catgtctaca tggcgtccgt gtgaccaggt      7860
tgaatccgcg gtcgcgtgga atacggcgt tgagcgtcag gacggcccga ctgcgcttat      7920
cctctcccgt cagaacctgg cgcagcagga acgaactgaa gagcaactgg caaacatcgc      7980
gcgcggtggt tatgtgctga agactgcgc cggtcagccg gaactgattt tcatcgctac      8040
cggttcagaa gttgaactgg ctgttgctgc ctacgaaaaa ctgactgccg aaggcgtgaa      8100
agcgcgcgtg gtgtccatgc cgtctaccga cgcatttgac aagcaggatg ctgcttaccg      8160
tgaatccgta ctgccgaaag cggttactgc acgcgttgct gtagaagcgg gtattgctga      8220
ctactggtac aagtatgttg gcctgaacgg tgctatcgtc ggtatgacca ccttcggtga      8280
atctgctccg gcagagctgc tgtttgaaga gttcggcttc actgttgata cgttgttgc      8340 gaaagcaaaa gaactgctgt aattagcatt tcgggtaaaa aggtcgcttc ggcgaccttt      8400
tttattacct tgatatgtcc gtttgcggac aagcaataga taaagcgtgt tgtagatcac      8460
aaatatttat atgcaataaa tatcaattat gtaatatgca tcacgatatg cgtattgaca      8520
tttgttgtta taactataac tcaatgttat ataagaaatt aacttgaaat aattaacaaa      8580
caaaggagtt acagttagaa attgtaggag agatctcgtt tttcgcgaca atctggcgtt      8640
tttcttgcta attccaggat taatccgttc atagtgtaaa accccgtta cacattctga      8700 cggaagatat agattggaag tattgcattc actaagataa gtatggcaac actggaacag      8760
acatgaatta tcagaacgac gatttacgca tcaaagaaat caaagagtta cttcctcctg      8820
tcgcattgct ggaaaaattc cccgctactg aaaatgccgc gaatacggtt gcccatgccc      8880
gaaaagcgat ccataagatc ctgaaaggta atgatgatcg cctgttggtt gtgattggcc      8940
catgctcaat tcatgatcct gtcgcggcaa aagagtatgc cactcgcttg ctggcgctgc      9000
gtgaagagct gaaagatgag ctggaaatcg taatgcgcgt ctattttgaa aagccgcgta      9060
ccacggtggg ctggaaaggg ctgattaacg atccgcatat ggataatagc ttccagatca      9120
```

```
acgacggtct gcgtatagcc cgtaaattgc tgcttgatat taacgacagc ggtctgccag   9180
cggcaggtga gtttctcgat atgatcaccc cacaatatct cgctgacctg atgagctggg   9240
gcgcaattgg cgcacgtacc accgaatcgc aggtgcaccg cgaactggca tcagggcttt   9300
cttgtccggt cggcttcaaa aatggcaccg acggtacgat taaagtggct atcgatgcca   9360
ttaatgccgc cggtgcgccg cactgcttcc tgtccgtaac gaaatggggg cattcggcga   9420
ttgtgaatac cagcggtaac ggcgattgcc atatcattct cgcgcggcgt aaagagccta   9480
actacagcgc gaagcacgtt gctgaagtga agaagggct gaacaaagca ggcctgccag   9540
cacaggtgat gatcgatttc agccatgcta actcgtccaa acaattcaaa aagcagatgg   9600
atgtttgtgc tgacgtttgc cagcagattg ccggtggcga aaaggccatt attggcgtga   9660
tggtggaaag ccatctggtg gaaggcaatc agagcctcga gagcggggag ccgctggcct   9720
acggtaagag catcaccgat gcctgcatcg gctgggaaga taccgatgct ctgttacgtc   9780
aactggcgaa tgcagtaaaa gcgcgtcgcg ggtaaggttt aattgtcgga tgcgccgtca   9840
gagtggcgta tccgatgaat caccacaggc ctgataagtc gcgcagcgtc gcatcaggca   9900
atgtgctcca ttgttagcaa caaaaaagcc gactcacttg cagtcggctt tctcattta   9960
aacgaatgac gtttacttcg ctttaccctg gtttgcaacc gccgctgctt cgctctcga  10020
ggctattgac gacagctatg gttcactgtc caccaaccaa aactgtgctc agtaccgcca  10080
atatttctcc cttgaggggt acaaagaggt gtccctagaa gagatccacg ctgtgtaaaa  10140
atttacaaa aaggtattga ctttccctac agggtgtgta ataatttaat tacaggcggg  10200
ggcaacccg cctgttctag aggaggagga atcgccatgg agaggattgt cgttactctc  10260
ggggaacgta gttacccaat taccatcgca tctggttttgt ttaatgaacc agcttcattc  10320
ttaccgctga atcgggcga gcaggtcatg ttggtcacca cgaaaccct ggctcctctg  10380
tatctcgata aggtccgcgg cgtacttgaa caggcgggtg ttaacgtcga tagcgttatc  10440
ctccctgacg gcgagcagta taaaagcctg gctgtactcg ataccgtctt tacggcgttg  10500
ttacaaaagc cgcatggtcg cgatactacg ctggtggcgc ttggcggcgg cgtagtgggc  10560
gatctgaccg gcttcgcggc ggcgagttat cagcgcggtt ttcgtttcat tcaagtcccg  10620
acgacgttac tgtcgcaggt cgattcctcc gttggcggca aaactgcggt caaccatccc  10680
ctcggtaaaa acatgattgg cgcgttctac cagcctgctt cagtggtggt ggatctcgac  10740
tgtctgaaaa cgcttccccc gcgtgagtta gcgtcggggc tggcagaagt catcaaatac  10800
ggcattattc ttgacggtgc gtttttcaac tggctgaag agaatctgga tgcgttgttg  10860
cgtctggacg gtccggcaat ggcgtactgt attcgccgtt gttgtgaact gaaggcagaa  10920
gttgtcgccg ccgacgagcg cgaaaccggg ttacgtgctt tactgaatct gggacacacc  10980
tttggtcatg ccattgaagc tgaaatgggg tatggcaatt ggttacatgg tgaagcggtc  11040
gctgcgggta tggtgatggc ggcgcggacg tcggaacgtc tcgggcagtt tagttctgcc  11100
gaaacgcagc gtattataac cctgctcacg cgggctgggt taccggtcaa tgggccgcgc  11160
gaaatgtccg cgcaggcgta tttaccgcat atgctgcgtg acaagaaagt ccttgcggga  11220
gagatgcgct taattcttcc gttggcaatt ggtaagagtg aagttcgcag cggcgtttcg  11280
cacgagcttg ttcttaacgc cattgccgat tgtcaatcag cgtaatcatc gttcatgcct  11340
gatgccgcta tgtaggccgg ataaggcgtt cacgccgcat ccggcaaccg atgcctgatg  11400
cgacgcggtc gcgtcttatc aggcctacag gtcgatgccg atatgtacat cgtattcggc  11460
```

-continued

| | |
|---|---|
| aattaataca tagca | 11475 |

<210> SEQ ID NO 33
<211> LENGTH: 7769
<212> TYPE: DNA
<213> ORGANISM: Escherichia coli
<220> FEATURE:
<221> NAME/KEY: misc_feature
<222> LOCATION: (1)..(7769)
<223> OTHER INFORMATION: DNA sequence of the plasmid YEP24

<400> SEQUENCE: 33

| | |
|---|---|
| gaattctgaa ccagtcctaa aacgagtaaa taggaccggc aattcttcaa gcaataaaca | 60 |
| ggaataccaa ttattaaaag ataacttagt cagatcgtac aataaagctt tgaagaaaaa | 120 |
| tgcgccttat tcaatctttg ctataaaaaa tggcccaaaa tctcacattg aagacattt | 180 |
| gatgacctca tttcttcaa tgaagggcct aacggagttg actaatgttg tgggaaattg | 240 |
| gagcgataag cgtgcttctg ccgtggccag gacaacgtat actcatcaga taacagcaat | 300 |
| acctgatcac tacttcgcac tagtttctcg gtactatgca tatgatccaa tatcaaagga | 360 |
| aatgatagca ttgaaggatg agactaatcc aattgaggag tggcagcata tagaacagct | 420 |
| aaagggtagt gctgaaggaa gcatacgata ccccgcatgg aatgggataa tatcacagga | 480 |
| ggtactagac tacctttcat cctacataaa tagacgcata taagtacgca tttaagcata | 540 |
| aacacgcact atgccgttct tctcatgtat atatatatac aggcaacacg cagatatagg | 600 |
| tgcgacgtga acagtgagct gtatgtgcgc agctcgcgtt gcattttcgg aagcgctcgt | 660 |
| tttcggaaac gctttgaagt tcctattccg aagttcctat tctctagaaa gtataggaac | 720 |
| ttcagagcgc ttttgaaaac caaaagcgct ctgaagacgc actttcaaaa aaccaaaaac | 780 |
| gcaccggact gtaacgagct actaaaatat tgcgaatacc gcttccacaa acattgctca | 840 |
| aaagtatctc tttgctatat atctctgtgc tatatccta tataacctac ccatccacct | 900 |
| ttcgctcctt gaacttgcat ctaaactcga cctctacatt ttttatgttt atctctagta | 960 |
| ttactcttta gacaaaaaaa ttgtagtaag aactattcat agagtgaatc gaaaacaata | 1020 |
| cgaaaatgta aacatttcct atacgtagta tatagacaca aaatagaaga aaccgttcat | 1080 |
| aattttctga ccaatgaaga atcatcaacg ctatcacttt ctgttcacaa agtatgcgca | 1140 |
| atccacatcg gtatagaata taatcgggga tgcctttatc ttgaaaaaat gcacccgcag | 1200 |
| cttcgctagt aatcagtaaa cgcgggaagt ggagtcaggc tttttttatg gaagagaaaa | 1260 |
| tagacaccaa agtagccttc ttctaacctt aacggaccta cagtgcaaaa agttatcaag | 1320 |
| agactgcatt atagagcgca caaggagaa aaaagtaat ctaagatgct tgttagaaa | 1380 |
| aatagcgctc tcgggatgca tttttgtaga acaaaaaaga agtatagatt ctttgttggt | 1440 |
| aaaatagcgc tctcgcgttg catttctgtt ctgtaaaaat gcagctcaga ttctttgttt | 1500 |
| gaaaaattag cgctctcgcg ttgcattttt gttttacaaa aatgaagcac agattcttcg | 1560 |
| ttggtaaaat agcgctttcg cgttgcattt ctgttctgta aaaatgcagc tcagattctt | 1620 |
| tgtttgaaaa attagcgctc tcgcgttgca ttttgttct acaaaatgaa gcacagatgc | 1680 |
| ttcgttaaca aagatatgct attgaagtgc aagatggaaa cgcagaaaat gaaccggggga | 1740 |
| tgcgacgtgc aagattacct atgcaataga tgcaatagtt tctccaggaa ccgaaataca | 1800 |
| tacattgtct tccgtaaagc gctagactat atattattat acaggttcaa atatactatc | 1860 |
| tgtttcaggg aaaactccca ggttcggatg ttcaaaattc aatgatgggt aacaagtacg | 1920 |
| atcgtaaatc tgtaaaacag tttgtcggat attaggctgt atctcctcaa agcgtattcg | 1980 |

-continued

```
aatatcattg agaagctgca gcgtcacatc ggataataat gatggcagcc attgtagaag    2040
tgccttttgc atttctagtc tctttctcgg tctagctagt tttactacat cgcgaagata    2100
gaatcttaga tcacactgcc tttgctgagc tggatcaata gagtaacaaa agagtggtaa    2160
ggcctcgtta aaggacaagg acctgagcgg aagtgtatcg tacagtagac ggagtatact    2220
agtatagtct atagtccgtg gaattctcat gtttgacagc ttatcatcga taagcttttc    2280
aattcaattc atcattttt tttattctt tttttgatt tcggtttctt tgaaatttt    2340 ttgattcggt aatctccgaa cagaaggaag aacgaaggaa ggagcacaga cttagattgg    2400
tatatatacg catatgtagt gttgaagaaa catgaaattg cccagtattc ttaacccaac    2460
tgcacagaac aaaaacctgc aggaaacgaa gataaatcat gtcgaaagct acatataagg    2520
aacgtgctgc tactcatcct agtcctgttg ctgccaagct atttaatatc atgcacgaaa    2580
agcaaacaaa cttgtgtgct tcattggatg ttcgtaccac caaggaatta ctggagttag    2640
ttgaagcatt aggtcccaaa atttgtttac taaaaacaca tgtggatatc ttgactgatt    2700
tttccatgga gggcacagtt aagccgctaa aggcattatc cgccaagtac aattttttac    2760
tcttcgaaga cagaaaattt gctgacattg gtaatacagt caaattgcag tactctgcgg    2820
gtgtatacag aatagcagaa tgggcagaca ttacgaatgc acacggtgtg gtgggcccag    2880
gtattgttag cggtttgaag caggcggcag aagaagtaac aaaggaacct agaggccttt    2940
tgatgttagc agaattgtca tgcaagggct ccctatctac tggagaatat actaagggta    3000
ctgttgacat tgcgaagagc gacaaagatt ttgttatcgg ctttattgct caaagagaca    3060
tgggtggaag agatgaaggt tacgattggt tgattatgac acccggtgtg ggtttagatg    3120
acaagggaga cgcattgggt caacagtata gaaccgtgga tgatgtggtc tctacaggat    3180
ctgacattat tattgttgga agaggactat ttgcaaaggg aagggatgct aaggtagagg    3240
gtgaacgtta cagaaaagca ggctgggaag catatttgag aagatgcggc cagcaaaact    3300
aaaaaactgt attataagta aatgcatgta tactaaactc acaaattaga gcttcaattt    3360
aattatatca gttattaccc gggaatctcg gtcgtaatga ttttataat gacgaaaaaa    3420 aaaaaattgg aaagaaaaag ctttaatgcg gtagtttatc acagttaaat tgctaacgca    3480
gtcaggcacc gtgtatgaaa tctaacaatg cgctcatcgt catcctcggc accgtcaccc    3540
tggatgctgt aggcataggc ttggttatgc cggtactgcc gggcctcttg cgggatatcg    3600
tccattccga cagcatcgcc agtcactatg gcgtgctgct agcgctatat gcgttgatgc    3660
aatttctatg cgcacccgtt ctcggagcac tgtccgaccg ctttggccgc cgcccagtcc    3720
tgctcgcttc gctacttgga gccactatcg actacgcgat catggcgacc acacccgtcc    3780
tgtggatcct ctacgccgga cgcatcgtgg ccggcatcac cggcgccaca ggtgcggttg    3840
ctggcgccta tcgccgacat caccgatg gggaagatcg gctcgccac ttcgggctca    3900 tgagcgcttg tttcggcgtg ggtatggtgg caggccccgt ggccggggga ctgttgggcg    3960
ccatctcctt gcatgcacca ttccttgcgg cggcggtgct caacggcctc aacctactac    4020
tgggctgctt cctaatgcag gagtcgcata agggagagcg tcgaccgatg cccttgagag    4080
ccttcaaccc agtcagctcc ttccggtggg cgcggggcat gactatcgtc gccgcactta    4140
tgactgtctt ctttatcatg caactcgtag gacaggtgcc ggcagcgctc tgggtcattt    4200
tcggcgagga ccgctttcgc tggagcgcga cgatgatcgg cctgtcgctt gcggtattcg    4260
gaatcttgca cgccctcgct caagccttcg tcactggtcc cgccaccaaa cgtttcggcg    4320
```

```
agaagcaggc cattatcgcc ggcatggcgg ccgacgcgct gggctacgtc ttgctggcgt   4380
tcgcgacgcg aggctggatg gccttcccca ttatgattct tctcgcttcc ggcggcatcg   4440
ggatgcccgc gttgcaggcc atgctgtcca ggcaggtaga tgacgaccat cagggacagc   4500
ttcaaggatc gctcgcggct cttaccagcc taacttcgat cactggaccg ctgatcgtca   4560
cggcgattta tgccgcctcg gcgagcacat ggaacgggtt ggcatggatt gtaggcgccg   4620
ccctatacct tgtctgcctc cccgcgttgc gtcgcggtgc atggagccgg gccacctcga   4680
cctgaatgga agccggcggc acctcgctaa cggattcacc actccaagaa ttggagccaa   4740
tcaattcttg cggagaactg tgaatgcgca aaccaaccct tggcagaaca tatccatcgc   4800
gtccgccatc tccagcagcc gcacgcggcg catctcgggc agcgttgggt cctggccacg   4860
ggtgcgcatg atcgtgctcc tgtcgttgag gacccggcta ggctggcggg gttgccttac   4920
tggttagcag aatgaatcac cgatacgcga gcgaacgtga agcgactgct gctgcaaaac   4980
gtctgcgacc tgagcaacaa catgaatggt cttcggtttc cgtgtttcgt aaagtctgga   5040
aacgcggaag tcagcgccct gcaccattat gttccggatc tgcatcgcag gatgctgctg   5100
gctaccctgt ggaacaccta catctgtatt aacgaagcgc tggcattgac cctgagtgat   5160
ttttctctgg tcccgccgca tccataccgc cagttgttta ccctcacaac gttccagtaa   5220
ccgggcatgt tcatcatcag taacccgtat cgtgagcatc ctctctcgtt tcatcggtat   5280
cattaccccc atgaacagaa attccccctt acacggaggc atcaagtgac caaacaggaa   5340
aaaaccgccc ttaacatggc ccgctttatc agaagccaga cattaacgct tctggagaaa   5400
ctcaacgagc tggacgcgga tgaacaggca gacatctgtg aatcgcttca cgaccacgct   5460
gatgagcttt accgcagctg cctcgcgcgt ttcggtgatg acggtgaaaa cctctgacac   5520
atgcagctcc cggagacggt cacagcttgt ctgtaagcgg atgccgggag cagacaagcc   5580
cgtcagggcg cgtcagcggg tgttggcggg tgtcggggcg cagccatgac ccagtcacgt   5640
agcgatagcg gagtgtatac tggcttaact atgcggcatc agagcagatt gtactgagag   5700
tgcaccatat gcggtgtgaa ataccgcaca gatgcgtaag gagaaaatac cgcatcaggc   5760
gctcttccgc ttcctcgctc actgactcgc tgcgctcggt cgttcggctg cggcgagcgg   5820
tatcagctca ctcaaaggcg gtaatacggt tatccacaga atcaggggat aacgcaggaa   5880
agaacatgtg agcaaaaggc cagcaaaagg ccaggaaccg taaaaaggcc gcgttgctgg   5940 cgttttttcca taggctccgc cccctgacg agcatcacaa aaatcgacgc tcaagtcaga   6000
ggtggcgaaa cccgacagga ctataaagat accaggcgtt tccccctgga agctccctcg   6060
tgcgctctcc tgttccgacc ctgccgctta ccggatacct gtccgccttt ctcccttcgg   6120
gaagcgtggc gctttctcat agctcacgct gtaggtatct cagttcggtg taggtcgttc   6180
gctccaagct gggctgtgtg cacgaacccc ccgttcagcc cgaccgctgc gccttatccg   6240
gtaactatcg tcttgagtcc aacccggtaa gacacgactt atcgccactg gcagcagcca   6300
ctggtaacag gattagcaga gcgaggtatg taggcggtgc tacagagttc ttgaagtggt   6360
ggcctaacta cggctacact agaaggacag tatttggtat ctgcgctctg ctgaagccag   6420
ttaccttcgg aaaaagagtt ggtagctctt gatccggcaa acaaaccacc gctggtagcg   6480
gtggtttttt tgtttgcaag cagcagatta cgcgcagaaa aaaaggatct caagaagatc   6540
ctttgatctt ttctacgggg tctgacgctc agtggaacga aaactcacgt taagggattt   6600
tggtcatgag attatcaaaa aggatcttca cctagatcct tttaaattaa aaatgaagtt   6660
ttaaatcaat ctaaagtata tatgagtaaa cttggtctga cagttaccaa tgcttaatca   6720
```

```
gtgaggcacc tatctcagcg atctgtctat ttcgttcatc catagttgcc tgactccccg    6780
tcgtgtagat aactacgata cgggagggct taccatctgg ccccagtgct gcaatgatac    6840
cgcgagaccc acgctcaccg gctccagatt tatcagcaat aaaccagcca gccggaaggg    6900
ccgagcgcag aagtggtcct gcaactttat ccgcctccat ccagtctatt aattgttgcc    6960
gggaagctag agtaagtagt tcgccagtta atagtttgcg caacgttgtt gccattgctg    7020
caggcatcgt ggtgtcacgc tcgtcgtttg gtatggcttc attcagctcc ggttcccaac    7080
gatcaaggcg agttacatga tcccccatgt tgtgcaaaaa agcggttagc tccttcggtc    7140
ctccgatcgt tgtcagaagt aagttggccg cagtgttatc actcatggtt atggcagcac    7200
tgcataattc tcttactgtc atgccatccg taagatgctt ttctgtgact ggtgagtact    7260
caaccaagtc attctgagaa tagtgtatgc ggcgaccgag ttgctcttgc ccggcgtcaa    7320
cacgggataa taccgcgcca catagcagaa ctttaaaagt gctcatcatt ggaaaacgtt    7380
cttcggggcg aaaactctca aggatcttac cgctgttgag atccagttcg atgtaaccca    7440
ctcgtgcacc caactgatct tcagcatctt ttactttcac cagcgtttct gggtgagcaa    7500
aaacaggaag gcaaaatgcc gcaaaaaagg gaataagggc gacacggaaa tgttgaatac    7560
tcatactctt cctttttcaa tattattgaa gcatttatca gggttattgt ctcatgagcg    7620
gatacatatt tgaatgtatt tagaaaaata aacaaatagg ggttccgcgc acatttcccc    7680
gaaaagtgcc acctgacgtc taagaaacca ttattatcat gacattaacc tataaaaata    7740
ggcgtatcac gaggcccttt cgtcttcaa                                       7769
```

<210> SEQ ID NO 34
<211> LENGTH: 2000
<212> TYPE: DNA
<213> ORGANISM: Escherichia coli
<220> FEATURE:
<221> NAME/KEY: gene
<222> LOCATION: (1)..(2000)
<223> OTHER INFORMATION: DNA sequence of the deleted aroE region

<400> SEQUENCE: 34

```
actacgtccg tcctctgaaa tcttcagcgg atggacatat cgtcaaagtt ctggaggggc      60
aggtttgccc tgcatgtggc gcaaatctgg tattacgcca gggacgcttt ggtatgttta     120
ttggttgcat taactaccct gaatgcgaac ataccgaact tatcgataaa ccggacgaaa     180
cagcaattac atgcccccaa tgtcggacgg ccatctggt ccagcgccgc tcccgttatg     240
gcaaaacatt tcactcttgt gatcgctacc cggagtgtca atttgccatt aacttcaaac     300
ccatagctgg agaatgccct gagtgtcatt atccgctact catcgaaaag aaaaccgcgc     360
agggtgtaaa acacttttgt gccagtaaac aatgtgaaaa gccggtttcg gcggaataat     420
aacgtgaata ataacctgca aagagacgct atcgcagctg cgatagatgt tctcaatgaa     480
gaacgtgtca tcgcctatcc aacggaagcc gttttcggtt tgggtgcga tcctgatagc     540 gaaacagcag tgatgcgact gttggagtta aaacagcgtc cggttgataa ggggctgatt     600
ttaatcgcag caattacga gcagcttaaa ccctatattg atgacaccat gttgactgac     660
gtgcagcgtg aaaccatttt tcccgctgg ccaggtcctg tcacctttgt ctttcccgcg     720
cctgcgacaa caccgcgctg gttgacgggc cgctttgatt cgcttgctgt acgagtcacc     780
gaccatccgt tggtggttgc tttgtgccag gcttatggta aaccgctggt ttctaccagt     840
gccaacttga gtggattgcc accttgtcga acagtagacg aagttcgcgc acaatttggc     900
```

```
gcggcgttcc cggttgtgcc tggtgaaacg ggggggcgtt taaatccttc agaaatccgc    960
gatgccctga cgggtgaact gtttcgacag gggtaacata atcaggccat ccagtttccg   1020
gacagggaag agtgggacga gaataaaaaa tgtgtatgtt ttcccgctct cgtgaatggt   1080
atgcaactga catgcgcgat ctctggcgag agtctggcgt atcgctttac tggagatacg   1140
ccagaacagt ggttagcgag ttttcgtcag catcgctggg acctggaaga agaagcggaa   1200
aacttaattc aggaacaaag tgaagatgat caaggctggg tctggttacc ctgatccaga   1260
tattcgtcct tccatttcac gtaattattc gcggaatagc gtaacccagc cttctcttca   1320
tcacttaacg gcggatctg tttgacgggg ctaccgagat acagatatcc gctctccagc    1380
cgtttatttt gtgggaccag actacccgca ccaatcatca catcatcttc tactattgcg   1440
ccatcaagta aaattgagcc catcccaacc aaaactcgat tgccaatggt gcagccgtgg   1500
agcatcacct tgtgaccaac agtgacatct tcgccaatgg ttaatgggtt gccatctggg   1560
ttgtacgagg atttatgagt gacatgcaac atactgccat cctggatatt ggtgcgtgct   1620
ccgatctgta cataatgtac atctccacga atcacaacga gcggcagat cccacatca    1680 tcagccagac gaacgtcacc aatcacgaca ctgctatcgt cgatcattac gcgctgaccg   1740
atttgtggaa aaagatcgcg gtatgggcgt aaaacatcag acatacttac ctcagcaata   1800
aatgatttac taatgacttt gggggcatta ttggccttgt gcaagtcttt tagtatgcaa   1860
aaaagcaccg ttttgtgtgc gattgcagca aaaagggtga aaaacaaca acagaaaaa    1920 aagatcaaaa aaatacttgt gcaaaaaatt gggatcccta taatgcgcct ccgttgagac   1980
gacaacgtga aacacttcac                                               2000
```

<210> SEQ ID NO 35
<211> LENGTH: 2460
<212> TYPE: DNA
<213> ORGANISM: Escherichia coli
<220> FEATURE:
<221> NAME/KEY: gene
<222> LOCATION: (1)..(2460)
<223> OTHER INFORMATION: DNA sequence of the integrated cassette
ack::P15aroB

<400> SEQUENCE: 35

```
gatcggcggc ataaaacgga tcgcataacg cgtcatcttg ataacgcgat tttcgacaaa     60
gaccggggca aggcgttttt ccagcggcca cgtctttgag taatgctgtc cccggcgaaa    120
caagctaaaa aaattaacag aacgattatc cggcgttgac atgcttcacc tcaacttcac    180
atataaagat tcaaaaattt gtgcaaattc acaactcagc gggacaacgt tcaaaacatt    240
ttgtcttcca tacccactat caggtatcct ttagcagcct gaaggcctaa gtagtacata    300
ttcattgagt cgtcaaattc atatacatta tgccattggc tgaaaattac gcaaaatggc    360
atagactcaa gatatttctt ccatcatgca aaaaaaaatt tgcagtgcat gatgttaatc    420
ataaatgtcg gtgtcatcat gcgctacgct ctatggctcc ctgacgtttt tttagccacg    480
tatcaattat aggtacttcc ctcgaggcta ttgacgacag ctatggttca ctgtccacca    540
accaaaactg tgctcagtac cgccaatatt tctcccttga ggggtacaaa gaggtgtccc    600
tagaagagat ccacgctgtg taaaaatttt acaaaaaggt attgactttc cctacagggt    660
gtgtaataat ttaattacag gcggggggcaa ccccgcctgt tctagaggag gaggaatcgc    720
catggagagg attgtcgtta ctctcgggga acgtagttac ccaattacca tcgcatctgg    780 tttgttttaat gaaccagctt cattcttacc gctgaaatcg ggcgagcagg tcatgttggt    840
```

```
caccaacgaa accctggctc ctctgtatct cgataaggtc cgcggcgtac ttgaacaggc    900
gggtgttaac gtcgatagcg ttatcctccc tgacggcgag cagtataaaa gcctggctgt    960
actcgatacc gtctttacgg cgttgttaca aaagccgcat ggtcgcgata ctacgctggt   1020
ggcgcttggc ggcggcgtag tgggcgatct gaccggcttc cgcggcggcga gttatcagcg   1080
cggtgttcgt ttcattcaag tcccgacgac gttactgtcg caggtcgatt cctccgttgg   1140
cggcaaaact gcggtcaacc atccctcgg taaaaacatg attggcgcgt tctaccagcc   1200
tgcttcagtg gtggtggatc tcgactgtct gaaaacgctt ccccgcgtg agttagcgtc   1260
ggggctggca gaagtcatca aatacggcat tattcttgac ggtgcgtttt tcaactggct   1320
ggaagagaat ctggatgcgt tgttgcgtct ggacggtccg gcaatggcgt actgtattcg   1380
ccgttgttgt gaactgaagg cagaagttgt cgccgccgac gagcgcgaaa ccgggttacg   1440
tgctttactg aatctgggac acacctttgg tcatgccatt gaagctgaaa tggggtatgg   1500
caattggtta catggtgaag cggtcgctgc gggtatggtg atggcggcgc ggacgtcgga   1560
acgtctcggg cagtttagtt ctgccgaaac gcagcgtatt ataaccctgc tcacgcgggc   1620
tgggttaccg gtcaatgggc cgcgcgaaat gtccgcgcag gcgtatttac cgcatatgct   1680
gcgtgacaag aaagtccttg cgggagagat gcgcttaatt cttccgttgg caattggtaa   1740
gagtgaagtt cgcagcggcg tttcgcacga gcttgttctt aacgccattg ccgattgtca   1800
atcagcgtaa tcatcgttca tgcctgatgc cgctatgtag gccggataag gcgttcacgc   1860
cgcatccggc aaccgatgcc tgatgcgacg cggtcgcgtc ttatcaggcc tacaggtcga   1920
tgccgatatg tacatcgtat tcggcaatta atacatagca tttcacaccg ccagctcagc   1980
tggcggtgct gttttgtaac ccgccaaatc ggcggtaacg aaagaggata aaccgtgtcc   2040
cgtattatta tgctgatccc taccggaacc agcgtcggtc tgaccagcgt cagccttggc   2100
gtgatccgtg caatggaacg caaaggcgtt cgtctgagcg ttttcaaacc tatcgctcag   2160
ccgcgtaccg gtgcgatgc gcccgatcag actacgacta cgtgcgtgc gaactcttcc   2220
accacgacgg ccgctgaacc gctgaaaatg agctacgttg aaggtctgct ttccagcaat   2280
cagaaagatg tgctgatgga agagatcgtc gcaaactacc acgctaacac caaagacgct   2340
gaagtcgttc tggttgaagg tctggtcccg acacgtaagc accagtttgc ccagtctctg   2400
aactacgaaa tcgctaaaac gctgaatgcg gaaatcgtct cgttatgtc tcagggcact   2460
```

<210> SEQ ID NO 36
<211> LENGTH: 1000
<212> TYPE: DNA
<213> ORGANISM: Escherichia coli
<220> FEATURE:
<221> NAME/KEY: gene
<222> LOCATION: (1)..(1000)
<223> OTHER INFORMATION: DNA sequence of the poxB region
<400> SEQUENCE: 36

```
gcggcccggc tccgtatatg gattgggtag agcaggaagt gaaagcgctc ggcgtgacgc     60
gtttctttaa agagaaattc ttcaccccag tagcggaagc agcgaccagc ggtctgaaat    120
tcaccaaact gcaaccggca cgagaatttt acgcccgtt tggcaccacg ctactggagg    180
cgctggaaag caataacgtt ccggttgtcg ccgcctgccg tgcgggtgtt tgcggctgct    240
gtaagacaaa agtggtttcc ggtgaatata cggtgagcag cacaatgacg ctgaccgacg    300
ccgaaatcgc tgaaggttac gtactggcct gctcctgcca tccgcagggg gatttggttc    360
tcgcataatc gccttatgcc cgatgatatt cctttcatcg ggctatttaa ccgttagtgc    420
```

```
ctcctttctc tcccatccct tccccctccg tcagatgaac taaacttgtt accgttatca      480
cattcaggag atggagaacc aaagggtggc atttcccgtc ataataagga catgccatga      540
ttgatttacg cagtgatacc gttacccgac cgagccgcgc catgctcgaa gcaatgatgg      600
ccgccccggt tggggacgac gtttacggag acgaccctac cgttaatgct ctgcaggact      660
acgccgcaga gctttccggt aaagaagccg ccattttctc gccgaccggc actcaggcca      720
acctggtcgc tctgctcagt cactgcgaac gtggcgaaga gtatattgtc ggtcaggccg      780
cgcataacta tctgtttgaa gccggtggcg cagcggtgct gggcagtatt cagccgcaac      840
ccatcgacgc ggctgccgac ggcacgctac cgctggataa agtggcgatg aaaatcaaac      900
ccgacgatat ccatttcgcc cgcaccaaat tactcagtct ggaaaacacc cacaacggca      960
aagtgctgcc gcgtgaatac ctgaaagaag catgggaatt                            1000
```

<210> SEQ ID NO 37
<211> LENGTH: 3392
<212> TYPE: DNA
<213> ORGANISM: Escherichia coli
<220> FEATURE:
<221> NAME/KEY: gene
<222> LOCATION: (1)..(3392)
<223> OTHER INFORMATION: DNA sequence of the integrated cassette poxB::tktA

<400> SEQUENCE: 37

```
gcggcccggc tccgtatatg gattgggtag agcaggaagt gaaagcgctc ggcgtgacgc       60
gtttctttaa agagaaattc ttcaccccag tagcggaagc agcgaccagc ggtctgaaat      120
tcaccaaact gcaaccggca cgagaatttt acgccccggt tggcaccacg ctactggagg      180
cgctggaaag caataacgtt ccggttgtcg ccgcctgccg tgcgggtgtt tgcggctgct      240
gtaagacaaa agtggtttcc ggtgaatata cggtgagcag cacaatgacg ctgaccgacg      300
ccgaaatcgc tgaaggttac gtactggcct gctcctgcca tccgcagggg gatttggttc      360
tcgcataatc gccttatgcc cgatgatatt cctttcatcg ggctatttaa ccgttagtgc      420
ctcctttctc tcccatccct tccccctccg tcagatgaac taaacttgtt accgttatca      480
cattcaggag atggagaacc aaggaaaagc gcaacggacg ggcgagtaga ttgcgcaaca      540
tgcgagcatg atccagagat ttctgaagca gcaaaaggat gttccatgta catgacgcgc      600
ggcttgcggt aaattgttgg caaattttcc ggcgtagccc aaaacgcgct gtcgtcaagt      660
cgttaagggc gtgcccttca tcatccgatc tggagtcaaa atgtcctcac gtaaagagct      720
tgccaatgct attcgtgcgc tgagcatgga cgcagtacag aaagccaaat ccggtcaccc      780
gggtgcccct atgggtatgg ctgacattgc cgaagtcctg tggcgtgatt tcctgaaaca      840
caacccgcag aatccgtcct gggctgaccg tgaccgcttc gtgctgtcca acggccacgg      900
ctccatgctg atctacagcc tgctgcacct caccggttac gatctgccga tggaagaact      960
gaaaaacttc cgtcagctgc actctaaaac tccgggccac ccggaagtag gttataccgc     1020
tggtgtggaa accaccaccg gtccgctggg tcagggtatt gccaacgcag tcggtatggc     1080
gattgcagaa aaaacgctgg cggcgcagtt taaccgtcca ggtcacgaca ttgtcgacca     1140
ctacacctac gccttcatgg gcgacggctg catgatggaa ggcatctccc acgaagtttg     1200
ctctctggcg ggtacgctga agctgggtaa actgattgcg ttctacgatg acaacggtat     1260
ctcaatcgat ggtcacgttg aaggctggtt cactgacgac accgcaatgc gtttcgaagc     1320
ttacggctgg cacgttattc gcgacatcga cggtcatgac gcggcatcca tcaaacgcgc     1380
```

```
agtagaagaa gcgcgcgcag tgactgacaa accgtccctg ctgatgtgca aaaccatcat    1440
cggtttcggt tccccgaaca aagccggtac ccacgactcc cacggtgcgc cgctgggcga    1500
cgctgaaatt gccctgaccc gcgaacagct gggctggaaa tacgcgccgt tcgaaatccc    1560
gtctgaaatc tatgctcagt gggatgcgaa agaagcaggc caggcgaaag aatctgcatg    1620
gaatgagaag tttgcggctt acgcgaaagc ttatccgcag gaagcggctg aatttacccg    1680
ccgtatgaaa ggcgaaatgc cgtctgactt cgacgccaaa gcgaaagagt ttatcgctaa    1740
actgcaggct aatccggcga aaatcgccag ccgtaaagcg tcgcagaatg ctatcgaagc    1800
gttcggcccg ctgttgcctg aattcctcgg cggctctgct gacctggcac cgtctaacct    1860
gaccctgtgg tctggttcta aagcaatcaa cgaagatgct gcaggtaact acatccacta    1920
cggtgttcgc gagttcggta tgaccgcgat tgctaacgat atctccctgc acggtggttt    1980
cctgccgtac acctccacct tcctgatgtt cgtggaatac gcacgtaacg ccgtacgtat    2040
ggctgcgctg atgaaacagc gtcaggtgat ggtttacacc cacgactcca tcggtctggg    2100
cgaagatggc ccgactcacc agccggttga gcaggtcgct tctctgcgcg tgaccccgaa    2160
catgtctaca tggcgtccgt gtgaccaggt tgaatccgcg gtcgcgtgga aatacggcgt    2220
tgagcgtcag gacggcccga ctgcgcttat cctctcccgt cagaacctgg cgcagcagga    2280
acgaactgaa gagcaactgg caaacatcgc gcgcggtggt tatgtgctga agactgcgc    2340 cggtcagccg gaactgattt tcatcgctac cggttcagaa gttgaactgg ctgttgctgc    2400
ctacgaaaaa ctgactgccg aaggcgtgaa agcgcgcgtg gtgtccatgc cgtctaccga    2460
cgcatttgac aagcaggatg ctgcttaccg tgaatccgta ctgccgaaag cggttactgc    2520
acgcgttgct gtagaagcgg gtattgctga ctactggtac aagtatgttg gcctgaacgg    2580
tgctatcgtc ggtatgacca ccttcggtga atctgctccg gcagagctgc tgtttgaaga    2640
gttcggcttc actgttgata cgttgttgc gaaagcaaaa gaactgctgt aattagcatt    2700
tcgggtaaaa aggtcgcttc ggcgaccttt tttattacct tgatatgtcc gtttgcggac    2760
aagcaataga taaagcgtgt tgtagatcac aaatatttat atgcaataaa tatcaattat    2820
gtaatatgca tcacgatatg cgtattgaca tttgttgtta taactataac tcaatgttat    2880
ataagaaatt aaaagggtg gcatttcccg tcataataag gacatgccat gattgattta    2940
cgcagtgata ccgttacccg accgagccgc gccatgctcg aagcaatgat ggccgccccg    3000
gttggggacg acgtttacgg agacgaccct accgttaatg ctctgcagga ctacgccgca    3060
gagctttccg gtaaagaagc cgccattttt ctgccgaccg gcactcaggc caacctggtc    3120
gctctgctca gtcactgcga acgtggcgaa gagtatattg tcggtcaggc cgcgcataac    3180
tatctgtttg aagccggtgg cgcagcgtg ctgggcagta ttcagccgca acccatcgac    3240
gcggctgccg acggcacgct accgctggat aaagtggcga tgaaaatcaa acccgacgat    3300
atccatttcg cccgcaccaa attactcagt ctggaaaaca cccacaacgg caaagtgctg    3360
ccgcgtgaat acctgaaaga agcatgggaa tt                                  3392
```

<210> SEQ ID NO 38
<211> LENGTH: 1045
<212> TYPE: DNA
<213> ORGANISM: Escherichia coli
<220> FEATURE:
<221> NAME/KEY: gene
<222> LOCATION: (1)..(1045)
<223> OTHER INFORMATION: DNA sequence of the ptsHI region

<400> SEQUENCE: 38

```
gaagatgaaa gctttaccaa caagaatatt gtggttattc taccatcatc gggtgagcgt    60
tatttaagca ccgcattgtt tgccgatctc ttcactgaga aagaattgca acagtaatgc   120
cagcttgtta aaaatgcgta aaaaagcacc tttttaggtg cttttttgtg gcctgcttca   180
aactttcgcc cctcctggca ttgattcagc ctgtcggaac tggtatttaa ccagactaat   240
tattttgatg cgcgaaatta atcgttacag gaaaagccaa agctgaatcg attttatgat   300
ttggttcaat tcttccttta gcggcataat gtttaatgac gtacgaaacg tcagcggtca   360
acacccgcca gcaatggact gtattgcgct cttcgtgcgt cgcgtctgtt aaaaactggc   420
gctaacaata caggctaaag tcgaaccgcc aggctagact ttagttccac aacactaaac   480
ctataagttg gggaaataca atgttccagc aagaagttac cattaccgct ccgacaatct   540
gctaatccac gagatgcggc ccaatttact gcttaggaga agatcatggg tttgttcgat   600
aaactgaaat ctctggtttc cgacgacaag aaggataccg gaactattga gatcattgct   660
ccgctctctg gcgagatcgt caatatcgaa gacgtgccgg atgtcgtttt tgcggaaaaa   720
atcgttggtg atggtattgc tatcaaacca acgggtaaca aaatggtcgc gccagtagac   780
ggcaccattg gtaaaatctt tgaaaccaac cacgcattct ctatcgaatc tgatagcggc   840
gttgaactgt tcgtccactt cggtatcgac accgttgaac tgaaaggcga aggcttcaag   900
cgtattgctg aagaaggtca gcgcgtgaaa gttggcgata ctgtcattga atttgatctg   960
ccgctgctgg aagagaaagc caagtctacc ctgactccgg ttgttatctc caacatggac  1020
gaaatcaaag aactgatcaa actgt                                        1045
```

<210> SEQ ID NO 39
<211> LENGTH: 4595
<212> TYPE: DNA
<213> ORGANISM: Escherichia coli
<220> FEATURE:
<221> NAME/KEY: gene
<222> LOCATION: (1)..(4595)
<223> OTHER INFORMATION: DNA sequence of the integrated cassette
tdc::glf-glk

<400> SEQUENCE: 39

```
ctgatttctt tgtcgctgat cccttactgg aactctgcag ttatcgacca ggttgacctc    60
ggttcgctgt cgttaaccgg tcatgacggt atcctgatca ctgtctggct ggggattttcc   120
atcatggttt tctcctttaa cttctcgcca atcgtctctt ccttcgtggt ttctaaacgt   180
gaaagagtatg agaaagactt cggtcgcgac ttcaccgaac gtaaatgttc ccaaatcatt   240
tctcgtgcca gcatgctgat ggttgcagtg gtgatgttct ttgcctttag ctgcctgttt   300
actctgtctc cggccaacat ggcggaagcc aaagcgcaga atattccagt gctttcttat   360
ctggctaacc acttttgcgtc catgaccggt accaaaacaa cgttcgcgat tacactggaa   420
tatgcggctt ccatcatcgc actcgtggct atcttcaaat cttttcttcgg tcactatctg   480
gggacgctgg aaggcttgaa tggtctgatt ctgaagttcg ttataaagg tgacaaaacc   540
aaagtgtcgc tgggtaaaact gaatactctc agcatgatct tcatcatggg ctccacctgg   600
gttgttgcct acgccaaccc gaacatcctc gacctgattg aagccatggg cgcaccgatt   660
atcgcatccc tgctgtgcct gttgccgatg tatgccatcc gtaaagcgcc gtctctggcg   720
aaataccgtg gtcgtctgga taacgtgttt gttaccgtga ttggtctgct gaccatcctg   780
aacatcgtat acaaactgtt ttaatccgta actcaggatg agaaaagaga tgaatgaatt   840
```

```
tccggttgtt ttggttatta actgtggttc gtcttcgatt aagttttccg tactcgatgc    900
cagcgactgt gaagtattaa tgtcaggtat tgccgacggt attaactcgg aaaatgcatt    960
cttatccgta aatgggggag agccagcacc gctggctcac cacagctacg aaggtgcatt   1020
gaaggcaatt gcatttgaac tggaaaaacg gagtttaaat gacagcgtgg ccttaattgg   1080
tgcaaaagtg gctgtgactg taaaagaaa tcgaaaaga ccgttttgtg tgaaaacggt    1140 cttttttgttt cctttttaacc aactgccata actcgaggcc tacctagctt ccaagaaaga   1200
tatcctaaca gcacaagagc ggaaagatgt tttgttctac atccagaaca acctctgcta   1260
aaattcctga aaattttgc aaaaagttgt tgactttatc tacaaggtgt ggtataataa    1320
tcttaacaac agcaggacgc tctagaggga gaggaatcgc catgagttct gaaagtagtc   1380
agggtctagt cacgcgacta gccctaatcg ctgctatagg cggcttgctt ttcggttacg   1440
attcagcggt tatcgctgca atcggtacac cggttgatat ccattttatt gcccctcgtc   1500
acctgtctgc tacggctgcg gcttcccttt ctgggatggt cgttgttgct gttttggtcg   1560
gttgtgttac cggttctttg ctgtctggct ggattgtat tcgcttcggt cgtcgcggcg   1620
gattgttgat gagttccatt tgtttcgtcg ccgccggttt tggtgctgcg ttaaccgaaa   1680
aattatttgg aaccggtggt tcggctttac aaattttttg ctttttccgg tttcttgccg   1740
gtttaggtat cggtgtcgtt tcaaccttga ccccaaccta tattgctgaa attgctccgc   1800
cagacaaacg tggtcagatg gttctggtc agcagatggc cattgtgacg ggtgctttaa   1860
ccggttatat ctttacctgg ttactggctc atttcggttc tatcgattgg gttaatgcca   1920
gtggttggtg ctggtctccg gcttcagaag gcctgatcgg tattgccttc ttattgctgc   1980
tgttaaccgc accggatacg ccgcattggt tggtgatgaa gggacgtcat tccgaggcta   2040
gcaaaatcct tgctcgtctg gaaccgcaag ccgatcctaa tctgacgatt caaaagatta   2100
aagctggctt tgataaagcc atggacaaaa gcagcgcagg tttgtttgct tttggtatca   2160
ccgttgtttt tgccggtgta tccgttgctg ccttccagca gttagtcggt attaacgccg   2220
tgctgtatta tgcaccgcag atgttccaga atttaggttt tggagctgat acggcattat   2280
tgcagaccat ctctatcggt gttgtgaact tcatcttcac catgattgct tcccgtgttg   2340
ttgaccgctt cggccgtaaa cctctgctta tttggggtgc tctcggtatg gctgcaatga   2400
tggctgtttt aggctgctgt ttctggttca aagtcggtgg tgttttgcct ttggcttctg   2460
tgcttcttta tattgcagtc tttggtatgt catggggccc tgtctgctgg gttgttctgt   2520
cagaaatgtt cccgagttcc atcaagggcg cagctatgcc tatcgctgtt accggacaat   2580
ggttagctaa tatcttggtt aacttcctgt ttaaggttgc cgatggttct ccagcattga   2640
atcagacttt caaccacggt ttctcctatc tcgttttcgc agcattaagt atcttaggtg   2700
gcttgattgt tgctcgcttc gtgccggaaa ccaaaggtcg gagcctggat gaaatcgagg   2760
agatgtggcg ctcccagaag tagttaaact tgctttggct gaatcctttt gtctttttta   2820
gataagtctt aaccaattat acttttgtt tacaacgatg gtataaagcg ggcggactta   2880
ttttacctgt tgggtagcct tctgatttca gaaaggaatt attatggaaa ttgttgcgat   2940
tgacatcggt ggaacgcatg cgcgtttctc tattgcggaa gtaagcaatg gtcgggttct   3000
ttctcttgga gaagaaacaa cttttaaaac ggcagaacat gctagcttgc agttagcttg   3060
ggaacgtttc ggtgaaaaac tgggtcgtcc tctgccacgt gccgcagcta ttgcatgggc   3120
tggcccggtt catggtgaag ttttaaaact taccaataac ccttgggtat aagaccagc    3180 tactctgaat gaaaagctgg acatcgatac gcatgttctg atcaatgact tcggcgcggt   3240
```

```
tgcccacgcg gttgcgcata tggattcttc ttatctggat catatttgtg gtcctgatga    3300
agcgcttcct agcgatggtg ttatcactat tcttggtccg ggaacgggct tgggtgttgc    3360
ccatctgttg cggactgaag gccgttattt cgtcatcgaa actgaaggcg gtcatatcga    3420
cttcgctccg cttgacagac ttgaagacaa aattctggca cgtttacgtg aacgtttccg    3480
ccgcgtttct atcgaacgca ttatttctgg cccgggtctt ggtaatatct acgaagcact    3540
ggctgccatt gaaggcgttc cgttcagctt gctggatgat attaaattat ggcagatggc    3600
tttggaaggt aaagacaacc ttgctgaagc cgctttggat cgcttctgct tgagccttgg    3660
cgctatcgct ggtgatcttg ctttggcaca gggtcgaacc agtgttgtta ttggcggtgg    3720
tgtcggtctt cgtatcgctt cccatttgcc agaatctggt ttccgtcagc gctttgtttc    3780
aaaaggacgc tttgaacgcg tcatgtccaa gattccggtt aagttgatta cttatccgca    3840
gcctggactg ttgggtgcgc agctgcctat gccaacaaat attctgaagt tgaataatat    3900
tttttaatat tatgaactga atttaagagg ctgccttccg ataaaatcgg gaggtggcct    3960
tttttatatt ttttactaaa aaatgaagac aaaaaagtct taagtaagaa taatattatt    4020
attaactttt gatatatttt gtattagtgg atccgccctc ccgctggaaa ttgaagccat    4080
cgcagtacgt agtgcgtaaa gcctcgtgag cgggacggtc gtaaggtcgt tccgctccac    4140
ttcactgaac ggcaatccga gggtgtggat atgattagtg cattcgatat tttcaaaatt    4200
gggattggtc cctccagttc gcataccgtg gggccaatga atgccggaaa agttttatt    4260 gatcggctgg aaagtagcgg cttattaacc gcgacgagcc atattgtggt cgatctgtac    4320
gggtcgttgt cactgacggg caaaggccat gccacggatg tcgccatcat catgggactg    4380
gcaggaaaca gtccgcagga tgttgtcatt gatgagatcc ctgcatttat agagttagta    4440
acgcgcagcg ggcggctgcc agtggcatct ggtgcgcata ttgttgattt tcctgtagca    4500
aagaacatta tcttccatcc cgaaatgttg cctcgccatg agaacggaat gcggatcact    4560
gcctggaagg gacaggaaga gctattaagt aaaac                               4595
```

<210> SEQ ID NO 40
<211> LENGTH: 1069
<212> TYPE: DNA
<213> ORGANISM: Escherichia coli
<220> FEATURE:
<221> NAME/KEY: gene
<222> LOCATION: (1)..(1069)
<223> OTHER INFORMATION: DNA sequence of the galP region

<400> SEQUENCE: 40

```
actttggtcg tgaacatttc ccgtgggaaa aaaccgacaa agcgcagctg ctgcgcgatg     60
ctgccggtct gaagtaatct ttcttcacct gcgttcaaag gccagcctcg cgctggcctt    120
tttcttttgg ataggcgttc acgccgcatc cggcaaaaaa accgcccgca caataacatc    180
attcttcctg atcacgtttc accgcagatt atcatcacaa ctgaaaccga ttacaccaac    240
cacaacagac aaagatttgt aatattttca tattattatt cggttttcac agttgttaca    300
tttcttttca gtaaagtctt aattgcagat aacagcgttt aatctatgat gatataactc    360
aattattttc atgcacttaa atcataacta agataaatgt tagtgtaagc gattacactg    420
atgtgatttg cttcacatct ttttacgtcg tactcaccta tcttaattca caataaaaaa    480
taaccatatt ggagggcatc atgcctgacg ctaaaaaaca ggggcggtca acaaggcaa    540 tgacgtttga ataggcgct cacgattaat ctccccaagc ttcctcccat cgcggaggaa    600
```

```
gccacctctt gcagtcatct tttcttcgct ctatcctctg ccgctatgaa acatcccgt      660 ctccctatcg ccatccaaca ggccgttatg cgtcgcctgc gggaaaaact cgcccaggcc    720
aacctgaagc tagggcgtaa ctacccggag ccaaaactct cttacaccca gcgcggaacc    780
tccgccggaa cggcctggct ggaaagctat gaaattcgcc tcaatcccgt tttgctgttg    840
gaaaacagtg aagcttttat tgaagaagtg gtaccgcacg aactggcaca tttgctggta    900
tggaaacatt tcggccgcgt agcgccacat ggcaaagagt ggaagtggat gatgaaaaac    960
gtgctgggtg ttcccgcccg tcgtacgcat cagttcgaac tgcaatccgt gcgtcgcaac   1020
accttcccct accgctgcaa gtgccaggag catcagctta ccgtacgcc               1069
```

```
<210> SEQ ID NO 41
<211> LENGTH: 6100
<212> TYPE: DNA
<213> ORGANISM: Escherichia coli
<220> FEATURE:
<221> NAME/KEY: gene
<222> LOCATION: (1)..(6100)
<223> OTHER INFORMATION: MYR352  adhE::P15-catAX , PR-aroY, P26-quiC

<400> SEQUENCE: 41
```

```
ttgattttca taggttaagc aaatcatcac cgcactgact atactctcgt attcgagcag      60
atgatttact aaaaaagttt aacattatca ggagagcatt agcttgctat tgacgacagc    120
tatggttcac tgtccaccaa ccaaaactgt gctcagtacc gccaatattt ctcccttgag    180
gggtacaaag aggtgtccct agaagagatc cacgctgtgt aaaaatttta caaaaaggta    240
ttgactttcc ctacagggtg tgtaataatt taattacagg cggggggcaac cccgcctgtt   300 ctgcagagga ggaatatagc catggaagtg aaaatcttca acacccagga tgttcaggat    360
tttctgcgtg ttgcaagcgg tctggaacaa gagggtggta atccgcgtgt taaacaaatt    420
attcatcgtg ttctgagcga cctgtataaa gcaattgaag atctgaatat caccagcgac    480
gaatattggg caggcgttgc atatctgaat cagctgggtg caaatcaaga agcaggtctg    540
ctgagtccgg gtctgggttt tgatcattat ctggatatgc gtatggatgc agaagatgca    600
gcactgggta ttgaaaatgc aacaccgcgt accattgaag gtccgctgta tgttgcgggt    660
gcaccggaaa gcgttggtta tgcacgcatg gatgatggta gcgatccgaa tggtcatacc    720
ctgattctgc atggcaccat ttttgatgca atggtaaaac gctgccgaa tgcaaaagtt    780 gaaatttggc atgcaaacac caaaggcttt tatagccatt ttgatccgac cggtgaacag    840
caggccttta atatgcgtcg tagcattatt ccgatgaga atggtcagta tcgtgttcgt    900
accattctgc ctgccggtta tggttgtcct ccggaaggtc cgacccagca actgctgaac    960
caactgggtc gtcatggtaa tcgtccggca catattcatt attttgttag cgcagatggt   1020
caccgtaaac tgaccaccca gattaatgtt gccggtgatc cgtataccta tgatgatttt   1080
gcatatgcca cccgtgaagg tctggttgtt gatgcagttg aacataccga tccggaagca   1140
attaaagcca atgatgtgga aggtcctttt gccgaaatgg tgtttgatct gaaactgacc   1200
cgtctggttg atggtgttga taatcaggtt gtggatcgtc cgcgtctggc agtttaatac   1260
accaaaatgg ttcaaaatta tcaggcgagt gatcatgatc actggcctgt ttttatttca   1320
gggaagggtg gagacaatta cgtggataat cagatcatcc aagaaaccgt ggataaaatt   1380
ctgagcgttc tgccgaatca ggcaggtcag ctggcacgtc tggtgcgtct gatgcaattt   1440
gcatgcgatc cgaccattac cgttattggc aaatataacc atggtaaaag ccgtctgctg   1500
aatgaactga ttggcaccga tatctttagc gttgcagata aacgtgaaac cattcagctg   1560
```

```
gccgaacata aacaggatca ggttcgttgg ctggatgcac ctggtctgga tgccgatgtt    1620
gcagcagttg atgatcgtca tgcatttgaa gcagtttgga cccaggcaga tattcgtctg    1680
tttgttcata gcgttcgtga aggtgaactg gatgcaaccg aacaccatct gctgcaacag    1740
ctgattgaag atgccgatca tagccgtcgt cagaccattc tggttctgac ccagattgat    1800
cagattccgg atcagaccat cctgacacag attaaaacca gcattgcaca gcaggttccg    1860
aaactggata tttgggcagt tagcgcaacc cgtcatcgtc agggcattga aaacggtaaa    1920
accctgctga tcgaaaaaag cggtattggt gcactgcgcc ataccctgga caggcactg     1980 gcacaggtgc cgagcgcacg tacctatgaa aaaaatcgtc tgctgtcaga tctgcaccat    2040
cagctgaaac aactgctgct ggatcagaaa catgttctgc aacaactgca acagacacag    2100
caacagcagc tgcatgattt tgataccggt ctgattaaca ttctggacaa aattcgtgtt    2160
gatctggaac cgattgtgaa tattgatggt caggatcaag cactgaatcc ggatagcttt    2220
gcaaccatgt ttaaaaacac cgcagcaaaa cagcagcgtg ccaaagttca gattgcatat    2280
agccgtgcat gcattgaaat caacagccat ctgattcgcc atggtgttgt tggtctgcct    2340
gcggaacagc agaccaccat taaaagcatt gataccgtga ttgttgccgt gtttggtatc    2400
agcgttaaat ttcgtgatca gctgcgtgcc ctgttttata ccgataccga acgtcagcgt    2460
ctgcaacgtg aatttcgttt ctattttgaa aaaagtgccg gtcgcatgat tctggcagca    2520
aaaattgaac agaccatgcg tcagcagggc tgtattcaga atgccatgat ggcactgcaa    2580 caaatgaaa gcgcagcata aaaacacgga cgccgcaaac ggcgtccgaa tttcttggtc     2640
gaccgttaaa tctatcaccg caagggataa atatctaaca ccgtgcgtgt tgactatttt    2700
acctctggcg gtgataatgg ttgcatgtac taatctagat aaggaatata gccatgaccg    2760
caccgattca ggatctgcgt gatgcaattg ccctgctgca acagcatgat aatcagtatc    2820
tggaaaccga tcatccggtt gatccgaatg cagaactggc aggcgtttat cgtcatattg    2880
gtgccggtgg caccgttaaa cgtccgaccc gtattggtcc ggcaatgatg tttaataaca    2940
ttaaaggtta tccgcacagc cgtattctgg ttggtatgca tgcaagccgt cagcgtgcag    3000
cactgctgct gggttgtgaa gcaagtcagc tggcactgga agttggtaaa gcagttaaaa    3060
aaccggttgc accggtggtt gttccggcaa gcagcgcacc gtgtcaagag cagattttc     3120 tggcagatga tccggatttt gatctgcgta ccctgctgcc tgcacatacc aatacccga     3180 ttgatgcagg tccgtttttt tgtctgggtc tggccctggc aagcgatccg gtggatgcaa    3240
gcctgaccga tgttaccatt catcgtctgt gtgttcaggg tcgtgatgaa ctgagcatgt    3300
tcctggcagc aggtcgccat attgaagttt ttcgtcagaa agcagaagca gcaggtaaac    3360
cgctgccgat taccattaat atgggtctgg acccagcaat ctatattggc gcatgttttg    3420
aagcaccgac cacccccgttt ggttataatg aactgggtgt tgccggtgca ctgcgtcagc   3480
gtccggttga actggttcag ggtgttagcg ttccggaaaa agcaattgca cgtgccgaaa    3540
ttgttattga aggtgaactg ctgcctggtg ttcgtgttcg tgaagatcag cataccaatt    3600
caggtcatgc aatgccggaa tttccggggtt attgtggtgg tgcaaatccg agcctgccgg   3660
ttattaaagt taaagccgtt accatgcgca ataacgcaat tctgcaaacc ctggttggtc    3720
cgggtgaaga acataccacc ctggcaggtc tgccgaccga agcaagcatt tggaatgcag    3780
ttgaagcagc aattccgggt tttctgcaaa atgtttatgc ccataccgca ggcgttggta    3840
aatttctggg tattctgcaa gtgaaaaaac gtcagcctgc cgatgaaggt cgtcagggtc    3900
```

```
aggcagccct gctggcgctg caacctata gcgaactgaa aaatatcatt ctggtggatg    3960
aggatgtgga cattttttgat agtgatgata ttctgtgggc aatgaccacc cgtatgcagg    4020
gtgatgttag cattaccacc attccgggta ttcgcggtca tcagctggac ccgagccaga    4080
caccggaata ttcaccgagc attcgtggta atggtattag ctgcaaaacc atctttgatt    4140
gtaccgttcc gtgggcactg aaaagccatt tgaacgtgc accgtttgca gatgttgatc    4200
cgcgtccgtt tgcacctgaa tattttgcac gtctggaaaa aaatcagggc agcgcaaaat    4260
aagctaataa caggcctgct ggtaatcgca ggaatttta tttggatgga tccgcctacc    4320
tagcttccaa gaaagatatc ctaacagcac aagagcggaa agatgttttg ttctacatcc    4380
agaacaacct ctgctaaaat tcctgaaaaa ttttgcaaaa agttgttgac tttatctaca    4440
aggtgtggta taataatctt aacaacagca ggacgctccc gggttgagga aaacctaatg    4500
aaactgacca gcctgcgtgt tagcctgctg gcactgggtc tggttaccag cggttttgca    4560
gcagcagaaa cctataccgt tgatcgttat caggatgata gcgaaaaagg tagcctgcgt    4620
tgggcaattg aacagagcaa tgcaaatagc gcacaagaaa accagattct gattcaggca    4680
gttggtaaag caccgtatgt tatcaaagtt gataaaccgc tgcctccgat taaaagcagc    4740
gttaaaatca ttggcaccga gtgggataaa accggtgaat ttattgcaat tgatggcagc    4800
aactatatca aaggcgaagg tgaaaaagca tgtccgggtg caaatccggg tcagtatggc    4860
accaatgttc gtaccatgac cctgcctggt ctggttctgc aagatgttaa tggtgttacc    4920
ctgaaaggtc tggatgttca tcgttttttgt attggtgttc tggttaatcg cagcagcaat    4980
aacctgattc agcataatcg tatcagcaac aattatggtg gtgccggtgt tatgattacc    5040
ggtgatgatg gtaaaggtaa tccgaccagc accaccacca ataataacaa agttctggat    5100
aacgtgttca tcgataatgg tgatggtctg gaactgaccc gtggtgcagc atttaatctg    5160
attgcaaata acctgtttac cagcacaaaa gccaatccgg aaccgagcca gggtattgaa    5220
attctgtggg gtaatgataa tgccgtggtg ggtaacaaat tcgaaaacta ttcagatggc    5280
ctgcaaatca attggggtaa acgtaactat atcgcctata cgaactgac caataacagc    5340 ctgggtttca atctgacagg tgatggtaac attttcgaca gcaataaagt gcatggtaac    5400
cgtattggta ttgccattcg tagtgaaaaa gatgccaatg cacgtattac cctgaccaaa    5460
aatcagattt gggataacgg caaagatatc aaacgttgtg aagccggtgg tagctgtgtt    5520
ccgaatcagc gtctgggtgc aattgttttt ggtgttccgg cactggaaca tgaaggtttt    5580
gttggtagcc gtggcggtgg tgttgttatt gaaccggcaa aactgcaaaa acctgcacc    5640 cagccgaacc agcagaattg taatgcaatt cctaatcagg gtattcaggc accgaaactg    5700
acagttagca aaaaacagct gaccgttgaa gttaaaggca cccctaatca gcgttataat    5760
gtggaatttt ttggcaatcg taatgccagc agcagcgaag cagaacagta tctgggtagc    5820
attgttgttg ttaccgatca tcagggtctg gcaaaagcaa attgggctcc gaaagttagc    5880
atgccgagcg ttaccgcaaa tgtgacagat catctgggtg cgaccagcga actgagcagc    5940
gcagttaaaa tgcgttaaat gcatgcgcgc cgcgttcgcg cggcgctttt ttttggtact    6000
cagtagcgct gtctggcaac ataaacggcc ccttctgggc aatgccgatc agttaaggat    6060
tagttgaccg atccttaaac tgaggcacta taacggcttc                         6100
```

<210> SEQ ID NO 42
<211> LENGTH: 594
<212> TYPE: DNA
<213> ORGANISM: Klebsiella pneumoniae

```
<220> FEATURE:
<221> NAME/KEY: gene
<222> LOCATION: (1)..(594)
<223> OTHER INFORMATION: Nucleotide sequence of Klebsiella pneumoniae
      kpdB gene.

<400> SEQUENCE: 42
atgaaactga ttattgggat gacgggggcc accggggcac cgcttggggt ggcattgctg      60
caggcgctgc gcgatatgcc ggaggtggaa acccatctgg tgatgtcgaa atgggccaaa     120
accaccatcg agctggaaac gccctggacg gcgcgcgaag tggccgcgct ggcggacttt     180
tcccacagcc cggcagacca ggccgccacc atctcatccg gttcatttcg taccgacggc     240
atgatcgtta ttccctgcag tatgaaaacg cttgcaggca ttcgcgcggg ttatgccgaa     300
gggctggtgg gccgcgcggc ggacgtggtg ctcaaagagg ggcgcaagct ggtgttggtc     360
ccgcgggaaa tgccgctcag cacgatccat ctggagaaca tgctggcgct gtcccgcatg     420
ggcgtggcga tggtcccgcc gatgccagct tactacaacc acccggagac ggttgacgat     480
atcaccaatc atatcgtcac ccgggtgctg gatcagtttg gcctcgacta tcacaaagcg     540
cgccgctgga acggcttgcg cacggcagaa caatttgcac aggagatcga ataa           594

<210> SEQ ID NO 43
<211> LENGTH: 197
<212> TYPE: PRT
<213> ORGANISM: Klebsiella pneumoniae
<220> FEATURE:
<221> NAME/KEY: PEPTIDE
<222> LOCATION: (1)..(197)
<223> OTHER INFORMATION: Amino acid sequence of KpdB protein of
      Klebsiella pneumoniae

<400> SEQUENCE: 43

Met Lys Leu Ile Ile Gly Met Thr Gly Ala Thr Gly Ala Pro Leu Gly
1               5                   10                  15

Val Ala Leu Leu Gln Ala Leu Arg Asp Met Pro Glu Val Glu Thr His
            20                  25                  30

Leu Val Met Ser Lys Trp Ala Lys Thr Thr Ile Glu Leu Glu Thr Pro
        35                  40                  45

Trp Thr Ala Arg Glu Val Ala Ala Leu Ala Asp Phe Ser His Ser Pro
    50                  55                  60

Ala Asp Gln Ala Ala Thr Ile Ser Ser Gly Ser Phe Arg Thr Asp Gly
65                  70                  75                  80

Met Ile Val Ile Pro Cys Ser Met Lys Thr Leu Ala Gly Ile Arg Ala
                85                  90                  95

Gly Tyr Ala Glu Gly Leu Val Gly Arg Ala Ala Asp Val Val Leu Lys
            100                 105                 110

Glu Gly Arg Lys Leu Val Leu Val Pro Arg Glu Met Pro Leu Ser Thr
        115                 120                 125

Ile His Leu Glu Asn Met Leu Ala Leu Ser Arg Met Gly Val Ala Met
    130                 135                 140

Val Pro Pro Met Pro Ala Tyr Tyr Asn His Pro Glu Thr Val Asp Asp
145                 150                 155                 160

Ile Thr Asn His Ile Val Thr Arg Val Leu Asp Gln Phe Gly Leu Asp
                165                 170                 175

Tyr His Lys Ala Arg Arg Trp Asn Gly Leu Arg Thr Ala Glu Gln Phe
            180                 185                 190

Ala Gln Glu Ile Glu
        195
```

<210> SEQ ID NO 44
<211> LENGTH: 570
<212> TYPE: DNA
<213> ORGANISM: Escherichia coli
<220> FEATURE:
<221> NAME/KEY: gene
<222> LOCATION: (1)..(570)
<223> OTHER INFORMATION: Nucleotide sequence of Escherichia coli ubiX gene

<400> SEQUENCE: 44

```
atgaaacgac tcattgtagg catcagcggt gccagcggcg cgatttatgg cgtgcgctta      60
ttacaggttc tgcgcgatgt cgcagatatc gaaacgcatc tggtgatgag ccaggcggcg     120
cgccagacct tatccctcga aacgggtttt tccctgcgcg aagtgcaggc attagctgat     180
gtcacgcacg atgcgcgcga tattgccgcc agcatctctt ccggttcttt ccagacgctg     240
gggatggtta ttttaccctg ttcaatcaaa acccttccg gcattgtcca tagctacacc      300
gatggtttac tgacccgtgc ggcagatgtg gtgctgaaag agcgtcgccc gttggtgctc     360
tgcgtgcgtg aaacaccatt gcacttaggc catctgcgtt taatgactca ggcagcagaa     420
atcggtgcgg tgattatgcc tcccgttccg gcgttttatc atcgcccaca gtcccttgat     480
gatgtgataa atcagacggt taatcgtgtt cttgaccagt ttgcgataac ccttcctgaa     540
gatctctttg cccgctggca gggcgcataa                                       570
```

<210> SEQ ID NO 45
<211> LENGTH: 189
<212> TYPE: PRT
<213> ORGANISM: Escherichia coli
<220> FEATURE:
<221> NAME/KEY: PEPTIDE
<222> LOCATION: (1)..(189)

<400> SEQUENCE: 45

```
Met Lys Arg Leu Ile Val Gly Ile Ser Gly Ala Ser Gly Ala Ile Tyr
1               5                   10                  15

Gly Val Arg Leu Leu Gln Val Leu Arg Asp Val Ala Asp Ile Glu Thr
            20                  25                  30

His Leu Val Met Ser Gln Ala Ala Arg Gln Thr Leu Ser Leu Glu Thr
        35                  40                  45

Gly Phe Ser Leu Arg Glu Val Gln Ala Leu Ala Asp Val Thr His Asp
    50                  55                  60

Ala Arg Asp Ile Ala Ala Ser Ile Ser Ser Gly Ser Phe Gln Thr Leu
65                  70                  75                  80

Gly Met Val Ile Leu Pro Cys Ser Ile Lys Thr Leu Ser Gly Ile Val
                85                  90                  95

His Ser Tyr Thr Asp Gly Leu Leu Thr Arg Ala Ala Asp Val Val Leu
            100                 105                 110

Lys Glu Arg Arg Pro Leu Val Leu Cys Val Arg Glu Thr Pro Leu His
        115                 120                 125

Leu Gly His Leu Arg Leu Met Thr Gln Ala Ala Glu Ile Gly Ala Val
    130                 135                 140

Ile Met Pro Pro Val Pro Ala Phe Tyr His Arg Pro Gln Ser Leu Asp
145                 150                 155                 160

Asp Val Ile Asn Gln Thr Val Asn Arg Val Leu Asp Gln Phe Ala Ile
                165                 170                 175

Thr Leu Pro Glu Asp Leu Phe Ala Arg Trp Gln Gly Ala
            180                 185
```

<210> SEQ ID NO 46
<211> LENGTH: 594
<212> TYPE: DNA
<213> ORGANISM: Escherichia coli
<220> FEATURE:
<221> NAME/KEY: gene
<222> LOCATION: (1)..(594)
<223> OTHER INFORMATION: Nucleotide sequence of Escherichia coli Wstrain elw gene

<400> SEQUENCE: 46

```
atgaaactga tcgtcgggat gacaggggct accggtgcgc tcttggtgt ggcattactg    60
caagcgctgc gggagatgcc gaatgtcgag actcatctgg tgatgtcgaa gtgggcgaaa   120
accaccattg aactggaaac gccttacagc gctcgcgatg ttgctgccct cgcagacttc   180
agccataacc cggcggatca ggcggcgatc atctcatccg gttcttttcg taccgacggc   240
atgatcgtta ttccgtgcag tatgaaaacg ctcgccggta tccgcgctgg ttacgccgat   300
ggcctggtag gcgcgcggc ggacgtcgtg ctcaaagaag ccgcaaaact ggtgctggtg    360
ccgcgtgaaa tgccgcttag caccatccat ctcgaaaata tgctcgcact ttcacgcatg   420
ggcgtggcga tggtgccgcc gatgcctgcc ttttataacc atcccgaaac ggtagatgac   480
attgtccacc atgtggtagc ccgcgtgctg atcaatttg gcctcgaaca tccccacgcc    540
aggcgctggc aaggattgcc gcaggcccgg aattttctc aggagaatga ataa           594
```

<210> SEQ ID NO 47
<211> LENGTH: 197
<212> TYPE: PRT
<213> ORGANISM: Escherichia coli
<220> FEATURE:
<221> NAME/KEY: PEPTIDE
<222> LOCATION: (1)..(197)
<223> OTHER INFORMATION: Amino acid sequence of Elw protein of Escherichia coli W strain

<400> SEQUENCE: 47

Met Lys Leu Ile Val Gly Met Thr Gly Ala Thr Gly Ala Pro Leu Gly
1               5                   10                  15

Val Ala Leu Leu Gln Ala Leu Arg Glu Met Pro Asn Val Glu Thr His
            20                  25                  30

Leu Val Met Ser Lys Trp Ala Lys Thr Thr Ile Glu Leu Glu Thr Pro
        35                  40                  45

Tyr Ser Ala Arg Asp Val Ala Leu Ala Asp Phe Ser His Asn Pro
    50                  55                  60

Ala Asp Gln Ala Ala Ile Ile Ser Ser Gly Ser Phe Arg Thr Asp Gly
65                  70                  75                  80

Met Ile Val Ile Pro Cys Ser Met Lys Thr Leu Ala Gly Ile Arg Ala
                85                  90                  95

Gly Tyr Ala Asp Gly Leu Val Gly Arg Ala Ala Asp Val Val Leu Lys
            100                 105                 110

Glu Gly Arg Lys Leu Val Leu Val Pro Arg Glu Met Pro Leu Ser Thr
        115                 120                 125

Ile His Leu Glu Asn Met Leu Ala Leu Ser Arg Met Gly Val Ala Met
    130                 135                 140

Val Pro Pro Met Pro Ala Phe Tyr Asn His Pro Glu Thr Val Asp Asp
145                 150                 155                 160

Ile Val His His Val Val Ala Arg Val Leu Asp Gln Phe Gly Leu Glu 165                 170                 175
His Pro His Ala Arg Arg Trp Gln Gly Leu Pro Gln Ala Arg Asn Phe
            180                 185                 190

Ser Gln Glu Asn Glu
        195

<210> SEQ ID NO 48
<211> LENGTH: 579
<212> TYPE: DNA
<213> ORGANISM: Klebsiella oxytoca
<220> FEATURE:
<221> NAME/KEY: gene
<222> LOCATION: (1)..(579)
<223> OTHER INFORMATION: Nucleotide sequence of Klebsiella oxytoca kox
      gene

<400> SEQUENCE: 48
atgacggcac gcatcatcat tggtatcagc ggcgcatccg gtttcagta cggcgttaag      60 gcgctggagc tactgcgccc gcatcccgtt gaagtccacc tggtcgtctc taaaggcgcg    120
gaaaaaacct gcgagctgga gacggatcac cgcctggacg aggtgatggc gctggccgac    180
gtggtgcatc ccatcgcgaa tcttggggcg gctatctcca gcggttcgtt taaaacgctg    240
ggaatgttga tcgcgccgtg ttcaatgcgt tctttaggcg ccatcgccca ctgcctgacc    300
gacaacctgc tcacccgcgc tgcggacgtg gtgctgaaag agcgtcgccg cctggtgctg    360
ctggcccggg aaacaccgct gaaccttggc catatccgca atatggccgc cgtaaccgaa    420
atgggcggaa ttatctttcc gccggtcccg gcactttacc agcgtccgca aacggcggac    480
gacatcgtta cccatagcgt caatcgcgcg ctcgatctgt tgacctgca ggtcaacaac    540 atcccccgct ggggtgaagg cgagctacgt tttaattaa                           579

<210> SEQ ID NO 49
<211> LENGTH: 192
<212> TYPE: PRT
<213> ORGANISM: Klebsiella oxytoca
<220> FEATURE:
<221> NAME/KEY: PEPTIDE
<222> LOCATION: (1)..(192)
<223> OTHER INFORMATION: Amino acid sequence of Kox protein of
      Klebsiella oxytoca.

<400> SEQUENCE: 49

Met Thr Ala Arg Ile Ile Gly Ile Ser Gly Ala Ser Gly Phe Gln
1               5                  10                  15

Tyr Gly Val Lys Ala Leu Glu Leu Leu Arg Pro His Pro Val Glu Val
            20                  25                  30

His Leu Val Val Ser Lys Gly Ala Glu Lys Thr Cys Glu Leu Glu Thr
        35                  40                  45

Asp His Arg Leu Asp Glu Val Met Ala Leu Ala Asp Val Val His Pro
    50                  55                  60

Ile Ala Asn Leu Gly Ala Ala Ile Ser Ser Gly Ser Phe Lys Thr Leu
65                  70                  75                  80

Gly Met Leu Ile Ala Pro Cys Ser Met Arg Ser Leu Gly Ala Ile Ala
                85                  90                  95

His Cys Leu Thr Asp Asn Leu Leu Thr Arg Ala Ala Asp Val Val Leu
            100                 105                 110

Lys Glu Arg Arg Arg Leu Val Leu Leu Ala Arg Glu Thr Pro Leu Asn
        115                 120                 125

Leu Gly His Ile Arg Asn Met Ala Ala Val Thr Glu Met Gly Gly Ile

```
                  130                 135                 140
Ile Phe Pro Pro Val Pro Ala Leu Tyr Gln Arg Pro Gln Thr Ala Asp
145                 150                 155                 160

Asp Ile Val Thr His Ser Val Asn Arg Ala Leu Asp Leu Phe Asp Leu
                165                 170                 175

Gln Val Asn Asn Ile Pro Arg Trp Gly Glu Gly Glu Leu Arg Phe Asn
                180                 185                 190

<210> SEQ ID NO 50
<211> LENGTH: 564
<212> TYPE: DNA
<213> ORGANISM: Lactobacillus plantarum
<220> FEATURE:
<221> NAME/KEY: gene
<222> LOCATION: (1)..(564)
<223> OTHER INFORMATION: Nucleotide sequence of Lactobacillus plantarum
      lpl gene

<400> SEQUENCE: 50
atgaaacgaa ttgttgtggg aatcacggga gcgtccggta cgatttacgc ggtcgactta      60
ttagaaaagt tacatcagcg gccagatgtt gaagttcatc tggtaatgag tgcgtgggct     120
aaaaaaaact tggagttaga gactgattac tcgctcgcgc agctgacggc gctcgcggat     180
gctacttatc gggctaatga ccaaggcgca gcgattgcca gcggttcgtt tttgaatgac     240
ggaatggtca ttgtcccagc tagtatgaag acggtagcag ggattgcgta cggcttcggt     300
gataatttaa tatcgcgggc tgctgatgtc acgattaaag aacaacgtaa acttgtgatt     360
gttccacgtg aaaacaccgt taagcgtgat catttagaaa atctaacgaa gttggcaaaa     420
ctcggtgccc aaattattcc accgattccc gcgtttttata atcatccgca atccattcag     480
gatctggtca atcatcaaac catgaaaatt ttagatgcgt tcatattcaa taatgaaact     540
gatcgccgtt gggaggggga ttaa                                            564

<210> SEQ ID NO 51
<211> LENGTH: 187
<212> TYPE: PRT
<213> ORGANISM: Lactobacillus plantarum
<220> FEATURE:
<221> NAME/KEY: PEPTIDE
<222> LOCATION: (1)..(187)
<223> OTHER INFORMATION: Amino acid sequence of Lpl protein of
      Lactobacillus plantarum

<400> SEQUENCE: 51

Met Lys Arg Ile Val Val Gly Ile Thr Gly Ala Ser Gly Thr Ile Tyr
1               5                   10                  15

Ala Val Asp Leu Leu Glu Lys Leu His Gln Arg Pro Asp Val Glu Val
                20                  25                  30

His Leu Val Met Ser Ala Trp Ala Lys Lys Asn Leu Glu Leu Glu Thr
            35                  40                  45

Asp Tyr Ser Leu Ala Gln Leu Thr Ala Leu Ala Asp Ala Thr Tyr Arg
        50                  55                  60

Ala Asn Asp Gln Gly Ala Ala Ile Ala Ser Gly Ser Phe Leu Asn Asp
65                  70                  75                  80

Gly Met Val Ile Val Pro Ala Ser Met Lys Thr Val Ala Gly Ile Ala
                85                  90                  95

Tyr Gly Phe Gly Asp Asn Leu Ile Ser Arg Ala Ala Asp Val Thr Ile
                100                 105                 110

Lys Glu Gln Arg Lys Leu Val Ile Val Pro Arg Glu Thr Pro Leu Ser
```

|  |  | 115 |  |  | 120 |  |  | 125 |  |  |  |

Val Ile His Leu Glu Asn Leu Thr Lys Leu Ala Lys Leu Gly Ala Gln
    130                 135                 140

Ile Ile Pro Pro Ile Pro Ala Phe Tyr Asn His Pro Gln Ser Ile Gln
145                 150                 155                 160

Asp Leu Val Asn His Gln Thr Met Lys Ile Leu Asp Ala Phe His Ile
                165                 170                 175

His Asn Glu Thr Asp Arg Arg Trp Glu Gly Asp
            180                 185

<210> SEQ ID NO 52
<211> LENGTH: 200
<212> TYPE: DNA
<213> ORGANISM: Escherichia coli
<220> FEATURE:
<221> NAME/KEY: promoter
<222> LOCATION: (1)..(200)
<223> OTHER INFORMATION: Nucleotide sequence of Pgi promoter

<400> SEQUENCE: 52
agcggggcgg ttgtcaacga tggggtcatg cggattttc atccactcct ggcggtcagt     60
agttcagcta ataaatgctt cactgcgcta agggtttaca ctcaacatta cgctaacggc    120
actaaaacca tcacattttt ctgtgactgg cgctacaatc ttccaaagtc acaattctca    180
tgcagaggag gaatatagcc                                                 200

<210> SEQ ID NO 53
<211> LENGTH: 3537
<212> TYPE: DNA
<213> ORGANISM: Saccharomyces cerevisiae
<220> FEATURE:
<221> NAME/KEY: gene
<222> LOCATION: (1)..(3537)
<223> OTHER INFORMATION: Nucleotide sequence of Saccharomyces cerevisiae
      pyc gene

<400> SEQUENCE: 53
atgtcgcaaa gaaaattcgc cggcttgaga gataacttca atctcttggg tgaaaagaac     60
aaaatattgg tggctaatag aggagaaatt ccaatcagaa ttttcgtac cgctcatgaa    120 ctgtctatgc agacggtagc tatatattct catgaagatc gtctttcaac gcacaaacaa    180
aaggctgacg aagcatacgt cataggtgaa gtaggccaat ataccccgt cggcgcttat    240 ttggccattg acgaaatcat ttccattgcc caaaacacc aggtagattt catccatcca    300
ggttatgggt tcttgtctga aaattcggaa tttgccgaca agtagtgaa ggccggtatc    360 acttggattg gccctccagc tgaagttatt gactccgtgg gtgataaggt ctcagctaga    420
aacctggcag caaaagctaa tgtgcccacc gttcctggta caccaggtcc tatagaaact    480
gtagaggaag cacttgactt cgtcaatgaa tacggctacc cggtgatcat taaggccgcc    540
tttggtggtg gtggtagagg tatgagagtc gttagaagg tgacgacgt ggcagatgcc    600 tttcaacgtg ctacctccga agcccgtact gccttcggta atggtacctg ctttgtggaa    660
agattcttgg acaagccaaa gcatattgaa gttcaattgt tggccgataa ccacggaaac    720
gtggttcatc ttttcgaaag agactgttcc gtgcagagaa gacaccaaaa ggttgtcgaa    780
gtggccccag caaagacttt acccgtgaa gtccgtgacg ccattttgac agatgcagtt    840
aaattggcca agagtgtgg ctacagaaat gcgggtactg ctgaattctt ggttgataac    900
caaaatagac actatttcat tgaaattaat ccaagaatcc aagtgaaaca taccatcaca    960

```
gaagaaatta ccggtataga tattgtggcg gctcagatcc aaattgcggc aggtgcctct    1020
ctaccccagc tgggcctatt ccaggacaaa attacgactc gtggctttgc cattcagtgc    1080
cgtattacca cggaagaccc tgctaagaac ttccaaccag ataccggtag aatagaagtg    1140
taccgttctg caggtggtaa tggtgttaga ctggatggtg gtaacgccta tgcaggaaca    1200
ataatctcac ctcattacga ctcaatgctg gtcaaatgct catgctccgg ttccacctac    1260
gaaatcgttc gtagaaaaat gattcgtgca ttaatcgagt tcagaattag aggtgtcaag    1320
accaacattc ccttcctatt gactcttttg accaatccag tatttattga gggtacatac    1380
tggacgactt ttattgacga cacccacaa ctgttccaaa tggtttcatc acaaaacaga    1440
gcccaaaaac ttttacatta cctcgccgac gtggcagtca atggttcatc tatcaagggt    1500
caaattggct tgccaaaatt aaaatcaaat ccaagtgtcc cccatttgca cgatgctcag    1560
ggcaatgtca tcaacgttac aaagtctgca ccaccatccg gatggaggca agtgctacta    1620 gaaaagggc cagctgaatt tgccagacaa gttagacagt tcaatggtac tttattgatg    1680
gacaccacct ggagagacgc tcatcaatct ctacttgcaa caagagtcag aacccacgat    1740
ttggctacaa tcgctccaac aaccgcacat gcccttgcag gtcgtttcgc cttagaatgt    1800
tggggtggtg ccacattcga tgttgcaatg agatttttgc atgaggatcc atgggaacgt    1860
ttgagaaaat taagatctct ggtgcctaat attccattcc aaatgttatt gcgtggtgcc    1920
aatggtgtgg cttattcttc attgcctgac aatgctattg accatttcgt caagcaagcc    1980
aaggataatg gtgttgatat atttagagtc tttgatgcct taaatgactt ggaacaattg    2040
aaggtcggtg tagatgctgt gaagaaggca ggtggtgttg tagaagccac tgtttgtttc    2100
tctggggata tgcttcagcc aggcaagaaa tacaatttgg attactactt ggaaattgct    2160
gaaaaaattg tccaaatggg cactcatatc ctgggtatca agatatggc aggtaccatg    2220 aagccagcag ctgccaaact actgattgga tctttgaggg ctaagtaccc tgatctccca    2280
atacatgttc acactcacga ttctgcaggt actgctgttg catcaatgac tgcgtgtgct    2340
ctggcgggcg ccgatgtcgt tgatgttgcc atcaactcaa tgtctggttt aacttcacaa    2400
ccatcaatca atgctctgtt ggcttcatta gaaggtaata ttgacactgg tattaacgtt    2460
gagcatgtcc gtgaactaga tgcatattgg gcagagatga gattgttata ctcttgtttc    2520
gaggctgact tgaagggccc agatccagaa gtttatcaac atgaaatccc aggtggtcaa    2580
ttgacaaact tgttgtttca gcccaacaa ttgggtcttg agaacaatg ggccgaaaca    2640 aaaagagctt acagagaagc caattattta ttgggtgata ttgtcaaagt taccccaact    2700
tcgaaggtcg ttggtgatct ggcacaattt atggtctcca ataaattaac ttccgatgat    2760
gtgagacgcc tggctaattc tttggatttc cctgactctg ttatgatt cttcgaaggc    2820 ttaatcggcc aaccatatgg tgggttccca gaaccattta gatcagacgt tttaaggaac    2880 aagaaagaa agttgacttg tcgtccaggc ctggaactag agccatttga tctcgaaaaa    2940
attagagaag acttgcagaa tagattggt gatgttgatg agtgcgacgt tgcttcttat    3000
aacatgtacc caagagttta tgaagacttc caaaagatga gagaaacgta tggtgattta    3060
tctgtattgc caacaagaag cttttttgtct ccactagaga ctgacgaaga aattgaagtt    3120
gtaatcgaac aaggtaaaac gctaattatc aagctacagg ctgtgggtga tttgaacaaa    3180
aagaccggtg aaagagaagt ttactttgat ttgaatggtg aaatgagaaa aattcgtgtt    3240
gctgacagat cacaaaaagt ggaaactgtt actaaatcca aagcagacat gcatgatcca    3300
ttacacattg gtgcaccaat ggcaggtgtc attgttgaag ttaaagttca taaaggatca    3360
```

```
ctaataaaga agggccaacc tgtagccgta ttaagcgcca tgaaaatgga aatgattata    3420
tcttctccat ccgatggaca agttaaagaa gtgtttgtct ctgatggtga aaatgtggac    3480
tcttctgatt tattagttct attagaagac caagttcctg ttgaaactaa ggcatga      3537
```

<210> SEQ ID NO 54
<211> LENGTH: 1178
<212> TYPE: PRT
<213> ORGANISM: Escherichia coli
<220> FEATURE:
<221> NAME/KEY: PEPTIDE
<222> LOCATION: (1)..(1178)
<223> OTHER INFORMATION: Amino acid sequence of Pyc protein of
      Saccharomyces cerevisiae

<400> SEQUENCE: 54

```
Met Ser Gln Arg Lys Phe Ala Gly Leu Arg Asp Asn Phe Asn Leu Leu
1               5                   10                  15

Gly Glu Lys Asn Lys Ile Leu Val Ala Asn Arg Gly Glu Ile Pro Ile
            20                  25                  30

Arg Ile Phe Arg Thr Ala His Glu Leu Ser Met Gln Thr Val Ala Ile
        35                  40                  45

Tyr Ser His Glu Asp Arg Leu Ser Thr His Lys Gln Lys Ala Asp Glu
    50                  55                  60

Ala Tyr Val Ile Gly Glu Val Gly Gln Tyr Thr Pro Val Gly Ala Tyr
65                  70                  75                  80

Leu Ala Ile Asp Glu Ile Ile Ser Ile Ala Gln Lys His Gln Val Asp
                85                  90                  95

Phe Ile His Pro Gly Tyr Gly Phe Leu Ser Glu Asn Ser Glu Phe Ala
            100                 105                 110

Asp Lys Val Val Lys Ala Gly Ile Thr Trp Ile Gly Pro Pro Ala Glu
        115                 120                 125

Val Ile Asp Ser Val Gly Asp Lys Val Ser Ala Arg Asn Leu Ala Ala
    130                 135                 140

Lys Ala Asn Val Pro Thr Val Pro Gly Thr Pro Gly Pro Ile Glu Thr
145                 150                 155                 160

Val Glu Glu Ala Leu Asp Phe Val Asn Glu Tyr Gly Tyr Pro Val Ile
                165                 170                 175

Ile Lys Ala Ala Phe Gly Gly Gly Gly Arg Gly Met Arg Val Val Arg
            180                 185                 190

Glu Gly Asp Asp Val Ala Asp Ala Phe Gln Arg Ala Thr Ser Glu Ala
        195                 200                 205

Arg Thr Ala Phe Gly Asn Gly Thr Cys Phe Val Glu Arg Phe Leu Asp
    210                 215                 220

Lys Pro Lys His Ile Glu Val Gln Leu Leu Ala Asp Asn His Gly Asn
225                 230                 235                 240

Val Val His Leu Phe Glu Arg Asp Cys Ser Val Gln Arg Arg His Gln
                245                 250                 255

Lys Val Val Glu Val Ala Pro Ala Lys Thr Leu Pro Arg Glu Val Arg
            260                 265                 270

Asp Ala Ile Leu Thr Asp Ala Val Lys Leu Ala Lys Glu Cys Gly Tyr
        275                 280                 285

Arg Asn Ala Gly Thr Ala Glu Phe Leu Val Asp Asn Gln Asn Arg His
    290                 295                 300

Tyr Phe Ile Glu Ile Asn Pro Arg Ile Gln Val Glu His Thr Ile Thr
305                 310                 315                 320
```

-continued

Glu Glu Ile Thr Gly Ile Asp Ile Val Ala Ala Gln Ile Gln Ile Ala
              325                 330                 335

Ala Gly Ala Ser Leu Pro Gln Leu Gly Leu Phe Gln Asp Lys Ile Thr
              340                 345                 350

Thr Arg Gly Phe Ala Ile Gln Cys Arg Ile Thr Thr Glu Asp Pro Ala
              355                 360                 365

Lys Asn Phe Gln Pro Asp Thr Gly Arg Ile Glu Val Tyr Arg Ser Ala
              370                 375                 380

Gly Gly Asn Gly Val Arg Leu Asp Gly Gly Asn Ala Tyr Ala Gly Thr
385                 390                 395                 400

Ile Ile Ser Pro His Tyr Asp Ser Met Leu Val Lys Cys Ser Cys Ser
              405                 410                 415

Gly Ser Thr Tyr Glu Ile Val Arg Arg Lys Met Ile Arg Ala Leu Ile
              420                 425                 430

Glu Phe Arg Ile Arg Gly Val Lys Thr Asn Ile Pro Phe Leu Leu Thr
              435                 440                 445

Leu Leu Thr Asn Pro Val Phe Ile Glu Gly Thr Tyr Trp Thr Thr Phe
              450                 455                 460

Ile Asp Asp Thr Pro Gln Leu Phe Gln Met Val Ser Ser Gln Asn Arg
465                 470                 475                 480

Ala Gln Lys Leu Leu His Tyr Leu Ala Asp Val Ala Val Asn Gly Ser
              485                 490                 495

Ser Ile Lys Gly Gln Ile Gly Leu Pro Lys Leu Lys Ser Asn Pro Ser
              500                 505                 510

Val Pro His Leu His Asp Ala Gln Gly Asn Val Ile Asn Val Thr Lys
              515                 520                 525

Ser Ala Pro Pro Ser Gly Trp Arg Gln Val Leu Leu Glu Lys Gly Pro
              530                 535                 540

Ala Glu Phe Ala Arg Gln Val Arg Gln Phe Asn Gly Thr Leu Leu Met
545                 550                 555                 560

Asp Thr Thr Trp Arg Asp Ala His Gln Ser Leu Leu Ala Thr Arg Val
              565                 570                 575

Arg Thr His Asp Leu Ala Thr Ile Ala Pro Thr Thr Ala His Ala Leu
              580                 585                 590

Ala Gly Arg Phe Ala Leu Glu Cys Trp Gly Gly Ala Thr Phe Asp Val
              595                 600                 605

Ala Met Arg Phe Leu His Glu Asp Pro Trp Glu Arg Leu Arg Lys Leu
610                 615                 620

Arg Ser Leu Val Pro Asn Ile Pro Phe Gln Met Leu Leu Arg Gly Ala
625                 630                 635                 640

Asn Gly Val Ala Tyr Ser Ser Leu Pro Asp Asn Ala Ile Asp His Phe
              645                 650                 655

Val Lys Gln Ala Lys Asp Asn Gly Val Asp Ile Phe Arg Val Phe Asp
              660                 665                 670

Ala Leu Asn Asp Leu Glu Gln Leu Lys Val Gly Val Asp Ala Val Lys
              675                 680                 685

Lys Ala Gly Gly Val Val Glu Ala Thr Val Cys Phe Ser Gly Asp Met
              690                 695                 700

Leu Gln Pro Gly Lys Lys Tyr Asn Leu Asp Tyr Tyr Leu Glu Ile Ala
705                 710                 715                 720

Glu Lys Ile Val Gln Met Gly Thr His Ile Leu Gly Ile Lys Asp Met
              725                 730                 735

Ala Gly Thr Met Lys Pro Ala Ala Lys Leu Leu Ile Gly Ser Leu
                740                 745                 750

Arg Ala Lys Tyr Pro Asp Leu Pro Ile His Val His Thr His Asp Ser
            755                 760                 765

Ala Gly Thr Ala Val Ala Ser Met Thr Ala Cys Ala Leu Ala Gly Ala
        770                 775                 780

Asp Val Val Asp Val Ala Ile Asn Ser Met Ser Gly Leu Thr Ser Gln
785                 790                 795                 800

Pro Ser Ile Asn Ala Leu Leu Ala Ser Leu Glu Gly Asn Ile Asp Thr
                805                 810                 815

Gly Ile Asn Val Glu His Val Arg Glu Leu Asp Ala Tyr Trp Ala Glu
            820                 825                 830

Met Arg Leu Leu Tyr Ser Cys Phe Glu Ala Asp Leu Lys Gly Pro Asp
        835                 840                 845

Pro Glu Val Tyr Gln His Glu Ile Pro Gly Gly Gln Leu Thr Asn Leu
    850                 855                 860

Leu Phe Gln Ala Gln Gln Leu Gly Leu Gly Glu Gln Trp Ala Glu Thr
865                 870                 875                 880

Lys Arg Ala Tyr Arg Glu Ala Asn Tyr Leu Leu Gly Asp Ile Val Lys
                885                 890                 895

Val Thr Pro Thr Ser Lys Val Val Gly Asp Leu Ala Gln Phe Met Val
            900                 905                 910

Ser Asn Lys Leu Thr Ser Asp Asp Val Arg Arg Leu Ala Asn Ser Leu
        915                 920                 925

Asp Phe Pro Asp Ser Val Met Asp Phe Phe Glu Gly Leu Ile Gly Gln
    930                 935                 940

Pro Tyr Gly Gly Phe Pro Glu Pro Phe Arg Ser Asp Val Leu Arg Asn
945                 950                 955                 960

Lys Arg Arg Lys Leu Thr Cys Arg Pro Gly Leu Glu Leu Glu Pro Phe
                965                 970                 975

Asp Leu Glu Lys Ile Arg Glu Asp Leu Gln Asn Arg Phe Gly Asp Val
            980                 985                 990

Asp Glu Cys Asp Val Ala Ser Tyr Asn Met Tyr Pro Arg Val Tyr Glu
        995                 1000                1005

Asp Phe Gln Lys Met Arg Glu Thr Tyr Gly Asp Leu Ser Val Leu
    1010                1015                1020

Pro Thr Arg Ser Phe Leu Ser Pro Leu Glu Thr Asp Glu Glu Ile
    1025                1030                1035

Glu Val Val Ile Glu Gln Gly Lys Thr Leu Ile Ile Lys Leu Gln
    1040                1045                1050

Ala Val Gly Asp Leu Asn Lys Lys Thr Gly Glu Arg Glu Val Tyr
    1055                1060                1065

Phe Asp Leu Asn Gly Glu Met Arg Lys Ile Arg Val Ala Asp Arg
    1070                1075                1080

Ser Gln Lys Val Glu Thr Val Thr Lys Ser Lys Ala Asp Met His
    1085                1090                1095

Asp Pro Leu His Ile Gly Ala Pro Met Ala Gly Val Ile Val Glu
    1100                1105                1110

Val Lys Val His Lys Gly Ser Leu Ile Lys Lys Gly Gln Pro Val
    1115                1120                1125

Ala Val Leu Ser Ala Met Lys Met Glu Met Ile Ile Ser Ser Pro
    1130                1135                1140

Ser Asp Gly Gln Val Lys Glu Val Phe Val Ser Asp Gly Glu Asn

```
       1145                1150                1155

Val Asp Ser Ser Asp Leu Leu Val Leu Leu Glu Asp Gln Val Pro
        1160                1165                1170

Val Glu Thr Lys Ala
        1175

<210> SEQ ID NO 55
<211> LENGTH: 6273
<212> TYPE: DNA
<213> ORGANISM: Escherichia coli
<220> FEATURE:
<221> NAME/KEY: misc_feature
<222> LOCATION: (1)..(6273)
<223> OTHER INFORMATION: DNA sequence of the plasmid pCAT350

<400> SEQUENCE: 55
tgaatgacct ttaatagatt atattactaa ttaattgggg accctagagg tccccttttt      60
tattttaaaa attttttcac aaaacggttt acaagcatac gttggccgat tcattaatgc     120
agctggcacg acaggtttcc cgactggaaa gcgggcagtg agcgcaacgc aattaatgtg     180
agttagctca ctcattaggc accccaggct ttacacttta tgcttccggc tcgtatgttg     240
tgtggaattg tgagcggata caatttcac acaggaaaca gctatgacca tgattacgcc      300
aagcttgcat gcctgcaggt cgactctaga ggatccccgg gtaccgagct cgaattcact     360
ggccgtcgtt ttacaacgtc gtgactggga aaaccctggc gttacccaac ttaatcgcct     420
tgcagcacat cccccttccg ccagctggcg taatagcgaa gaggcccgca ccgatcgccc     480
ttcccaacag ttgcgcagcc tgaatggcga atggcgcctg atgcggtatt ttctccttac     540
gcatctgtgc ggtatttcac accgcatatg gtgcactctc agtacaatct gctctgatgc     600
cgcatagtta agccagcccc gacacccgcc aacacccgct gacgaattcg ttgacagtaa     660
gacgggtaag cctgttgatg ataccgctgc cttactgggt gcattagcca gtctgaatga     720
cctgtcacgg gataatccga agtggtcaga ctggaaaatc agagggcagg aactgctgaa     780
cagcaaaaag tcagatagca ccacatagca gacccgccat aaaacgccct gagaagcccg     840
tgacgggctt tcttgtatt atgggtagtt tccttgcatg aatccataaa aggcgcctgt      900
agtgccattt accccccattc actgccagag ccgtgagcgc agcgaactga atgtcacgaa     960
aaagacagcg actcaggtgc ctgatggtcg gagacaaaag gaatattcag cgatttgccc    1020
gagcttgcga gggtgctact taagccttta gggttttaag gtctgttttg tagaggagca    1080
aacagcgttt gcgacatcct tttgtaatac tgcggaactg actaaagtag tgagttatac    1140
acagggctgg gatctattct ttttatcttt ttttattctt tctttattct ataaattata    1200
accacttgaa tataaacaaa aaaacacac aaaggtctag cggaatttac agagggtcta     1260
gcagaattta caagttttcc agcaaaggtc tagcagaatt tacagatacc cacaactcaa    1320
aggaaaagga ctagtaatta tcattgacta gcccatctca attggtatag tgattaaaat    1380
cacctagacc aattgagatg tatgtctgaa ttagttgttt tcaaagcaaa tgaactagcg    1440
attagtcgct atgacttaac ggagcatgaa accaagctaa ttttatgctg tgtggcacta    1500
ctcaacccca cgattgaaaa ccctacaagg aaagaacgga cggtatcgtt cacttataac    1560
caatacgctc agatgatgaa catcagtagg gaaaatgctt atggtgtatt agctaaagca    1620
accagagagc tgatgacgag aactgtggaa atcaggaatc ctttggttaa aggctttgag    1680
attttccagt ggacaaacta tgccaagttc tcaagcgaaa attagaatt agttttagt     1740 gaagagatat tgccttatct tttccagtta aaaaaattca taaatataa tctggaacat    1800
```

-continued

```
gttaagtctt tgaaaacaa atactctatg aggatttatg agtggttatt aaaagaacta    1860
acacaaaaga aaactcacaa ggcaaatata gagattagcc ttgatgaatt taagttcatg    1920
ttaatgcttg aaaataacta ccatgagttt aaaaggctta accaatgggt tttgaaacca    1980
ataagtaaag atttaaacac ttacagcaat atgaaattgg tggttgataa gcgaggccgc    2040
ccgactgata cgttgatttt ccaagttgaa ctagatagac aaatggatct cgtaaccgaa    2100
cttgagaaca accagataaa aatgaatggt gacaaaatac caacaaccat tacatcagat    2160
tcctacctac gtaacggact aagaaaaaca ctacacgatg ctttaactgc aaaaattcag    2220
ctcaccagtt tgaggcaaa attttttgagt gacatgcaaa gtaagcatga tctcaatggt    2280
tcgttctcat ggctcacgca aaaacaacga accacactag agaacatact ggctaaatac    2340
ggaaggatct gaggttctta tggcaaaacac ggacgccgca aacggcgtcc gaatttcttg    2400
gtcgaccgtt aaatctatca ccgcaaggga taaatatcta acaccgtgcg tgttgactat    2460
tttacctctg gcggtgataa tggttgcatg tactaatcta gataaggaat atagccatgg    2520
aagtgaaaat cttcaacacc caggatgttc aggattttct gcgtgttgca gcggtctgg    2580
aacaagaggg tggtaatccg cgtgttaaac aaattattca tcgtgttctg agcgacctgt    2640
ataaagcaat tgaagatctg aatatcacca gcgacgaata ttgggcaggc gttgcatatc    2700
tgaatcagct gggtgcaaat caagaagcag gtctgctgag tccgggtctg ggttttgatc    2760
attatctgga tatgcgtatg gatgcagaag atgcagcact gggtattgaa aatgcaacac    2820
cgcgtaccat tgaaggtccg ctgtatgttg cgggtgcacc ggaaagcgtt ggttatgcac    2880
gcatggatga tggtagcgat ccgaatggtc ataccctgat tctgcatggc accattttg    2940
atgcagatgg taaaccgctg ccgaatgcaa aagttgaaat ttggcatgca acaccaaag    3000
gcttttatag ccattttgat ccgaccggtg aacagcaggc cttaatatg cgtcgtagca    3060
ttattaccga tgagaatggt cagtatcgtg ttcgtaccat tctgcctgcc ggttatggtt    3120
gtcctccgga aggtccgacc cagcaactgc tgaaccaact gggtcgtcat ggtaatcgtc    3180
cggcacatat tcattatttt gttagcgcag atggtcaccg taaactgacc acccagatta    3240
atgttgccgg tgatccgtat acctatgatg attttgcata tgccacccgt gaaggtctgg    3300
ttgttgatgc agttgaacat accgatccgg aagcaattaa agccaatgat gtggaaggtc    3360
cttttgccga aatggtgttt gatctgaaac tgacccgtct ggttgatggt gttgataatc    3420
aggttgtgga tcgtccgcgt ctggcagttt aatacaccaa aatggttcaa aattatcagg    3480
cgagtgatca tgatcactgg cctgttttta tttcagggaa gggtggagac aattacgtgg    3540
ataatcagat catccaagaa accgtggata aaattctgag cgttctgccg aatcaggcag    3600
gtcagctggc acgtctggtg cgtctgatgc aatttgcatg cgatccgacc attaccgtta    3660
ttggcaaata taaccatggt aaaagccgtc tgctgaatga actgattggc accgatatct    3720
ttagcgttgc agataaacgt gaaaccattc agctggccga acataaacag gatcaggttc    3780
gttggctgga tgcacctggt ctggatgccg atgttgcagc agttgatgat cgtcatgcat    3840
ttgaagcagt ttggacccag gcagatattc gtctgtttgt tcatagcgtt cgtgaaggtg    3900
aactggatgc aaccgaacac catctgctgc aacagctgat tgaagatgcc gatcatagcc    3960
gtcgtcagac cattctggtt ctgacccaga ttgatcagat tccggatcag accatcctga    4020
cacagattaa aaccagcatt gcacagcagg ttccgaaact ggatatttgg cagttagcg    4080
caacccgtca tcgtcagggc attgaaaacg gtaaaaccct gctgatcgaa aaaagcggta    4140
```

```
ttggtgcact gcgccatacc ctggaacagg cactggcaca ggtgccgagc gcacgtacct    4200
atgaaaaaaa tcgtctgctg tcagatctgc accatcagct gaaacaactg ctgctggatc    4260
agaaacatgt tctgcaacaa ctgcaacaga cacagcaaca gcagctgcat gattttgata    4320
ccggtctgat taacattctg gacaaaattc gtgttgatct ggaaccgatt gtgaatattg    4380
atggtcagga tcaagcactg aatccggata gctttgcaac catgtttaaa aacaccgcag    4440
caaaacagca gcgtgccaaa gttcagattg catatagccg tgcatgcatt gaaatcaaca    4500
gccatctgat tcgccatggt gttgttggtc tgcctgcgga acagcagacc accattaaaa    4560
gcattgatac cgtgattgtt gccgtgtttg gtatcagcgt taaatttcgt gatcagctgc    4620
gtgccctgtt ttataccgat accgaacgtc agcgtctgca acgtgaattt cgtttctatt    4680
ttgaaaaaag tgccggtcgc atgattctgg cagcaaaaat tgaacagacc atgcgtcagc    4740
agggctgtat tcagaatgcc atgatggcac tgcaacaaat ggaaagcgca gcataagtct    4800
gacaggtgcc ggatttcata tccggcactt actttcctta actcttcgcc ttaacgcaaa    4860
atctcacact gatgatcctg aatttcctcg gctgaagcac ggttaagcgt cagtagattt    4920
cgttgtgtcg ccagcaatac aaatgatgga cataagcctg ttcggttcgt aagctgtaat    4980
gcaagtagcg tatgcgctca cgcaactggt ccagaacctt gaccgaacgc agcggtggta    5040
acggcgcagt ggcggttttc atggcttgtt atgactgttt ttttggggta cagtctatgc    5100
ctcgggcatc caagcagcaa gcgcgttacg ccgtgggtcg atgtttgatg ttatggagca    5160
gcaacgatgt tacgcagcag ggcagtcgcc ctaaaacaaa gttaaacatc atgagggaag    5220
cggtgatcgc cgaagtatcg actcaactat cagaggtagt tggcgtcatc gagcgccatc    5280
tcgaaccgac gttgctggcc gtacatttgt acggctccgc agtggatggc ggcctgaagc    5340
cacacagtga tattgatttg ctggttacgg tgaccgtaag gcttgatgaa acaacgcggc    5400
gagctttgat caacgacctt ttggaaactt cggcttcccc tggagagagc gagattctcc    5460
gcgctgtaga agtcaccatt gttgtgcacg acgacatcat tccgtggcgt tatccagcta    5520
agcgcgaact gcaatttgga gaatggcagc gcaatgacat tcttgcaggt atcttcgagc    5580
cagccacgat cgacattgat ctggctatct tgctgacaaa agcaagagaa catagcgttg    5640
ccttggtagg tccagcggcg gaggaactct ttgatccggt tcctgaacag gatctatttg    5700
aggcgctaaa tgaaacctta acgctatgga actcgccgcc cgactgggct ggcgatgagc    5760
gaaatgtagt gcttacgttg tcccgcattt ggtacagcgc agtaaccggc aaaatcgcgc    5820
cgaaggatgt cgctgccgac tgggcaatgg agcgcctgcc ggcccagtat cagcccgtca    5880
tacttgaagc tagacaggct tatcttggac aagaagaaga tcgcttggcc tcgcgcgcag    5940
atcagttgga agaatttgtc cactacgtga aaggcgagat caccaaggta gtcggcaaat    6000
aatgtctaac aattcgttca agccgacgcc gcttcgcggc gcggcttaac tcaagcgtta    6060
gatgcactaa gcacataatt gctcacagcc aaactatcag gtcaagtctg cttttattat    6120
ttttaagcgt gcataataag ccctacacaa attgggagat atatcatgaa aggctggctt    6180
tttcttgtta tcgcaatagt tggcgaagta atcgcaacat ccgcattaaa atctagcgag    6240
ggctttacta agctgatccg gtggatgacc ttt                                  6273
```

<210> SEQ ID NO 56
<211> LENGTH: 3943
<212> TYPE: DNA
<213> ORGANISM: Escherichia coli
<220> FEATURE:
<221> NAME/KEY: misc_feature
<222> LOCATION: (1)..(3943)
<223> OTHER INFORMATION: DNA sequence of the plasmid pCP165

<400> SEQUENCE: 56

```
tgaatgacct ttaatagatt atattactaa ttaattgggg accctagagg tccccttttt      60
tattttaaaa attttttcac aaaacggttt acaagcatac gttggccgat tcattaatgc     120
agctggcacg acaggtttcc cgactggaaa gcgggcagtg agcgcaacgc aattaatgtg     180
agttagctca ctcattaggc accccaggct ttacactttta tgcttccggc tcgtatgttg     240
tgtggaattg tgagcggata acaatttcac acaggaaaca gctatgacca tgattacgcc     300
aagcttgcat gcctgcaggt cgactctaga ggatccccgg gtaccgagct cgaattcact     360
ggccgtcgtt ttacaacgtc gtgactggga aaaccctggc gttacccaac ttaatcgcct     420
tgcagcacat ccccctttcg ccagctggcg taatagcgaa gaggcccgca ccgatcgccc     480
ttcccaacag ttgcgcagcc tgaatggcga atggcgcctg atgcggtatt ttctccttac     540
gcatctgtgc ggtatttcac accgcatatg gtgcactctc agtacaatct gctctgatgc     600
cgcatagtta agccagcccc gacacccgcc aacacccgct gacgaattcg ttgacagtaa     660
gacgggtaag cctgttgatg ataccgctgc cttactgggt gcattagcca gtctgaatga     720
cctgtcacgg gataatccga gtggtcaga ctggaaaatc agagggcagg aactgctgaa     780
cagcaaaaag tcagatagca ccacatagca gacccgccat aaaacgccct gagaagcccg     840
tgacgggctt ttcttgtatt atgggtagtt ccttgcatg aatccataaa aggcgcctgt     900
agtgccattt accccattc actgccgag ccgtgagcgc agcgaactga atgtcacgaa     960
aaagacagcg actcaggtgc ctgatggtcg gagacaaaag gaatattcag cgatttgccc    1020
gagcttgcga gggtgctact taagccttta gggttttaag gtctgttttg tagaggagca    1080
aacagcgttt gcgacatcct tttgtaatac tgcggaactg actaaagtag tgagttatac    1140
acagggctgg gatctattct ttttatcttt ttttattctt tctttattct ataaattata    1200
accacttgaa tataaacaaa aaaacacac aaaggtctag cggaatttac agagggtcta    1260
gcagaattta caagttttcc agcaaaggtc tagcagaatt tacagatacc cacaactcaa    1320
aggaaaagga ctagtaatta tcattgacta gcccatctca attggtatag tgattaaaat    1380
cacctagacc aattgagatg tatgtctgaa ttagttgttt tcaaagcaaa tgaactagcg    1440
attagtcgct atgacttaac ggagcatgaa accaagctaa ttttatgctg tgtggcacta    1500
ctcaaccca cgattgaaaa ccctacaagg aaagaacgga cggtatcgtt cacttataac    1560
caatacgctc agatgatgaa catcagtagg gaaaatgctt atggtgtatt agctaaagca    1620
accagagagc tgatgacgag aactgtggaa atcaggaatc ctttggttaa aggctttgag    1680
attttccagt ggacaaacta tgccaagttc tcaagcgaaa aattagaatt agttttagt    1740
gaagagatat tgccttatct tttccagtta aaaaaattca taaatataa tctggaacat    1800
gttaagtctt ttgaaaacaa atactctatg aggatttatg agtggttatt aaagaaacta    1860
acacaaaaga aaactcacaa ggcaaatata gagattagcc ttgatgaatt taagttcatg    1920
ttaatgcttg aaaataacta ccatgagttt aaaaggctta accatggggt tttgaaacca    1980
ataagtaaag atttaaacac ttcagcaat atgaaattgg tggttgataa gcgaggccgc    2040
ccgactgata cgttgatttt ccaagttgaa ctagatagac aaatggatct cgtaaccgaa    2100
cttgagaaca accagataaa aatgaatggt gacaaaatac caacaaccat tacatcagat    2160
tcctacctac gtaacggact aagaaaaaca ctacacgatg ctttaactgc aaaaattcag    2220
```

| | |
|---|---|
| ctcaccagtt ttgaggcaaa attttttgagt gacatgcaaa gtaagcatga tctcaatggt | 2280 |
| tcgttctcat ggctcacgca aaaacaacga accacactag agaacatact ggctaaatac | 2340 |
| ggaaggatct gaggttctta tggcaaacac ggacgccgca aacggcgtcc gaatttcttg | 2400 |
| gtcgaccgtt aaatctatca ccgcaaggga taaatatcta acaccgtgcg tgttgactat | 2460 |
| tttacctctg gcggtgataa tggttgcatg tactaatcta gataaggaat atagccttag | 2520 |
| atttgactga aatcgtacag taaaaagcgt acaataaagg ctccacgaaa gtggggcctt | 2580 |
| ttttagcgcg agagcctttt ttgtcagcta tctatatgga cataagcctg ttcggttcgt | 2640 |
| aagctgtaat gcaagtagcg tatgcgctca cgcaactggt ccagaacctt gaccgaacgc | 2700 |
| agcggtggta acggcgcagt ggcggttttc atggcttgtt atgactgttt ttttgggggta | 2760 |
| cagtctatgc ctcgggcatc caagcagcaa gcgcgttacg ccgtgggtcg atgtttgatg | 2820 |
| ttatggagca gcaacgatgt tacgcagcag ggcagtcgcc ctaaaacaaa gttaaacatc | 2880 |
| atgagggaag cggtgatcgc cgaagtatcg actcaactat cagaggtagt tggcgtcatc | 2940 |
| gagcgccatc tcgaaccgac gttgctggcc gtacatttgt acggctccgc agtggatggc | 3000 |
| ggcctgaagc cacacagtga tattgatttg ctggttacgg tgaccgtaag gcttgatgaa | 3060 |
| acaacgcggc gagctttgat caacgacctt ttggaaactt cggcttcccc tggagagagc | 3120 |
| gagattctcc gcgctgtaga agtcaccatt gttgtgcacg acgacatcat tccgtggcgt | 3180 |
| tatccagcta agcgcgaact gcaatttgga gaatggcagc gcaatgacat tcttgcaggt | 3240 |
| atcttcgagc cagccacgat cgacattgat ctggctatct tgctgacaaa agcaagagaa | 3300 |
| catagcgttg ccttggtagg tccagcggcg gaggaactct tgatccggt tcctgaacag | 3360 |
| gatctatttg aggcgctaaa tgaaacctta acgctatgga actcgccgcc cgactgggct | 3420 |
| ggcgatgagc gaaatgtagt gcttacgttg tcccgcattt ggtacagcgc agtaaccggc | 3480 |
| aaaatcgcgc cgaaggatgt cgctgccgac tgggcaatgg agcgcctgcc ggcccagtat | 3540 |
| cagcccgtca tacttgaagc tagacaggct tatcttggac aagaagaaga tcgcttggcc | 3600 |
| tcgcgcgcag atcagttgga agaatttgtc cactacgtga aaggcgagat caccaaggta | 3660 |
| gtcggcaaat aatgtctaac aattcgttca agccgacgcc gcttcgcggc gcggcttaac | 3720 |
| tcaagcgtta gatgcactaa gcacataatt gctcacagcc aaactatcag gtcaagtctg | 3780 |
| cttttattat tttttaagcgt gcataataag ccctacacaa attgggagat atatcatgaa | 3840 |
| aggctggctt tttcttgtta tcgcaatagt tggcgaagta atcgcaacat ccgcattaaa | 3900 |
| atctagcgag ggctttacta agctgatccg gtggatgacc ttt | 3943 |

<210> SEQ ID NO 57
<211> LENGTH: 10863
<212> TYPE: DNA
<213> ORGANISM: Escherichia coli
<220> FEATURE:
<221> NAME/KEY: misc_feature
<222> LOCATION: (1)..(10863)
<223> OTHER INFORMATION: DNA sequence of the plasmid pCP140

<400> SEQUENCE: 57

| | |
|---|---|
| tggacataag cctgttcggt tcgtaagctg taatgcaagt agcgtatgcg ctcacgcaac | 60 |
| tggtccagaa ccttgaccga acgcagcggt ggtaacggcg cagtggcggt tttcatggct | 120 |
| tgttatgact gtttttttgg ggtacagtct atgcctcggg catccaagca gcaagcgcgt | 180 |
| tacgccgtgg gtcgatgttt gatgttatgg agcagcaacg atgttacgca gcagggcagt | 240 |
| cgccctaaaa caaagttaaa catcatgagg gaagcggtga tcgccgaagt atcgactcaa | 300 |

```
ctatcagagg tagttggcgt catcgagcgc catctcgaac cgacgttgct ggccgtacat      360
ttgtacggct ccgcagtgga tggcggcctg aagccacaca gtgatattga tttgctggtt      420
acggtgaccg taaggcttga tgaaacaacg cggcgagctt tgatcaacga ccttttggaa      480
acttcggctt cccctggaga gagcgagatt ctccgcgctg tagaagtcac cattgttgtg      540
cacgacgaca tcattccgtg gcgttatcca gctaagcgcg aactgcaatt tggagaatgg      600
cagcgcaatg acattcttgc aggtatcttc gagccagcca cgatcgacat tgatctggct      660
atcttgctga caaaagcaag agaacatagc gttgccttgg taggtccagc ggcggaggaa      720
ctctttgatc cggttcctga acaggatcta tttgaggcgc taaatgaaac cttaacgcta      780
tggaactcgc cgcccgactg ggctggcgat gagcgaaatg tagtgcttac gttgtcccgc      840
atttggtaca gcgcagtaac cggcaaaatc gcgccgaagg atgtcgctgc cgactgggca      900
atggagcgcc tgccggccca gtatcagccc gtcatacttg aagctagaca ggcttatctt      960
ggacaagaag aagatcgctt ggcctcgcgc gcagatcagt tggaagaatt tgtccactac     1020
gtgaaaggcg agatcaccaa ggtagtcggc aaataatgtc taacaattcg ttcaagccga     1080
cgccgcttcg cggcgcggct taactcaagc gttagatgca ctaagcacat aattgctcac     1140
agccaaacta tcaggtcaag tctgctttta ttatttttaa gcgtgcataa taagccctac     1200
acaaattggg agatatatca tgaaaggctg gcttttcctt gttatcgcaa tagttggcga     1260
agtaatcgca acatccgcat taaaatctag cgagggcttt actaagctga tccggtggat     1320
gaccttttga atgacctttta atagattata ttactaatta attggggacc ctagaggtcc     1380
ccttttttat tttaaaaatt ttttcacaaa acggtttaca agcatacgtt ggccgattca     1440
ttaatgcagc tggcacgaca ggtttcccga ctggaaagcg ggcagtgagc gcaacgcaat     1500
taatgtgagt tagctcactc attaggcacc ccaggcttta cactttatgc ttccggctcg     1560
tatgttgtgt ggaattgtga gcggataaca atttcacaca ggaaacagct atgaccatga     1620
ttacgccatc gaccgttaaa tctatcaccg caagggataa atatctaaca ccgtgcgtgt     1680
tgactatttt acctctggcg gtgataatgg ttgcatgtac taatctagat aaggaatata     1740
gccatggaag tgaaaatctt caacacccag gatgttcagg attttctgcg tgttgcaagc     1800
ggtctggaac aagagggtgg taatccgcgt gttaaacaaa ttattcatcg tgttctgagc     1860
gacctgtata aagcaattga agatctgaat atcaccagcg acgaatattg gcaggcgtt      1920 gcatatctga atcagctggg tgcaaatcaa gaagcaggtc tgctgagtcc gggtctgggt     1980
tttgatcatt atctggatat gcgtatggat gcagaagatg cagcactggg tattgaaaat     2040
gcaacaccgc gtaccattga aggtccgctg tatgttgcgg gtgcaccgga aagcgttggt     2100
tatgcacgca tggatgatgg tagcgatccg aatggtcata ccctgattct gcatggcacc     2160 attttgatg cagatggtaa accgctgccg aatgcaaaag ttgaaatttg gcatgcaaac     2220
accaaaggct tttatagcca ttttgatccg accggtgaac agcaggcctt taatatgcgt     2280
cgtagcatta ttaccgatga gaatggtcag tatcgtgttc gtaccattct gcctgccggt     2340
tatggttgtc ctccggaagg tccgacccag caactgctga accaactggg tcgtcatggt     2400
aatcgtccgg cacatattca ttattttgtt agcgcagatg tcaccgtaa actgaccacc     2460 cagattaatg ttgccggtga tccgtatacc tatgatgatt ttgcatatgc cacccgtgaa     2520
ggtctggttg ttgatgcagt tgaacatacc gatccggaag caattaaagc caatgatgtg     2580
gaaggtcctt ttgccgaaat ggtgtttgat ctgaaactga cccgtctggt tgatggtgtt     2640
```

```
gataatcagg ttgtggatcg tccgcgtctg gcagtttaat acaccaaaat ggttcaaaat    2700
tatcaggcga gtgatcatga tcactggcct gtttttattt cagggaaggg tggagacaat    2760
tacgtggata atcagatcat ccaagaaacc gtggataaaa ttctgagcgt tctgccgaat    2820
caggcaggtc agctggcacg tctggtgcgt ctgatgcaat ttgcatgcga tccgaccatt    2880
accgttattg gcaaatataa ccatggtaaa agccgtctgc tgaatgaact gattggcacc    2940
gatatcttta gcgttgcaga taaacgtgaa accattcagc tggccgaaca taaacaggat    3000
caggttcgtt ggctggatgc acctggtctg gatgccgatg ttgcagcagt tgatgatcgt    3060
catgcatttg aagcagtttg gacccaggca gatattcgtc tgtttgttca tagcgttcgt    3120
gaaggtgaac tggatgcaac cgaacaccat ctgctgcaac agctgattga agatgccgat    3180
catagccgtc gtcagaccat tctggttctg acccagattg atcagattcc ggatcagacc    3240
atcctgacac agattaaaac cagcattgca cagcaggttc gaaactgga tatttgggca    3300
gttagcgcaa cccgtcatcg tcagggcatt gaaaacggta aaaccctgct gatcgaaaaa    3360
agcggtattg gtgcactgcg ccataccctg gaacaggcac tggcacaggt gccgagcgca    3420
cgtacctatg aaaaaaatcg tctgctgtca gatctgcacc atcagctgaa caactgctg    3480
ctggatcaga aacatgttct gcaacaactg caacagacac agcaacagca gctgcatgat    3540
tttgataccg gtctgattaa cattctggac aaaattcgtg ttgatctgga accgattgtg    3600
aatattgatg gtcaggatca agcactgaat ccggatagct ttgcaaccat gtttaaaaac    3660
accgcagcaa acagcagcg tgccaaagtt cagattgcat atagccgtgc atgcattgaa    3720
atcaacagcc atctgattcg ccatggtgtt gttggtctgc ctgcggaaca gcagaccacc    3780
attaaaagca ttgataccgt gattgttgcc gtgtttggta tcagcgttaa atttcgtgat    3840
cagctgcgtg ccctgtttta taccgatacc gaacgtcagc gtctgcaacg tgaatttcgt    3900
ttctattttg aaaaaagtgc cggtcgcatg attctggcag caaaaattga acagaccatg    3960
cgtcagcagg gctgtattca gaatgccatg atggcactgc aacaaatgga aagcgcagca    4020
taaaaacacg gacgccgcaa acggcgtccg aattctctgg tcgactctag aggatccccg    4080
ggtaccgagc tcgaattcac tggccgtcgt tttacaacgt cgtgactggg aaaaccctgg    4140
cgttacccaa cttaatcgcc ttgcagcaca tcccccttc gccagctggc gtaatagcga    4200
agaggcccgc accgatcgcc cttcccaaca gttgcgcagc ctgaatggcg aatggcgcct    4260
gatgcggtat tttctcctta cgcatctgtg cggtatttca caccgcatat ggtgcactct    4320
cagtacaatc tgctctgatg ccgcatagtt aagccagccc cgacacccgc caacacccgc    4380
tgacgaattc gttgacagta agacgggtaa gcctgttgat gataccgctg ccttactggg    4440
tgcattagcc agtctgaatg acctgtcacg ggataatccg aagtggtcag actgaaaat    4500
cagagggcag gaactgctga acagcaaaaa gtcagatagc accacatagc agacccgcca    4560
taaaacgccc tgagaagccc gtgacgggct tttcttgtat tatgggtagt ttccttgcat    4620
gaatccataa aaggcgcctg tagtgccatt taccccatt cactgccaga gccgtgagcg    4680
cagcgaactg aatgtcacga aaagacagc gactcaggtg cctgatggtc ggagacaaaa    4740
ggaatattca gcgatttgcc cgagcttgcg agggtgctac ttaagccttt agggttttaa    4800
ggtctgtttt gtagaggagc aaacagcgtt tgcgacatcc ttttgtaata ctgcggaact    4860
gactaaagta gtgagttata cacagggctg gatctattc tttttatctt ttttattct    4920
ttctttattc tataaattat aaccacttga atataaacaa aaaaaacaca caagggtcta    4980
gcggaattta cagagggtct agcagaattt acaagttttc cagcaaaggt ctagcagaat    5040
```

```
ttacagatac ccacaactca aaggaaaagg actagtaatt atcattgact agcccatctc    5100
aattggtata gtgattaaaa tcacctagac caattgagat gtatgtctga attagttgtt    5160
ttcaaagcaa atgaactagc gattagtcgc tatgacttaa cggagcatga aaccaagcta    5220
attttatgct gtgtggcact actcaacccc acgattgaaa accctacaag gaagaacgg     5280 acggtatcgt tcacttataa ccaatacgct cagatgatga acatcagtag ggaaaatgct    5340
tatggtgtat tagctaaagc aaccagagag ctgatgacga gaactgtgga aatcaggaat    5400
cctttggtta aaggctttga gattttccag tggacaaact atgccaagtt ctcaagcgaa    5460
aaattagaat tagttttttag tgaagagata ttgccttatc ttttccagtt aaaaaaattc    5520
ataaaatata atctggaaca tgttaagtct tttgaaaaca aatactctat gaggatttat    5580
gagtggttat taaaagaact aacacaaaag aaaactcaca aggcaaatat agagattagc    5640
cttgatgaat ttaagttcat gttaatgctt gaaaataact accatgagtt taaaaggctt    5700
aaccaatggg ttttgaaacc aataagtaaa gatttaaaca cttacagcaa tatgaaattg    5760
gtggttgata agcgaggccg cccgactgat acgttgattt tccaagttga actagataga    5820
caaatggatc tcgtaaccga acttgagaac aaccagataa aaatgaatgg tgacaaaata    5880
ccaacaacca ttacatcaga ttcctaccta cgtaacggac taagaaaaac actacacgat    5940
gctttaactg caaaaattca gctcaccagt tttgaggcaa aattttttgag tgacatgcaa    6000 agtaagcatg atctcaatgg ttcgttctca tggctcacgc aaaaacaacg aaccacacta    6060
gagaacatac tggctaaata cggaaggatc tgaggttctt atggcccggc gtagcccaaa    6120
acgcgctgtc gtcaagtcgt taagggcgtg cccttcatca tccgatctgg agtcaaaatg    6180
tcctcacgta aagagcttgc caatgctatt cgtgcgctga gcatggacgc agtacagaaa    6240
gccaaatccg gtcacccggg tgcccctatg ggtatggctg acattgccga agtcctgtgg    6300
cgtgatttcc tgaaacacaa cccgcagaat ccgtcctggg ctgaccgtga ccgcttcgtg    6360
ctgtccaacg gccacggctc catgctgatc tacagcctgc tgcacctcac cggttacgat    6420
ctgccgatgg aagaactgaa aaacttccgt cagctgcact ctaaaactcc gggccacccg    6480
gaagtaggtt ataccgctgg tgtggaaacc accaccggtc cgctgggtca gggtattgcc    6540
aacgcagtcg gtatggcgat tgcagaaaaa acgctggcgg cgcagtttaa ccgtccaggt    6600
cacgacattg tcgaccacta cacctacgcc ttcatgggcg acggctgcat gatggaaggc    6660
atctcccacg aagtttgctc tctggcgggt acgctgaagc tgggtaaact gattgcgttc    6720
tacgatgaca acggtatctc aatcgatggt cacgttgaag gctggttcac tgacgacacc    6780
gcaatgcgtt tcgaagctta cggctggcac gttattcgcg acatcgacgg tcatgacgcg    6840
gcatccatca aacgcgcagt agaagaagcg cgcgcagtga ctgacaaacc gtccctgctg    6900
atgtgcaaaa ccatcatcgg tttcggttcc ccgaacaaag ccggtaccca cgactcccac    6960
ggtgcgccgc tgggcgacgc tgaaattgcc ctgaccgcg aacagctggg ctggaaatac    7020
gcgccgttcg aaatcccgtc tgaaatctat gctcagtggg atgcgaaaga agcaggccag    7080
gcgaaagaat ctgcatggaa tgagaagttt gcggcttacg cgaaagctta tccgcaggaa    7140
gcggctgaat ttaccccgccg tatgaaaggc gaaatgccgt ctgacttcga cgccaaagcg    7200
aaagagttta tcgctaaact gcaggctaat ccggcgaaaa tcgccagccg taaagcgtcg    7260
cagaatgcta tcgaagcgtt cggcccgctg ttgcctgaat tcctcggcgg ctctgctgac    7320
ctggcaccgt ctaacctgac cctgtggtct ggttctaaag caatcaacga agatgctgca    7380
```

```
ggtaactaca tccactacgg tgttcgcgag ttcggtatga ccgcgattgc taacggtatc    7440
tccctgcacg gtggtttcct gccgtacacc tccaccttcc tgatgttcgt ggaatacgca    7500
cgtaacgccg tacgtatggc tgcgctgatg aaacagcgtc aggtgatggt ttacacccac    7560
gactccatcg gtctgggcga agatggcccg actcaccagc cggttgagca ggtcgcttct    7620
ctgcgcgtga ccccgaacat gtctacatgg cgtccgtgtg accaggttga atccgcggtc    7680
gcgtggaaat acggcgttga gcgtcaggac ggcccgactg cgcttatcct ctcccgtcag    7740
aacctggcgc agcaggaacg aactgaagag caactggcaa acatcgcgcg cggtggttat    7800
gtgctgaaag actgcgccgg tcagccggaa ctgattttca tcgctaccgg ttcagaagtt    7860
gaactggctg ttgctgccta cgaaaaactg actgccgaag gcgtgaaagc gcgcgtggtg    7920
tccatgccgt ctaccgacgc atttgacaag caggatgctg cttaccgtga atccgtactg    7980
ccgaaagcgg ttactgcacg cgttgctgta gaagcgggta ttgctgacta ctggtacaag    8040
tatgttggcc tgaacggtgc tatcgtcggt atgaccacct tcggtgaatc tgctccggca    8100
gagctgctgt ttgaagagtt cggcttcact gttgataacg ttgttgcgaa agcaaaagaa    8160
ctgctgtaat tagcatttcg ggtaaaaagg tcgcttcggc gacctttttt attaccttga    8220
tatgtccgtt tgcggacaag caatagataa agcgtgttgt agatcacaaa tatttatatg    8280
caataaatat caattatgta atatgcatca cgatatgcgt attgacattt gttgttataa    8340
ctataactca atgttatata agaaattaac tcgaggctat tgacgacagc tatggttcac    8400
tgtccaccaa ccaaaactgt gctcagtacc gccaatattt ctcccttgag gggtacaaag    8460
aggtgtccct agaagagatc cacgctgtgt aaaaatttta caaaaaggta ttgactttcc    8520
ctacagggtg tgtaataatt taattacagg cggggcaac cccgcctgtt ctagaggagg     8580
aggaatcgcc atgagagga ttgtcgttac tctcggggaa cgtagttacc caattaccat     8640
cgcatctggt ttgtttaatg aaccagcttc attcttaccg ctgaaatcgg gcgagcaggt    8700
catgttggtc accaacgaaa ccctggctcc tctgtatctc gataaggtcc gcggcgtact    8760
tgaacaggcg ggtgttaacg tcgatagcgt tatcctccct gacggcgagc agtataaaag    8820
cctggctgta ctcgataccg tctttacggc gttgttacaa aagccgcatg gtcgcgatac    8880
tacgctggtg gcgcttggcg gcggcgtagt gggcgatctg accggcttcg cggcggcgag    8940
ttatcagcgc ggtgttcgtt tcattcaagt cccgacgacg ttactgtcgc aggtcgattc    9000
ctccgttggc ggcaaaactg cggtcaacca tcccctcggt aaaaacatga ttggcgcgtt    9060
ctaccagcct gcttcagtgg tggtggatct cgactgtctg aaaacgcttc ccccgcgtga    9120
gttagcgtcg gggctggcag aagtcatcaa atacggcatt attcttgacg gtgcgttttt    9180
caactggctg gaagagaatc tggatgcgtt gttgcgtctg gacggtccgg caatggcgta    9240
ctgtattcgc cgttgttgtg aactgaaggc agaagttgtc gccgccgacg agcgcgaaac    9300
cgggttacgt gctttactga atctgggaca caccttggt catgccattg aagctgaaat    9360
ggggtatggc aattggttac atggtgaagc ggtcgctgcg ggtatggtga tggcggcgcg    9420
gacgtcggaa cgtctcgggc agtttagttc tgccgaaacg cagcgtatta accctgct     9480
cacgcgggct gggttaccgg tcaatgggcc gcgcgaaatg tccgcgcagg cgtatttacc    9540
gcatatgctg cgtgacaaga aagtccttgc gggagagatg cgcttaattc ttccgttggc    9600
aattggtaag agtgaagttc gcagcggcgt ttcgcacgag cttgttctta acgccattgc    9660
cgattgtcaa tcagcgtaat catcgttcat gcctgatgcc gctatgtagg ccggataagg    9720
cgttcacgcc gcatccggca accgatgcct gatgcgacgc ggtcgcgtct tatcaggcct    9780
```

| | | | | |
|---|---|---|---|---|
| acaggtcgat | gccgatatgt | acatcgtatt | cggcaattaa | tacatagcac tcgaggccta | 9840 |
| cctagcttcc | aagaaagata | tcctaacagc | acaagagcgg | aaagatgttt tgttctacat | 9900 |
| ccagaacaac | ctctgctaaa | attcctgaaa | aattttgcaa | aaagttgttg actttatcta | 9960 |
| caaggtgtgg | tataataatc | ttaacaacag | caggacgctc | tagaatgaaa accgtaactg | 10020 |
| taaaagatct | cgtcattggt | acgggcgcac | ctaaaatcat | cgtctcgctg atggcgaaag | 10080 |
| atatcgccag | cgtgaaatcc | gaagctctcg | cctatcgtga | agcggacttt gatattctgg | 10140 |
| aatggcgtgt | ggaccactat | gccgacctct | ccaatgtgga | gtctgtcatg gcggcagcaa | 10200 |
| aaattctccg | tgagaccatg | ccagaaaaac | cgctgctgtt | taccttccgc agtgccaaag | 10260 |
| aaggcggcga | gcaggcgatt | tccaccgagg | cttatattgc | actcaatcgt gcagccatcg | 10320 |
| acagcggcct | ggttgatatg | atcgatctgg | agttatttac | cggtgatgat caggttaaag | 10380 |
| aaaccgtcgc | ctacgcccac | gcgcatgatg | tgaaagtagt | catgtccaac catgacttcc | 10440 |
| ataaaacgcc | ggaagccgaa | gaaatcattg | cccgtctgcg | caaaatgcaa tccttcgacg | 10500 |
| ccgatattcc | taagattgcg | ctgatgccgc | aaagtaccag | cgatgtgctg acgttgcttg | 10560 |
| ccgcgaccct | ggagatgcag | gagcagtatg | ccgatcgtcc | aattatcacg atgtcgatgg | 10620 |
| caaaaactgg | cgtaatttct | cgtctggctg | gtgaagtatt | tggctcggcg gcaacttttg | 10680 |
| gtgcggtaaa | aaaagcgtct | gcgccagggc | aaatctcggt | aaatgatttg cgcacggtat | 10740 |
| taactatttt | acaccaggca | taagcaataa | tatttcggcg | ggaacaccct ccccgccgaa | 10800 |
| ctaaaaaata | tattcaatcg | tatttaataa | aaatatttcg | tgagtctctg tgcgctaatt | 10860 |
| ctc | | | | | 10863 |

<210> SEQ ID NO 58
<211> LENGTH: 5500
<212> TYPE: DNA
<213> ORGANISM: Escherichia coli
<220> FEATURE:
<221> NAME/KEY: gene
<222> LOCATION: (1)..(5500)
<223> OTHER INFORMATION: Nucleotide sequence of ppc::PR-pyc

<400> SEQUENCE: 58

| | | | | |
|---|---|---|---|---|
| cgaaccgacg | tcactacaac | cggtacgcgc | acataaaggt | catatctcta acgccatccg | 60 |
| tattcagggc | cagtcggggc | actccagcga | tccagcacgc | ggagttaacg ctatcgaact | 120 |
| aatgcacgac | gccatcgggc | atattttgca | attgcgcgat | aacctgaaag aacgttatca | 180 |
| ctacgaagcg | tttaccgtgc | cataccctac | gctcaacctc | gggcatattc acggtggcga | 240 |
| cgcttctaac | cgtatttgcg | cttgctgtga | gttgcatatg | gatattcgtc cgctgcctgg | 300 |
| catgacactc | aatgaactta | atggtttgct | caacgatgca | ttggctccgg tgagcgaacg | 360 |
| ctggccgggt | cgtctgacgg | tcgacgagct | gcatccgccg | atccctggct atgaatgccc | 420 |
| accgaatcat | caactggttg | aagtggttga | gaaattgctc | ggagcaaaaa ccgaagtggt | 480 |
| gaactactgt | accgaagcgc | cgtttattca | aacgttatgc | ccgacgctgg tgttggggcc | 540 |
| tggctcaatt | aatcaggctc | atcaacctga | tgaatatctg | gaaacacggt ttatcaagcc | 600 |
| cacccgcgaa | ctgataaccc | aggtaattca | ccattttgc | tggcattaaa acgtaggcc | 660 |
| gataaggcgc | tcgcgccgca | tccggcactg | ttgccaaact | ccagtgccgc aataatgtcg | 720 |
| gatgcgatac | ttgcgcatct | tatccgacct | acacctttgg | tgttacttgg ggcgattttt | 780 |
| taacatttcc | ataagttacg | cttatttaaa | gcgtcgtgaa | tttaatgacg taaattcctg | 840 |

```
ctatttattc gttcgttaaa tctatcaccg caagggataa atatctaaca ccgtgcgtgt       900
tgactatttt acctctggcg gtgataatgg ttgcatgtac taatctagat aaggaatata       960
gccatgtcgc aaagaaaatt cgccggcttg agagataact tcaatctctt gggtgaaaag      1020
aacaaaatat tggtggctaa tagaggagaa attccaatca gaattttcg taccgctcat       1080
gaactgtcta tgcagacggt agctatatat tctcatgaag atcgtctttc aacgcacaaa      1140
caaaaggctg acgaagcata cgtcataggt gaagtaggcc aatataccc cgtcggcgct       1200
tatttggcca ttgacgaaat catttccatt gcccaaaaac accaggtaga tttcatccat      1260
ccaggttatg ggttcttgtc tgaaaattcg gaatttgccg acaaagtagt gaaggccggt      1320
atcacttgga ttggccctcc agctgaagtt attgactccg tgggtgataa ggtctcagct      1380
agaaacctgg cagcaaaagc taatgtgccc accgttcctg gtacaccagg tcctatagaa      1440
actgtagagg aagcacttga cttcgtcaat gaatacggct acccggtgat cattaaggcc      1500
gcctttggtg gtggtggtag aggtatgaga gtcgttagag aaggtgacga cgtggcagat      1560
gcctttcaac gtgctacctc cgaagcccgt actgccttcg gtaatggtac ctgctttgtg      1620
gaaagattct tggacaagcc aaagcatatt gaagttcaat tgttggccga taaccacgga      1680
aacgtggttc atcttttcga aagagactgt tccgtgcaga gaagacacca aaaggttgtc      1740
gaagtggccc cagcaaagac tttacccccgt gaagtccgtg acgccatttt gacagatgca      1800
gttaaattgg ccaaagagtg tggctacaga atgcgggta ctgctgaatt cttggttgat       1860
aaccaaaata gacactattt cattgaaatt aatccaagaa tccaagtgga acataccatc      1920
acagaagaaa ttaccggtat agatattgtg gcggctcaga tccaaattgc ggcaggtgcc      1980
tctctacccc agctgggcct attccaggac aaaattacga ctcgtggctt tgccattcag      2040
tgccgtatta ccacggaaga ccctgctaag aacttccaac cagataccgg tagaatagaa      2100
gtgtaccgtt ctgcaggtgg taatggtgtt agactggatg gtggtaacgc ctatgcagga      2160
acaataatct cacctcatta cgactcaatg ctggtcaaat gctcatgctc cggttccacc      2220
tacgaaatcg ttcgtagaaa aatgattcgt gcattaatcg agttcagaat tagaggtgtc      2280
aagaccaaca ttcccttcct attgactctt ttgaccaatc cagtatttat tgagggtaca      2340
tactggacga cttttattga cgacaccccc aactgttcc aaatggtttc atcacaaaac       2400
agagcccaaa aacttttaca ttacctcgcc gacgtggcag tcaatggttc atctatcaag      2460
ggtcaaattg gcttgccaaa attaaaatca atccaagtg tccccatt gcacgatgct        2520
cagggcaatg tcatcaacgt tacaaagtct gcaccaccat ccggatggag gcaagtgcta      2580
ctagaaaagg ggccagctga atttgccaga caagttagac agttcaatgg tacttattg      2640
atggacacca cctggagaga cgctcatcaa tctctacttg caacaagagt cagaacccac      2700
gatttggcta caatcgctcc aacaaccgca catgccctg caggtcgttt cgccttagaa       2760
tgttggggtg gtgccacatt cgatgttgca atgagatttt tgcatgagga tccatgggaa      2820
cgtttgagaa aattaagatc tctggtgcct aatattccat tccaaatgtt attgcgtggt      2880
gccaatggtg tggcttattc ttcattgcct gacaatgcta ttgaccattt cgtcaagcaa      2940
gccaaggata atggtgttga tatttaga gtctttgatg ccttaaatga cttggaacaa        3000
ttgaaggtcg gtgtagatgc tgtgaagaag gcaggtggtg ttgtagaagc cactgttgt       3060
ttctctgggg atatgcttca gccaggcaag aaatacaatt tggattacta cttggaaatt      3120
gctgaaaaaa ttgtccaaat gggcactcat atcctgggta tcaaagatat ggcaggtacc      3180
atgaagccag cagctgccaa actactgatt ggatctttga gggctaagta ccctgatctc      3240
```

```
ccaatacatg ttcacactca cgattctgca ggtactgctg ttgcatcaat gactgcgtgt    3300
gctctggcgg gcgccgatgt cgttgatgtt gccatcaact caatgtctgg tttaacttca    3360
caaccatcaa tcaatgctct gttggcttca ttagaaggta atattgacac tggtattaac    3420
gttgagcatg tccgtgaact agatgcatat tgggcagaga tgagattgtt atactcttgt    3480
ttcgaggctg acttgaaggg cccagatcca gaagtttatc aacatgaaat cccaggtggt    3540
caattgacaa acttgttgtt tcaagcccaa caattgggtc ttggagaaca atgggccgaa    3600
acaaaaagag cttacagaga agccaattat ttattgggtg atattgtcaa agttacccca    3660
acttcgaagg tcgttggtga tctggcacaa tttatggtct ccaataaatt aacttccgat    3720
gatgtgagac gcctggctaa ttcttttggat ttccctgact ctgttatgga tttcttcgaa    3780
ggcttaatcg gccaaccata tggtgggttc ccagaaccat ttagatcaga cgttttaagg    3840
aacaagagaa gaaagttgac ttgtcgtcca ggcctggaac tagagccatt tgatctcgaa    3900
aaaattagag aagacttgca gaatagattt ggtgatgttg atgagtgcga cgttgcttct    3960
tataacatgt acccaagagt ttatgaagac ttccaaaaga tgagagaaac gtatggtgat    4020
ttatctgtat tgccaacaag aagcttttg tctccactag agactgacga agaaattgaa    4080
gttgtaatcg aacaaggtaa aacgctaatt atcaagctac aggctgtggg tgatttgaac    4140
aaaaagaccg gtgaaagaga agtttacttt gatttgaatg gtgaaatgag aaaaattcgt    4200
gttgctgaca gatcacaaaa agtggaaact gttactaaat ccaaagcaga catgcatgat    4260
ccattacaca ttggtgcacc aatggcaggt gtcattgttg aagttaaagt tcataaagga    4320
tcactaataa agaagggcca acctgtagcc gtattaagcg ccatgaaaat ggaaatgatt    4380
atatcttctc catccgatgg acaagttaaa gaagtgtttg tctctgatgg tgaaaatgtg    4440
gactcttctg atttattagt tctattagaa gaccaagttc ctgttgaaac taaggcatga    4500
tcttcctctt ctgcaaaccc tcgtgctttt gcgcgagggt tttctgaaat acttctgttc    4560
taacacccct gttttcaata tatttctgtc tgcatttat tcaaattctg aatataccct    4620
cagatatcct taaggaattg tcgttacatt cggcgatatt ttttcaagac aggttcttac    4680
tatgcattcc acagaagtcc aggctaaacc tctttttagc tggaaagccc tgggttgggc    4740
actgctctac ttttggtttt tctctactct gctacaggcc attatttaca tcagtggtta    4800
tagtggcact aacggcattc gcgactcgct gttattcagt tcgctgtggt tgatcccggt    4860
attcctcttt ccgaagcgga ttaaaattat tgccgcagta atcggcgtgg tgctatgggc    4920
ggcctctctg gcgcgctgt gctactacgt catctacggt caggagttct cgcagagcgt    4980
tctgtttgtg atgttcgaaa ccaacaccaa cgaagccagc gagtatttaa gccagtattt    5040
cagcctgaaa attgtgctta tcgcgctggc ctatacggcg gtggcagttc tgctgtggac    5100
acgcctgcgc ccggtctata ttccaaagcc gtggcgttat gttgtctctt tgccctgct    5160 ttatggcttg attctgcatc cgatcgccat gaatacgttt atcaaaaaca gccgtttga    5220 gaaaacgttg gataacctgg cctcgcgtat ggagcctgcc gcaccgtggc aattcctgac    5280
cggctattat cagtatcgtc agcaactaaa ctcgctaaca aagttactga atgaaaataa    5340
tgccttgccg ccactggcta atttcaaaga tgaatcgggt aacgaaccgc gcactttagt    5400
gctggtgatt ggcgagtcga cccagcgcgg acgcatgagt ctgtacggtt atccgcgtga    5460
aaccacgccg gagctggatg cgctgcataa aaccgatccg                           5500
```

<210> SEQ ID NO 59

-continued

```
<211> LENGTH: 200
<212> TYPE: DNA
<213> ORGANISM: Escherichia coli
<220> FEATURE:
<221> NAME/KEY: promoter
<222> LOCATION: (1)..(200)
<223> OTHER INFORMATION: Nucleotide sequence of acpP promoter

<400> SEQUENCE: 59
cacaaaatgc tcatgttgcg cgcagtctgc gtggttatga gtaataatta gtgcaaaatg      60
atttgcgtta ttgggggggta aggcctcaaa ataacgtaaa atcgtggtaa gacctgccgg    120
gatttagttg caaatttttc aacattttat acactacgaa aaccatcgcg aaagcgagtt    180
ttgataggaa atttaagagt                                                 200

<210> SEQ ID NO 60
<211> LENGTH: 200
<212> TYPE: DNA
<213> ORGANISM: Escherichia coli
<220> FEATURE:
<221> NAME/KEY: promoter
<222> LOCATION: (1)..(200)
<223> OTHER INFORMATION: Nuclotide sequence of rplU promoter

<400> SEQUENCE: 60
ttatggttag gaatataggg tgattgtact gaaaaaatgg cacagataaa cgttaccgta      60
caagttgtgt ttttttttctt cgtgtattga ctgtagcact tgtcaaaggc gtgcgttttg    120
cgtaatattc gcgccctatt gtgaatattt atagcgcact ctgaatcatt gaaaaggtgt    180
gcgcggaagc ggagttttat                                                 200

<210> SEQ ID NO 61
<211> LENGTH: 60
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(60)
<223> OTHER INFORMATION: Sequence of DNA primer MS604

<400> SEQUENCE: 61
aacgccgtat aatgggcgca gattaagagg ctacagtggg cttacatggc gatagctaga     60

<210> SEQ ID NO 62
<211> LENGTH: 60
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(60)
<223> OTHER INFORMATION: Sequence of DNA Primer MS605

<400> SEQUENCE: 62
tgtcggatcg ataaataggg caaaacaaac gcgcatcccg gaaaacgatt ccgaagccca     60

<210> SEQ ID NO 63
<211> LENGTH: 60
<212> TYPE: DNA
<213> ORGANISM: Artificial Sequence
<220> FEATURE:
<223> OTHER INFORMATION: Primer
<220> FEATURE:
<221> NAME/KEY: primer_bind
```

<222> LOCATION: (1)..(60)
<223> OTHER INFORMATION: Sequence of DNA Primer MS608

<400> SEQUENCE: 63
aaagtctgcc tgcaagtctg acagggcaac tatttgtggg cttacatggc gatagctaga    60

<210> SEQ ID NO 64
<211> LENGTH: 60
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(60)
<223> OTHER INFORMATION: Sequence of DNA Primer MS609

<400> SEQUENCE: 64
ttgcaaaatt gccctgaaac agggcaacag cggagtcccg gaaaacgatt ccgaagccca    60

<210> SEQ ID NO 65
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(25)
<223> OTHER INFORMATION: Sequence of DNA Primer MS461

<400> SEQUENCE: 65
ggctatattc cttatctaga ttagt    25

<210> SEQ ID NO 66
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(25)
<223> OTHER INFORMATION: Sequence of DNA Primer MS346

<400> SEQUENCE: 66
gtctgacagg tgccggattt catat    25

<210> SEQ ID NO 67
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer RP712

<400> SEQUENCE: 67
tctagataag gaatatagcc atgaccgcac cgattcagga tctgc    45

<210> SEQ ID NO 68
<211> LENGTH: 45
<212> TYPE: DNA
<213> ORGANISM: Artificial Sequence
<220> FEATURE:
<223> OTHER INFORMATION: Primer
<220> FEATURE:

<221> NAME/KEY: primer_bind
<222> LOCATION: (1)..(45)
<223> OTHER INFORMATION: Sequence of DNA Primer RP714

<400> SEQUENCE: 68
aaatccggca cctgtcagac ttattttgcg ctaccctggt ttttt         45

<210> SEQ ID NO 69
<211> LENGTH: 60
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(60)
<223> OTHER INFORMATION: Sequence of DNA Primer RP731

<400> SEQUENCE: 69
catgtactaa tctagataag gaatatagcc atgaaactga ttattgggat gacgggggcc    60

<210> SEQ ID NO 70
<211> LENGTH: 60
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(60)
<223> OTHER INFORMATION: Sequence of DNA Primer RP732

<400> SEQUENCE: 70
gccggatatg aaatccggca cctgtcagac ttattcgatc tcctgtgcaa attgttctgc    60

<210> SEQ ID NO 71
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequenc of DNA Primer MS669

<400> SEQUENCE: 71
tctagataag gaatatagcc atgaaacgac tcattgtagg catca         45

<210> SEQ ID NO 72
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer MS666

<400> SEQUENCE: 72
accgaacagg cttatgtcca gatagcaggt atagcggttg aatcg         45

<210> SEQ ID NO 73
<211> LENGTH: 24
<212> TYPE: DNA
<213> ORGANISM: Artificial Sequence
<220> FEATURE:
<223> OTHER INFORMATION: Primer

```
<220> FEATURE:
<221> NAME/KEY: primer_bind
<222> LOCATION: (1)..(24)
<223> OTHER INFORMATION: Sequence of DNA Primer RP607

<400> SEQUENCE: 73
tggacataag cctgttcggt tcgt                                          24

<210> SEQ ID NO 74
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(25)
<223> OTHER INFORMATION: Sequence of DNA Primer RP621

<400> SEQUENCE: 74
ttagatttga ctgaaatcgt acagt                                         25

<210> SEQ ID NO 75
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer MS676

<400> SEQUENCE: 75
tctagataag gaatatagcc atgaaactga tcgtcgggat gacag                   45

<210> SEQ ID NO 76
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer MS680

<400> SEQUENCE: 76
acgatttcag tcaaatctaa ttattcattc tcctgagaaa aattc                   45

<210> SEQ ID NO 77
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer MS686

<400> SEQUENCE: 77
tctagataag gaatatagcc atgacggcac gcatcatcat tggta                   45

<210> SEQ ID NO 78
<211> LENGTH: 45
<212> TYPE: DNA
<213> ORGANISM: Artificial Sequence
<220> FEATURE:
```

```
<223> OTHER INFORMATION: Primer
<220> FEATURE:
<221> NAME/KEY: primer_bind
<222> LOCATION: (1)..(45)
<223> OTHER INFORMATION: Sequence of DNA Primer MS684

<400> SEQUENCE: 78
acgatttcag tcaaatctaa ttaattaaaa cgtagctcgc cttca          45

<210> SEQ ID NO 79
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer MS692

<400> SEQUENCE: 79
tctagataag gaatatagcc atgaaacgaa ttgttgtggg aatca          45

<210> SEQ ID NO 80
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer MS691

<400> SEQUENCE: 80
acgatttcag tcaaatctaa ttaatccccc tcccaacggc gatca          45

<210> SEQ ID NO 81
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer RP677

<400> SEQUENCE: 81
acgatttcag tcaaatctaa ttaatccccc tcccaacggc gatca          45

<210> SEQ ID NO 82
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(25)
<223> OTHER INFORMATION: Sequence of DNA Primer RP671

<400> SEQUENCE: 82
ttaatcgcct tgcagcacat ccccc                                25

<210> SEQ ID NO 83
<211> LENGTH: 24
<212> TYPE: DNA
<213> ORGANISM: Artificial Sequence
```

<220> FEATURE:
<223> OTHER INFORMATION: Primer
<220> FEATURE:
<221> NAME/KEY: primer_bind
<222> LOCATION: (1)..(24)
<223> OTHER INFORMATION: Sequenc of DNA primer RP664

<400> SEQUENCE: 83
acgaaccgaa caggcttatg tcca                                      24

<210> SEQ ID NO 84
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer RP702

<400> SEQUENCE: 84
gccgtcgttt tacaacgtcg gatccgccta cctagcttcc aagaa               45

<210> SEQ ID NO 85
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer RP783

<400> SEQUENCE: 85
cctacaatga gtcgtttcat taggttttcc tcaacccggg agcgt               45

<210> SEQ ID NO 86
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA primer RP781

<400> SEQUENCE: 86 cccggggttga ggaaaaccta atgaaacgac tcattgtagg catca              45

<210> SEQ ID NO 87
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer 780

<400> SEQUENCE: 87
atgtgctgca aggcgattaa gatagcaggt atagcggttg aatcg               45

<210> SEQ ID NO 88
<211> LENGTH: 45
<212> TYPE: DNA

```
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer RP700

<400> SEQUENCE: 88
gccgtcgttt tacaacgtcg agcggggcgg ttgtcaacga tgggg            45

<210> SEQ ID NO 89
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(45)
<223> OTHER INFORMATION: Sequence of DNA Primer RP784

<400> SEQUENCE: 89
cctacaatga gtcgtttcat ggctatattc ctcctctgca tgaga            45

<210> SEQ ID NO 90
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequenc of DNA Primer RP779

<400> SEQUENCE: 90
tgcagaggag gaatatagcc atgaaacgac tcattgtagg catca            45

<210> SEQ ID NO 91
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer MS1383

<400> SEQUENCE: 91
gatggggtgt ctggggtaat atgtcgcaaa gaaaattcgc cggct            45

<210> SEQ ID NO 92
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer MS1384

<400> SEQUENCE: 92
gggtttgcag aagaggaaga tcatgcctta gtttcaacag gaact            45

<210> SEQ ID NO 93
<211> LENGTH: 45
```

```
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer MS1429

<400> SEQUENCE: 93
attcctgcta tttattcgtt cgttaaatct atcaccgcaa gggat          45

<210> SEQ ID NO 94
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: primer_bind
<222> LOCATION: (1)..(45)
<223> OTHER INFORMATION: Sequence of DNA Primer MS1430

<400> SEQUENCE: 94
gcgaattttc tttgcgacat ggctatattc cttatctaga ttagt          45

<210> SEQ ID NO 95
<211> LENGTH: 14
<212> TYPE: DNA
<213> ORGANISM: Escherichia coli
<220> FEATURE:
<221> NAME/KEY: misc_feature
<222> LOCATION: (1)..(14)
<223> OTHER INFORMATION: RBS in front of the E. coli pykA gene

<400> SEQUENCE: 95
cggagtatta catg          14

<210> SEQ ID NO 96
<211> LENGTH: 14
<212> TYPE: DNA
<213> ORGANISM: Artificial Sequence
<220> FEATURE:
<223> OTHER INFORMATION: Mutated RBS in front of pykA gene

<400> SEQUENCE: 96
cagagtatta catg          14

<210> SEQ ID NO 97
<211> LENGTH: 14
<212> TYPE: DNA
<213> ORGANISM: Artificial Sequence
<220> FEATURE:
<223> OTHER INFORMATION: Mutated RBS in front of pykA gene

<400> SEQUENCE: 97
caaagtatta catg          14

<210> SEQ ID NO 98
<211> LENGTH: 14
<212> TYPE: DNA
<213> ORGANISM: Artificial Sequence
<220> FEATURE:
<223> OTHER INFORMATION: Mutated RBS in front of pykA gene

<400> SEQUENCE: 98
caatgtatta catg          14
```

```
<210> SEQ ID NO 99
<211> LENGTH: 14
<212> TYPE: DNA
<213> ORGANISM: Artificial Sequence
<220> FEATURE:
<223> OTHER INFORMATION: Mutated RBS in front of pykA gene

<400> SEQUENCE: 99
caatatatta catg                                                        14
```